US008791107B2

(12) United States Patent
Chang et al.

(10) Patent No.: US 8,791,107 B2
(45) Date of Patent: Jul. 29, 2014

(54) N-SUBSTITUTED OXAZINOPTERIDINES AND OXAZINOPTERIDINONES

(75) Inventors: Edcon Chang, San Diego, CA (US); Tony Gibson, San Diego, CA (US); Bohan Jin, San Diego, CA (US); Nicholas Scorah, South Diego, CA (US); Qing Dong, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 184 days.

(21) Appl. No.: 13/404,958

(22) Filed: Feb. 24, 2012

(65) Prior Publication Data
US 2012/0220575 A1 Aug. 30, 2012

Related U.S. Application Data

(60) Provisional application No. 61/446,949, filed on Feb. 25, 2011.

(51) Int. Cl.
*A61K 31/5383* (2006.01)
*C07D 498/14* (2006.01)

(52) U.S. Cl.
USPC ........................................ 514/230.2; 544/101

(58) Field of Classification Search
USPC ........................................ 544/101; 514/230.2
See application file for complete search history.

(56) References Cited

U.S. PATENT DOCUMENTS

| | | | |
|---|---|---|---|
| 6,806,272 | B2 | 10/2004 | Bauer et al. |
| 6,861,422 | B2 | 3/2005 | Hoffmann et al. |
| 7,238,807 | B2 | 7/2007 | Duran et al. |
| 7,241,889 | B2 | 7/2007 | Hoffmann et al. |
| 7,371,753 | B2 | 5/2008 | Stadtmueller |
| 8,163,755 | B2 * | 4/2012 | Jin et al. ............... 514/252.16 |
| 8,268,819 | B2 | 9/2012 | Jin |
| 2004/0029885 | A1 | 2/2004 | Bauer et al. |
| 2004/0176380 | A1 | 9/2004 | Hoffmann et al. |
| 2006/0014751 | A1 | 1/2006 | Hoffmann et al. |
| 2006/0035903 | A1 | 2/2006 | Mohr et al. |
| 2006/0046990 | A1 | 3/2006 | Stadtmueller et al. |
| 2006/0122393 | A1 | 6/2006 | Duran et al. |
| 2008/0177066 | A1 | 7/2008 | Linz et al. |

FOREIGN PATENT DOCUMENTS

| | | |
|---|---|---|
| WO | WO/03/076440 | 9/2003 |
| WO | WO/2004/042002 | 5/2004 |
| WO | WO/2005/026158 | 3/2005 |
| WO | WO/2006/005915 | 1/2006 |
| WO | WO/2006/018185 | 2/2006 |
| WO | WO2006018182 | 2/2006 |
| WO | WO/2006/086464 | 8/2006 |
| WO | WO/2007/014838 | 2/2007 |
| WO | WO/2008/023180 | 2/2008 |
| WO | WO/2009/046383 | 4/2009 |
| WO | WO/2011/025889 | 3/2011 |
| WO | WO2011/079114 | 6/2011 |
| WO | WO2011/079118 | 6/2011 |

OTHER PUBLICATIONS

L.C. Cantley, Science 296:1655-57 (2002).
C. Jimenez, et al., J. Biol. Chem., 277(44):41556-62 (2002).
C. Brock, et al., J. Cell. Biol., 160(1):89-99 (2003).
B. Vanhaesebroeck, et al., Trends Biochem. Sci. 30:194-204 (2005).
Eduardo Vilar et al. "Pushing the Envelope in the mTOR Pathway: The Second Generation of Inhibitors" Mol Cancer Ther 2011;10:395-403. Published OnlineFirst Jan. 7,2011.
C. Rommel et al., Nature Rev. Immunology, 7:191-201 (2007).
A. Ghigo et al., BioEssays 32:185-196 (2010).
M. Camps et al., Nature Med. 11:936-43 (2005).
G. S. Firestein, N. Engl. J. Med. 354:80-82 (2006).
S. Hayer et al., FASEB J 23:4288-98 (2009) (RA).
D. F. Barber et al., Nature Med. 11:933-35 (2005) (SLE).
A. Fougerat et al., Circulation 117:1310-17. 2008.
T. M. Randis et al., Eur. J. Immunol. 38:1215-24 (2008) (RA).
K. S. Lee et al., FASEB J. 20:455-65 (2006).
H. S. Farghaly et al., Mol. Pharmacol. 73:1530-37 (2008) (asthma).
K. Ali et al., Nature 431:1007-11 (2004) (anaphylaxis).
J. Doukas et al., J. Pharmacol. Exp. Ther. 328:758-65 (2009) (asthma and COPD).
Y. Samuels et al., Science 304:554 (2004).
Y. Samuels & K. Ericson, Curr. Opin. Oncol. 18(1):77-82 (2006).
S. Kang et al., Proc. Nat'l Acad. Sci. USA 102(3):802-7 (2005).

(Continued)

*Primary Examiner* — Kahsay Habte
(74) *Attorney, Agent, or Firm* — Matthew J. Russo

(57) ABSTRACT

Disclosed are compounds of Formula 1,

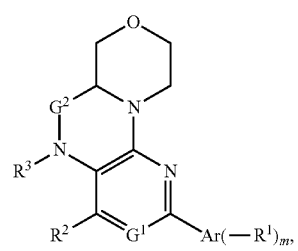

and pharmaceutically acceptable salts thereof, wherein Ar, $R^1$, $R^2$, $R^3$, $G^1$, $G^2$, and m are defined in the specification. This disclosure also relates to materials and methods for preparing compounds of Formula 1, to pharmaceutical compositions which contain them, and to their use for treating inflammatory disorders, cardiovascular disease, cancer, and other conditions associated with PI3Kδ.

13 Claims, No Drawings

(56) References Cited

OTHER PUBLICATIONS

A. Bader et al., Proc. Nat'l Acad. Sci. USA 103(5):1475-79 (2006).
P. Sujobert et al., Blood 106(3):1063-66 (2005).
C. Billottet et al., Oncogene 25(50):6648-59 (2006).
F. Hickey & T. Cotter, J. Biol. Chem. 281(5):2441-50 (2006).
C. Benistant et al., Oncogene, 19(44):5083-90 (2000).
M. Mizoguchi et al., Brain Pathology 14(4):372-77 (2004).
C. Knobbe et al, Neuropathology Appl. Neurobiolgy 31(5):486-90 (2005).
J. Doukas et al., Proc. Nat'l Acad. Sci. USA 103:19866-71 (2006) (MI).

* cited by examiner

N-SUBSTITUTED OXAZINOPTERIDINES AND OXAZINOPTERIDINONES

CROSS REFERENCE TO RELATED APPLICATION

This application claims the benefit of U.S. Provisional Application No. 61/446,949, filed Feb. 25, 2011, which is incorporated herein by reference.

FIELD OF THE INVENTION

This invention relates to N-substituted oxazinopteridines, N-substituted oxazinopteridinones, and related compounds, which are inhibitors of PI3Kδ, to pharmaceutical compositions which contain them, and to the use of the inhibitors to treat diseases, disorders, and conditions associated with PI3Kδ, including inflammatory disorders, cancer, and cardiovascular disease.

BACKGROUND OF THE INVENTION

The phosphoinositide 3-kinases (PI3Ks) are lipid and protein kinases involved in intracellular signal transduction. They act primarily through phosphorylation of phosphoinositides at the D3 position of the inositol ring, and are typically grouped into three classes (I, II, and III) based on their structure, function, and substrate specificity. The class I PI3Ks, denoted PI3Kα, PI3Kβ, PI3Kγ, and PI3Kδ, catalyze the phosphorylation of phosphatidylinositol-4,5-bisphosphate to phosphatidylinositol-3,4,5-trisphosphate, which functions as a second messenger whose binding to proteins containing pleckstrin homology domains, such as AKT, PDK1, Btk, GTPase activating proteins, and guanine nucleotide exchange factors, triggers a cascade of cellular processes involved with cell growth, survival, proliferation, apoptosis, adhesion, and migration, among others. See L. C. Cantley, *Science* 296:1655-57 (2002). Class I PI3K isoforms exist as heterodimers composed of a catalytic subunit, p110, and an associated regulatory subunit that controls their expression, activation, and subcellular localization. PI3Kα, PI3Kβ, and PI3Kδ associate with a regulatory subunit, p85, and are activated by growth factors and cytokines through a tyrosine kinase-dependent mechanism; PI3Kγ associates with two regulatory subunits, p101 and p84, and is activated by G-protein-coupled receptors. See C. Jimenez, et al., *J. Biol. Chem.*, 277(44):41556-62 (2002) and C. Brock, et al., *J. Cell. Biol.*, 160(1):89-99 (2003).

Although PI3Kα and PI3Kβ are expressed in many tissue types, PI3Kγ and PI3Kδ are predominantly expressed in leukocytes and are therefore thought to be attractive targets for treating inflammatory disorders and other diseases related to the immune system. See B. Vanhaesebroeck, et al., *Trends Biochem. Sci.* 30:194-204 (2005), C. Rommel et al., *Nature Rev. Immunology*, 7:191-201 (2007), and A. Ghigo et al., *BioEssays* 32:185-196 (2010). Recent preclinical studies support this view. For example, treatments with selective PI3Kγ inhibitors suppress the progression of joint inflammation and damage in mouse models of rheumatoid arthritis (RA), and reduce glomerulonephritis and extend survival in the MRL-lpr mouse model of systemic lupus erythematosus (SLE). See M. Camps et al., *Nature Med.* 11:936-43 (2005), G. S. Firestein, *N. Engl. J. Med.* 354:80-82 (2006), and S. Hayer et al., *FASEB J* 23:4288-98 (2009) (RA); see also D. F. Barber et al., *Nature Med.* 11:933-35 (2005) (SLE). A selective PI3Kγ inhibitor has also been shown to reduce formation and size of lesions in mouse models of early- and advanced-stage atherosclerosis, and to stabilize plaque formation thereby minimizing risks of plaque rupture and subsequent thrombosis and myocardial infarction. See A. Fougerat et al., *Circulation* 117:1310-17.2008. Treatments with PI3Kδ-selective inhibitors significantly reduce inflammation and associated bone and cartilage erosion following injection of wild type mice with an arthritogenic serum, attenuate allergic airway inflammation and hyper-responsiveness in a mouse model of asthma, and protect mice against anaphylactic allergic responses. See T. M. Randis et al., *Eur. J. Immunol.* 38:1215-24 (2008) (RA); K. S. Lee et al., *FASEB J.* 20:455-65 (2006) and H. S. Farghaly et al., *Mol. Pharmacol.* 73:1530-37 (2008) (asthma); K. Ali et al., *Nature* 431:1007-11 (2004) (anaphylaxis). Administration of a PI3Kγ and PI3Kδ dual selective inhibitor has been shown to be efficacious in murine models of allergic asthma and chronic obstructive pulmonary disease (COPD) and is cardioprotective in murine and porcine models of myocardial infraction (MI). See J. Doukas et al., *J. Pharmacol. Exp. Ther.* 328:758-65 (2009) (asthma and COPD); J. Doukas et al., *Proc. Nat'l Acad. Sci. USA* 103: 19866-71 (2006) (MI).

Studies also suggest targeting one or more of the four class I PI3K isoforms may yield useful treatments for cancer. The gene encoding p110α is mutated frequently in common cancers, including breast, brain, prostate, colon, gastric, lung, and endometrial cancers. See Y. Samuels et al., *Science* 304: 554 (2004) and Y. Samuels & K. Ericson, *Curr. Opin. Oncol.* 18(1):77-82 (2006). One of three amino acid substitutions in the helical or kinase domains of the enzyme are responsible for 80 percent of these mutations, which lead to significant upregulation of kinase activity and result in oncogenic transformation in cell culture and in animal models. See S. Kang et al., *Proc. Nat'l Acad. Sci. USA* 102(3):802-7 (2005) and A. Bader et al., *Proc. Nat'l Acad. Sci. USA* 103(5):1475-79 (2006). No such mutations have been identified in the other PI3K isoforms, though there is evidence they can contribute to the development and progression of malignancies. PI3Kδ is consistently overexpressed in acute myeloblastic leukemia and inhibitors of PI3Kδ can prevent the growth of leukemic cells. See P. Sujobert et al., *Blood* 106(3):1063-66 (2005); C. Billottet et al., *Oncogene* 25(50):6648-59 (2006). PI3Kγ expression is elevated in chronic myeloid leukemia. See F. Hickey & T. Cotter, *J. Biol. Chem.* 281(5):2441-50 (2006). Alterations in expression of PI3Kβ, PI3Kγ, and PI3Kδ have also been observed in cancers of the brain, colon and bladder. See C. Benistant et al., *Oncogene*, 19(44):5083-90 (2000), M. Mizoguchi et al., *Brain Pathology* 14(4):372-77 (2004), and C. Knobbe et al, *Neuropathology Appl. Neurobiology* 31(5): 486-90 (2005). Moreover, all of these isoforms have been shown to be oncogenic in cell culture. See S. Kang et al. (2006).

Certain inhibitors of PI3K are described in WO2006/005915 and WO 2008/023180.

SUMMARY OF THE INVENTION

This invention provides N-substituted oxazinopteridines, N-substituted oxazinopteridinones, and related compounds, and pharmaceutically acceptable salts thereof. This invention also provides pharmaceutical compositions that contain the N-substituted oxazinopteridines and oxazinopteridinones and provides for their use to treat diseases, disorders and conditions associated with PI3Kδ inhibition, including inflammatory disorders, cancer, and cardiovascular disease.

One aspect of the invention provides compounds of Formula 1:

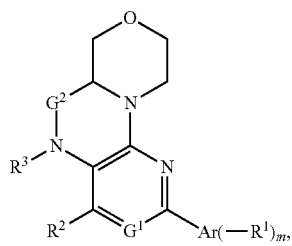

or a pharmaceutically acceptable salt therefore, wherein:
$G^1$ is selected from N and $CR^7$;
$G^2$ is selected from C=O and $CH_2$;
Ar is selected from $C_{6-14}$ aryl and $C_{1-10}$ heteroaryl;
m is 0, 1, 2, 3, or 4;
n is 0, 1, 2 or 3;
each $R^1$ is independently selected from cyano, halo, hydroxy, nitro, oxo, optionally substituted $C_{1-6}$ alkyl, optionally substituted $C_{1-4}$ alkoxy, optionally substituted $C_{2-4}$ alkenyl, optionally substituted $C_{2-4}$ alkynyl, optionally substituted $C_{3-8}$ cycloalkyl, optionally substituted $C_{3-6}$ heterocyclyl, optionally substituted $C_{6-14}$ aryl, optionally substituted $C_{6-14}$ aryloxy, optionally substituted $C_{1-10}$ heteroaryl, optionally substituted $C_{1-10}$ heteroaryloxy, —C(O)OR$^4$, —OC(O)R$^4$, —N(R$^4$)R$^5$, —NHC(O)N(R$^8$)R$^9$, —S(O)$_2$R$^6$, —S(O)$_2$N(R$^4$)R$^5$, —C(O)N(R$^8$)R$^9$, —NHC(O)OR$^{10}$, —NHS(O)$_2$NHR$^8$, —NHS(O)$_2$R$^6$, —NHC(O)NHN(R$^8$)R$^9$, —NHC(S)N(R$^8$)R$^9$, —NHC(=NR$^{11}$)N(R$^8$)R$^9$, —NHC(SR$^{12}$)N(R$^8$)R$^9$, and —NHC(=NR$^{11}$)OR$^{13}$;
$R^2$ is selected from hydrogen, cyano, halo, hydroxy, nitro, optionally substituted $C_{1-6}$ alkyl, optionally substituted $C_{1-4}$ alkoxy, optionally substituted $C_{2-4}$ alkenyl, optionally substituted $C_{2-4}$ alkynyl, optionally substituted $C_{3-6}$ heterocyclyl, optionally substituted $C_{6-14}$ aryl, optionally substituted $C_{6-14}$ aryloxy, optionally substituted $C_{1-10}$ heteroaryl, —C(O)OR$^4$, —OC(O)R$^4$, —N(R$^4$)R$^5$, and —S(O)$_2$R$^6$;
$R^3$ is selected from hydrogen, optionally substituted $C_{1-6}$ alkyl, optionally substituted $C_{3-8}$ cycloalkyl, optionally substituted $C_{3-6}$ heterocyclyl, optionally substituted $C_{6-14}$ aryl, optionally substituted $C_{1-10}$ heteroaryl, —(CH$_2$)$_n$N(R$^4$)R$^5$, —(CH$_2$)$_n$C(O)N(R$^4$)R$^5$, and —S(O)$_2$R$^6$;
each $R^4$ and $R^5$ is independently selected from hydrogen, optionally substituted $C_{1-6}$ alkyl, optionally substituted $C_{3-8}$ cycloalkyl, optionally substituted phenyl, optionally substituted $C_{3-6}$ heterocyclyl, and optionally substituted $C_{1-10}$ heteroaryl;
each $R^6$ is independently selected from optionally substituted $C_{1-6}$ alkyl, optionally substituted $C_{3-8}$ cycloalkyl, optionally substituted phenyl, optionally substituted $C_{3-6}$ heterocyclyl, and optionally substituted $C_{1-10}$ heteroaryl;
$R^7$ is selected from hydrogen, cyano, halo, hydroxy, nitro, optionally substituted $C_{1-4}$ alkyl, optionally substituted $C_{1-4}$ alkoxy, —C(O)OR$^4$, —C(O)N(R$^4$)R$^5$, —N(R$^4$)R$^5$, —NHC(O)R$^4$, —NHC(O)N(R$^4$)R$^5$, —OC(O)N(R$^4$)R$^5$, —NHC(O)OR$^6$, —S(O)$_2$R$^6$, —NHS(O)$_2$R$^6$, and —S(O)$_2$N(R$^4$)R$^5$;
each $R^8$ and $R^9$ is independently selected from hydrogen, optionally substituted $C_{1-6}$ alkyl, optionally substituted $C_{3-8}$ cycloalkyl, optionally substituted $C_{6-14}$ aryl, optionally substituted $C_{3-6}$ heterocyclyl, and optionally substituted $C_{1-10}$ heteroaryl;

each $R^{10}$ is independently selected from optionally substituted $C_{1-6}$ alkyl, optionally substituted $C_{3-8}$ cycloalkyl, optionally substituted $C_{6-14}$ aryl, optionally substituted $C_{3-6}$ heterocyclyl, and optionally substituted $C_{1-10}$ heteroaryl;
each $R^{11}$ is independently selected from hydrogen, cyano, nitro, optionally substituted $C_{1-6}$ alkyl, optionally substituted $C_{1-4}$ alkoxy, optionally substituted $C_{3-8}$ cycloalkyl, optionally substituted $C_{3-6}$ heterocyclyl, optionally substituted $C_{6-14}$ aryl, and optionally substituted $C_{1-10}$ heteroaryl;
each $R^{12}$ is independently selected from optionally substituted $C_{1-6}$ alkyl and optionally substituted phenyl;
each $R^{13}$ is independently selected from optionally substituted $C_{1-6}$ alkyl, optionally substituted $C_{3-8}$ cycloalkyl, and optionally substituted $C_{6-14}$ aryl;
each $R^{14}$ and $R^{15}$ is independently selected from hydrogen, $C_{1-6}$ alkyl, $C_{3-8}$ cycloalkyl, optionally substituted phenyl, $C_{3-6}$ heterocyclyl, and $C_{1-10}$ heteroaryl; and
each $R^{16}$ is independently selected from $C_{1-6}$ alkyl, $C_{3-8}$ cycloalkyl, optionally substituted phenyl, $C_{3-6}$ heterocyclyl, and $C_{1-10}$ heteroaryl;
wherein:
each optionally substituted $C_{1-6}$ alkyl is independently substituted with from 0 to 7 substituents independently selected from cyano, halo, hydroxy, oxo, optionally substituted $C_{1-4}$ alkyl, $C_{1-4}$ alkoxy, $C_{2-4}$ alkenyl, optionally substituted $C_{3-8}$ cycloalkyl, optionally substituted $C_{3-6}$ heterocyclyl, optionally substituted $C_{1-10}$ heteroaryl, optionally substituted phenyl, optionally substituted $C_{6-14}$ aryloxy, —SR$^{14}$, —C(O)OR$^{14}$, —N(R$^{14}$)R$^{15}$, —C(O)N(R$^{14}$)R$^{15}$, and —S(O)$_2$R$^{16}$;
each optionally substituted $C_{1-4}$ alkoxy is independently substituted with from 0 to 6 substituents independently selected from cyano, halo, hydroxy, oxo, $C_{2-4}$ alkenyl, $C_{1-4}$ alkoxy, optionally substituted $C_{3-8}$ cycloalkyl, optionally substituted $C_{1-10}$ heteroaryl, optionally substituted phenyl, —C(O)N(R$^{14}$)R$^{15}$, and —C(O)OR$^{14}$;
each optionally substituted $C_{2-4}$ alkenyl is independently substituted with from 0 to 3 substituents independently selected from cyano, halo, hydroxy, oxo, $C_{1-4}$ alkoxy, $C_{3-8}$ cycloalkyl, optionally substituted $C_{1-10}$ heteroaryl, optionally substituted phenyl, —C(O)N(R$^{14}$)R$^{15}$, and —C(O)OR$^{14}$;
each optionally substituted $C_{2-4}$ alkynyl is independently substituted with from 0 to 3 substituents independently selected from cyano, halo, hydroxy, oxo, $C_{1-4}$ alkoxy, $C_{3-8}$ cycloalkyl, optionally substituted $C_{1-10}$ heteroaryl, optionally substituted phenyl, —C(O)N(R$^{14}$)R$^{15}$, and —C(O)OR$^{14}$;
each optionally substituted $C_{3-8}$ cycloalkyl is independently substituted with from 0 to 6 substituents independently selected from cyano, halo, hydroxy, nitro, oxo, optionally substituted $C_{1-4}$ alkyl, $C_{1-4}$ alkoxy, $C_{2-4}$ alkenyl, $C_{3-8}$ cycloalkyl, $C_{3-8}$ cycloalkoxy, optionally substituted $C_{1-10}$ heteroaryl, optionally substituted phenyl, —C(O)N(R$^{14}$)R$^{15}$, —C(O)N(R$^{14}$)R$^{15}$, —N(R$^{14}$)R$^{15}$, —NHC(O)R$^{14}$, —NHC(O)OR$^{14}$, and —C(O)OR$^{14}$;
each optionally substituted $C_{1-10}$ heteroaryl is independently substituted with from 0 to 5 substituents independently selected from cyano, halo, hydroxy, oxo, nitro, optionally substituted $C_{1-4}$ alkyl, $C_{1-4}$ alkoxy, $C_{3-8}$ cycloalkyl, optionally substituted $C_{3-6}$ heterocyclyl, $C_{1-10}$ heteroaryl, optionally substituted phenyl, —C(O)N(R$^{14}$)R$^{15}$, —N(R$^{14}$)R$^{15}$, —C(O)N(R$^{14}$)R$^{15}$, —OC(O)NR$^{14}$R$^{15}$, —NHC(O)OR$^{16}$, —NHS(O)$_2$R$^{16}$, —S(O)$_2$N(R$^{14}$)R$^{15}$, —NHC(O)N(R$^{14}$)R$^{15}$, —C(O)OR$^{14}$, and —S(O)$_2$R$^{16}$;

each optionally substituted $C_{1-10}$ heteroaryloxy is independently substituted with from 0 to 5 substituents independently selected from cyano, halo, hydroxy, nitro, oxo, optionally substituted $C_{1-4}$ alkyl, $C_{1-4}$ alkoxy, trifluoromethyl, optionally substituted phenyl, and —S(O)$_2$R$^{16}$;

each optionally substituted $C_{3-6}$ heterocyclyl is independently substituted with from 0 to 4 substituents independently selected from cyano, halo, hydroxy, nitro, oxo, optionally substituted $C_{1-4}$ alkyl, optionally substituted $C_{1-4}$ alkoxy, $C_{2-4}$ alkenyl, optionally substituted $C_{3-8}$ cycloalkyl, $C_{3-8}$ cycloalkoxy, $C_{3-6}$ heterocyclyl, $C_{1-10}$ heteroaryl, optionally substituted phenyl, —C(O)N(R$^{14}$)R$^{15}$, —C(O)N(R$^{14}$)R$^{15}$, —N(R$^{14}$)R$^{15}$, and —C(O)OR$^{14}$;

each optionally substituted $C_{1-4}$ alkyl is independently substituted with from 0 to 5 substituents independently selected from cyano, halo, hydroxy, nitro, oxo, optionally substituted $C_{1-4}$ alkoxy, $C_{2-4}$ alkenyl, $C_{3-8}$ cycloalkyl, $C_{3-8}$ cycloalkoxy, $C_{3-6}$ heterocyclyl, $C_{1-10}$ heteroaryl, phenyl, —SR$^{14}$, —C(O)N(R$^{14}$)R$^{15}$, —N(R$^{14}$)R$^{15}$, —C(O)OR$^{14}$, and —S(O)$_2$R$^{16}$;

each optionally substituted $C_{6-14}$ aryl is independently substituted with from 0 to 5 substituents independently selected from cyano, halo, hydroxy, nitro, oxo, optionally substituted $C_{1-4}$ alkyl, $C_{1-4}$ alkoxy, $C_{2-4}$ alkenyl, $C_{1-10}$ heteroaryl, trifluoromethyl, trifluoromethoxy, —N(R$^{14}$)R$^{15}$, —C(O)N(R$^{14}$)R$^{15}$, —OC(O)N(R$^{14}$)R$^{15}$, —NHC(O)OR$^{16}$, —NHS(O)$_2$R$^{16}$, —S(O)$_2$N(R$^{14}$)R$^{15}$, —NHC(O)N(R$^{14}$)R$^{15}$, —C(O)OR$^{14}$, and —S(O)$_2$R$^{16}$;

each optionally substituted $C_{6-14}$ aryloxy is independently substituted with from 0 to 5 substituents independently selected from cyano, halo, hydroxy, nitro, oxo, optionally substituted $C_{1-4}$ alkyl, $C_{1-4}$ alkoxy, $C_{2-4}$ alkenyl, trifluoromethyl, trifluoromethoxy, —N(R$^{14}$)R$^{15}$, —C(O)N(R$^{14}$)R$^{15}$, —OC(O)N(R$^{14}$)R$^{15}$, —NHC(O)OR$^{16}$, —NHS(O)$_2$R$^{16}$, —S(O)$_2$N(R$^{14}$)R$^{15}$, —NHC(O)N(R$^{14}$)R$^{15}$, —C(O)OR$^{14}$, and —S(O)$_2$R$^{16}$;

each optionally substituted phenyl is independently substituted with from 0 to 5 substituents independently selected from cyano, halo, hydroxy, nitro, optionally substituted $C_{1-4}$ alkyl, $C_{1-4}$ alkoxy, $C_{2-4}$ alkenyl, $C_{1-10}$ heteroaryl, trifluoromethyl, trifluoromethoxy, —N(R$^{14}$)R$^{15}$, —C(O)N(R$^{14}$)R$^{15}$, —OC(O)N(R$^{14}$)R$^{15}$, —NHC(O)OR$^{16}$, —NHS(O)$_2$R$^{16}$, —S(O)$_2$N(R$^{14}$)R$^{15}$, —NHC(O)N(R$^{14}$)R$^{15}$, —C(O)OR$^{14}$, and —S(O)$_2$R$^{16}$;

each of the aforementioned heteroaryl and heteroaryloxy moieties has independently one to four ring heteroatoms independently selected from N, O, and S, and each of the aforementioned heterocyclyl moieties is independently saturated or partially unsaturated and has one or two ring heteroatoms independently selected from N, O, and S; and provided the compound of Formula 1 is not 1-methyl-3-(4-(6-oxo-5-(tetrahydro-2H-pyran-4-yl)-5,6,6a,7,9,10-hexahydro-[1,4]oxazino[3,4-h]pteridin-2-yl)phenyl)urea.

Another aspect of the invention provides a compound which is selected from the compounds described in the examples, their pharmaceutically acceptable salts, and stereoisomers of any of the compounds in the examples and their pharmaceutically acceptable salts.

A further aspect of the invention provides a pharmaceutical composition which includes: a compound of Formula 1 or a pharmaceutically acceptable salt as defined above, or a compound selected from the group of compounds and their pharmaceutically acceptable salts as defined in the preceding paragraph; and a pharmaceutically acceptable excipient.

An additional aspect of the invention provides a compound of Formula 1 or a pharmaceutically acceptable salt as defined above, or of a compound selected from the group of compounds and their pharmaceutically acceptable salts as defined above, for use as a medicament.

Another aspect of the invention provides a compound of Formula 1 or a pharmaceutically acceptable salt as defined above, or of a compound selected from the group of compounds and their pharmaceutically acceptable salts as defined above, for use in the treatment of a disease or condition associated with PI3Kδ.

Still another aspect of the invention provides a use of a compound of Formula 1 or a pharmaceutically acceptable salt as defined above, or of a compound selected from the group of compounds and their pharmaceutically acceptable salts as defined above, for the manufacture of a medicament for the treatment of a disease or condition associated with PI3Kδ.

A further aspect of the invention provides a method of treating a disease or condition associated with PI3Kδ, the method comprising administering to the subject an effective amount of a compound of Formula 1 or a pharmaceutically acceptable salt as defined above, or of a compound selected from the group of compounds and their pharmaceutically acceptable salts as defined above.

An additional aspect of the invention provides a method of treating a disease or condition in a subject, the method comprising administering to the subject an effective amount of a compound of Formula 1 or a pharmaceutically acceptable salt as defined above, or of a compound selected from the group of compounds and their pharmaceutically acceptable salts as defined above, wherein the disease or condition is selected from inflammatory disorders, cancer, and cardiovascular disease.

Another aspect of the invention provides a method of treating a disease or condition in a subject, the method comprising administering to the subject an effective amount of a compound of Formula 1 or a pharmaceutically acceptable salt as defined above, or of a compound selected from the group of compounds and their pharmaceutically acceptable salts as defined above, wherein the disease or condition is selected from allergic rhinitis, asthma, atopic dermatitis, rheumatoid arthritis, multiple sclerosis, systemic lupus erythematosus, psoriasis, immune thrombocytopenic purpura, inflammatory bowel disease, chronic obstructive pulmonary disease, Sjögren's syndrome, ankylosing spondylitis, Behcet's disease, atherosclerosis, myocardial infarction, and thrombosis.

A further aspect of the invention provides a combination of an effective amount of a compound of Formula 1 or a pharmaceutically acceptable salt as defined above, or of a compound selected from the group of compounds and their pharmaceutically acceptable salts as defined above, and at least one additional pharmacologically active agent.

DETAILED DESCRIPTION OF THE INVENTION

Unless otherwise indicated, this disclosure uses definitions provided below. Certain formulae may include one or more asterisks ("*") to indicate stereogenic (asymmetric or chiral) centers, although the absence of an asterisk does not indicate that the compound lacks a stereocenter. Such formulae may refer to the racemate or to individual enantiomers or to individual diastereomers, which may or may not be pure or substantially pure. Other formulae may include one or more wavy bonds ("〰〰"). When attached to a stereogenic center, the wavy bonds refer to both stereoisomers, either individually or as mixtures. Likewise, when attached to a double bond, the wavy bonds indicate a Z-isomer, an E-isomer, or a mixture of Z and E isomers.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-3}$ alkyl refers to an alkyl group having 1 to 3 carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Alkoxy" refers to to alkyl-O—, where alkyl is defined above. Examples of alkoxy groups include methoxy, ethoxy, n-propoxy, i-propoxy, n-butoxy, s-butoxy, t-butoxy, n-pentoxy, and s-pentoxy.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include trifluoromethyl, trichloromethyl, pentafluoroethyl, pentachloroethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached to a parent group or to a substrate at any ring atom unless such attachment would violate valence requirements. In addition, the cycloalkyl group may include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkoxy" refers to cycloalkyl-O—, where cycloalkyl is defined above. Examples of cycloalkoxy groups include cyclopropoxy, cyclobutoxy, cyclopentoxy, and cyclohexoxy.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Aryloxy" refers to aryl-O—, where aryl is defined above. An example is phenoxy.

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. The nitrogen and sulfur heteroatoms may optionally be oxidized. Both the monocyclic and bicyclic groups generally have a specified number of carbon atoms in their ring or rings (e.g., $C_{3-6}$ heterocyclyl refers to a heterocyclyl group having 3 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached to a parent group or to a substrate at any ring atom and may include one or more non-hydrogen substituents unless such attachment or substitution would violate valence requirements. Examples of monocyclic heterocyclyl groups include oxiranyl, thiaranyl, aziridinyl (e.g., aziridin-1-yl and aziridin-2-yl), oxetanyl, thiatanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

"Heteroaryl" and "heteroarylene" refer, respectively, to monovalent and divalent unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. The nitrogen and sulfur heteroatoms may optionally be oxidized. Both the monocyclic and polycyclic groups generally have a specified number of carbon atoms as ring members (e.g., $C_{1-10}$ heteroaryl refers to a heteroaryl group having 1 to 10 carbon atoms and 1 to 4 heteroatoms as ring members) and include any bicyclic group in which any of the above-listed monocyclic heterocycles are fused to a benzene ring. The heteroaryl group may be attached to a parent group or to a substrate at any ring atom and may include one or more non-hydrogen substituents unless such attachment or substitution would violate valence requirements. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzo[d][1,3]dioxole, benzothiopheneyl, benzo[c]thiopheneyl, indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-c]pyridinyl, imidazo[1,5-c]pyridinyl, pyrazolo[1,5-c]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

"Heteroaryloxy" refers to heteroaryl-O—, where heteroaryl is defined above. An example is imidazol-2-yloxy.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Opposite enantiomer" refers to a molecule that is a nonsuperimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with PI3Kδ" and similar phrases relate to a disease, disorder or condition in a subject for which inhibition of PI3Kδ may provide a therapeutic or prophylactic benefit.

The following abbreviations are used throughout the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); dba (dibenzylideneacetone); DCC (1,3-dicyclohexylcarbodiimide); DCM (dichloromethane); DIPEA (N,N-diisopropylethylamine, Hüig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); dppf (1,1'-bis(diphenylphosphino)ferrocene); DTT (dithiothreitol); EDA ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); Et$_3$N (triethyl-amine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-ol); IC$_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMP (N-methyl-2-pyrrolidinone), PE (petroleum ether); Ph (phenyl); pIC$_{50}$ (–log$_{10}$(IC$_{50}$), where IC$_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl)phosphine); TFA (trifluoroacetic acid); TFAA (2,2,2-trifluoroacetic anhydride); THF (tetrahydrofuran); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating inflammatory disorders, cancer, cardiovascular disorders, and conditions associated with PI3Kδ or other PI3K isoforms.

In addition to the specific compounds in the examples, compounds of Formula 1 include those in which: (a) G$^1$ is N; (b) G$^2$ is CH$_2$; (c) Ar is C$_{1-10}$ heteroaryl; or (d) m is 0, 1 or 2; or combinations of structural features (a) through (d).

In addition, or as an alternative to one or more of embodiments (a) through (d) in the preceding paragraph, compounds of Formula 1 include those in which: (e) Ar is a bicyclic C$_{5-9}$ heteroaryl having from 1 to 4 nitrogen heteroatoms.

In addition, or as an alternative to one or more of embodiments (a) through (d) in the preceding paragraphs, compounds of Formula 1 include those in which: (f) Ar is a bicyclic C$_{7-9}$ heteroaryl having from 1 to 2 nitrogen heteroatoms.

In addition, or as an alternative to one or more of embodiments (a) through (d) in the preceding paragraphs, compounds of Formula 1 include those in which: (g) Ar is selected from indolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, benzimidazolyl, and indazolyl.

In addition, or as an alternative to one or more of embodiments (a) through (d) in the preceding paragraphs, compounds of Formula 1 include those in which: (h) Ar is selected from indol-4-yl, 1H-pyrrolo[2,3-b]pyridin-4-yl, 1H-pyrrolo[2,3-c]pyridin-4-yl, and 1H-pyrrolo[3,2-c]pyridin-4-yl.

In addition, or as an alternative to one or more of embodiments (a) through (d) in the preceding paragraphs, compounds of Formula 1 include those in which: (i) Ar is indolyl.

In addition, or as an alternative to one or more of embodiments (a) through (d) in the preceding paragraphs, compounds of Formula 1 include those in which: (j) Ar is indol-4-yl.

In addition, or as an alternative to one or more of embodiments (a) through (j) in the preceding paragraphs, compounds of Formula 1 include those in which: (k) R$^3$ is selected from optionally substituted C$_{1-6}$ alkyl, optionally substituted C$_{6-14}$ aryl, optionally substituted C$_{1-10}$ heteroaryl, —(CH$_2$)$_n$C(O)N(R$^4$)R$^5$, and —S(O)$_2$R$^6$.

In addition, or as an alternative to one or more of embodiments (a) through (j) in the preceding paragraphs, compounds of Formula 1 include those in which: (1) R$^3$ is C$_{1-6}$ alkyl, which is substituted with from 1 to 7 substituents independently selected from cyano, halo, hydroxy, oxo, optionally substituted C$_{1-4}$ alkoxy, C$_{2-4}$ alkenyl, optionally substituted C$_{3-8}$ cycloalkyl, optionally substituted C$_{3-6}$ heterocyclyl, optionally substituted C$_{1-10}$ heteroaryl, optionally substituted phenyl, —SR$^{14}$, —C(O)OR$^{14}$, —N(R$^{14}$)R$^{15}$, —C(O)N(R$^{14}$)R$^{15}$, and —S(O)$_2$R$^{16}$.

In addition, or as an alternative to one or more of embodiments (a) through (j) in the preceding paragraphs, compounds of Formula 1 include those in which: (m) R$^3$ is —(CH$_2$)$_n$C(O)N(R$^4$)R$^5$.

In addition, or as an alternative to one or more of embodiments (a) through (j) in the preceding paragraphs, compounds of Formula 1 include those in which: (n) R$^3$ is —CH$_2$C(O)N(R$^4$)R$^5$.

In addition, or as an alternative to one or more of embodiments (a) through (j) in the preceding paragraphs, compounds of Formula 1 include those in which: (o)R$^3$ is C$_{1-6}$ alkyl, which is substituted with optionally substituted phenyl.

In addition, or as an alternative to one or more of embodiments (a) through (j) in the preceding paragraphs, compounds of Formula 1 include those in which: (p) R$^3$ is optionally substituted phenyl-methyl.

In addition, or as an alternative to one or more of embodiments (a) through (p) in the preceding paragraphs, compounds of Formula 1 include those in which: (q) R$^2$ is hydrogen.

In addition, or as an alternative to one or more of embodiments (b) through (q) in the preceding paragraphs, compounds of Formula 1 include those in which: (r) G$^1$ is CR$^7$.

In addition, or as an alternative to one or more of embodiments (b) through (r) in the preceding paragraphs, compounds of Formula 1 include those in which: (s) G$^1$ is CR$^7$ and R$^7$ is hydrogen.

In addition, or as an alternative to one or more of embodiments (a) and (c) through (s) in the preceding paragraphs, compounds of Formula 1 include those in which: (t) G$^2$ is C=O.

In addition, or as an alternative to one or more of embodiments (a) and (c) through (s) in the preceding paragraphs, compounds of Formula 1 include those in which: (u) G$^2$ is C=O and each R$^1$ is independently selected from cyano, halo, hydroxy, nitro, optionally substituted C$_{1-6}$ alkyl, optionally substituted C$_{1-4}$ alkoxy, optionally substituted C$_{2-4}$ alkenyl, optionally substituted C$_{2-4}$ alkynyl, optionally substituted C$_{3-8}$ cycloalkyl, optionally substituted C$_{3-6}$ heterocyclyl, optionally substituted C$_{6-14}$ aryl, optionally substituted C$_{6-14}$ aryloxy, optionally substituted C$_{1-10}$ heteroaryl, optionally substituted C$_{1-10}$ heteroaryloxy, —C(O)OR$^4$, —OC(O)R$^4$, —N(R$^4$)R$^5$, S(O)$_2$R$^6$, —S(O)$_2$N(R$^4$)R$^5$, —C(O)N(R$^8$)R$^9$, —NHC(O)OR$^{10}$, —NHS(O)$_2$NHR$^8$, —NHS(O)$_2$R$^6$, —NHC(O)NHN(R$^8$)R$^9$, —NHC(S)N(R$^8$)R$^9$, —NHC(=NR$^{11}$)N(R$^8$)R$^9$, —K NHC(SR$^{12}$)N(R$^8$)R$^9$, and —NHC(=NR$^{11}$)OR$^{13}$.

In addition, or as an alternative to one or more of embodiments (a) through (u) in the preceding paragraphs, compounds of Formula 1 include those which have (v) the stereochemical configuration shown in Formula 1A or Formula 1B:

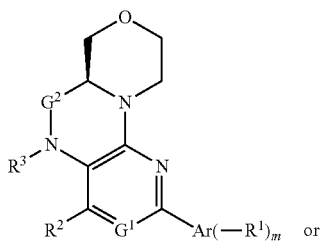

where substituents $R^1$, $R^2$, $R^3$, $G^1$, $G^2$, Ar, and m in Formula 1A and Formula 1B are as defined for Formula 1.

Compounds of Formula 1 include embodiments (a) through (v) described in the preceding paragraphs and all compounds specifically named above and in the examples, and generally include all salts, complexes, solvates, hydrates, and liquid crystals of the compounds of Formula 1. Likewise, all references to compounds of Formula 1 include all complexes, solvates, hydrates, and liquid crystals of the salts of the compounds of Formula 1.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8): 1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., $-COO^-Na^+$, $-COO^-K^+$, $-SO_3^-Na^+$) or polar non-ionic moiety (such as $-N^-N^+$ $(CH_3)_3$). See, e.g., N. H. Hartshorne and A. Stuart, *Crystals and the Polarizing Microscope* (4th ed, 1970).

Compounds of Formula 1 also include all polymorphs and crystal habits, prodrugs, metabolites, stereoisomers, and tautomers thereof, as well as all isotopically-labeled compounds thereof.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 include all stereoisomers, whether they are pure, substantially pure, or mixtures, and result from the presence of one or more stereogenic centers, one or more double bonds, or both. Such stereoisomers may also result from acid addition or base salts in which the counter-ion is optically active, for example, when the counter-ion is D-lactate or L-lysine.

Compounds of Formula 1 also include all tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 also include all isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2H$ and $^3H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; isotopes of chlorine, such as $^{36}Cl$, and isotopes of iodine, such as $^{123}I$ and $^{125}I$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (rt) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., $R^1$, $R^3$, $R^4$, $G^1$, Ar, m, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include an $R^3$ that is a moiety having a potentially reactive amine. In such cases, $R^3$ would include the moiety with or without, say, a Boc or Cbz group attached to the amine.

Scheme A

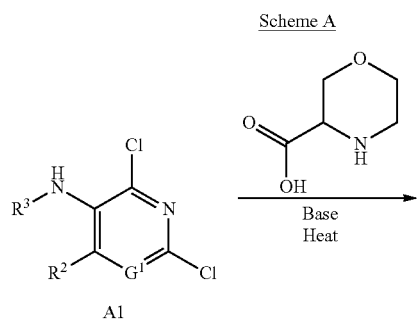

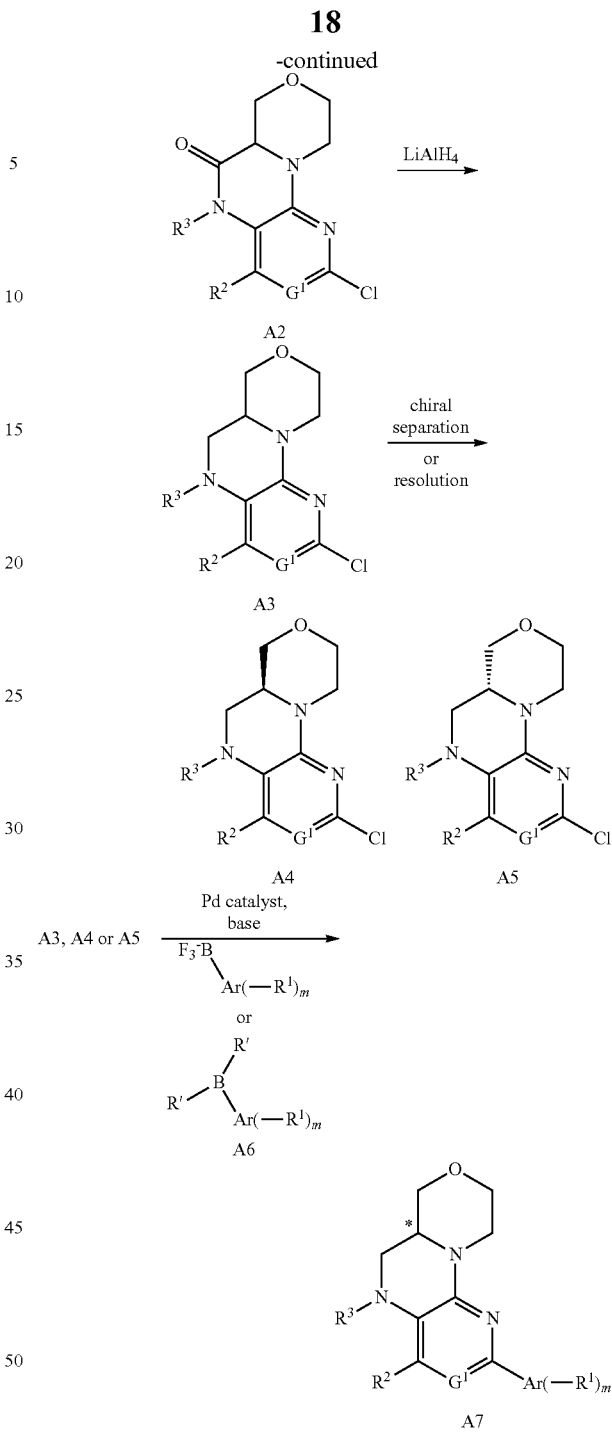

Scheme A shows a method for preparing compounds of Formula A7. According to the method, a 5-amino-substituted 2,4-dichloropyrimidine or a 3-amino-substituted 2,6-dichloropyridine A1 is reacted with morpholine-3-carboxylic acid at elevated temperature (e.g., about 100° C.) in a solvent (e.g., DMSO) and in the presence of a non-nucleophilic base (e.g., DIPEA or similar tertiary amine). An oxo moiety of the resulting cyclocondensation product A2 is subsequently reduced with LiAlH$_4$ to give a chloro-substituted oxazinopteridine or oxazinopyridopyrazine intermediate A3, which may be resolved or purified by chiral column chromatography, such as supercritical fluid chromatography (SFC), to give enantiomer A4 or A5. Palladium-catalyzed (e.g., Pd(PPh$_3$)$_4$, (PPh$_3$)$_2$PdCl$_2$, etc.) coupling of compound A3, A4 or A5 with an arylboronic acid, an arylboronate ester (A6) or an aryl trifluoroborate gives compound A7 with the corresponding stereochemistry. The Suzuki-type coupling is carried out at elevated temperature (e.g., about 90°-100° C.), typically in the presence of a base (e.g., KF or Na$_2$CO$_3$) and an organic solvent (e.g., dioxane, DMF, etc.). In Formula A6, R' is OH or R'—R' is pinocol, and in formula A7, the asterisk ("*") represents a stereogenic center.

Scheme B

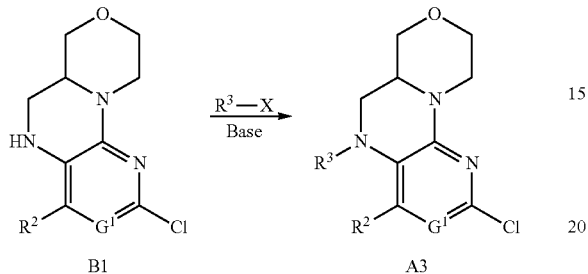

Scheme B shows a method for preparing intermediates of Formula A3 when R$^3$ is optionally substituted C$_{1-6}$ alkyl, —S(O)$_2$R$^6$ or substituted acyl (i.e., 1-oxo-C$_{1-6}$ alkyl). According to the method, chloro-substituted oxazinopteridine or oxazinopyridopyrazine B1 is treated, respectively, with an alkyl halide, sulfonyl halide or acid halide (R$^3$—X, where X is Cl, Br or I) in the presence of a base, with or without heating, to give the N-substituted intermediate A3, which may be used to prepare compounds of Formula A7 in Scheme A.

Scheme C

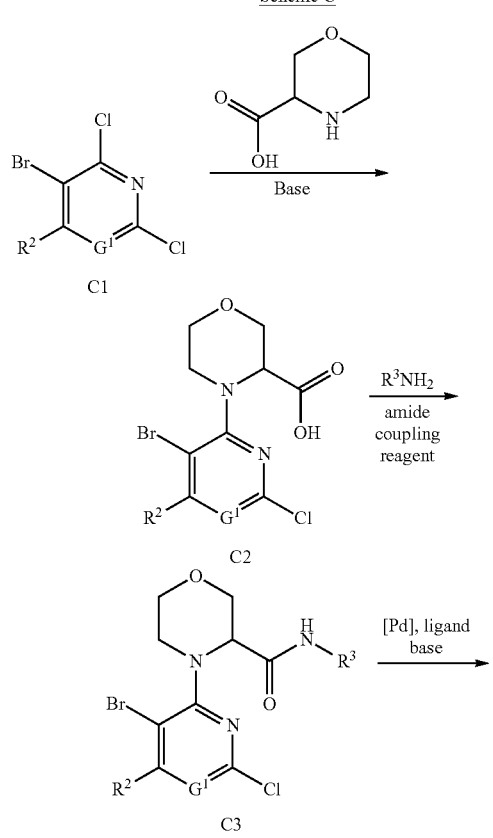

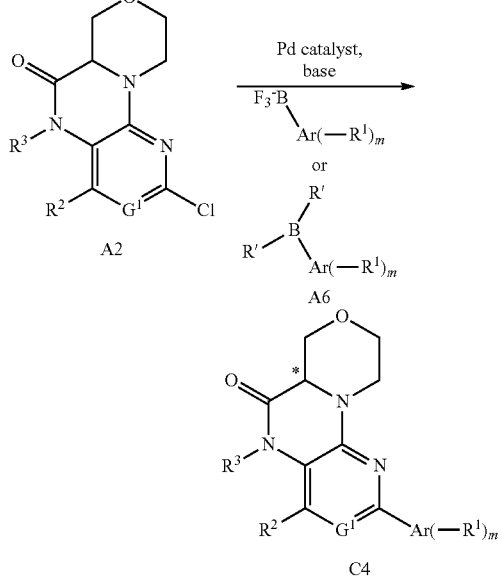

Scheme C shows a method for preparing compounds of formula C4. In the method, a 5-bromo-2,4-dichloropyrimidine or a 3-bromo-2,6-dichloropyridine C1 is reacted with morpholine-3-carbocyclic acid in the presence of a non-nucleophilic base (e.g., DIPEA or similar tertiary amine) and solvent (e.g., ethanol) to give an acid intermediate C2. The carboxylic acid intermediate C2 is converted to an amide C3 via reaction with a primary amine R$^3$NH$_2$ in the presence of an amide coupling reagent, such as HATU or EDC. Ring closure is effected via Buchwald amidation by heating intermediate C3 at a temperature of about 90-180° C. for about 3 to 18 hours in a solvent (e.g., 1-4 dioxane and/or tert-butanol) and in the presence of a palladium pre-catalyst (e.g., Pd(OAc)$_2$), a ligand (e.g., Xanthphos or BINAP), and a base (e.g., potassium phosphate tribasic or cesium carbonate). As in Scheme A, palladium-catalyzed coupling of the cyclized product A2 with an arylboronic acid, an arylboronate ester (A6) or an aryl trifluoroborate gives compound C4, where the asterisk ("*") in Formula C4 represents a stereogenic center.

Scheme D

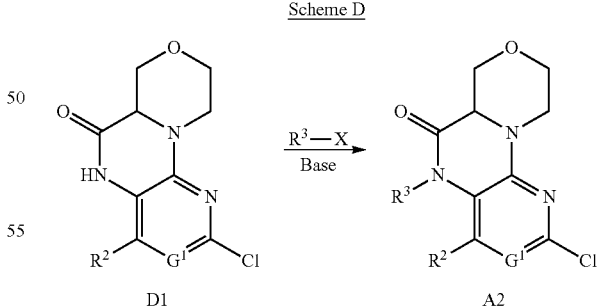

Scheme D shows a method for preparing intermediate A2 when R$^3$ is an optionally substituted C$_{1-6}$ alkyl. The method includes treating a chloro-substituted oxazinopteridinone or oxazinopyridopyrazinone D1 with an alkyl halide (R$^3$—X, where X is Cl, Br or I) in the presence of a non-nucleohilic base (e.g., LiHMDS) with or without heating, to give the N-substituted intermediate 1-2, which may be used to prepare compounds of Formula C4 in Scheme C.

Scheme E shows a method for preparing compounds of Formula E4. The method includes reacting intermediate C2 with an imidazole or benzimidazole derivative E1 (where $R^1$ may be attached to carbon atoms on either or both rings) at elevated temperature (e.g., about 120° C.) in the presence of a base (e.g., cesium carbonate) to give acid intermediate E2. As in Scheme C, the carboxylic acid intermediate E2 is converted to an amide E3 via reaction with a primary amine $R^3NH_2$ in the presence of an amide coupling reagent, such as HATU or EDC. Similarly, compound E4 is obtained via Buchwald amidation by heating intermediate E3 at a temperature of about 90-180° C. for about 3 to 18 hours in a solvent (e.g., 1-4 dioxane and/or tert-butanol) and in the presence of a palladium pre-catalyst (e.g., Pd(OAc)$_2$), a ligand (e.g., Xanthphos or BINAP), and a base (e.g., potassium phosphate tribasic or cesium carbonate).

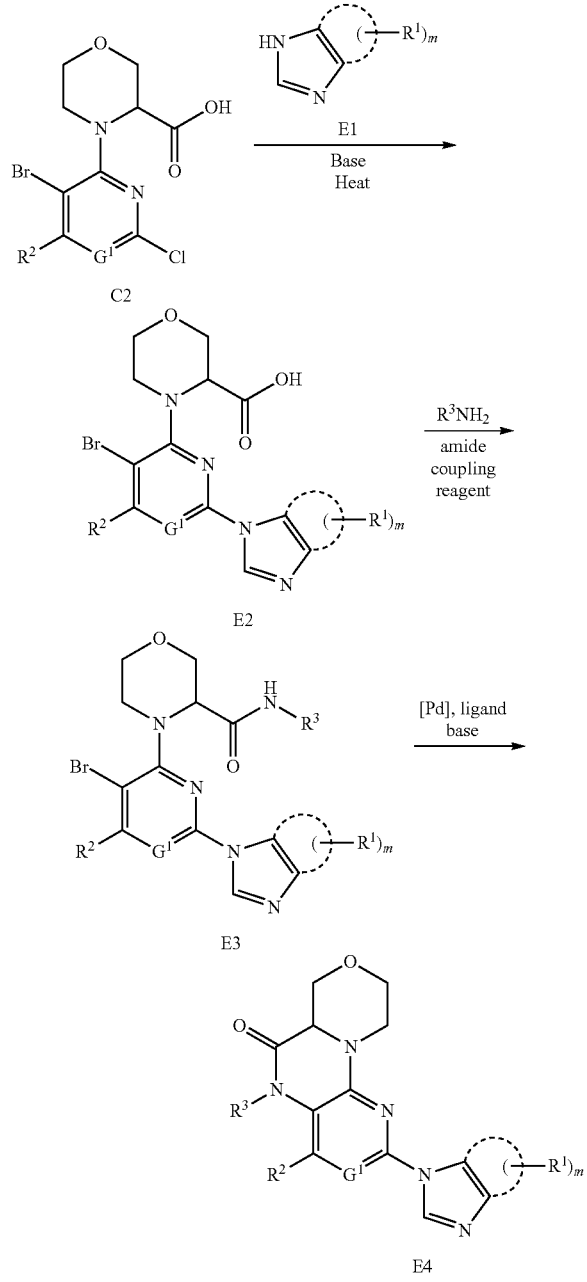

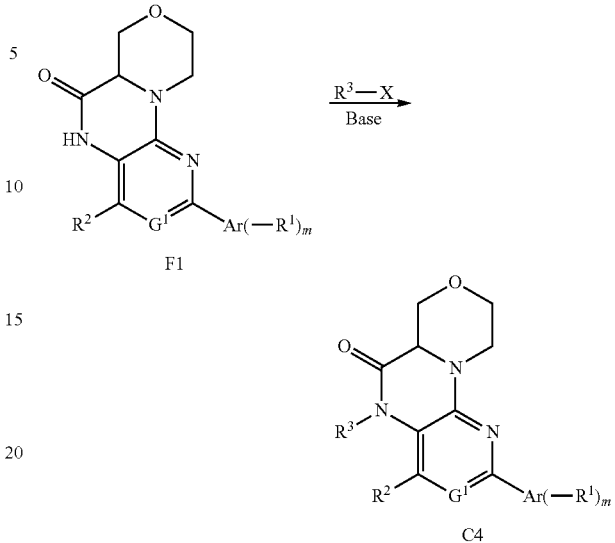

Scheme F shows a method for preparing compounds of Formula C4 when $R^3$ is optionally substituted $C_{1-6}$ alkyl. According to the method, treating an aryl- or heteroaryl-substituted oxazinopteridinone or oxazinopyridopyrazinone F1 with an alkyl halide ($R^3$—X, where X is Cl, Br or I) in the presence of a hindered base (e.g., LiHMDS) and solvent (e.g., DMF) with or without heating, gives compound C4.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology, Vol.* 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic) acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, J. Pharm. Sci. 88(10):955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 μg to about 20 mg of the API per actuation and the actuation volume may vary from about 1 μL, to about 100 μL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 μg to about 1000 μg of the API. The overall daily dose will typically range from about 100 μg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat disorders, diseases, and conditions for which inhibition of PI3Kδ is indicated. Such disorders, diseases, and conditions generally relate to any unhealthy or abnormal state in a subject for which the inhibition of PI3Kδ provides a therapeutic benefit. More particularly, such disorders, diseases, and conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); inflammation of the lung (chronic obstructive pulmonary disease) and thrombosis. The compounds of Formula 1 may also be used to treat disorders, diseases, and conditions related to abnormal cell growth, including hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma), as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the compounds of Formula 1 may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the compounds of Formula 1 may also be used to treat other diseases related to abnormal cell growth, including non-malignant proliferative diseases such as benign prostatic hypertrophy, restinosis, hyperplasia, synovial proliferation disorder, retinopathy or other neovascular disorders of the eye, among others.

The compounds of Formula 1 may also be used to treat autoimmune disorders in addition to those listed above. Such disorders, diseases, and conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, Sjögren's syndrome, temporal arteritis, ulcerative colitis, vasculitis, and Wegener's granulomatosis, among others.

Furthermore, compounds of Formula 1 may be used to treat inflammatory disorders including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemtic inflammatory response syndrome.

The compounds of Formula 1 may also be used to treat specific diseases that may fall within one or more general disorders described above, including arthritis. In addition to rheumatoid arthritis, Sjögren's syndrome, systemic lupus erythematosus, SLE in children and adolescents, compounds of Formula 1 may also be used to treat other arthritis diseases, including ankylosing spondylitis, avascular necrosis, Behcet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

The claimed and disclosed compounds may be combined with one or more other pharmacologically active compounds or therapies for the treatment of one or more disorders, diseases or conditions for which PI3Kδ is indicated, including disorders, diseases, and conditions involving the immune system, inflammation, and abnormal cell growth. For example, compounds of Formula 1, which include compounds specifically named above, and their pharmaceutically acceptable complexes, salts, solvates and hydrates, may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the compounds of Formula 1 may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the compounds of Formula 1 may be combined with one or more disease modifying antirheumatic drugs (DMARDs), and when treating osteoarthritis, the compounds of Formula 1 may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, and sulfasalazine. Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include a compound of Formula 1 and methotrexate; a compound of Formula 1 and one or more biological response modifiers, such as lefluonomide, etanercept, adalimumab, and infliximab; or a compound of Formula 1, methotrexate, and one or more biological response modifiers, such as lefluonomide, etanercept, adalimumab, and infliximab.

For the treatment of thrombis and restensosis, the compounds of Formula 1 may be combined with one or more cardiovascular agents such as calcium channel blockers, statins, fibrates, beta-blockers, ACE inhibitors, and platelet aggregation inhibitors.

The compounds of Formula 1 may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkone sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and streptomyces (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); hymidylate synthase inhibitors (e.g., raltitrexed and pemetrexed); folinic acid (e.g., leucovorin); adenosine deaminase inhibitors (e.g., pentostatin); halogenated/ribonucleotide reductase inhibitors (e.g., cladribine, clofarabine, and fludarabine); thiopurines (e.g, thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include vinca alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (filgrastim) and granulocyte macrophage CSF (sargramostim). Other immuno-modulating agents include bacillus Calmette-Guerin, levamisole, and octreotide; monoclonal antibodies against tumor antigens, such as trastruzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha (TGF$_\alpha$), TGF$_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hetaptocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependant kinase (CDK), Akt, extracellular signal-regulated kinases (ERK), poly(ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogensis, such as bevacizumab, sorafenib, and sunitinib; agents that help the immune system destroy cancel cells, such as rituximab and alemtuzumab; and monoclonal antibodies which deliver toxic molecules to cancer cells, such as gemtuzumab ozogamicin, tositumomab, 131I-tositumoab, and ibritumomab tiuxetan.

Biological Activity

The activity of compounds as PI3Kδ inhibitors may be determined by a variety of methods, including in vitro and in vivo methods. The following in vitro assay measures a test compound's ability to inhibit PI3Kδ-mediated phosphorylation of PIP2 and ATP.

Recombinant GST-tagged PIK3CD is purchased from Invitrogen (Part Number: PV5274). The protein is full length and co-expressed with untagged PIK3R1, phosphoinositide-3-kinase regulatory subunit 1 (p85α). The protein is stored at −20° C. in 50 mM TRIS (pH 7.5), 150 mM NaCl, 0.5 mM EDTA, 0.02% Triton® X-100, 2 mM DTT, and 50% glycerol.

A modified PIK3CD Adapta® assay (Invitrogen, Carlsbad, Calif.) is used to measure PI3Kδ inhibition of the example compounds. The assay has two phases. In the first phase, kinase reaction components, which include the enzyme (PIK3CD), substrates (PIP2, ATP), test compound (inhibitor), and assay buffer are added to each well, and the reaction is allowed to incubate for a pre-determined period of time. After reaction, a detection solution composed of an Eu (europium)-labeled anti-ADP antibody, Alexa Fluor® 647-labeled ADP tracer, and EDTA (to stop the kinase reaction) is added to each assay well. In this second phase, ADP formed by the kinase reaction displaces the Alexa Fluor® 647-labeled ADP tracer from the antibody, resulting in a decrease in time-resolved fluorescence resonance energy transfer (TR-FRET) signal. In the presence of the inhibitor, the amount of ADP formed by the kinase reaction is reduced, and the resulting intact antibody-tracer interaction maintains a high TR-FRET signal.

The assay uses black Greiner® 384-well plates (784076). The reaction buffer contains 50 mM Hepes (pH 7.5), 3 mM MgCl$_2$, 1 mM EGTA, 100 mM NaCl, 0.03% CHAPS; 2 mM DTT is added fresh prior to each experiment. Enzyme (4 μL, estimated 1.5 nM in buffer) is first added to the wells of the plate. Next, test compounds (2 μL) from a source plate (5% dilution plate) are introduced into the wells. The final DMSO concentration in each assay well is 1%. The dilution plate contains 5% DMSO in the bottom half of columns 23 and 24, which serve as negative (non-inhibited) controls; the top half contains a known inhibitor concentration (positive control) that gives >98% inhibition of the kinase reaction. Other wells contain test compounds serially diluted across the plate 11 times for a total of 12 data points. The kinase reactions are carried out at room temperature and are initiated by the addition of 4 μL of solution containing 2 μM ATP and 50 μM PIP2. Each reaction is stopped after 1 hour±10 minutes via addition of 10 μL stop solution, which contains a final assay concentration of 3 nM Alexa Fluor® 647-labeled ADP tracer, 2 nM Eu-anti-ADP Antibody, and 10 mM EDTA. After allowing the solutions to equilibrate for 30±10 minutes, a PHERAstar plate reader is used to excite the Eu donor (at 337 nm) and to detect emission from the Alexa Fluor® 647 at 665 nm. This emission signal is referenced or "ratioed" to the emission from Eu at 620 nm. The emission ratio (665 nm/620 nm) from each well is collected and converted to percent conversion using a standard curve for the assay conditions: % conversion=B×(C+A−emission ratio)/(emission ratio−C), where "A" and "C" are the maximum and minimum values of the emission ratio obtained from the standard curve of emission ratio vs. % conversion (ATP-ADP); "B" is the emission ratio corresponding to the % conversion at the EC$_{50}$ value for the ADP Tracer-Eu anti-ADP antibody complex. The percent inhibition for a given inhibitor concentration is computed from % conversion for the reaction and for the positive and negative controls. Corresponding IC$_{50}$ values are calculated by non-linear curve fitting of the compound concentrations and values of percent inhibition to the standard IC$_{50}$ equation and are reported as pIC$_{50}$, i.e., −log(IC$_{50}$), where IC$_{50}$ is molar concentration at 50% inhibition.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: CDCl$_3$ (deuterochloroform), DMSO-d$_6$ (deuterodimethylsulfoxide), CD$_3$OD (deuteromethanol), and THF-d$_8$ (deuterotetrahydrofuran). The mass spectra ([M+H]$^+$) were recorded using either electrospray ionization (ESI) or atmospheric pressure chemical ionization.

Where indicated, products of certain preparations and examples are purified by mass-triggered HPLC (e.g., Pump: Waters™ 2525; MS: ZQ™; Software: MassLynx™), flash chromatography or preparative thin layer chromatography (TLC). Reverse phase chromatography is typically carried out on a column (Gemini™ 5μ, C18 110A, Axia™, 30×75 mm, 5μ) under acidic conditions, eluting with ACN and water mobile phases containing 0.035% and 0.05% trifluoroacetic acid (TFA), respectively, or under basic conditions, eluting with water and 20/80 (v/v) water/acetonitrile mobile phases, both containing 10 mM NH$_4$HCO$_3$. Preparative TLC is typically carried out on silica gel 60 F$_{254}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., H$_2$) atmosphere are typically carried out at a pressure of about 1 atmosphere (14.7 psi).

PREPARATION x1: 2-chloro-6a,7,9,10-tetrahydro-[1,4]oxazino[3,4-h]pteridin-6(5H)-one

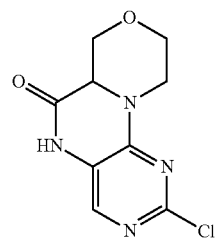 [SMILES: O=C1Nc2cnc(Cl)nc2N2CCOCC12]

2,4-Dichloropyrimidin-5-amine (25 g, 152 mmol) and morpholine-3-carboxylic acid hydrochloride (28.1 g, 168 mmol) were dissolved in DMSO (200 mL) to give a yellow suspension. To the suspension was added N,N-diisopropylethylamine (106 mL, 610 mmol) and the mixture was heated to 100° C. for 18 hours. The mixture was cooled to room temperature and poured into ice. Water was added until the total volume was 1 L. The resulting beige suspension was stirred overnight before the solid was collected on a fritted-glass funnel of medium porosity. The solid was washed with water (3×) and then dried under a stream of nitrogen overnight to afford the title compound as a light yellow solid that was used without further purification (18.6 g, 51%). ESI-MS m/z [M+H]$^+$ calc'd for $C_9H_9ClN_4O_2$, 241.04. found 241.1.

PREPARATION x2: 2-chloro-5,6,6a,7,9,10-hexahydro-[1,4]oxazino[3,4-h]pteridine

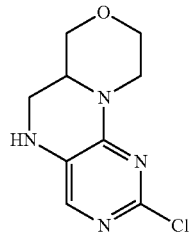 [SMILES: Clc1ncc2c(n1)N1CCOCC1CN2]

2-Chloro-6a,7,9,10-tetrahydro-[1,4]oxazino[3,4-h]pteridin-6(5H)-one (PREPARATION x1, 17.3 g, 71.9 mmol) was dissolved in THF (250 mL). To the resulting suspension was added lithium aluminum hydride in THF (2.0 M, 46.7 mL, 93 mmol) dropwise through an addition funnel at 0° C. to give a clear light-brown solution. The reaction mixture was allowed to warm to room temperature and was stirred for 3 hours. Ethyl acetate (~25 mL) was added at 0° C. in portions; a saturated aqueous solution of NH$_4$Cl (125 mL) was then added dropwise until bubbling ceased. The upper organic layer was decanted, concentrated in vacuo and then partitioned between brine and ethyl acetate. The murky bottom layer was then extracted with ethyl acetate (3×) and the combined organic layers were dried over MgSO$_4$, filtered, and concentrated. The product was triturated with ether/ethyl acetate and collected by filtration under nitrogen to give the title compound (9.6 g, 59%). $^1$H NMR (DMSO-d$_6$) δ 2.88-2.94 (m, 2H), 3.12 (t, 1H), 3.26-3.28 (m, 1H), 3.42-3.51 (m, 2H), 3.86-3.92 (m, 2H), 4.19-4.21 (d, J=8.0 Hz, 1H), 5.96 (br s, 1H), 7.36 (s, 1H). ESI-MS m/z [M+H]$^+$ calc'd for $C_9H_9ClN_4O_2$, 241.04. found 241.1.

PREPARATION x3: (R)-2-chloro-5,6,6a,7,9,10-hexahydro-[1,4]oxazino[3,4-h]pteridine

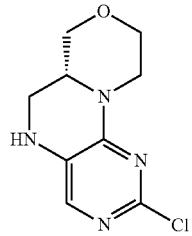 [SMILES: Clc1ncc2c(n1)N1CCOC[C@H]1CN2]

An enantiomeric mixture of 2-chloro-5,6,6a,7,9,10-hexahydro-[1,4]oxazino[3,4-h]pteridine (PREPARATION x2, 8 g) was dissolved in MeOH (400 mL) and was separated by supercritical fluid chromatography (SFC) (Chiralcel® AS-H (5 μm, 20×150 mm), 20% MeOH in liquid CO$_2$ at 55 mL/min, 3 mL/injection). The peak eluting at ~5 minutes was collected. The stereo-configuration was assigned based on a comparison of retention times of an enantiomerically-enriched sample synthesized in a manner similar to PREPARATION x1 and PREPARATION x2 using optically pure (S)-morpholine-3-carboxylic acid.

PREPARATION x4: (S)-2-chloro-5,6,6a,7,9,10-hexahydro-[1,4]oxazino[3,4-h]pteridine

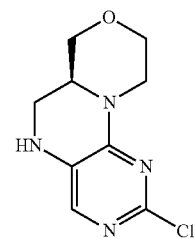 [SMILES: Clc1ncc2c(n1)N1CCOC[C@@H]1CN2]

The title compound was obtained as the peak eluting at ~3.5 minutes by chiral SFC chromatography in PREPARATION x3.

PREPARATION x5: 2-chloro-5-(cyclopropylmethyl)-5,6,6a,7,9,10-hexahydro-[1,4]oxazino[3,4-h]pteridine

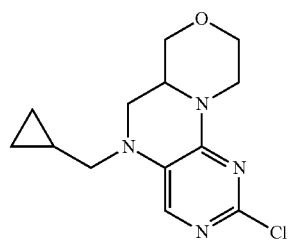 [SMILES: Clc1ncc2c(n1)N1CCOCC1CN2CC1CC1]

2-Chloro-5,6,6a,7,9,10-hexahydro-[1,4]oxazino[3,4-h]pteridine (PREPARATION x2, 200 mg, 0.882 mmol) was dissolved in DMSO (4.4 mL). Sodium tert-butoxide (102 mg, 1.059 mmol) was then added to give a brown solution. After 5 minutes, (bromomethyl)cyclopropane (86 μL, 0.882 mmol) was added dropwise. The reaction mixture was stirred for 2 hours at room temperature then quenched with aqueous saturated NH$_4$Cl. The reaction mixture was diluted with ethyl acetate and washed with aqueous saturated NH$_4$Cl (3×25 mL). The combined organic layers were dried over MgSO$_4$, filtered, and concentrated in vacuo. The crude product was loaded onto an ISCO® silica gel cartridge (12 g) and eluted with an ethyl acetate/hexane gradient. The product was collected and concentrated in vacuo to afford the title compound as a yellow oil (100 mg, 40%). ESI-MS m/z [M+H]$^+$ calc'd for $C_{13}H_{17}ClN_4O$, 281.1. found 281.3.

PREPARATION x6: 2-chloro-5-(2-chloro-4-(methylsulfonyl)benzyl)-5,6,6a,7,9,10-hexahydro-[1,4]oxazino[3,4-h]pteridine

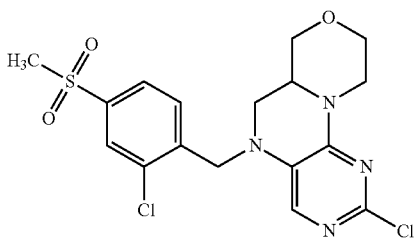 [SMILES: CS(=O)(=O)c1ccc(CN2CC3COCCN3c3nc(Cl)ncc32)c(Cl)c1]

2-Chloro-5,6,6a,7,9,10-hexahydro-[1,4]oxazino[3,4-h]pteridine (PREPARATION x2, 200 mg, 0.882 mmol) was dissolved in DMSO (4.4 mL). Sodium tert-butoxide (102 mg, 1.059 mmol) was then added to give a brown solution. After 5 minutes, 1-(bromomethyl)-2-chloro-4-(methylsulfonyl)benzene (250 mg, 0.882 mmol) was added dropwise. The reaction mixture was stirred for 18 hours. Additional sodium tert-butoxide (0.5 eq) was added and the reaction mixture was stirred for an additional 18 hours. The reaction mixture was subsequently diluted with ethyl acetate and was washed with aqueous saturated NH$_4$Cl (3×25 mL). The combined organic layers were dried over MgSO$_4$, filtered, and concentrated in vacuo. The crude product was loaded onto an ISCO® silica gel cartridge (12 g) and eluted with an ethyl acetate/hexane gradient. The product was collected and concentrated in vacuo to afford the title compound as a yellow oil (143 mg, 37%). ESI-MS m/z [M+H]$^+$ calc'd for C$_{17}$H$_{18}$Cl$_2$N$_4$O$_3$S, 430.3. found 431.3.

PREPARATION x7: methyl 4-((2-chloro-6a,7,9,10-tetrahydro-[1,4]oxazino[3,4-h]pteridin-5(6H)-yl)methyl)benzoate

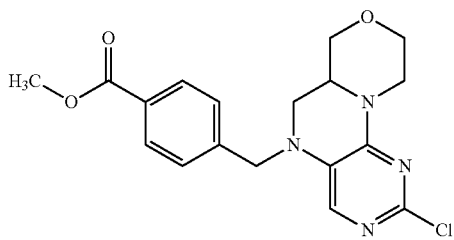 [SMILES: COC(=O)c1ccc(CN2CC3COCCN3c3nc(Cl)ncc32)cc1]

2-Chloro-5,6,6a,7,9,10-hexahydro-[1,4]oxazino[3,4-h]pteridine (PREPARATION x2, 350 mg, 1.544 mmol) was dissolved in DMSO (10 mL). Sodium tert-butoxide (223 mg, 2.316 mmol) was added, followed 5 minutes later by the addition of methyl 4-(bromomethyl)benzoate (531 mg, 2.316 mmol) to give a brown suspension. The reaction mixture was heated to 100° C. in a microwave on high absorbance for 30 minutes. The reaction mixture was diluted with ethyl acetate and washed with aqueous saturated NH$_4$Cl (2×15 mL) and brine (2×15 mL). The combined organic layers were dried over MgSO$_4$, filtered, and concentrated in vacuo. The crude product was loaded onto an ISCO® silica gel cartridge (24 g) and eluted using an ethyl acetate/hexane gradient. The product was collected and concentrated in vacuo to afford the title compound as a yellow oil (133 mg, 23%). ESI-MS m/z [M+H]$^+$ calc'd for C$_{18}$H$_{19}$ClN$_4$O$_3$, 375.1. found 375.4.

PREPARATION x8: 2-(4-((2-chloro-6a,7,9,10-tetrahydro-[1,4]oxazino[3,4-h]pteridin-5(6H)-yl)methyl)phenyl)propan-2-ol

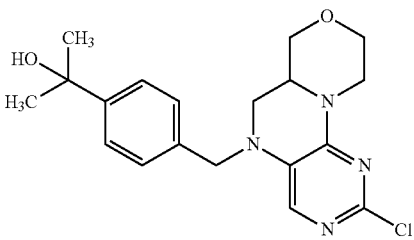 [SMILES: CC(C)(O)c1ccc(CN2CC3COCCN3c3nc(Cl)ncc32)cc1]

To an oven dried flask was added methyl 4-((2-chloro-6a,7,9,10-tetrahydro-[1,4]oxazino[3,4-h]pteridin-5(6H)-yl)methyl)benzoate (PREPARATION x7, 128 mg, 0.341 mmol) in THF (2.3 mL). The flask was evacuated, flushed with N$_2$, and cooled to 0° C. Methylmagnesium bromide (250 µL, 0.751 mmol) was added dropwise at 0° C. and the reaction mixture was stirred for 30 minutes. The crude reaction mixture was washed with Rochelle salts (2×10 mL) and brine (2×10 mL). The combined organic layers were dried over MgSO$_4$, filtered, and concentrated in vacuo. The crude product was loaded onto an ISCO® silica gel cartridge (4 g) and eluted using an ethyl acetate/hexane gradient. The product was collected and concentrated in vacuo to afford the title compound as a yellow oil (39 mg, 31%). $^1$H NMR (400 MHz, DMSO-d$_6$) δ 1.40 (s, 6H), 2.93-2.99 (m, 1H), 3.00-3.07 (m, 1H), 3.11-3.20 (m, 1H), 3.25-3.27 (m, 1H), 3.42-3.51 (m, 1H), 3.62-3.64 (m, 1H), 3.85-3.99 (m, 2H), 4.24-4.26 (m, 1H), 4.34-4.40 (m, 2H), 4.94-4.97 (m, 1H), 7.19-7.26 (m, 2H), 7.35-7.38 (m, 1H), 7.40-7.45 (m, 2H). ESI-MS m/z [M+H]$^+$ calc'd for C$_{19}$H$_{23}$ClN$_4$O$_2$, 375.15. found 375.4.

PREPARATION x9: 2-chloro-5-(4-(methylsulfonyl)benzyl)-5,6,6a,7,9,10-hexahydro-[1,4]oxazino[3,4-h]pteridine

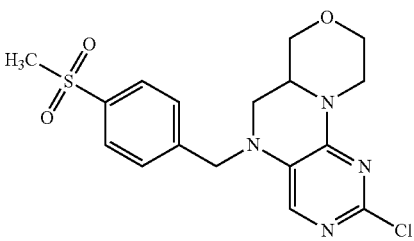 [SMILES: CS(=O)(=O)c1ccc(CN2CC3COCCN3c3nc(Cl)ncc32)cc1]

2-Chloro-5,6,6a,7,9,10-hexahydro-[1,4]oxazino[3,4-h]pteridine (PREPARATION x2, 580 mg, 2.56 mmol) was dissolved in DMSO (20 mL). Sodium tert-butoxide (295 mg, 3.07 mmol) was added, followed by 1-(bromomethyl)-4-(methylsulfonyl)benzene (669 mg, 2.69 mmol) to give a brown solution. The reaction mixture was stirred overnight at room temperature. The reaction mixture was quenched with aqueous saturated NH$_4$Cl, diluted with ethyl acetate, and washed with aqueous saturated NH$_4$Cl (3×20 mL). The combined organic layers were dried over MgSO$_4$, filtered, and concentrated. The crude product was loaded onto an ISCO® silica gel cartridge (40 g) and eluted using an ethyl acetate/hexane gradient. The product was collected and concentrated in vacuo to afford the title compound as a yellow solid (403 mg, 40%). ESI-MS m/z [M+H]$^+$ calc'd for C$_{17}$H$_{19}$ClN$_4$O$_3$S, 395.09. found 395.4.

PREPARATION x10: (R)-2-chloro-5-(4-(methylsulfonyl)benzyl)-5,6,6a,7,9,10-hexahydro-[1,4]oxazino[3,4-h]pteridine

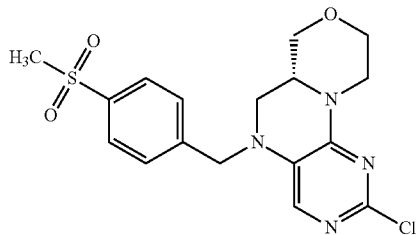 [SMILES: CS(=O)(=O)c1ccc(CN2C[C@@H]3COCCN3c3nc(Cl)ncc32)cc1]

4-Methylsulphonylbenzyl bromide (121 mg, 0.485 mmol) was added to a mixture of (R)-2-chloro-5,6,6a,7,9,10-hexahydro-[1,4]oxazino[3,4-h]pteridine (PREPARATION x3, 100 mg, 0.441 mmol) and potassium tert-butoxide (59.4 mg, 0.529 mmol) in DMSO (2206 µL) at room temperature. The resultant mixture was stirred overnight at room temperature and subsequently diluted with EtOAc and water. The mixture was extracted twice with EtOAc. The combined extracts were washed with brine, dried over $Na_2SO_4$, filtered, and concentrated in vacuo. The residue was purified by column chromatography ($SiO_2$, eluting with 0-10% MeOH/$CHCl_3$ gradient) to afford the title compound as an off-white solid (55.9 mg, 32%).

$^1$H NMR (400 MHz, DMSO-$d_6$) δ 2.94-3.06 (m, 1H), 3.08-3.29 (m, 5H), 3.35-3.52 (m, 2H), 3.67-3.76 (m, 1H), 3.86-4.01 (m, 2H), 4.25 (dd, J=13.64, 1.77 Hz, 1H), 4.55 (s, 2H), 7.30 (s, 1H), 7.57 (d, J=8.34 Hz, 2H), 7.87-7.92 (m, 2H). ESI-MS m/z [M+H]$^+$ calc'd for $C_{17}H_{19}ClN_4O_3S$, 395.09. found 395.2.

PREPARATION x11: 2-chloro-5-tosyl-5,6,6a,7,9,10-hexahydro-[1,4]oxazino[3,4-h]pteridine

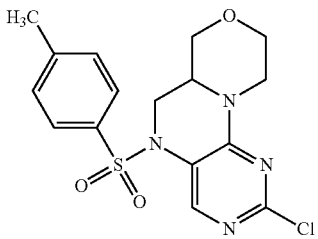 [SMILES: Cc1ccc(S(=O)(=O)N2CC3COCCN3c3nc(Cl)ncc32)cc1]

2-Chloro-5,6,6a,7,9,10-hexahydro-[1,4]oxazino[3,4-h]pteridine (PREPARATION x2, 300 mg, 1.324 mmol) was dissolved in DMSO (20 mL). Sodium tert-butoxide (153 mg, 1.588 mmol) was added followed by 4-methylbenzene-1-sulfonyl chloride (278 mg, 1.456 mmol). The reaction mixture was heated to 50° C. and stirred for 18 hours. Additional 4-methylbenzene-1-sulfonyl chloride (0.5 eq) was added and the reaction mixture was stirred for 18 hours at 50° C. The reaction mixture was subsequently quenched with aqueous saturated $NH_4Cl$, diluted with ethyl acetate, and washed with aqueous saturated $NH_4Cl$ (3×20 mL). The combined organic layers were dried over $MgSO_4$, filtered, and concentrated. The crude product was loaded onto an ISCO® silica gel cartridge (12 g) and eluted using an ethyl acetate/hexane gradient. The product was collected and concentrated in vacuo to afford the title compound as a yellow solid (68 mg, 14%). ESI-MS m/z [M+H]$^+$ calc'd for $C_{16}H_{17}ClN_4O_3S$, 381.07. found 381.3.

PREPARATION x12: 2-(1-(tert-butyldimethylsilyl)-1H-indol-4-yl)-5,6,6a,7,9,10-hexahydro-[1,4]oxazino[3,4-h]pteridine

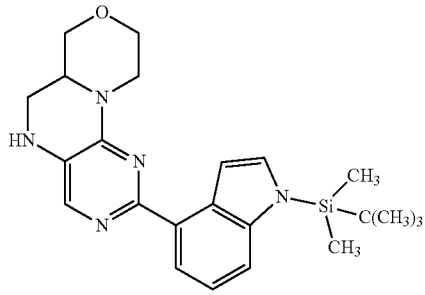 [SMILES: CC(C)(C)[Si](C)(C)n1ccc2c(-c3ncc4c(n3)N3CCOCC3CN4)cccc21]

2-Chloro-5,6,6a,7,9,10-hexahydro-[1,4]oxazino[3,4-h]pteridine (PREPARATION x2, 75 mg, 0.331 mmol), 1-(tert-butyldimethylsilyl)-1H-indol-4-ylboronic acid (182 mg, 0.662 mmol) and $PdCl_2$(dppf) (12.11 mg, 0.017 mmol) were partially dissolved in dioxane (2 mL) and aqueous saturated $NaHCO_3$ (0.4 mL) to give a brown suspension. The reaction mixture was heated to 100° C. and stirred for 18 hours. Following reaction, the mixture was diluted with ethyl acetate and washed with aqueous saturated $NH_4Cl$ (3×5 mL). The combined organic layers were dried over $MgSO_4$, filtered, and concentrated. The crude product was loaded onto an ISCO® silica gel cartridge (12 g) and eluted using an ethyl acetate/hexane gradient. The product was collected and concentrated in vacuo to afford the title compound as a brown oil (43 mg, 30%). $^1$H NMR (400 MHz, DMSO-$d_6$) δ 0.62 (s, 6H), 0.88 (s, 9H), 2.96-3.08 (m, 1H), 3.16-3.25 (m, 1H), 3.39-3.62 (m, 2H), 3.85-3.97 (m, 2H), 4.00-4.07 (m, 2H), 4.43-4.55 (m, 1H), 5.90-5.96 (m, 1H), 7.10-7.18 (m, 1H), 7.34-7.39 (m, 1H), 7.49-7.56 (m, 2H), 7.71 (s, 1H), 7.89-7.96 (m, 1H). ESI-MS m/z [M+H]$^+$ calc'd for $C_{23}H_{31}ClN_5OSi$, 422.23. found 422.5.

PREPARATION x13: 1-(2-(1-(tert-butyldimethylsilyl)-1H-indol-4-yl)-6a,7,9,10-tetrahydro-[1,4]oxazino[3,4-h]pteridin-5(6H)-yl)-2-(4-methoxyphenyl)ethanone

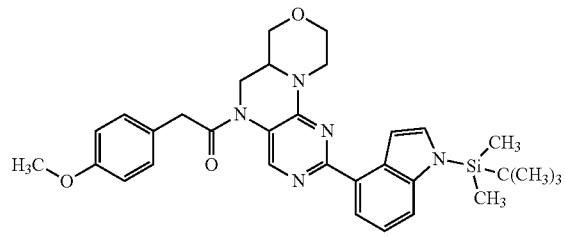 [SMILES: COc1ccc(CC(=O)N2CC3COCCN3c3nc(-c4cccc5c4ccn5[Si](C)(C)C(C)(C)C)ncc32)cc1]

2-(1-(tert-Butyldimethylsilyl)-1H-indol-4-yl)-5,6,6a,7,9,10-hexahydro-[1,4]oxazino[3,4-h]pteridine (PREPARATION x12, 42 mg, 0.100 mmol) in $CH_2Cl_2$ (1 mL) was cooled to 0° C. 2-(4-Methoxyphenyl)acetyl chloride (0.018 mL, 0.120 mmol) was added, followed by triethylamine (0.028 mL, 0.199 mmol) to give a yellow solution. The reaction mixture was stirred for 2 hours at 0° C. The solvent was subsequently removed in vacuo and the resulting concentrate was loaded onto an ISCO® silica gel cartridge (4 g) and eluted using an ethyl acetate/hexane gradient. The product was collected and concentrated in vacuo to afford the title compound as a yellow oil (42 mg, 74%). $^1$H NMR (400 MHz, DMSO-$d_6$) δ 0.64 (s, 6H), 0.89 (s, 9H), 3.02-3.22 (m, 4H), 3.42-3.61 (m, 2H), 3.66-3.78 (m, 3H), 3.87-3.92 (m, 2H), 3.91-3.98 (m, 1H), 4.30-4.47 (m, 1H), 4.64-4.75 (m, 1H), 6.79-6.93 (m, 2H), 7.00-7.30 (m, 3H), 7.42-7.51 (m, 2H), 7.61-7.68 (m, 1H), 8.02-8.07 (m, 1H), 8.32-9.02 (m, 1H). ESI-MS m/z [M+H]$^+$ calc'd for C$_{32}$H$_{39}$N$_5$O$_3$Si, 570.28. found 570.6.

PREPARATION x14: 3-((2-chloro-6a,7,9,10-tetrahydro-[1,4]oxazino[3,4-h]pteridin-5(6H)-yl)methyl)benzonitrile

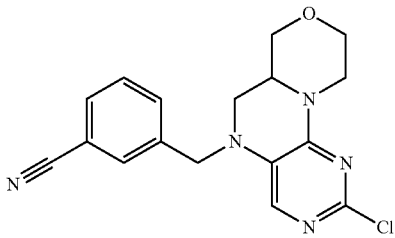 [SMILES: N#Cc1cccc(CN2CC3COCCN3c3nc(Cl)ncc32)c1]

The title compound was made in a manner similar to PREPARATION x9 using 2-chloro-5,6,6a,7,9,10-hexahydro-[1,4]oxazino[3,4-h]pteridine (PREPARATION x2, 75 mg, 0.331 mmol), sodium tert-butoxide (35.0 mg, 0.364 mmol), and 3-(bromomethyl)benzonitrile (78 mg, 0.397 mmol) in DMSO (2 mL). $^1$H NMR (400 MHz, DMSO-d$_6$) δ 2.99 (m, 3H), 3.34-3.39 (m, 1H), 3.41-3.53 (m, 1H), 3.65-3.77 (m, 1H), 3.84-3.99 (m, 2H), 4.19-4.28 (m, 1H), 4.46 (s, 2H), 7.29 (s, 1H), 7.53-7.60 (m, 1H), 7.63-7.69 (m, 1H), 7.79 (m, 2H). ESI-MS m/z [M+H]$^+$ calc'd for C$_{17}$H$_{16}$ClN$_5$O, 342.10. found 342.2.

PREPARATION x15: 3-((2-chloro-6a,7,9,10-tetrahydro-[1,4]oxazino[3,4-h]pteridin-5(6H)-yl)methyl)-4-fluorobenzonitrile

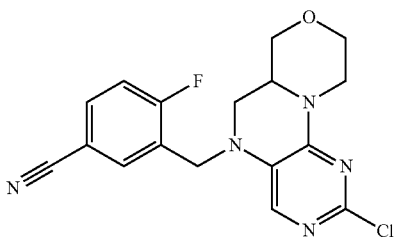 [SMILES: N#Cc1ccc(F)c(CN2CC3COCCN3c3nc(Cl)ncc32)c1]

The title compound was made in a manner similar to PREPARATION x9 using 2-chloro-5,6,6a,7,9,10-hexahydro-[1,4]oxazino[3,4-h]pteridine (PREPARATION x2, 75 mg, 0.331 mmol), sodium tert-butoxide (38.2 mg, 0.397 mmol), and 3-(bromomethyl)-4-fluorobenzonitrile (78 mg, 0.364 mmol) in DMSO (2 mL). $^1$H NMR (400 MHz, DMSO-d$_6$) δ 2.93-3.20 (m, 4H), 3.42-3.54 (m, 1H), 3.65-3.77 (m, 1H), 3.83-3.99 (m, 2H), 4.19-4.28 (m, 1H), 4.49 (m, 2H), 7.34 (s, 1H), 7.44-7.54 (m, 1H), 7.88 (m, 2H). ESI-MS m/z [M+H]$^+$ calc'd for C$_{17}$H$_{15}$ClFN$_5$O, 360.09. found 360.2.

PREPARATION x16: 5-benzyl-2-chloro-5,6,6a,7,9,10-hexahydro-[1,4]oxazino[3,4-h]pteridine

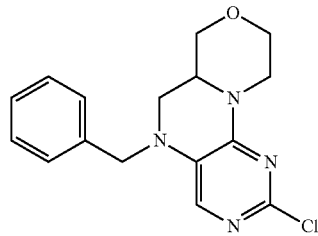 [SMILES: Clc1ncc2c(n1)N1CCOCC1CN2Cc1ccccc1]

To 2-chloro-5,6,6a,7,9,10-hexahydro-[1,4]oxazino[3,4-h]pteridine (PREPARATION x2, 82 mg, 0.362 mmol) in DMF (2 mL) was added N,N-diisopropylethylamine (0.076 mL, 0.434 mmol) and (bromomethyl)benzene (0.047 mL, 0.398 mmol) to give a yellow solution, which was stirred at room temperature for 48 hours. The mixture was subsequently diluted with ethyl acetate and then washed with aqueous saturated NH$_4$Cl (2×5 mL) and brine (2×5 mL). The combined organic layers were dried over MgSO$_4$, filtered, and concentrated. The crude product was loaded onto an ISCO® silica gel cartridge (4 g) and eluted using an ethyl acetate/hexane gradient. The product was collected and concentrated in vacuo to afford the title compound as a yellow solid (55 mg, 48%). $^1$H NMR (400 MHz, DMSO-d$_6$) δ 2.91-3.10 (m, 2H), 3.10-3.22 (m, 1H), 3.32 (s, 1H), 3.40-3.54 (m, 1H), 3.60-3.75 (m, 1H), 3.81-4.01 (m, 2H), 4.15-4.30 (m, 1H), 4.41 (s, 2H), 7.20-7.42 (m, 6H). ESI-MS m/z [M+H]$^+$ calc'd for C$_{16}$H$_{17}$ClN$_4$O, 317.11. found 317.3.

PREPARATION x17: 2-((2-chloro-6a,7,9,10-tetrahydro-[1,4]oxazino[3,4-h]pteridin-5(6H)-yl)methyl)benzonitrile

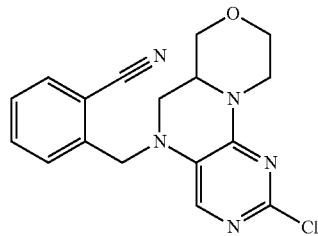 [SMILES: N#Cc1ccccc1CN1CC2COCCN2c2nc(Cl)ncc21]

The title compound was made in a manner similar to PREPARATION x9 using 2-chloro-5,6,6a,7,9,10-hexahydro-[1,4]oxazino[3,4-h]pteridine (PREPARATION x2, 200 mg, 0.882 mmol), sodium tert-butoxide (102 mg, 1.059 mmol) and 2-(bromomethyl)benzonitrile (190 mg, 0.971 mmol) in DMSO (5 mL). $^1$H NMR (400 MHz, DMSO-d$_6$) δ 2.94-3.10 (m, 2H), 3.16 (m, 1H), 3.28-3.32 (m, 1H), 3.42-3.52 (m, 1H), 3.65-3.76 (m, 1H), 3.82-4.00 (m, 2H), 4.22-4.31 (m, 1H), 4.58 (d, J=19.96 Hz, 2H), 7.34 (s, 1H), 7.46-7.56 (m, 2H), 7.68 (d, J=1.26 Hz, 1H), 7.88 (dd, J=7.71, 0.88 Hz, 1H). ESI-MS m/z [M+H]$^+$ calc'd for C$_{17}$H$_{16}$ClN$_5$O, 342.10. found 342.2.

PREPARATION x18: 2-((2-chloro-6a,7,9,10-tetrahydro-[1,4]oxazino[3,4-h]pteridin-5(6H)-yl)methyl)benzamide

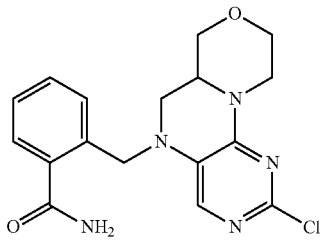 [SMILES: NC(=O)c1ccccc1CN1CC2COCCN2c2nc(Cl)ncc21]

2-((2-Chloro-6a,7,9,10-tetrahydro-[1,4]oxazino[3,4-h]pteridin-5(6H)-yl)methyl)benzonitrile (PREPARATION x17, 140 mg, 0.410 mmol) was dissolved in concentrated sulfuric acid (1 mL) and was stirred overnight at room temperature. Following reaction, the mixture was diluted with ethyl acetate and was washed with aqueous saturated $NaHCO_3$ (2×15 mL) and brine (2×5 mL). The combined organic layers were dried over $MgSO_4$, filtered, and concentrated. The product was purified by LC/MS using a gradient of 20-45% $CH_3CN$ (with 0.035% TFA) in $H_2O$ (with 0.05% TFA). The pure fractions were combined and lyophilized to afford the title compound as a white solid (147 mg, 99%). $^1$H NMR (400 MHz, DMSO-$d_6$) δ 2.91-3.05 (m, 2H), 3.10-3.19 (m, 1H), 3.22-3.29 (m, 1H), 3.44-3.49 (m, 1H), 3.63-3.73 (m, 1H), 3.81-3.99 (m, 2H), 4.21-4.29 (m, 1H), 4.36-4.61 (m, 2H), 7.19-7.24 (m, 1H), 7.30-7.50 (m, 5H), 7.78-7.87 (m, 1H). ESI-MS m/z [M+H]$^+$ calc'd for $C_{17}H_{18}ClN_5O_2$, 360.11. found 360.2.

PREPARATION x19: (R)-2-chloro-5-((5-ethyl-1,3,4-oxadiazol-2-yl)methyl)-5,6,6a,7,9,10-hexahydro-[1,4]oxazino[3,4-h]pteridine

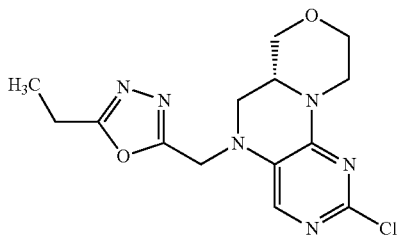 [SMILES: CCc1nnc(CN2C[C@@H]3COCCN3c3nc(Cl)ncc32)o1]

To a 50 mL round-bottom flask was added (R)-2-chloro-5,6,6a,7,9,10-hexahydro-[1,4]oxazino[3,4-h]pteridine (PREPARATION x3, 200 mg, 0.882 mmol) in DMSO (8 mL) followed by sodium tert-butoxide (102 mg, 1.059 mmol). The reaction mixture was stirred at room temperature for 10 minutes. 2-(Chloromethyl)-5-ethyl-1,3,4-oxadiazole (155 mg, 1.059 mmol) was then added to give an orange solution. After 1 hour, LC/MS indicated the reaction was complete. The reaction mixture was subsequently diluted with EtOAc and washed with aqueous saturated $NH_4Cl$ (3×). The combined organic layers were dried over $MgSO_4$, filtered, and concentrated. The product was purified by column chromatography (12 g $SiO_2$ column, EtOAc (20-80%)/hexane gradient) to give the title compound as a pale yellow solid (165 mg, 56%). $^1$H NMR (400 MHz, DMSO-$d_6$) δ 1.24 (t, J=7.58 Hz, 3H), 2.83 (d, J=7.33 Hz, 2H), 2.93-3.03 (m, 1H), 3.04-3.21 (m, 2H), 3.36-3.51 (m, 2H), 3.59-3.71 (m, 1H), 3.85-3.98 (m, 2H), 4.20-4.29 (m, 1H), 4.57-4.67 (m, 1H), 4.84-4.94 (m, 1H), 7.57 (s, 1H). ESI-MS m/z [M+H]$^+$ calc'd for $C_{14}H_{17}ClN_6O_2$, 337.78. found 337.2.

PREPARATION x20: 2-chloro-4-methyl-5,6,6a,7,9,10-hexahydro-[1,4]oxazino[3,4-h]pteridine

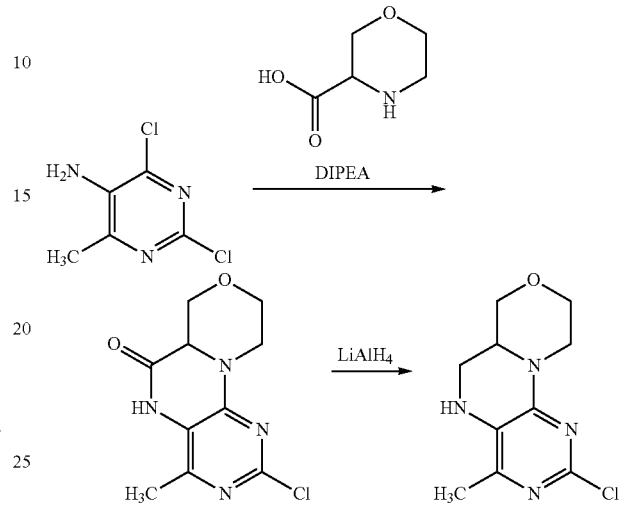

STEP A: 2-chloro-4-methyl-6a,7,9,10-tetrahydro-[1,4]oxazino[3,4-h]pteridin-6(5H)-one A round-bottom flask was charged with crude 2,4-dichloro-6-methylpyrimidin-5-amine (6.644 g, 37.3 mmol), morpholine-3-carboxylic acid hydrochloride (7.51 g, 44.8 mmol), DIPEA (26.1 mL, 149 mmol) and DMSO (49.0 mL). The flask was heated overnight at 100° C. The mixture was subsequently cooled to room temperature and then poured into ice. The solution was stirred while slowly warmed to room temperature. The mixture was subsequently filtered, and the filtrate was purified by preparatory HPLC using a gradient of 15-40% $CH_3CN$ (with 0.035% TFA) in $H_2O$ (with 0.05% TFA). The fractions were collected and concentrated in vacuo to give the title compound as a white solid (387 mg, 4.1%). $^1$H NMR (400 MHz, DMSO-$d_6$) δ 2.26 (s, 3H), 2.54 (s, 1H), 2.87-2.99 (m, 1H), 3.43-3.52 (m, 1H), 3.91 (dd, J=11.72, 3.42 Hz, 1H), 4.10-4.22 (m, 2H), 4.29 (dd, J=10.74, 3.91 Hz, 1H), 10.51 (s, 1H). ESI-MS m/z [M+H]$^+$ calc'd for $C_{10}H_{11}ClN_4O_2$, 255.06. found 255.5.

STEP B: 2-chloro-4-methyl-5,6,6a,7,9,10-hexahydro-[1,4]oxazino[3,4-h]pteridine

A round-bottom flask was charged with 2-chloro-4-methyl-6a,7,9,10-tetrahydro-[1,4]oxazino[3,4-h]pteridin-6(5H)-one (387 mg, 1.520 mmol) in THF (7.6 mL). To the resulting suspension was added lithium aluminum hydride in THF (1.0 M, 1975 μL, 1.975 mmol) dropwise at 0° C. The reaction mixture was allowed to warm to room temperature and was stirred overnight. Ethyl acetate (~1 mL) was subsequently added in portions at 0° C. Aqueous saturated $NH_4Cl$ (5 mL) was then added dropwise until bubbling stopped. The upper organic layer was decanted, concentrated, and then partitioned between brine and ethyl acetate. The murky bottom layer was extracted with ethyl acetate (3×) and the combined organic layers were dried over $MgSO_4$, filtered, and concentrated. The product was triturated with ether/EtOAc and filtered under N₂ to give the title compound as a yellow solid (264 mg, 72%). ESI-MS m/z [M+H]⁺ calc'd for $C_{10}H_{13}ClN_4O$, 241.08. found 241.6.

PREPARATION x21: 2-chloro-4-methyl-5-(4-(methylsulfonyl)benzyl)-5,6,6a,7,9,10-hexahydro-[1,4]oxazino[3,4-h]pteridine

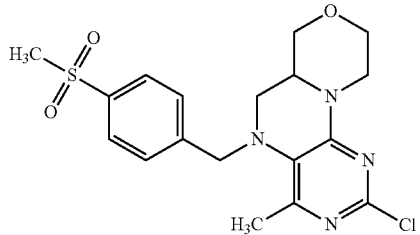 [SMILES: Cc1nc(Cl)nc2c1N(Cc1ccc(S(C)(=O)=O)cc1)CC1COCCN21]

To a round-bottom flask was added 2-chloro-4-methyl-5,6,6a,7,9,10-hexahydro-[1,4]oxazino[3,4-h]pteridine (PREPARATION x20, 264 mg, 1.097 mmol) in DMSO (8.6 mL). Sodium tert-butoxide (126 mg, 1.316 mmol) was then added, followed by 1-(bromomethyl)-4-(methylsulfonyl)benzene (287 mg, 1.152 mmol). The reaction mixture was stirred for 2 days at room temperature. The mixture was subsequently filtered and the filtrate was purified by preparatory HPLC using a gradient of 5-60% CH₃CN (with 0.035% TFA) in H₂O (with 0.05% TFA). The fractions were collected and concentrated in vacuo to give the title compound as a yellow solid (94 mg, 21%). ESI-MS m/z [M+H]⁺ calc'd for $C_{18}H_{21}ClN_4O_3S$, 409.1. found 409.6.

PREPARATION x22: 2-chloro-5-(cyclopropylmethyl)-4-methyl-5,6,6a,7,9,10-hexahydro-[1,4]oxazino[3,4-h]pteridine

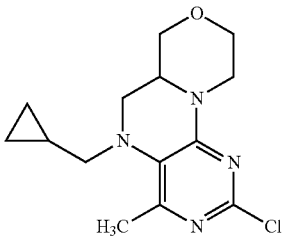 [SMILES: Cc1nc(Cl)nc2c1N(CC1CC1)CC1COCCN21]

To a round-bottom flask was added 2-chloro-4-methyl-5,6,6a,7,9,10-hexahydro-[1,4]oxazino[3,4-h]pteridine (PREPARATION x20, 248 mg, 1.030 mmol) in DMSO (4 mL). Sodium tert-butoxide (119 mg, 1.236 mmol) was added, followed by (bromomethyl)cyclopropane (0.105 mL, 1.082 mmol), and the reaction mixture was stirred overnight at room temperature. The mixture was subsequently filtered and the filtrate was purified by preparatory HPLC using a gradient of 25-50% CH₃CN (with 0.035% TFA) in H₂O (with 0.05% TFA). The fractions were collected and concentrated in vacuo to give the title compound as a brown solid (56 mg, 0.190 mmol, 18%). ESI-MS m/z [M+H]⁺ calc'd for $C_{14}H_{19}ClN_4O$, 295.12. found 295.6.

PREPARATION x23: tert-butyl (1r,4r)-4-((2-chloro-6a,7,9,10-tetrahydro-[1,4]oxazin[3,4-h]pteridin-5(6H)-yl)methyl)cyclohexylcarbamate

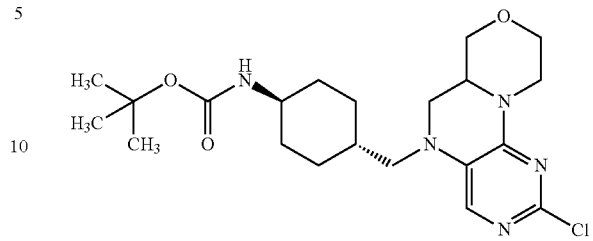

A vessel was charged with ((1r,4r)-4-(tert-butoxycarbonylamino)cyclohexyl)methyl 4-methylbenzenesulfonate (169 mg, 0.441 mmol), 2-chloro-5,6,6a,7,9,10-hexahydro-[1,4]oxazino[3,4-h]pteridine (PREPARATION x2, 100 mg, 0.441 mmol), and potassium 2-methylpropan-2-olate (59.4 mg, 0.529 mmol), and DMA (2.4 mL). The resulting mixture was stirred at 85° C. overnight. Additional ((1r,4r)-4-(tert-butoxycarbonylamino)cyclohexyl)methyl 4-methylbenzenesulfonate (169 mg, 0.441 mmol) and potassium 2-methylpropan-2-olate (59.4 mg, 0.529 mmol) were added and the reaction mixture was stirred at 85° C. for 1 hour. More ((1r,4r)-4-(tert-butoxycarbonylamino)cyclohexyl)methyl 4-methylbenzenesulfonate (216 mg, 0.564 mmol) and potassium 2-methylpropan-2-olate (76 mg, 0.676 mmol) were added and the reaction mixture was stirred at 85° C. for another 2 hours. The mixture was subsequently filtered and the filtrate was purified by preparatory HPLC using a gradient of 40-65% CH₃CN (with 0.035% TFA) in H₂O (with 0.05% TFA). The pure fractions were combined and concentrated to give the title compound as a yellow solid (31 mg, 16% yield). ESI-MS m/z [M+H]⁺ calc'd for $C_{21}H_{32}ClN_5O_3$, 438.22. found 438.5.

PREPARATION x24: (R)-tert-butyl 2-(2-chloro-6a,7,9,10-tetrahydro-[1,4]oxazino[3,4-h]pteridin-5(6H)-yl)acetate

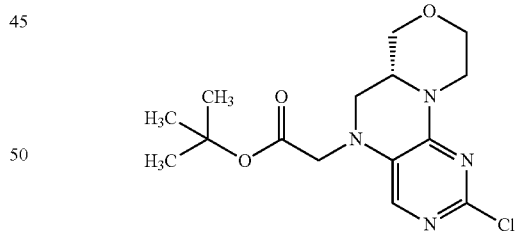

Sodium hydride (60% in oil, 19.41 mg, 0.485 mmol) was added to a solution of (R)-2-chloro-5,6,6a,7,9,10-hexahydro-[1,4]oxazino[3,4-h]pteridine (PREPARATION x3, 100 mg, 0.441 mmol) in DMF (1 mL) at 0° C. The resulting mixture was stirred at room temperature for 30 minutes, after which tert-butyl bromoacetate (0.078 mL, 0.529 mmol) was added at 0° C. The reaction mixture was stirred at room temperature for 30 minutes. Water was added and the mixture was extracted with EtOAc, washed with brine, dried over Na₂SO₄, filtered, and concentrated in vacuo. The residue was purified by column chromatography (SiO₂, 20-80% EtOAc/hexane gradient) to afford the title compound as an off-white solid (101 mg, 67.2%). ¹H NMR (400 MHz, CDCl₃) δ 1.44-1.49

(m, 9H), 3.01-3.11 (m, 1H), 3.15-3.29 (m, 2H), 3.37 (dd, J=11.37, 8.84 Hz, 1H), 3.58 (td, J=11.94, 2.91 Hz, 1H), 3.64-3.76 (m, 2H), 3.88-4.07 (m, 3H), 4.53 (dd, J=13.89, 2.02 Hz, 1H), 7.22 (s, 1H). ESI-MS m/z [M+H]+ calc'd for $C_{15}H_{21}ClN_4O_3$, 341.13. found 341.2

PREPARATION x25: (R)-2-(2-chloro-6a,7,9,10-tetrahydro-[1,4]oxazino[3,4-h]pteridin-5(6H)-yl)acetic acid, HCl

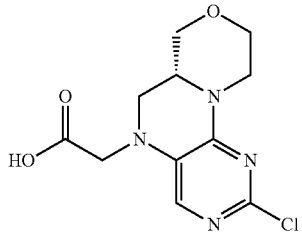 [SMILES: O=C(O)CN1C[C@@H]2COCCN2c2nc(Cl)ncc21]

A mixture of (R)-tert-butyl 2-(2-chloro-6a,7,9,10-tetrahydro-[1,4]oxazino[3,4-h]pteridin-5(6H)-yl)acetate (PREPARATION x24, 580 mg, 1.702 mmol) and HCl (4M in 1,4-dioxane) (15 mL, 60.0 mmol) was stirred at 70° C. for 1 hour and concentrated in vacuo to afford the title compound as a brown solid (590 mg, 108%). $^1$H NMR (400 MHz, DMSO-$d_6$) δ 2.95-3.04 (m, 1H), 3.09-3.20 (m, 2H), 3.32 (dd, J=11.62, 3.79 Hz, 1H), 3.43-4.00 (m, 5H), 4.19-4.29 (m, 2H), 7.35 (s, 1H)). ESI-MS m/z [M+H]+ calc'd for $C_{11}H_{13}ClN_4O_3$, 284.07. found 285.1.

PREPARATION x26: (R)-2-(2-chloro-6a,7,9,10-tetrahydro-[1,4]oxazino[3,4-h]pteridin-5(6H)-yl)-N-((tetrahydro-2H-pyran-4-yl)methyl)acetamide

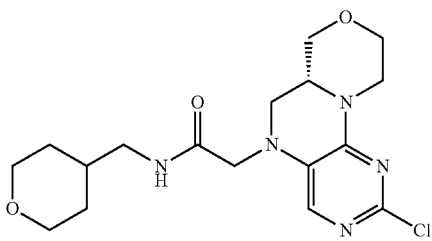 [SMILES: O=C(CN1C[C@@H]2COCCN2c2nc(Cl)ncc21)NCC1CCOCC1]

HATU (841 mg, 2.213 mmol) was added to a mixture of (R)-2-(2-(1H-indol-4-yl)-6a,7,9,10-tetrahydro-[1,4]oxazino[3,4-h]pteridin-5(6H)-yl)acetic acid, HCl (PREPARATION x25, 547 mg, 1.702 mmol), 4-aminomethyltetrahydropyran (294 mg, 2.55 mmol) and Et$_3$N (0.712 mL, 5.11 mmol) in DMF (6 mL) at room temperature. The resulting mixture was stirred at room temperature for 1 hour. The reaction mixture was subsequently diluted with EtOAc, washed with aqueous saturated NaHCO$_3$ and brine, dried over Na$_2$SO$_4$, filtered, and concentrated in vacuo to give a residue which was purified by column chromatography (SiO$_2$, 0-10% gradient of MeOH in CHCl$_3$) to afford the title compound as a white solid (478 mg, 73.5%). $^1$H NMR (400 MHz, DMSO-$d_6$) δ 1.05-1.18 (m, 2H), 1.46-1.55 (m, 2H), 1.54-1.69 (m, 1H), 2.89-3.02 (m, 3H), 3.09-3.31 (m, 5H), 3.47 (td, J=11.87, 2.78 Hz, 1H), 3.57-3.67 (m, 1H), 3.69-4.02 (m, 6H), 4.23 (dd, J=13.52, 1.89 Hz, 1H), 7.21 (s, 1H), 8.04 (t, J=5.81 Hz, 1H). ESI-MS m/z [M+H]+ calc'd for $C_{17}H_{24}ClN_5O_3$, 382.16. found 382.3.

PREPARATION x27: 5-((6-bromopyridin-2-yl)methyl)-2-chloro-5,6,6a,7,9,10-hexahydro-[1,4]oxazino[3,4-h]pteridine

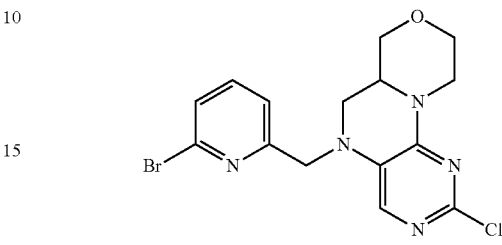

The title compound was prepared in a manner similar to PREPARATION x9 using 2-chloro-5,6,6a,7,9,10-hexahydro-[1,4]oxazino[3,4-h]pteridine (PREPARATION x2, 300 mg, 1.324 mmol) in DMSO (20 mL) followed by sodium tert-butoxide (153 mg, 1.588 mmol) and 2-bromo-6-(bromomethyl)pyridine (332 mg, 1.324 mmol). $^1$H NMR (400 MHz, DMSO-$d_6$) δ 2.92-3.04 (m, 1H), 3.12-3.24 (m, 2H), 3.40-3.53 (m, 2H), 3.62-3.72 (m, 1H), 3.86-4.00 (m, 2H), 4.19-4.28 (m, 1H), 4.42-4.64 (m, 2H), 7.31 (s, 4H), 7.36-7.43 (m, 4H), 7.56 (s, 3H), 7.72 (d, J=7.83 Hz, 4H). ESI-MS m/z [M+H]+ calc'd for $C_{15}H_{15}BrClN_5O$, 396.01. found 396.1.

PREPARATION x28: 2-chloro-5-((6-methylpyridin-2-yl)methyl)-5,6,6a,7,9,10-hexahydro-[1,4]oxazino[3,4-h]pteridine

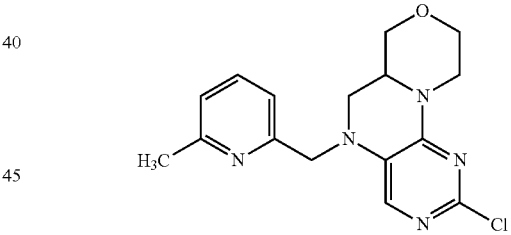

To a 10 mL vial was added 5-((6-bromopyridin-2-yl)methyl)-2-chloro-5,6,6a,7,9,10-hexahydro-[1,4]oxazino[3,4-h]pteridine (PREPARATION x27, 75 mg, 0.189 mmol), K$_2$CO$_3$ (52.3 mg, 0.378 mmol), PdCl$_2$(dppf) (13.83 mg, 0.019 mmol) and 2,4,6-trimethyl-1,3,5,2,4,6-trioxatriborinane (0.053 mL, 0.378 mmol) in dioxane (2 mL) and H$_2$O (0.4 mL) to give an orange suspension. The reaction vial was sealed, heated to 100° C., and stirred overnight. The reaction mixture was then diluted with ethyl acetate and washed with aqueous saturated NH$_4$Cl (3×10 mL). The combined organic layers were dried over MgSO$_4$, filtered, and concentrated in vacuo to give crude product, which was loaded onto an ISCO® silica gel cartridge (4 g) and eluted using an ethyl acetate/hexane gradient. The product was collected and concentrated in vacuo to afford the title compound as a yellow solid (36 mg, 57%). $^1$H NMR (400 MHz, DMSO-$d_6$) δ 2.45 (s, 3H), 2.92-3.05 (m, 1H), 3.12-3.27 (m, 2H), 3.40-3.52 (m, 2H), 3.61-3.74 (m, 1H), 3.85-4.00 (m, 2H), 4.18-4.28 (m, 1H), 4.35-4.58 (m, 2H), 7.10-7.17 (m, 2H), 7.30 (s, 1H), 7.60-7.68 (m, 1H). ESI-MS m/z [M+H]+ calc'd for C₁₆H₁₈ClN₅O, 331.12. found 331.2.

PREPARATION x29: 2-chloro-5-((5-cyclopropyl-1,3,4-oxadiazol-2-yl)methyl)-5,6,6a,7,9,10-hexahydro-[1,4]oxazino[3,4-h]pteridine

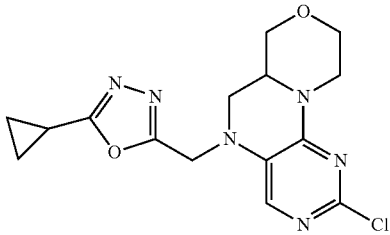 [SMILES: Clc1ncc2c(n1)N1CCOCC1CN2Cc1nnc(C2CC2)o1]

The title compound was prepared in a manner similar to PREPARATION x9 using 2-chloro-5,6,6a,7,9,10-hexahydro-[1,4]oxazino[3,4-h]pteridine (PREPARATION x2, 75 mg, 0.331 mmol) in DMSO (2 mL) followed by sodium tert-butoxide (35.0 mg, 0.364 mmol) and 2-(chloromethyl)-5-cyclopropyl-1,3,4-oxadiazole (68.2 mg, 0.430 mmol). ¹H NMR (400 MHz, DMSO-d₆) δ 0.92-1.00 (m, 2H), 1.07-1.16 (m, 2H), 2.14-2.25 (m, 1H), 2.92-3.03 (m, 1H), 3.03-3.11 (m, 1H), 3.11-3.20 (m, 1H), 3.34-3.51 (m, 1H), 3.53-3.58 (m, 1H), 3.59-3.72 (m, 1H), 3.85-4.00 (m, 2H), 4.20-4.29 (m, 1H), 4.53-4.63 (m, 1H), 4.79-4.88 (m, 1H), 7.56 (s, 1H). ESI-MS m/z [M+H]+ calc'd for C₁₅H₁₇ClN₆O₂, 348.11. found 348.2.

PREPARATION x30: 4-(5-bromo-2-chloropyrimidin-4-yl)morpholine-3-carboxylic acid

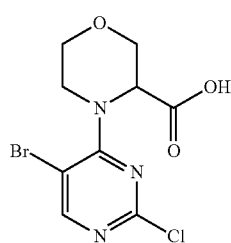 [SMILES: O=C(O)C1COCCN1c1nc(Cl)ncc1Br]

5-Bromo-2,4-dichloropyrimidine (28.5 g, 125 mmol) and morpholine-3-carboxylic acid, HCl (23.06 g, 138 mmol) were dissolved in EtOH (125 mL) at room temperature. N,N-diisopropylethylamine (54.5 mL, 313 mmol) was added and the mixture was stirred for 2 hours. Brine (500 mL) was added and the pH was adjusted to about 2-3 with 1M HCl (aq). The resulting precipitate was collected on a fitted glass filter with vacuum suction. The solid was washed with water (3×) and then dried in a stream of nitrogen overnight to give the title compound as a light brown solid that was used without further purification (31.4 g, 78%). ESI-MS m/z [M+H]+ calc'd for C₉H₉BrClN₃O₃, 321.95. found 322.1.

PREPARATION x31: 4-(5-bromo-2-chloropyrimidin-4-yl)-N—((R)-1-(4-chlorophenyl)ethyl)morpholine-3-carboxamide

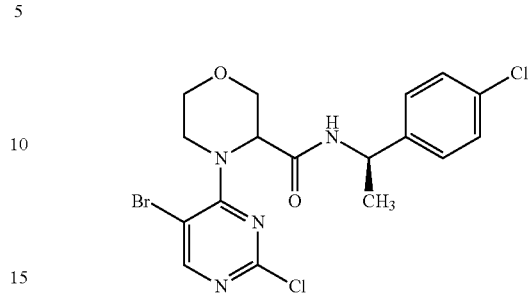

4-(5-Bromo-2-chloropyrimidin-4-yl)morpholine-3-carboxylic acid (PREPARATION x30, 1 g, 3.10 mmol), EDC (0.892 g, 4.65 mmol), HOBt (0.712 g, 4.65 mmol), (R)-1-(4-chlorophenyl)ethanamine (0.724 g, 4.65 mmol) and triethylamine (1.296 mL, 9.30 mmol) were dissolved in DMF (15 mL). The resulting brown solution was stirred at room temperature for 18 hours and was subsequently diluted with ethyl acetate and washed with aqueous saturated NH₄Cl (3×25 mL). The combined organic layers were dried over MgSO₄, filtered, and concentrated in vacuo to give a crude product which was loaded onto an ISCO® silica gel cartridge (40 g) and eluted using an ethyl acetate/hexane gradient. The product was collected and concentrated in vacuo to afford the title compound as a yellow foam (574 mg, 40%). ¹H NMR (400 MHz, DMSO-d₆) δ 1.38 (dd, J=7.07, 4.29 Hz, 3H), 3.55 (d, J=6.32 Hz, 2H), 3.68-3.79 (m, 1H), 3.84-3.91 (m, 1H), 4.22-4.39 (m, 2H), 4.86 (m, 1H), 4.89-5.03 (m, 1H), 7.31-7.41 (m, 4H), 8.45 (d, J=10.61 Hz, 2H).

PREPARATION x32: 4-(5-bromo-2-chloropyrimidin-4-yl)-N—((S)-1-(p-tolyl)ethyl)morpholine-3-carboxamide

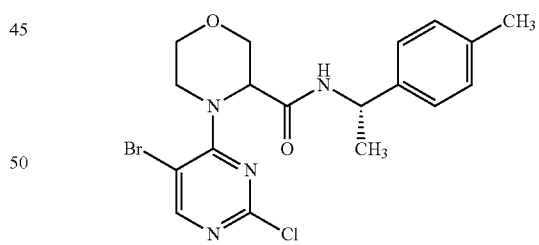

The title compound was prepared in a manner similar to PREPARATION x31 using 4-(5-bromo-2-chloropyrimidin-4-yl)morpholine-3-carboxylic acid (PREPARATION x30, 1 g, 3.10 mmol), EDC (0.892 g, 4.65 mmol), HOBt (0.712 g, 4.65 mmol), triethylamine (1.296 mL, 9.30 mmol) and (S)-1-p-tolylethanamine (0.629 g, 4.65 mmol) in DMF (15 mL). ¹H NMR (400 MHz, DMSO-d₆) δ 1.37 (dd, J=6.95, 3.66 Hz, 3H), 2.27 (s, 3H), 3.55 (d, J=9.35 Hz, 2H), 3.66-3.77 (m, 1H), 3.82-3.92 (m, 1H), 4.21-4.39 (m, 2H), 4.83-5.01 (m, 2H), 7.12 (d, J=7.83 Hz, 2H), 7.16-7.28 (m, 2H), 8.45 (d, J=10.86 Hz, 2H). ESI-MS m/z [M+H]+ calc'd for C₁₈H₂₀BrClN₄O₂, 439.05. found 439.2.

PREPARATION x33: 4-(5-bromo-2-chloropyrimidin-4-yl)-N-(1-(4-chlorophenyl)cyclopropyl)morpholine-3-carboxamide

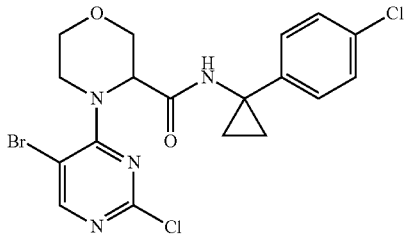 [SMILES: O=C(NC1(c2ccc(Cl)cc2)CC1)C1COCCN1c1nc(Cl)ncc1Br]

The title compound was prepared in a manner similar to PREPARATION x31 using 4-(5-bromo-2-chloropyrimidin-4-yl)morpholine-3-carboxylic acid (PREPARATION x30, 0.244 g, 0.756 mmol), EDC (0.174 g, 0.908 mmol), HOBt (0.123 g, 0.908 mmol), N,N-diisopropylethylamine (0.138 mL, 0.794 mmol), and 1-(4-chlorophenyl)cyclopropanamine, HCl (0.185 g, 0.908 mmol) in THF (8 mL). ESI-MS m/z [M+H]$^+$ calc'd for $C_{18}H_{17}BrCl_2N_4O_2$, 470.99. found 471.3.

PREPARATION x34: 2-chloro-5-((R)-1-(4-chlorophenyl)ethyl)-6a,7,9,10-tetrahydro-[1,4]oxazino[3,4-h]pteridin-6(5H)-one

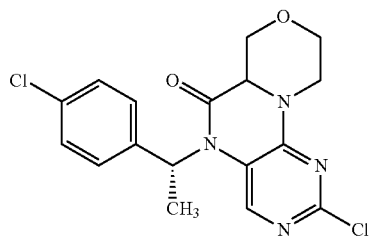 [SMILES: C[C@H](c1ccc(Cl)cc1)N1C(=O)C2COCCN2c2nc(Cl)ncc21]

To an oven dried vial were added 4-(5-bromo-2-chloropyrimidin-4-yl)-N—((R)-1-(4-chlorophenyl)ethyl)morpholine-3-carboxamide (PREPARATION x31, 574 mg, 1.247 mmol), Xantphos (54.1 mg, 0.094 mmol), potassium phosphate tribasic (265 mg, 1.247 mmol) and palladium(II)acetate (14.00 mg, 0.062 mmol) in dioxane (5 mL) and tert-butanol (1 mL). The reaction mixture was degassed for 5 minutes with N$_2$. The vial was then sealed and heated to 105° C. and the contents were stirred for 72 hours to give a brown suspension. The reaction mixture was subsequently diluted with ethyl acetate and washed with aqueous saturated NH$_4$Cl (3×5 mL) and brine (3×5 mL). The combined organic layers were dried over MgSO$_4$, filtered, and concentrated in vacuo to give a crude product which was loaded onto an ISCO® silica gel cartridge (40 g) and eluted using an ethyl acetate/hexane gradient. The product was collected and concentrated in vacuo to afford the title compound as a white solid (58 mg, 12%). $^1$H NMR (400 MHz, DMSO-d$_6$) δ 1.68-1.80 (m, 3H), 2.91-3.02 (m, 1H), 3.46-3.64 (m, 1H), 3.64-3.76 (m, 1H), 3.88-4.01 (m, 1H), 4.13-4.27 (m, 2H), 4.41-4.60 (m, 1H), 5.99-6.24 (m, 1H), 7.27-7.49 (m, 4H), 7.50-7.57 (m, 1H). ESI-MS m/z [M+H]$^+$ calc'd for $C_{17}H_{16}Cl_2N_4O_2$, 379.07. found 379.3.

PREPARATION x35: 2-chloro-54(5)-1-(p-tolyl)ethyl)-6a,7,9,10-tetrahydro-[1,4]oxazino[3,4-h]pteridin-6(5H)-one

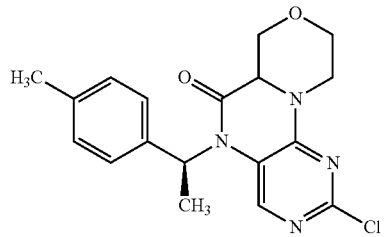 [SMILES: Cc1ccc([C@H](C)N2C(=O)C3COCCN3c3nc(Cl)ncc32)cc1]

To an oven dried vial were added 4-(5-bromo-2-chloropyrimidin-4-yl)-N—((S)-1-p-tolylethyl)morpholine-3-carboxamide (PREPARATION x32, 588 mg, 1.337 mmol), potassium phosphate tribasic (284 mg, 1.337 mmol), Xantphos (58.0 mg, 0.100 mmol) and palladium(II)acetate (15.01 mg, 0.067 mmol) in dioxane (15 mL) and tert-butanol (3 mL). The reaction mixture was degassed for 5 minutes with N$_2$. The vial was then sealed and heated to 105° C. and the contents were stirred for 18 hours to give a brown suspension. The reaction mixture was subsequently diluted with ethyl acetate and washed with aqueous saturated NH$_4$Cl (3×5 mL and brine (3×5 mL). The combined organic layers were dried over MgSO$_4$, filtered, and concentrated in vacuo. The crude product was loaded onto an ISCO® silica gel cartridge (40 g) and eluted using an ethyl acetate/hexane gradient to give two diastereomers whose absolute configuration was not assigned (Diastereomer 1, higher R$_f$, 97 mg; Diastereomer 2, lower R$_f$, 91 mg; 39% overall). Diastereomer 1: $^1$H NMR (400 MHz, DMSO-d$_6$) δ 1.69 (d, J=7.33 Hz, 3H), 2.29 (s, 3H), 2.89-3.04 (m, 1H), 3.46-3.67 (m, 2H), 3.89-4.01 (m, 1H), 4.13-4.27 (m, 2H), 4.50-4.63 (m, 1H), 6.16-6.30 (m, 1H), 7.13-7.29 (m, 4H), 7.29-7.38 (m, 1H); ESI-MS m/z [M+H]$^+$ calc'd for $C_{18}H_{19}ClN_4O_2$, 359.12. found 359.3. Diastereomer 2: $^1$H NMR (400 MHz, DMSO-d$_6$) δ 1.75 (d, J=7.07 Hz, 3H), 2.28 (s, 3H), 2.90-3.04 (m, 1H), 3.51-3.62 (m, 1H), 3.64-3.75 (m, 1H), 3.89-3.98 (m, 1H), 4.16-4.26 (m, 2H), 4.43-4.51 (m, 1H), 6.06-6.17 (m, 1H), 7.18 (d, J=2.53 Hz, 4H), 7.47 (s, 1H); ESI-MS m/z [M+H]$^+$ calc'd for $C_{18}H_{19}ClN_4O$, 359.12. found 359.3.

PREPARATION x36: 2-chloro-5-(1-(4-chlorophenyl)cyclopropyl)-6a,7,9,10-tetrahydro-[1,4]oxazino[3,4-h]pteridin-6(5H)-one

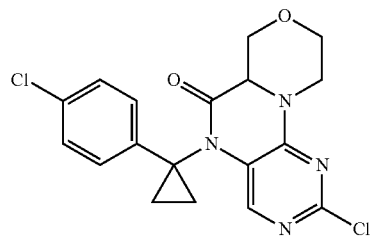 [SMILES: O=C1C2COCCN2c2nc(Cl)ncc2N1C1(c2ccc(Cl)cc2)CC1]

The title compound was prepared in a manner similar to PREPARATION x35 using 4-(5-bromo-2-chloropyrimidin-4-yl)-N-(1-(4-chlorophenyl)cyclopropyl)morpholine-3-carboxamide (PREPARATION x33, 300 mg, 0.635 mmol), 9,9- dimethyl-4,5-bis(diphenylphosphino)xanthene (27.6 mg, 0.048 mmol), palladium (II)acetate (7.13 mg, 0.032 mmol), and potassium phosphate, tribasic (189 mg, 0.890 mmol) in dioxane (2.5 mL) and tert-butanol (0.5 mL). ESI-MS m/z [M+H]$^+$ calc'd for $C_{19}H_{17}Cl_2N_3O_2$, 391.07. found 391.0.

PREPARATION x37: 1-methyl-3-(4-(6-oxo-5,6,6a,7,9,10-hexahydro-[1,4]oxazino[3,4-h]pteridin-2-yl)phenyl)urea

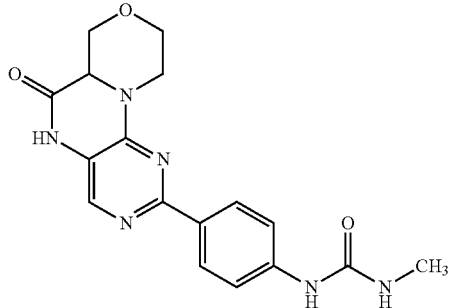 [SMILES: CNC(=O)Nc1ccc(-c2ncc3c(n2)N2CCOCC2C(=O)N3)cc1]

2-Chloro-6a,7,9,10-tetrahydro-[1,4]oxazino[3,4-h]pteridin-6(5H)-one (PREPARATION x1, 1 g, 4.16 mmol), 1-methyl-3-(4-(4,4,5,5-tetramethyl-1,3,2-dioxaborolan-2-yl)phenyl)urea (2.295 g, 8.31 mmol) and PdCl$_2$(dppf) (0.152 g, 0.208 mmol) were suspended in dioxane (10 mL) and aqueous saturated NaHCO$_3$ (2 mL) to give a brown solution. The reaction vessel was sealed and the reaction mixture was heated to 75° C. for 48 hours. The crude reaction mixture was diluted with water (20 mL) and the solid was collected by vacuum filtration. The brown solid was carefully washed with a 1:4 ethanol/H$_2$O solution (5 mL) and was allowed to dry under a stream of nitrogen to give the title compound. ESI-MS m/z [M+H]$^+$ calc'd for $C_{17}H_{18}N_6O_3$, 355.14. found 355.3.

PREPARATION x38: 2-chloro-5-(4-(methylsulfonyl)benzyl)-6a,7,9,10-tetrahydro-[1,4]oxazino[3,4-h]pteridin-6(5H)-one

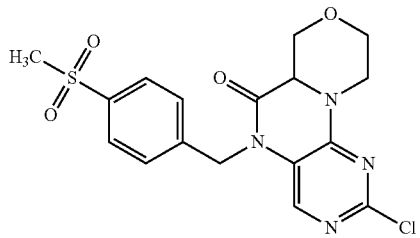 [SMILES: CS(=O)(=O)c1ccc(CN2C(=O)C3COCCN3c3nc(Cl)ncc32)cc1]

2-Chloro-6a,7,9,10-tetrahydro-[1,4]oxazino[3,4-h]pteridin-6(5H)-one (PREPARATION x1, 1.5 g, 6.23 mmol) was dissolved in DMF (25 mL) to give an orange solution. The mixture was cooled to 0° C. and lithium bis(trimethylsilyl)amide (1.04 g, 6.23 mmol), followed by 4-methylsulfonylbenzyl bromide (1.71 g, 6.86 mmol), were added. The reaction mixture was stirred at 0° C. for 1 hour and was subsequently diluted with ethyl acetate and washed with brine (100 mL) to give a suspension. An orange precipitate was collected on a fritted glass funnel and was washed with water (3×20 mL) and dried over night in a stream of nitrogen. The crude solid was triturated with hot ethyl acetate (2×) to give the title compound which was used without further purification (1.78 g, 69.8%). ESI-MS m/z [M+H]$^+$ calc'd for $C_{17}H_{17}ClN_4O_4S$, 409.07. found 409.3.

PREPARATION x39: 5-benzyl-2-chloro-6a,7,9,10-tetrahydro-[1,4]oxazino[3,4-h]pteridin-6(5H)-one

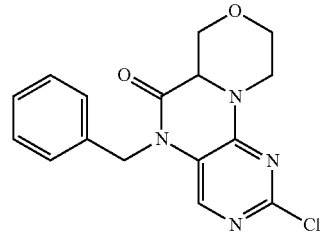 [SMILES: O=C1C2COCCN2c2nc(Cl)ncc2N1Cc1ccccc1]

The title compound was prepared in a manner similar to PREPARATION x38 using 2-chloro-6a,7,9,10-tetrahydro-[1,4]oxazino[3,4-h]pteridin-6(5H)-one (PREPARATION x1, 500 mg, 2.078 mmol), 1M lithium bis(trimethylsiylyamide) in hexanes (2.493 mL, 2.493 mmol) and (bromomethyl)benzene (0.271 mL, 2.286 mmol) in DMF (10 mL) at 0° C. for 18 hours. $^1$H NMR (400 MHz, DMSO-d$_6$) δ 2.94-3.06 (m, 1H), 3.50-3.61 (m, 1H), 3.62-3.72 (m, 1H), 3.90-3.99 (m, 1H), 4.17-4.32 (m, 2H), 4.56-4.67 (m, 1H), 5.02-5.22 (m, 2H), 7.29 (s, 5H), 7.72 (s, 1H). ESI-MS m/z [M+H]$^+$ calc'd for $C_{16}H_{15}ClN_4O_2$, 331.09. found 331.2.

PREPARATION x40: 4-(5-bromo-2-chloropyrimidin-4-yl)-N-(6-chloro-2,3-dihydro-1H-inden-1-yl)morpholine-3-carboxamide

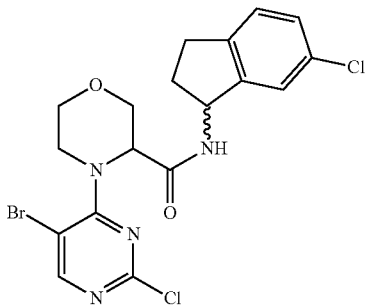 [SMILES: O=C(NC1CCc2ccc(Cl)cc21)C1COCCN1c1nc(Cl)ncc1Br]

The title compound was prepared in a manner similar to PREPARATION x31 using 4-(5-bromo-2-chloropyrimidin-4-yl)morpholine-3-carboxylic acid (PREPARATION x30, 750 mg, 2.325 mmol), EDC (669 mg, 3.49 mmol), HOBt (534 mg, 3.49 mmol), 6-chloro-2,3-dihydro-1H-inden-1-amine hydrochloride (712 mg, 3.49 mmol), and triethylamine (0.486 mL, 3.49 mmol) in DMF (15 mL). $^1$H NMR (400 MHz, DMSO-d$_6$) δ 1.78-1.95 (m, 1H), 2.36-2.47 (m, 1H), 2.70-2.96 (m, 2H), 3.48-3.80 (m, 3H), 3.86-3.98 (m, 1H), 4.21-4.44 (m, 2H), 4.77-4.93 (m, 1H), 5.28-5.43 (m, 1H), 7.27 (s, 3H), 8.47 (d, J=7.58 Hz, 2H). ESI-MS m/z [M+H]$^+$ calc'd for $C_{18}H_{17}Br_2Cl_2N_4O_2$, 470.99. found 471.3.

PREPARATION x41: 2-chloro-5-(6-chloro-2,3-dihydro-1H-inden-1-yl)-6a,7,9,10-tetrahydro-[1,4]oxazino[3,4-h]pteridin-6(5H)-one

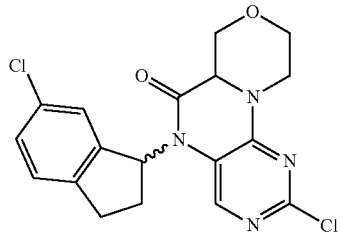 [SMILES: O=C1C2COCCN2c2nc(Cl)ncc2N1C1CCc2ccc(Cl)cc21]

The title compound was prepared in a manner similar to PREPARATION x35 using 4-(5-bromo-2-chloropyrimidin-4-yl)-N-(6-chloro-2,3-dihydro-1H-inden-1-yl)morpholine-3-carboxamide (PREPARATION x40, 567 mg, 1.201 mmol), Xantphos (52.1 mg, 0.090 mmol), palladium(II)acetate (13.48 mg, 0.060 mmol) and potassium phosphate (255 mg, 1.201 mmol) in dioxane (5 mL) and tert-butanol (1 mL). $^1$H NMR (400 MHz, DMSO-$d_6$) δ 2.21-2.48 (m, 3H), 2.87-3.05 (m, 2H), 3.05-3.21 (m, 1H), 3.47-3.65 (m, 2H), 3.88-4.01 (m, 1H), 4.08-4.32 (m, 2H), 4.39-4.56 (m, 1H), 7.16-7.42 (m, 4H). ESI-MS m/z [M+H]$^+$ calc'd for $C_{18}H_{16}Cl_2N_4O_2$, 391.07. found 391.3.

PREPARATION x42: 4-(5-bromo-2-chloropyrimidin-4-yl)-N-(6-methoxy-2,3-dihydro-1H-inden-1-yl)morpholine-3-carboxamide

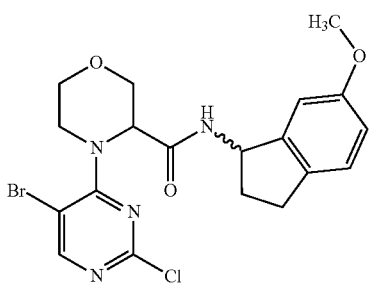 [SMILES: COc1ccc2c(c1)C(NC(=O)C1COCCN1c1nc(Cl)ncc1Br)CC2]

The title compound was prepared in a manner similar to PREPARATION x31 using 4-(5-bromo-2-chloropyrimidin-4-yl)morpholine-3-carboxylic acid (PREPARATION x30, 500 mg, 1.550 mmol), EDC (446 mg, 2.325 mmol), HOBt (356 mg, 2.325 mmol), 6-methoxy-2,3-dihydro-1H-inden-1-amine hydrochloride (464 mg, 2.325 mmol) and triethylamine (0.324 mL, 2.325 mmol) in DMF (10 mL). $^1$H NMR (400 MHz, DMSO-$d_6$) δ 1.76-1.94 (m, 1H), 2.30-2.47 (m, 1H), 2.62-2.93 (m, 2H), 3.48-3.65 (m, 2H), 3.70 (d, J=4.80 Hz, 3H), 3.87-3.96 (m, 1H), 4.24-4.43 (m, 2H), 4.89-5.01 (m, 1H), 5.26-5.41 (m, 1H), 6.70-6.82 (m, 2H), 7.08-7.18 (m, 1H), 8.45 (s, 2H). ESI-MS m/z [M+H]$^+$ calc'd for $C_{19}H_{20}BrClN_4O_3$, 467.04. found 467.3.

PREPARATION x43: 2-chloro-5-(6-methoxy-2,3-dihydro-1H-inden-1-yl)-6a,7,9,10-tetrahydro-[1,4]oxazino[3,4-h]pteridin-6(5H)-one

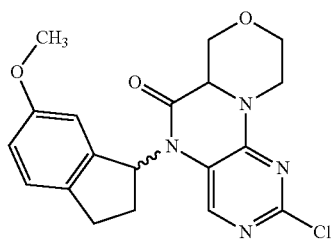 [SMILES: COc1ccc2c(c1)C(N1C(=O)C3COCCN3c3nc(Cl)ncc31)CC2]

The title compound was prepared in a manner similar to PREPARATION x35 using 4-(5-bromo-2-chloropyrimidin-4-yl)-N-(6-methoxy-2,3-dihydro-1H-inden-1-yl)morpholine-3-carboxamide (PREPARATION x42, 472 mg, 1.009 mmol), Xantphos (43.8 mg, 0.076 mmol), potassium phosphate (214 mg, 1.009 mmol) and palladium(II)acetate (11.33 mg, 0.050 mmol) in dioxane (5 mL) and tert-butanol (1 mL). ESI-MS m/z [M+H]$^+$ calc'd for $C_{19}H_{19}ClN_4O_3$, 387.11. found 387.4.

PREPARATION x44: 5-(4-(methylsulfonyl)benzyl)-2-(1-tosyl-1H-pyrrolo[2,3-b]pyridin-4-yl)-6a,7,9,10-tetrahydro-[1,4]oxazino[3,4-h]pteridin-6(5H)-one

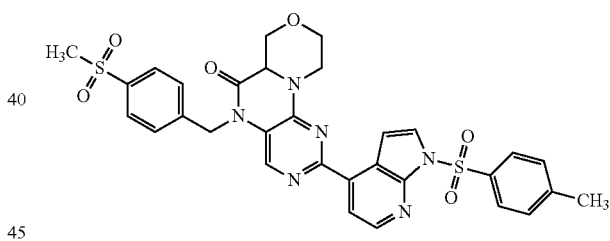

2-Chloro-5-(4-(methylsulfonyl)benzyl)-6a,7,9,10-tetrahydro-[1,4]oxazino[3,4-h]pteridin-6(5H)-one (PREPARATION x38, 250 mg, 0.611 mmol), 4-(4,4,5,5-tetramethyl-1,3,2-dioxaborolan-2-yl)-1-tosyl-1H-pyrrolo[2,3-b]pyridine (487 mg, 1.223 mmol), and PdCl$_2$(dppf) (35.8 mg, 0.049 mmol) were suspended in dioxane (2.5 mL) and aqueous saturated NaHCO$_3$ (0.5 mL). The reaction mixture was heated in a microwave at 100° C. on high absorbance for 1 hour and was subsequently diluted with ethyl acetate and washed with aqueous saturated NH$_4$Cl (3×2 mL) and brine (3×2 mL). The combined organic layers were dried over MgSO$_4$, filtered, and concentrated in vacuo to give a crude product which was loaded onto an ISCO® silica gel cartridge (4 g) and eluted using an ethyl acetate/hexane gradient. The product was collected and concentrated in vacuo to afford the title compound as a yellow foam (205 mg, 52%). ESI-MS m/z [M+H]$^+$ calc'd for $C_{31}H_{28}N_6O_6S_2$, 645.15. found 645.5.

PREPARATION x45: 4-(5-bromo-2-(2-(difluoromethyl)-1H-benzo[d]imidazol-1-yl)pyrimidin-4-yl)morpholine-3-carboxylic acid

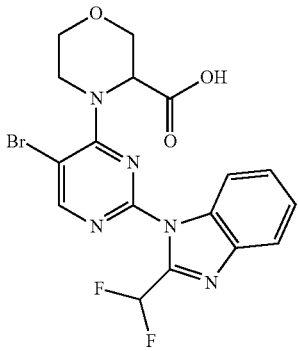 [SMILES: O=C(O)C1COCCN1c1nc(-n2c(C(F)F)nc3ccccc32)ncc1Br]

A mixture of 4-(5-bromo-2-chloropyrimidin-4-yl)morpholine-3-carboxylic acid (PREPARATION x30, 3 g, 9.3 mmol), 2-(difluoromethyl)-1H-benzo[d]imidazole (1.3 g, 11.1 mmol) and $Cs_2CO_3$ (10.28 g, 47.4 mmol) in DMA (50 mL) was stirred at 120° C. overnight. The mixture was subsequently concentrated and the crude material was converted to the methyl ester of the title compound by treatment with $CH_2N_2$. The methyl ester was purified and then hydrolyzed by LiOH to give the title compound which was used without further purification (310 mg, 7.6%).

PREPARATION x46: 4-(5-bromo-2-chloropyrimidin-4-yl)-N—((S)-1-phenylethyl)morpholine-3-carboxamide

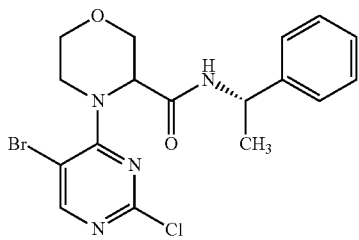 [SMILES: C[C@H](NC(=O)C1COCCN1c1nc(Cl)ncc1Br)c1ccccc1]

To a 50 mL round-bottom flask were added 4-(5-bromo-2-chloropyrimidin-4-yl)morpholine-3-carboxylic acid (PREPARATION x30, 300 mg, 0.930 mmol), 1-hydroxybenzotriazole (126 mg, 0.930 mmol), and (S)-1-phenylethanamine (118 µl, 0.930 mmol) in 1,4-dioxane (9.3 mL) to give a green solution. 1-Ethyl-(3-dimethylaminopropyl)carbodiimide hydrochloride (178 mg, 0.930 mmol) was added to the solution, which was allowed to react at room temperature for 6 hours. The mixture was subsequently partitioned between aqueous saturated $NaHCO_3$ and ethyl acetate. The aqueous layer was extracted with ethyl acetate and the combined organic layers were dried over $MgSO_4$, filtered, and concentrated to give the title compound, which was used without further purification. ESI-MS m/z $[M+H]^+$ calc'd for $C_{17}H_{18}BrClN_4O_2$, 425.03. found 425.2.

PREPARATION x47: (S)-2-chloro-5-(1-phenylethyl)-6a,7,9,10-tetrahydro-[1,4]oxazino[3,4-h]pteridin-6(5H)-one

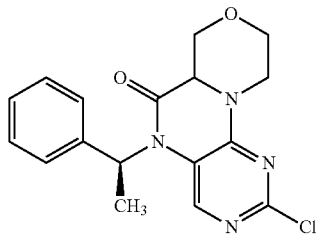 [SMILES: C[C@@H](c1ccccc1)N1C(=O)C2COCCN2c2nc(Cl)ncc21]

To a 5 mL microwave vial were added 4-(5-bromo-2-chloropyrimidin-4-yl)-N—((S)-1-phenylethyl)morpholine-3-carboxamide (PREPARATION x46, 0.394 g, 0.926 mmol), 9,9-dimethyl-4,5-bis(diphenylphosphino)xanthene (0.024 g, 0.042 mmol), and palladium (II) acetate (6.23 mg, 0.028 mmol). The vessel was evacuated, refilled with nitrogen, and sealed. Dioxane (3.9 mL) was added and the mixture was heated in a microwave to 120° C. for 3 hours. Additional catalyst was added and the reaction mixture was heated in the microwave to 120° C. for another 6 hours. The reaction mixture was then partitioned between aqueous saturated $NaHCO_3$ and ethyl acetate. The aqueous layer was extracted with ethyl acetate and the combined organic layers were dried over $MgSO_4$, filtered, and concentrated. The dark brown crude product was purified by normal phase column chromatography ($SiO_2$, 60 gram) eluting with a gradient of 50-100% EtOAc in hexanes over a 20 minute period. The product-containing fractions were combined and concentrated to give the title compound as a white foam (69 mg, 22%). ESI-MS m/z $[M+H]^+$ calc'd for $C_{17}H_{17}ClN_4O_2$, 345.10. found 345.3.

PREPARATION x48: 4-(5-bromo-2-chloropyrimidin-4-yl)-N—((S)-2,3-dihydro-1H-inden-1-yl)morpholine-3-carboxamide

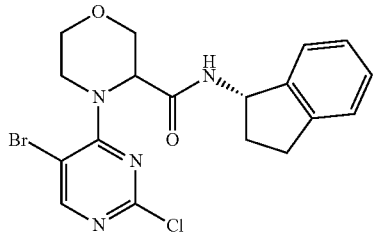 [SMILES: O=C(N[C@H]1CCc2ccccc21)C1COCCN1c1nc(Cl)ncc1Br]

To a 50 mL pear flask were added 4-(5-bromo-2-chloropyrimidin-4-yl)morpholine-3-carboxylic acid (PREPARATION x30, 300 mg, 0.930 mmol), 1-hydroxybenzotriazole (126 mg, 0.930 mmol), and (S)-2,3-dihydro-1H-inden-1-amine (0.119 mL, 0.930 mmol) in 1,4-dioxane (25 mL) to give a green solution. 1-Ethyl-(3-dimethylaminopropyl)carbodiimide hydrochloride (178 mg, 0.930 mmol) was added to the solution, which was allowed to reaction at room temperature for 6 hours. The reaction mixture was subsequently partitioned between aqueous saturated $NaHCO_3$ and ethyl acetate. The aqueous layer was extracted with ethyl acetate and the combined organic layers were dried over $MgSO_4$, filtered, and concentrated to give the title compound, which was used without further purification. ESI-MS m/z [M+H]+ calc'd for $C_{18}H_{18}BrClN_4O_2$, 437.03. found 437.2.

PREPARATION x49: (S)-2-chloro-5-(2,3-dihydro-1H-inden-1-yl)-6a,7,9,10-tetrahydro-[1,4]oxazino[3,4-h]pteridin-6(5H)-one

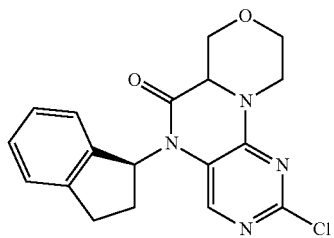 [SMILES: O=C1C2COCCN2c2nc(Cl)ncc2N1[C@H]1CCc2ccccc21]

To a 5 mL microwave vial were added 4-(5-bromo-2-chloropyrimidin-4-yl)-N—((S)-2,3-dihydro-1H-inden-1-yl)morpholine-3-carboxamide (PREPARATION x48, 407 mg, 0.93 mmol), 9,9-dimethyl-4,5-bis(diphenylphosphino)xanthene (26.9 mg, 0.047 mmol), palladium (II)acetate (6.26 mg, 0.028 mmol), and potassium phosphate, tribasic (276 mg, 1.302 mmol). The vessel was evacuated, refilled with nitrogen, and sealed. Dioxane (3.9 mL) and tert-butanol (0.78 mL) were added and the mixture was heated in a microwave to 120° C. for 90 minutes. An additional portion of catalyst was added, and the reaction mixture was heated in the microwave to 120° C. for another 6 hours. The reaction mixture was subsequently partitioned between aqueous saturated NaHCO$_3$ and ethyl acetate. The aqueous layer was extracted with ethyl acetate, and the combined organic layers were dried over MgSO$_4$, filtered, and concentrated. The dark brown crude product was purified by normal phase column chromatography (SiO$_2$, 60 g) eluting with a gradient of 50-100% EtOAc in hexanes over 20 minutes. The product-containing fractions were combined and concentrated to give the title compound as a white foam (88 mg, 26.5%). ESI-MS m/z [M+H]+ calc'd for $C_{17}H_{17}ClN_4O_2$, 357.10. found 357.3.

PREPARATION x50: 445-bromo-2-chloropyrimidin-4-yl)-N—((S)-1-(4-chlorophenyl)ethyl)morpholine-3-carboxamide

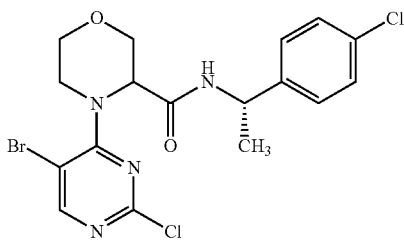 [SMILES: C[C@H](NC(=O)C1COCCN1c1nc(Cl)ncc1Br)c1ccc(Cl)cc1]

To a 50 mL round-bottom flask were added (R)-4-(5-bromo-2-chloropyrimidin-4-yl)morpholine-3-carboxylic acid (460 mg, 1.426 mmol), 1-hydroxybenzotriazole (193 mg, 1.426 mmol), and 1-ethyl-(3-dimethylaminopropyl)carbodiimide hydrochloride (328 mg, 1.711 mmol) in THF (10 mL) to give a beige solution. After 5 minutes (S)-1-(4-chlorophenyl)ethylamine (0.220 mL, 1.569 mmol) was added to the solution, which was allowed to react at room temperature for 1.5 hours. The reaction mixture was subsequently partitioned between brine and ethyl acetate. The aqueous layer was extracted with ethyl acetate and the combined organic layers were dried over MgSO$_4$, filtered, and concentrated. The residue was purified by normal phase column chromatography (20-50% EtOAc gradient in hexanes over 20 minutes) to give a diastereomeric mixture of the title compound as a white foam (474 mg, 72.2%). $^1$H NMR (400 MHz, DMSO-d$_6$) δ 1.35-1.42 (m, 3H), 3.50-3.63 (m, 2H), 3.69-3.79 (m, 1H), 3.83-3.93 (m, 1H), 4.23-4.39 (m, 2H), 4.85-4.89 (m, 1H), 4.90-5.03 (m, 1H), 7.33-7.41 (m, 4H), 8.44-8.48 (m, 1H), 8.48-8.57 (m, 1H). ESI-MS m/z [M+H]+ calc'd for $C_{17}H_{17}BrCl_2N_4O_2$, 458.99. found 459.3.

PREPARATION x51: 2-chloro-5-((S)-1-(4-chlorophenyl)ethyl)-6a,7,9,10-tetrahydro-[1,4]oxazino[3,4-h]pteridin-6(5H)-one

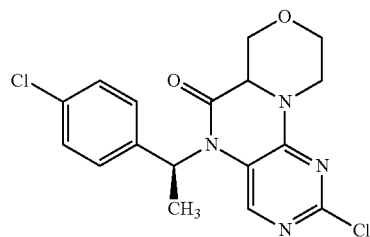 [SMILES: C[C@@H](c1ccc(Cl)cc1)N1C(=O)C2COCCN2c2nc(Cl)ncc21]

To a 20 mL microwave vial were added 9,9-dimethyl-4,5-bis(diphenylphosphino)xanthene (42.9 mg, 0.074 mmol), palladium (II)acetate (11.10 mg, 0.049 mmol), and potassium phosphate, tribasic (294 mg, 1.384 mmol). The vessel was evacuated and refilled with nitrogen. In a separate, nitrogen-filled flask was dissolved 4-(5-bromo-2-chloropyrimidin-4-yl)-N—((S)-1-(4-chlorophenyl)ethyl)morpholine-3-carboxamide (PREPARATION x50, 455 mg, 0.989 mmol) in dioxane (6 mL). The contents of the flask were transferred into the microwave vial via a syringe. Next, tert-Butanol (1.2 mL) was added to the microwave vial. The mixture was stirred for 15 minutes while bubbling nitrogen through it and was then heated in a microwave to 130° C. for 4 hours. The reaction was stopped even though HPLC showed it was about half done. The reaction mixture was then partitioned between brine and ethyl acetate. The aqueous layer was extracted with ethyl acetate and the combined organic layers were dried over MgSO$_4$, filtered, and concentrated. The dark brown crude product was purified by normal phase column chromatography (SiO$_2$, 60 g) eluting with a 20-75% EtOAc gradient in hexanes over a 20 minute period. The product-containing fractions were combined and concentrated to give a TFA salt of the title compound as a white solid (single diastereomer, 100 mg, 26.7%). Another spot with a higher R$_f$ appeared to be the other diastereomer, because of its nearly identical retention time and MW on the HPLC/MS. $^1$H NMR (400 MHz, DMSO-d$_6$) δ 1.78 (d, J=7.1 Hz, 3H), 2.88-3.04 (m, 1H), 3.58 (s, 1H), 3.70 (s, 1H), 3.90-4.00 (m, 1H), 4.21 (d, J=3.3 Hz, 2H), 4.47 (d, J=6.8 Hz, 1H), 6.02-6.11 (m, 1H), 7.31-7.37 (m, 6H), 7.40-7.45 (m, 7H), 7.54 (s, 3H). ESI-MS m/z [M+H]+ calc'd for $C_{17}H_{16}Cl_2N_4O_2$, 379.07. found 379.3.

PREPARATION x52: (S)-5-((S)-1-(4-chlorophenyl)ethyl)-2-(1H-indol-4-yl)-6a,7,9,10-tetrahydro-[1,4]oxazino[3,4-h]pteridin-6(5H)-one

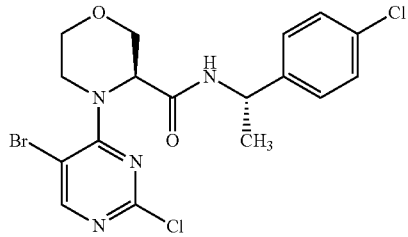

To a 50 mL round-bottom flask were added (S)-4-(5-bromo-2-chloropyrimidin-4-yl)morpholine-3-carboxylic acid (560 mg, 1.736 mmol), 1-hydroxybenzotriazole (235 mg, 1.736 mmol), and 1-ethyl-(3-dimethylaminopropyl)carbodiimide hydrochloride (399 mg, 2.083 mmol) in THF (10 mL) at 0° C. to give a beige solution. After 5 minutes, (S)-1-(4-chlorophenyl)ethylamine (0.268 mL, 1.910 mmol) was added to the solution, which was allowed to react at 0° C. for 2 hours. The reaction mixture was subsequently partitioned between brine and ethyl acetate. The aqueous layer was extracted with ethyl acetate and the combined organic layers were dried over MgSO$_4$, filtered, and concentrated. The residue was purified by normal phase column chromatography (20-50% EtOAc gradient in hexanes for 20 minutes) to give the title compound as a white foam (701 mg, 88%). ESI-MS m/z [M+H]$^+$ calc'd for $C_{17}H_{17}BrCl_2N_4O_2$, 458.99. found 459.3.

PREPARATION x53: 4-(5-bromo-2-(2-methyl-1H-imidazol-1-yl)pyrimidin-4-yl)morpholine-3-carboxylic acid

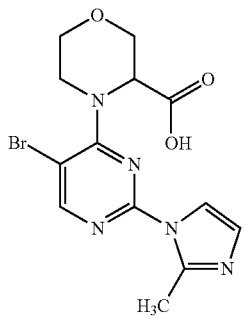 [SMILES: Cc1nccn1-c1ncc(Br)c(N2CCOCC2C(=O)O)n1]

A mixture of 4-(5-bromo-2-chloropyrimidin-4-yl)morpholine-3-carboxylic acid (PREPARATION x30, 1 g, 3.12 mmol), 2-methyl-1H-imidazole (0.54 g, 6.55 mmol) and Cs$_2$CO$_3$ (4 g, 12 mmol) in DMA (20 mL) was stirred at 120° C. for 2 days. Water was added and the mixture was concentrated, resulting in precipitation of solids. The solids were collected to give an HCl salt of the title compound as an off-white solid (0.47 g, 45%). $^1$H NMR (400 MHz, CD$_3$OD) δ 2.95 (s, 3H), 3.96-3.61 (m, 4H), 4.42-4.38 (m, 2H), 5.17-5.15 (m, 1H), 7.50 (d, J=2.0 Hz, 1H), 8.14 (d, J=2.0 Hz, 1H), 8.59 (s, 1H). ESI-MS m/z [M+H]$^+$ calc'd for $C_{13}H_{14}BrN_5O_3$, 368. found, 368.

PREPARATION x54: 4-(5-bromo-2-chloropyrimidin-4-yl)-N-(tetrahydro-2H-pyran-4-yl)morpholine-3-carboxamide

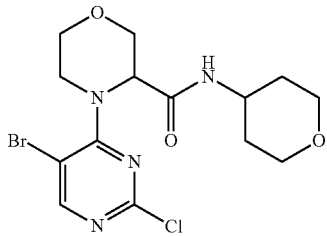 [SMILES: O=C(NC1CCOCC1)C1COCCN1c1nc(Cl)ncc1Br]

To a 200 mL round-bottom flask were added 4-(5-bromo-2-chloropyrimidin-4-yl)morpholine-3-carboxylic acid (PREPARATION x30, 2.5 g, 7.75 mmol) and 1-hydroxybenzotriazole (1.257 g, 9.30 mmol) in tetrahydrofuran (30 mL) to give a beige suspension. To this suspension were added 1-ethyl-(3-dimethylaminopropyl)carbodiimide hydrochloride (1.783 g, 9.30 mmol) and tetrahydro-2H-pyran-4-amine (0.802 mL, 7.75 mmol). After 1 hour at 0° C., HPLC showed the reaction was almost complete. The reaction mixture was subsequently partitioned between brine and ethyl acetate. The aqueous layer was extracted with ethyl acetate and the combined organic layers were dried over MgSO$_4$, filtered, and concentrated. The residue was purified by normal phase column chromatography (~50 g silica, 35-100% EtOAc gradient in hexanes) to give the title compound as a white foam (1.8 g, 57.2%).

PREPARATION x55: 2-chloro-5-(tetrahydro-2H-pyran-4-yl)-6a,7,9,10-tetrahydro-[1,4]oxazino[3,4-h]pteridin-6(5H)-one

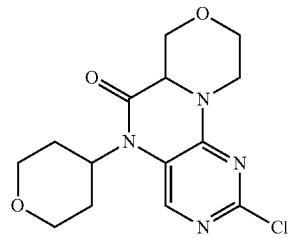 [SMILES: O=C1C2COCCN2c2nc(Cl)ncc2N1C1CCOCC1]

To a 5 mL microwave vial were added 4-(5-bromo-2-chloropyrimidin-4-yl)-N-(tetrahydro-2H-pyran-4-yl)morpholine-3-carboxamide (PREPARATION x54, 320 mg, 0.789 mmol), 9,9-dimethyl-4,5-bis(diphenylphosphino)xanthene (34.2 mg, 0.059 mmol), palladium(II)acetate (8.85 mg, 0.039 mmol), and potassium phosphate, tribasic (234 mg, 1.104 mmol). The vessel was sealed, evacuated, and refilled with nitrogen. To the vessel were added dioxane (2 mL) and tert-butanol (0.500 mL), and the mixture was heated in a microwave to 120° C. for 6 hours. The reaction mixture was subsequently partitioned between saturated brine and ethyl acetate. The aqueous layer was extracted with ethyl acetate and the combined organic layers were dried over MgSO4, filtered, and concentrated. The crude product was purified by normal phase column chromatography (SiO$_2$, 50-100% EtOAc gradient in hexanes over 20 minutes) to give the title compound (195 mg, 76%).

PREPARATION x56: (R)-methyl 4-bromo-2-((2-chloro-6a,7,9,10-tetrahydro-[1,4]oxazino[3,4-h]pteridin-5(6H)-yl)methyl)benzoate

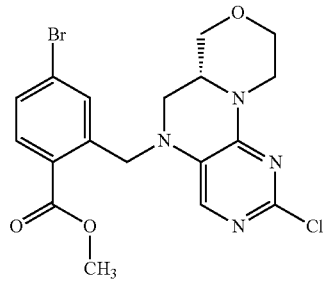 [SMILES: COC(=O)c1ccc(Br)cc1CN1C[C@@H]2COCCN2c2nc(Cl)ncc21]

(R)-2-chloro-5,6,6a,7,9,10-hexahydro-[1,4]oxazino[3,4-h]pteridine (200 mg, 0.882 mmol) (PREPARATION x2, 200 mg, 0.882 mmol) was dissolved in DMSO (5 mL). Sodium tert-butoxide (102 mg, 1.059 mmol) was then added to give a brown solution. After 5 minutes, methyl 4-bromo-2-(bromomethyl)benzoate (299 mg, 0.971 mmol) was added dropwise. The reaction was stirred overnight at room temperature, then quenched with aqueous saturated $NH_4Cl$. The reaction mixture was diluted with ethyl acetate and washed with aqueous saturated $NH_4Cl$ (3×25 mL). The combined organic layers were dried over $MgSO_4$, filtered, and concentrated in vacuo. The crude product was loaded onto an ISCO® silica gel cartridge (12 g) and eluted using an ethyl acetate/hexane gradient. The product was collected and concentrated in vacuo to afford the title compound as a white foam (164 mg, 41%). ESI-MS m/z $[M+H]^+$ calc'd for $C_{18}H_{18}BrClN_4O_3$, 453.04. found 453.2.

PREPARATION x57: (R)-methyl 2-((2-chloro-6a,7,9,10-tetrahydro-[1,4]oxazino[3,4-h]pteridin-5(6H)-yl)methyl)-4-methylbenzoate

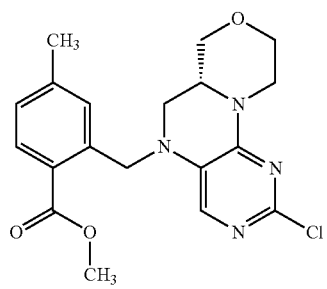 [SMILES: COC(=O)c1ccc(C)cc1CN1C[C@@H]2COCCN2c2nc(Cl)ncc21]

(R)-methyl 4-bromo-2-((2-chloro-6a,7,9,10-tetrahydro-[1,4]oxazino[3,4-h]pteridin-5(6H)-yl)methyl)benzoate (PREPARATION x56, 164 mg, 0.361 mmol), $K_2CO_3$ (100 mg, 0.723 mmol), $PdCl_2$(dppf) (13.22 mg, 0.018 mmol) and 2,4,6-trimethyl-1,3,5,2,4,6-trioxatriborinane (0.060 mL, 0.434 mmol) were dissolved in dioxane (2 mL) and water (0.4 mL) to give an orange suspension. The reaction mixture was heated to 100° C. and allowed to stir overnight, then quenched with aqueous saturated $NH_4Cl$. The reaction mixture was diluted with ethyl acetate and washed with aqueous saturated $NH_4Cl$ (3×15 mL). The combined organic layers were dried over $MgSO_4$, filtered, and concentrated in vacuo. The crude product was then loaded onto an ISCO® silica gel cartridge (12 g) and eluted using an ethyl acetate/hexane gradient. The product was collected and concentrated in vacuo to afford the title compound as a white foam (102 mg, 73%). ESI-MS m/z $[M+H]^+$ calc'd for $C_{19}H_{21}ClN_4O_3$, 389.14. found 389.2.

PREPARATION x58: (R)-4-(2-chloro-6a,7,9,10-tetrahydro-[1,4]oxazino[3,4-h]pteridin-5(6H)-yl)-2-methylbutan-2-ol

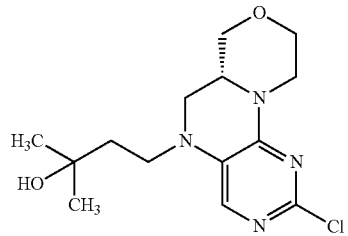 [SMILES: CC(C)(O)CCN1C[C@@H]2COCCN2c2nc(Cl)ncc21]

The title compound was prepared in a manner similar to PREPARATION x5 using (R)-2-chloro-5,6,6a,7,9,10-hexahydro-[1,4]oxazino[3,4-h]pteridine (PREPARATION x2, 300 mg, 1.324 mmol) in DMSO (7 mL), sodium tert-butoxide (153 mg, 1.588 mmol) and 4-bromo-2-methylbutan-2-ol (243 mg, 1.456 mmol) (306 mg, 74%). ESI-MS m/z $[M+H]^+$ calc'd for $C_{14}H_{21}ClN_4O_2$, 313.14. found 313.2.

PREPARATION x59: (R)-2-(2-chloro-6a,7,9,10-tetrahydro-[1,4]oxazino[3,4-h]pteridin-5(6H)-yl)ethanol

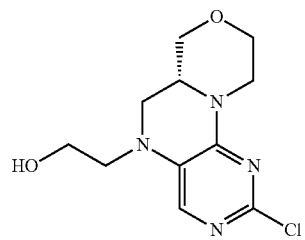 [SMILES: OCCN1C[C@@H]2COCCN2c2nc(Cl)ncc21]

The title compound was prepared in a manner similar to PREPARATION x5 using (R)-2-chloro-5,6,6a,7,9,10-hexahydro-[1,4]oxazino[3,4-h]pteridine (PREPARATION x2, 100 mg, 0.441 mmol) in DMSO (7 mL), sodium tert-butoxide (51 mg, 0.529 mmol) and bromoethyl acetate (81 mg, 0.485 mmol) (79 mg, 66%). ESI-MS m/z $[M+H]^+$ calc'd for $C_{11}H_{15}ClN_4O_2$, 271.09. found 271.1.

PREPARATION x60: (R)-2-chloro-5-((1-methyl-1H-pyrazol-4-yl)methyl)-5,6,6a,7,9,10-hexahydro-[1,4]oxazino[3,4-h]pteridine

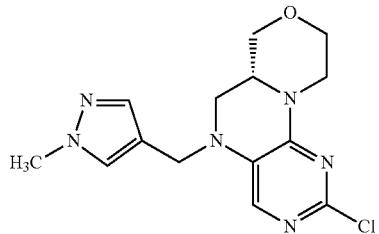 [SMILES: Cn1cc(CN2C[C@@H]3COCCN3c3nc(Cl)ncc32)cn1]

The title compound was prepared in a manner similar to PREPARATION x5 using (R)-2-chloro-5,6,6a,7,9,10-hexahydro-[1,4]oxazino[3,4-h]pteridine (PREPARATION x2, 300 mg, 1.324 mmol) in DMSO (6 mL), sodium tert-butoxide (153 mg, 1.588 mmol) and 4-(chloromethyl)-1-methyl-1H-pyrazole (190 mg, 1.456 mmol) (113 mg, 26%). ESI-MS m/z [M+H]$^+$ calc'd for $C_{41}H_{17}ClN_6O$, 321.12. found 321.2.

PREPARATION x61: (R)-2-chloro-5-(oxazol-5-ylmethyl)-5,6,6a,7,9,10-hexahydro-[1,4]oxazino[3,4-h]pteridine

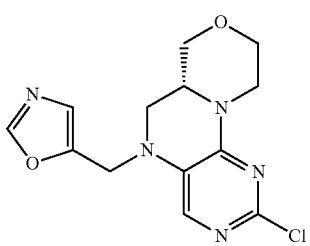 [SMILES: Clc1ncc2c(n1)N1CCOC[C@H]1CN2Cc1cnco1]

The title compound was prepared in a manner similar to PREPARATION x5 using (R)-2-chloro-5,6,6a,7,9,10-hexahydro-[1,4]oxazino[3,4-h]pteridine (PREPARATION x2, 351 mg, 1.547 mmol) in DMSO (10 mL), sodium tert-butoxide (178 mg, 1.856 mmol) and 5-(chloromethyl)oxazole (200 mg, 1.702 mmol) (171 mg, 36%). ESI-MS m/z [M+H]$^+$ calc'd for $C_{13}H_{14}ClN_5O_2$, 308.09. found 308.1.

PREPARATION x62: (R)-2-chloro-5-((3-ethylisoxazol-5-yl)methyl)-5,6,6a,7,9,10-hexahydro-[1,4]oxazino[3,4-h]pteridine

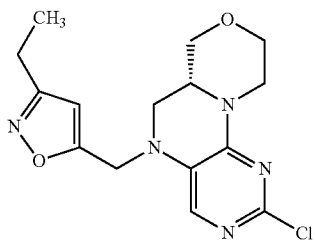 [SMILES: CCc1cc(CN2C[C@@H]3COCCN3c3nc(Cl)ncc32)on1]

The title compound was prepared in a manner similar to PREPARATION x5 using (R)-2-chloro-5,6,6a,7,9,10-hexahydro-[1,4]oxazino[3,4-h]pteridine (PREPARATION x2, 100 mg, 0.441 mmol) in DMSO (5 mL), sodium tert-butoxide (50.9 mg, 0.529 mmol) and 5-(chloromethyl)-3-ethylisoxazole (70.7 mg, 0.485 mmol) (120 mg, 81%). ESI-MS m/z [M+H]$^+$ calc'd for $C_{15}H_{18}ClN_5O_2$, 336.12. found 336.3.

PREPARATION x63: (R)-4-(2-chloro-6a,7,9,10-tetrahydro-[1,4]oxazino[3,4-h]pteridin-5(6H)-yl)cyclohexanol

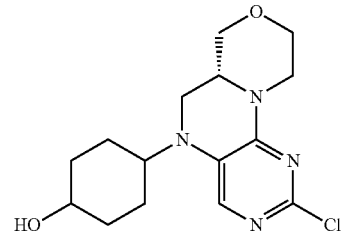 [SMILES: OC1CCC(N2C[C@@H]3COCCN3c3nc(Cl)ncc32)CC1]

To (R)-2-chloro-5,6,6a,7,9,10-hexahydro-[1,4]oxazino[3,4-h]pteridine (PREPARATION x2, 250 mg, 1.103 mmol) and 4-hydroxycyclohexanone (126 mg, 1.103 mmol) in $CH_2Cl_2$ (8 mL) was added titanium(IV) chloride in $CH_2Cl_2$ (1M, 2.427 mL, 2.427 mmol) dropwise to give an orange suspension. The reaction mixture was stirred at ambient temperature for 4 hours and then cooled to 0° C. Sodium triacetoxyhydroborate (514 mg, 2.427 mmol) was added in two portions. The reaction mixture was stirred for 1 hour and then quenched with aqueous saturated $NH_4Cl$ (1 mL). The reaction mixture was diluted with ethyl acetate and washed with aqueous saturated $NH_4Cl$ (3×10 mL). The combined organic layers were dried over $MgSO_4$, filtered, and concentrated in vacuo. The crude product was then loaded onto an ISCO® silica gel cartridge (12 g) and eluted using an ethyl acetate/hexane gradient. The product was collected and concentrated in vacuo to afford the title compound as a colorless foam (30 mg, 8%). ESI-MS m/z [M+H]$^+$ calc'd for $C_{15}H_{21}ClN_4O_2$, 325.14. found 325.2.

PREPARATION x64: (R)-2-chloro-5-(tetrahydro-2H-pyran-4-yl)-5,6,6a,7,9,10-hexahydro-[1,4]oxazino[3,4-h]pteridine

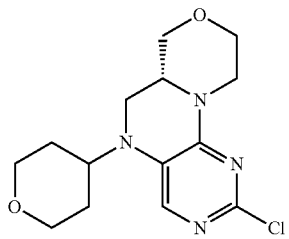 [SMILES: Clc1ncc2c(n1)N1CCOC[C@H]1CN2C1CCOCC1]

The title compound was prepared in a manner similar to PREPARATION x63 using (R)-2-chloro-5,6,6a,7,9,10-hexahydro-[1,4]oxazino[3,4-h]pteridine (PREPARATION x2, 250 mg, 1.103 mmol), dihydro-2H-pyran-4-(3H)-one (110 mg, 1.103 mmol), titanium(IV) chloride in $CH_2Cl_2$ (1M, 2.427 mL, 2.427 mmol) and sodium triacetoxyhydroborate (514 mg, 2.427 mmol) in $CH_2Cl_2$ (8 mL) (10 mg, 3%). ESI-MS m/z [M+H]$^+$ calc'd for $C_{14}H_{19}ClN_4O_2$, 311.13. found 311.2.

PREPARATION x65: (R)-tert-butyl 4-(2-(1H-indol-4-yl)-6a,7,9,10-tetrahydro-[1,4]oxazino[3,4-h]pteridin-5(6H)-yl)-1H-indole-1-carboxylate

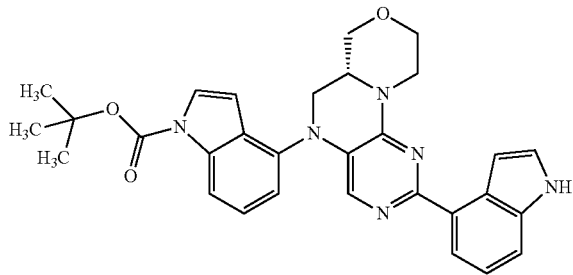 [SMILES: CC(C)(C)OC(=O)n1ccc2c(N3C[C@@H]4COCCN4c4nc(-c5cccc6[nH]ccc56)ncc43)cccc21]

The title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 60 mg, 0.142 mmol), cesium carbonate (93 mg, 0.285 mmol), palladium(II)acetate (1.59 mg, 0.007 mmol), dicyclohexyl(2',4',6'-triisopropylbiphenyl-2-yl)phosphine (10.2 mg, 0.021 mmol), and tert-butyl 4-bromo-1H-indole-1-carboxylate (126 mg, 0.427 mmol) in dioxane 2 mL (8 mg, 12%). ESI-MS m/z [M+H]$^+$ calc'd for $C_{30}H_{30}N_6O_3$, 523.24. found 523.3.

PREPARATION x66: (R)-5-(2-(1,3-dioxolan-2-yl)ethyl)-2-chloro-5,6,6a,7,9,10-hexahydro-[1,4]oxazino[3,4-h]pteridine

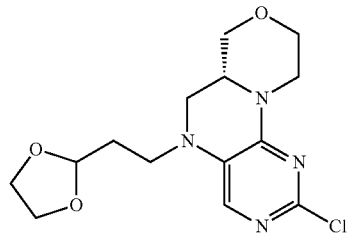 [SMILES: Clc1ncc2c(n1)N1CCOC[C@H]1CN2CCC1OCCO1]

The title compound was prepared in a manner similar to PREPARATION x5 using (R)-2-chloro-5,6,6a,7,9,10-hexahydro-[1,4]oxazino[3,4-h]pteridine (PREPARATION x2, 250 mg, 1.103 mmol) in DMSO (7 mL), sodium tert-butoxide (127 mg, 1.324 mmol), and 2-(2-bromoethyl)-1,3-dioxolane (220 mg, 1.213 mmol) (200 mg, 56%). ESI-MS m/z [M+H]$^+$ calc'd for $C_{14}H_{19}ClN_4O_3$, 327.12. found 327.2.

PREPARATION x67: (R)-methyl 4-(2-chloro-6a,7,9,10-tetrahydro-[1,4]oxazino[3,4-h]pteridin-5(6H)-yl)butanoate

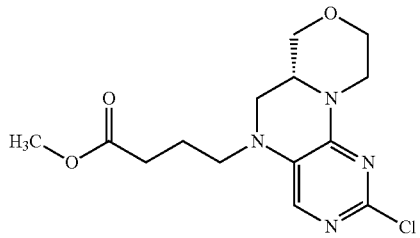 [SMILES: COC(=O)CCCN1C[C@@H]2COCCN2c2nc(Cl)ncc21]

The title compound was prepared in a manner similar to PREPARATION x63 using (R)-2-chloro-5,6,6a,7,9,10-hexahydro-[1,4]oxazino[3,4-h]pteridine (PREPARATION x2, 250 mg, 1.103 mmol), methyl 4-oxobutanoate (128 mg, 1.103 mmol), titanium(IV) chloride in $CH_2Cl_2$ (1M, 1.654 mL, 1.654 mmol) and sodium triacetoxyhydroborate (514 mg, 2.427 mmol) in $CH_2Cl_2$ (8 mL) (164 mg, 46%). ESI-MS m/z [M+H]$^+$ calc'd for $C_{14}H_{19}ClN_4O_3$, 327.12. found 327.2.

PREPARATION x68: benzyl ((1R,4r)-4-(4R)-2-chloro-6a,7,9,10-tetrahydro-[1,4]oxazino[3,4-h]pteridin-5(6H)-yl)methyl)cyclohexyl)carbamate

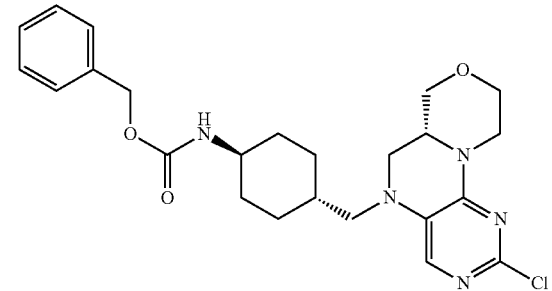 [SMILES: O=C(N[C@H]1CC[C@H](CN2C[C@@H]3COCCN3c3nc(Cl)ncc32)CC1)OCc1ccccc1]

The title compound was prepared in a manner similar to PREPARATION x63 using (R)-2-chloro-5,6,6a,7,9,10-hexahydro-[1,4]oxazino[3,4-h]pteridine (PREPARATION x2, 250 mg, 1.103 mmol), benzyl (1r,4r)-4-formylcyclohexylcarbamate (288 mg, 1.103 mmol), titanium(IV) chloride in $CH_2Cl_2$ (1M, 1.654 mL, 1.654 mmol) and sodium triacetoxyhydroborate (514 mg, 2.427 mmol) in $CH_2Cl_2$ (8 mL) (320 mg, 62%). ESI-MS m/z [M+H]$^+$ calc'd for $C_{24}H_{30}ClN_5O_3$, 472.21. found 472.4.

PREPARATION x69: benzyl ((1R,4r)-4-(4R)-2-(1H-indol-4-yl)-6a,7,9,10-tetrahydro-[1,4]oxazino[3,4-h]pteridin-5(6H)-yl)methyl)cyclohexyl)carbamate

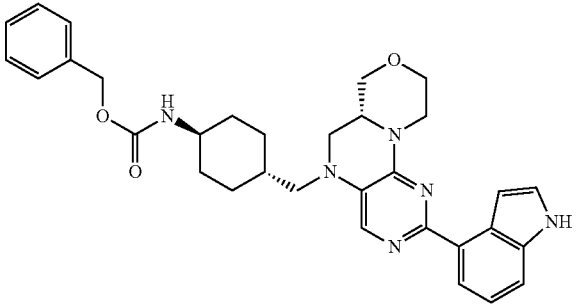 [SMILES: O=C(N[C@H]1CC[C@H](CN2C[C@@H]3COCCN3c3nc(-c4cccc5[nH]ccc45)ncc32)CC1)OCc1ccccc1]

The title compound was prepared in a manner similar to Example 2 using benzyl (1R,4r)-4-(((R)-2-chloro-6a,7,9,10-tetrahydro-[1,4]oxazino[3,4-h]pteridin-5(6H)-yl)methyl)cyclohexyl)carbamate (PREPARATION x68, 320 mg, 0.678 mmol), 1H-indol-4-ylboronic acid (218 mg, 1.356 mmol) and $PdCl_2$(dppf) (24.8 mg, 0.034 mmol) in dioxane (5 mL) and aqueous saturated $NaHCO_3$ (1 mL) (291 mg, 78%). ESI-MS m/z [M+H]$^+$ calc'd for $C_{32}H_{36}N_6O_3$, 553.29. found 553.5.

PREPARATION x70: (R)-2-(2-chloro-6a,7,9,10-tetrahydro-[1,4]oxazino[3,4-h]pteridin-5(6H)-yl)-N-(pyridin-4-yl)acetamide

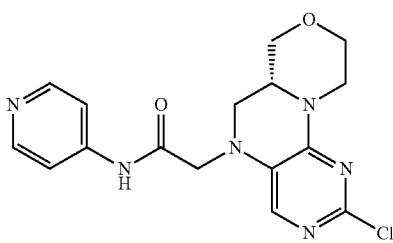 [SMILES: O=C(CN1C[C@@H]2COCCN2c2nc(Cl)ncc21)Nc1ccncc1]

The title compound was prepared in a manner similar to PREPARATION x26 using (R)-2-(2-chloro-6a,7,9,10-tetrahydro-[1,4]oxazino[3,4-h]pteridin-5(6H)-yl)acetic acid (PREPARATION x25, 50 mg, 0.176 mmol), HATU (87 mg, 0.228 mmol), 4-aminopyridine (25 mg, 0.263 mmol) and triethylamine (0.073 mL, 0.527 mmol) in DMF (2 mL). ESI-MS m/z [M+H]$^+$ calc'd for $C_{16}H_{17}ClN_6O_2$, 361.12. found 361.2.

PREPARATION x71: (R)-2-(2-chloro-6a,7,9,10-tetrahydro-[1,4]oxazino[3,4-h]pteridin-5(6H)-yl)-N-(2-methoxyethyl)acetamide

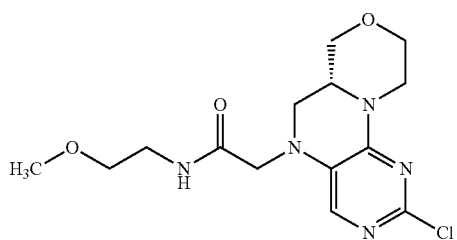 [SMILES: COCCNC(=O)CN1C[C@@H]2COCCN2c2nc(Cl)ncc21]

The title compound was prepared in a manner similar to PREPARATION x26 using (R)-2-(2-chloro-6a,7,9,10-tetrahydro-[1,4]oxazino[3,4-h]pteridin-5(6H)-yl)acetic acid (PREPARATION x25, 50 mg, 0.176 mmol), HATU (87 mg, 0.228 mmol), 2-methoxyethylamine (20 mg, 0.263 mmol) and triethylamine (0.073 mL, 0.527 mmol) in DMF (2 mL). ESI-MS m/z [M+H]$^+$ calc'd for $C_{14}H_{20}ClN_6O_3$, 342.13. found 342.2.

PREPARATION x72: (R)-2-(2-chloro-6a,7,9,10-tetrahydro-[1,4]oxazino[3,4-h]pteridin-5(6H)-yl)-N-(tetrahydro-2H-pyran-4-yl)acetamide

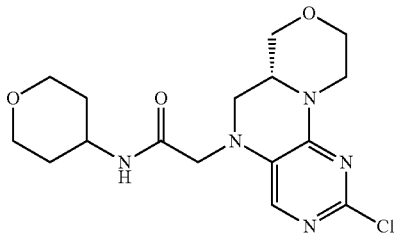 [SMILES: O=C(CN1C[C@@H]2COCCN2c2nc(Cl)ncc21)NC1CCOCC1]

The title compound was prepared in a manner similar to PREPARATION x26 using (R)-2-(2-chloro-6a,7,9,10-tetrahydro-[1,4]oxazino[3,4-h]pteridin-5(6H)-yl)acetic acid (PREPARATION x25, 50 mg, 0.176 mmol), HATU (87 mg, 0.228 mmol), 4-aminotetrahydrofuran (27 mg, 0.263 mmol) and triethylamine (0.073 mL, 0.527 mmol) in DMF (2 mL). ESI-MS m/z [M+H]$^+$ calc'd for $C_{16}H_{22}ClN_5O_3$, 368.15. found 368.3.

PREPARATION x73: (R)-2-(2-chloro-6a,7,9,10-tetrahydro-[1,4]oxazino[3,4-h]pteridin-5(6H)-yl)-N-(1-methyl-1H-pyrazol-4-yl)acetamide

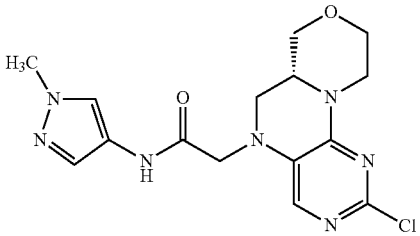 [SMILES: Cn1cc(NC(=O)CN2C[C@@H]3COCCN3c3nc(Cl)ncc32)cn1]

The title compound was prepared in a manner similar to PREPARATION x26 using (R)-2-(2-chloro-6a,7,9,10-tetrahydro-[1,4]oxazino[3,4-h]pteridin-5(6H)-yl)acetic acid (PREPARATION x25, 50 mg, 0.176 mmol), HATU (87 mg, 0.228 mmol), 1-methyl-1H-pyrazol-4-amine (26 mg, 0.263 mmol) and triethylamine (0.073 mL, 0.527 mmol) in DMF (2 mL). ESI-MS m/z [M+H]$^+$ calc'd for $C_{15}H_{18}ClN_7O_2$, 364.13. found 364.2.

PREPARATION x74: (R)-2-(2-chloro-6a,7,9,10-tetrahydro-[1,4]oxazino[3,4-h]pteridin-5(6H)-yl)-N-cyclopropylacetamide

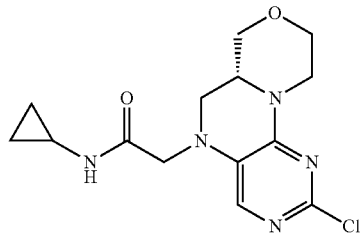 [SMILES: O=C(CN1C[C@@H]2COCCN2c2nc(Cl)ncc21)NC1CC1]

The title compound was prepared in a manner similar to PREPARATION x26 using (R)-2-(2-chloro-6a,7,9,10-tetrahydro-[1,4]oxazino[3,4-h]pteridin-5(6H)-yl)acetic acid (PREPARATION x25, 50 mg, 0.176 mmol), HATU (87 mg, 0.228 mmol), cyclopropylamine (15 mg, 0.263 mmol) and triethylamine (0.073 mL, 0.527 mmol) in DMF (2 mL). ESI-MS m/z [M+H]$^+$ calc'd for $C_{14}H_{18}ClN_5O_2$, 324.12. found 324.2.

PREPARATION x75: (R)-2-(2-chloro-6a,7,9,10-tetrahydro-[1,4]oxazino[3,4-h]pteridin-5(6H)-yl)-N-(2-cyanopropan-2-yl)acetamide

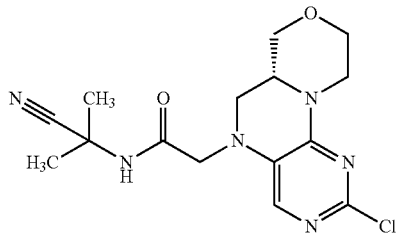 [SMILES: CC(C)(C#N)NC(=O)CN1C[C@@H]2COCCN2c2nc(Cl)ncc21]

The title compound was prepared in a manner similar to PREPARATION x26 using (R)-2-(2-chloro-6a,7,9,10-tetrahydro-[1,4]oxazino[3,4-h]pteridin-5(6H)-yl)acetic acid (PREPARATION x25, 50 mg, 0.176 mmol), HATU (87 mg, 0.228 mmol), 2-amino-2-methylpropionitrile (22 mg, 0.263 mmol) and triethylamine (0.073 mL, 0.527 mmol) in DMF (2 mL). ESI-MS m/z [M+H]$^+$ calc'd for $C_{15}H_{19}ClN_6O_2$, 351.13. found 351.2.

PREPARATION x76: 2-((R)-2-chloro-6a,7,9,10-tetrahydro-[1,4]oxazino[3,4-h]pteridin-5(6H)-yl)-N-(tetrahydrofuran-3-yl)acetamide

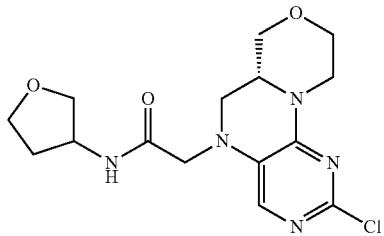 [SMILES: O=C(CN1C[C@@H]2COCCN2c2nc(Cl)ncc21)NC1CCOC1]

The title compound was prepared in a manner similar to PREPARATION x26 using (R)-2-(2-chloro-6a,7,9,10-tetrahydro-[1,4]oxazino[3,4-h]pteridin-5(6H)-yl)acetic acid (PREPARATION x25, 50 mg, 0.176 mmol), HATU (87 mg, 0.228 mmol), tetrahydro-furan-3-ylamine (23 mg, 0.263 mmol) and triethylamine (0.073 mL, 0.527 mmol) in DMF (2 mL). ESI-MS m/z [M+H]$^+$ calc'd for $C_{15}H_{20}ClN_6O_3$, 354.13. found 354.2.

PREPARATION x77: tert-butyl (1-((R)-2-chloro-6a,7,9,10-tetrahydro-[1,4]oxazino[3,4-h]pteridin-5(6H)-yl)-4,4-dimethylpentan-3-yl)carbamate

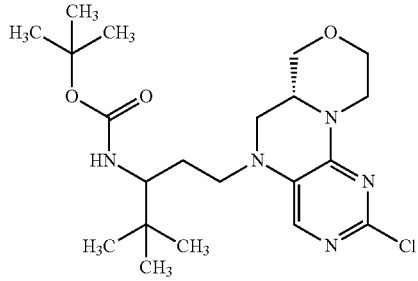 [SMILES: CC(C)(C)OC(=O)NC(CCN1C[C@@H]2COCCN2c2nc(Cl)ncc21)C(C)(C)C]

The title compound was prepared in a manner similar to PREPARATION x63 using (R)-2-chloro-5,6,6a,7,9,10-hexahydro-[1,4]oxazino[3,4-h]pteridine (PREPARATION x2, 115 mg, 0.507 mmol), tert-butyl 4,4-dimethyl-1-oxopentan-3-ylcarbamate (116 mg, 0.507 mmol), titanium(IV) chloride in $CH_2Cl_2$ (1M, 0.761 mL, 0.761 mmol) and sodium triacetoxyhydroborate (237 mg, 1.116 mmol) in $CH_2Cl_2$ (5 mL) (53 mg, 24%). ESI-MS m/z [M+H]$^+$ calc'd for $C_{21}H_{34}ClN_5O_3$, 440.24. found 440.4.

PREPARATION x78: tert-butyl (1-((R)-2-(1H-indol-4-yl)-6a,7,9,10-tetrahydro-[1,4]oxazino[3,4-h]pteridin-5(6H)-yl)-4,4-dimethylpentan-3-yl)carbamate

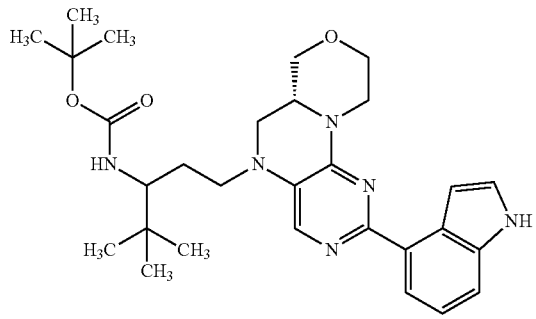 [SMILES: CC(C)(C)OC(=O)NC(CCN1C[C@@H]2COCCN2c2nc(-c3cccc4[nH]ccc34)ncc21)C(C)(C)C]

The title compound was prepared in a manner similar to Example 2 using tert-butyl (1-((R)-2-chloro-6a,7,9,10-tetrahydro-[1,4]oxazino[3,4-h]pteridin-5(6H)-yl)-4,4-dimethylpentan-3-yl)carbamate (PREPARATION x77, 53 mg, 0.120 mmol), 1H-indol-4-ylboronic acid (38.8 mg, 0.241 mmol) and $PdCl_2(dppf)$ (4.41 mg, 0.006 mmol) in dioxane (2 mL) and aqueous saturated $NaHCO_3$ (0.4 mL) (19 mg, 30%). ESI-MS m/z [M+H]$^+$ calc'd for $C_{29}H_{40}N_6O_3$, 521.32. found 521.5.

PREPARATION x79: (R)-2-(2-chloro-6a,7,9,10-tetrahydro-[1,4]oxazino[3,4-h]pteridin-5(6H)-yl)-N-methyl-N-((tetrahydro-2H-pyran-4-yl)methyl)acetamide

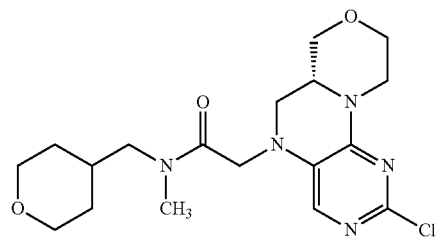 [SMILES: CN(CC1CCOCC1)C(=O)CN1C[C@@H]2COCCN2c2nc(Cl)ncc21]

Sodium hydride (60% in oil) (12.57 mg, 0.314 mmol) was added to a suspension of (R)-2-(2-chloro-6a,7,9,10-tetrahydro-[1,4]oxazino[3,4-h]pteridin-5(6H)-yl)-N-((tetrahydro-2H-pyran-4-yl)methyl)acetamide (PREPARATION x26, 100 mg, 0.262 mmol) in DMF (1 mL) at 0° C. The resultant mixture was stirred at room temperature for 30 minutes. Methyl iodide (0.021 mL, 0.340 mmol) was added to the reaction mixture at room temperature, and the resultant mixture was stirred at room temperature for 15 minutes. After addition of EtOAc, the resultant mixture was washed with water and brine, dried over $Na_2SO_4$, filtered and concentrated in vacuo. The residue was washed with EtOAc to afford the title compound as a white solid (73 mg, 70.4%). $^1$H NMR (400 MHz, DMSO-d$_6$) δ ppm 1.04-1.38 (m, 2H), 1.48 (d, J=11.12 Hz, 2H), 1.75-1.99 (m, 1H), 2.80-3.01 (m, 4H), 3.09-3.31 (m, 7H), 3.40-3.64 (m, 2H), 3.79-4.06 (m, 5H), 4.17-4.27 (m, 1H), 4.34-4.44 (m, 1H), 7.12-7.29 (m, 1H); ESI-MS m/z [M+H]$^+$ calc'd for $C_{18}H_{26}ClN_5O_3$, 396.18. found 396.3.

PREPARATION x80: (S)-tert-butyl 2-(2-chloro-6a,7,9,10-tetrahydro-[1,4]oxazino[3,4-h]pteridin-5(6H)-yl)acetate

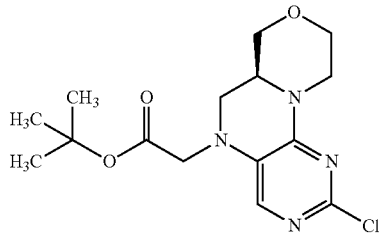 [SMILES: CC(C)(C)OC(=O)CN1C[C@H]2COCCN2c2nc(Cl)ncc21]

Potassium tert-butoxide in tert-BuOH (1M, 2.65 mL, 2.65 mmol) was added to a solution of (S)-2-chloro-5,6,6a,7,9,10-hexahydro-[1,4]oxazino[3,4-h]pteridine (PREPARATION x4, 500 mg, 2.206 mmol) in DMF (5 mL) at 0° C. The resultant mixture was stirred at room temperature for 30 minutes. tert-Butyl 2-bromoacetate (0.421 mL, 2.87 mmol) was added to the reaction mixture at 0° C. The resultant mixture was stirred at room temperature for 1 hour. After addition of water, the resultant mixture was extracted with EtOAc. The extract was washed with brine, dried over $Na_2SO_4$, filtered, and concentrated in vacuo. The residue was purified via flash column chromatography (gradient 20-80% EtOAc/hexane) to afford the title compound as an off-white solid (415 mg, 55.2%). $^1H$ NMR (400 MHz, $CDCl_3$) δ ppm 1.46 (s, 9H), 3.00-3.10 (m, 1H), 3.15-3.28 (m, 2H), 3.37 (dd, J=11.37, 8.84 Hz, 1H), 3.52-3.62 (m, 1H), 3.64-3.75 (m, 2H), 3.86-4.06 (m, 3H), 4.52 (dd, J=13.77, 1.89 Hz, 1H), 7.22 (s, 1H); ESI-MS m/z $[M+H]^+$ calc'd for $C_{15}H_{21}ClN_4O_3$, 341.14. found 341.2.

PREPARATION x81: (R)-5-(2-chloro-6a,7,9,10-tetrahydro-[1,4]oxazino[3,4-h]pteridin-5(6H)-yl)-2-methylpentan-2-yl acetate

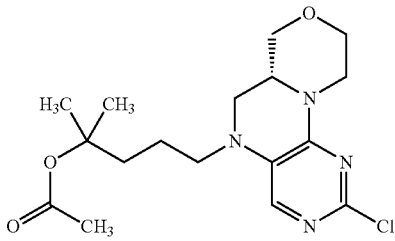 [SMILES: CC(=O)OC(C)(C)CCCN1C[C@@H]2COCCN2c2nc(Cl)ncc21]

(R)-2-Chloro-5,6,6a,7,9,10-hexahydro-[1,4]oxazino[3,4-h]pteridine (PREPARATION x3, 200 mg, 0.882 mmol) and 2-methyl-5-oxopentan-2-yl acetate (55.8 mg, 0.353 mmol) were combined in a 25 mL pear flask to give an orange suspension. Titanium(IV) chloride in DCM (1M, 0.971 mL, 0.971 mmol) was added at room temperature to give a deep-red suspension, which was stirred at room temperature for 1 hour before being cooled to 0° C. Sodium triacetoxyborohydride (281 mg, 1.324 mmol) was added at 0° C. in portions. The thick suspension slowly turned into a thinner, orange one with gas evolution. UPLC showed the reaction proceeded more than half-way after about 20 minutes. The reaction mixture was carefully quenched with brine, and was partitioned between saturated $NaHCO_3$ and ethyl acetate. The aqueous layer was extracted a second time with ethyl acetate. The combined organic layers were dried over $MgSO_4$, filtered, and concentrated to give the title compound, which was used without further purification. ESI-MS m/z $[M+H]^+$ calc'd for $C_{17}H_{25}ClN_4O_3$, 369.17. found 396.2.

PREPARATION x82: (R)-5-(2-(1H-indol-4-yl)-6a,7,9,10-tetrahydro-[1,4]oxazino[3,4-h]pteridin-5(6H)-yl)-2-methylpentan-2-yl acetate

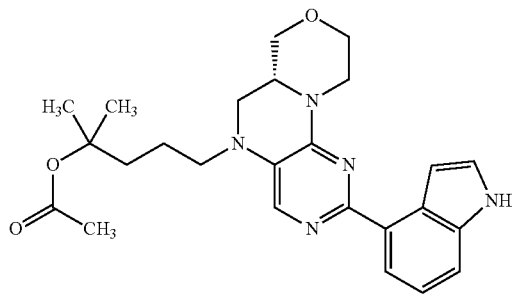 [SMILES: CC(=O)OC(C)(C)CCCN1C[C@@H]2COCCN2c2nc(-c3cccc4[nH]ccc34)ncc21]

To a 2 mL microwave vial were added (R)-5-(2-chloro-6a,7,9,10-tetrahydro-[1,4]oxazino[3,4-h]pteridin-5(6H)-yl)-2-methylpentan-2-yl acetate (PREPARATION x81, 148 mg, 0.401 mmol), indole-4-boronic acid (64.6 mg, 0.401 mmol) and [1,1'-bis(diphenylphosphino)ferrocene]-dichloropalladium(II) (16.50 mg, 0.020 mmol). The vial was evacuated and filled with nitrogen. After sealing the vial, dioxane (1600 µL) and saturated $NaHCO_3$ (400 µL) were added. The mixture was then heated in a microwave to 120° C. for 45 minutes. After the mixture was cooled to room temperature, ACN (4 mL) was added and the mixture was filtered by syringe filter. The crude product was purified by preparatory HPLC using a gradient of 20-40% $CH_3CN$ (with 0.035% TFA) in $H_2O$ (with 0.05% TFA). The collected fractions were pooled, neutralized with $NaHCO_3$, concentrated, and extracted with EtOAc. The combined organics were dried over $MgSO_4$, filtered, and concentrated to give the title compound (48 mg, 27%). ESI-MS m/z $[M+H]^+$ calc'd for $C_{25}H_{31}N_5O_3$, 450.25. found 450.3.

PREPARATION x83: 2-((2-chloro-6a,7,9,10-tetrahydro-[1,4]oxazino[3,4-h]pteridin-5(6H)-yl)methyl)-4-methylbenzonitrile

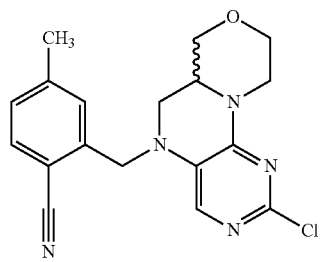 [SMILES: Cc1ccc(C#N)c(CN2CC3COCCN3c3nc(Cl)ncc32)c1]

STEP A: 4-bromo-2-((2-chloro-6a,7,9,10-tetrahydro-[1,4]oxazino[3,4-h]pteridin-5(6H)-yl)methyl)benzonitrile

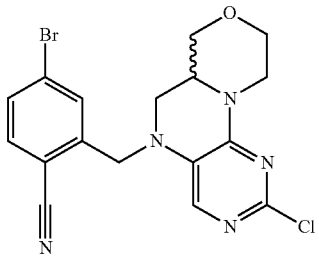 [SMILES: N#Cc1ccc(Br)cc1CN1CC2COCCN2c2nc(Cl)ncc21]

To a 10 mL vial charged with 2-chloro-5,6,6a,7,9,10-hexahydro-[1,4]oxazino[3,4-h]pteridine (PREPARATION x2, 100 mg, 0.441 mmol) in DMSO (2.5 mL) was added sodium tert-butoxide (50.9 mg, 0.529 mmol). The resulting orange solution was stirred for 5 minutes, after which 5-bromo-2-(bromomethyl)benzonitrile (133 mg, 0.485 mmol) was added. The reaction mixture was stirred overnight at room temperature, then diluted with EtOAc, and washed with saturated aq NH$_4$Cl (3×). The combined organic layers were dried over MgSO$_4$, filtered, and concentrated. The product was purified by flash chromatography (SiO$_2$, 12 g column, 2:8 EtOAc/Hexane to 100% EtOAc gradient) to give the title compound as a brown foam (105 mg, 57%). $^1$H NMR (400 MHz, DMSO-d$_6$) δ ppm 2.93-3.09 (m, 2H), 3.15 (s, 3H), 3.32 (s, 4H), 3.40-3.53 (m, 3H), 3.62-3.76 (m, 3H), 3.81-3.91 (m, 3H), 3.91-4.07 (m, 5H), 4.22-4.32 (m, 3H), 4.43-4.67 (m, 6H), 7.34 (s, 3H), 7.46 (d, J=8.34 Hz, 3H), 7.87 (dd, J=8.34, 2.02 Hz, 3H), 8.18 (d, J=2.02 Hz, 3H); ESI-MS m/z [M+H]$^+$ calc'd for C$_{17}$H$_{15}$BrClN$_5$O, 420.0. found 420.1.

STEP B: 2-((2-chloro-6a,7,9,10-tetrahydro-[1,4]oxazino[3,4-h]pteridin-5(6H)-yl)methyl)-4-methylbenzonitrile To a 20 mL vial were added 4-bromo-2-((2-chloro-6a,7,9,10-tetrahydro-[1,4]oxazino[3,4-h]pteridin-5(6H)-yl)methyl)benzonitrile (105 mg, 0.250 mmol), potassium carbonate (69.0 mg, 0.499 mmol), PdCl$_2$(dppf) (18.26 mg, 0.025 mmol), and 2,4,6-trimethyl-1,3,5,2,4,6-trioxatriborinane (0.042 mL, 0.300 mmol) in dioxane (2 mL) and water (0.4 mL). The resulting brown suspension was stirred overnight at 100° C. The reaction mixture was subsequently diluted with EtOAc and washed with saturated NH$_4$Cl (3×). The combined organic layers were dried over MgSO$_4$, filtered, and concentrated. The product was purified by flash chromatography (SiO$_2$, 4 g column, 2:8 to 8:2 EtOAc/Hexane gradient) to give the title compound as a tan solid (52 mg, 59%). $^1$H NMR (400 MHz, DMSO-d$_6$) δ ppm 2.33 (s, 3H), 2.92-3.08 (m, 3H), 3.10-3.20 (m, 2H), 3.24-3.32 (m, 2H), 3.40-3.52 (m, 2H), 3.62-3.75 (m, 2H), 3.81-3.90 (m, 2H), 3.91-4.00 (m, 2H), 4.21-4.31 (m, 2H), 4.41-4.63 (m, 3H), 7.30-7.38 (m, 2H), 7.38-7.55 (m, 3H), 7.67-7.73 (m, 1H); ESI-MS m/z [M+H]$^+$ calc'd for C$_{18}$H$_{18}$ClN$_5$O, 356.1. found 356.1.

PREPARATION x84: 2-((2-chloro-6a,7,9,10-tetrahydro-[1,4]oxazino[3,4-h]pteridin-5(6H)-yl)methyl)-4-methylbenzamide

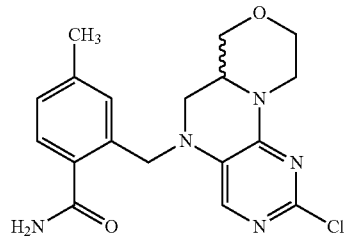 [SMILES: Cc1ccc(C(N)=O)c(CN2CC3COCCN3c3nc(Cl)ncc32)c1]

To a 20 mL round-bottomed flask charged with 2-((2-chloro-6a,7,9,10-tetrahydro-[1,4]oxazino[3,4-h]pteridin-5(6H)-yl)methyl)-4-methylbenzonitrile (PREPARATION x83, 52 mg, 0.146 mmol) was added sulfuric acid (1.6 mL, 29.2 mmol). The resulting yellow solution was stirred overnight at room temperature and was subsequently diluted with EtOAc and washed with saturated NaHCO$_3$ to adjust the pH to ~8. The combined organic layers were dried over MgSO$_4$, filtered, and concentrated to give an orange solid, which was used without further purification. $^1$H NMR (400 MHz, DMSO-d$_6$) δ ppm 2.88-3.02 (m, 5H), 3.09-3.18 (m, 3H), 3.19-3.28 (m, 2H), 3.41-3.51 (m, 3H), 3.59-3.71 (m, 2H), 3.80-3.91 (m, 3H), 3.91-4.00 (m, 2H), 4.19-4.29 (m, 3H), 4.30-4.58 (m, 2H), 7.16-7.29 (m, 10H), 7.37-7.45 (m, 2H), 7.73-7.82 (m, 2H); ESI-MS m/z [M+H]$^+$ calc'd for C$_{18}$H$_{20}$ClN$_5$O$_2$, 374.1. found 374.2.

PREPARATION x85: (6aR)-2-chloro-5-(1-(5-isobutyl-1,3,4-oxadiazol-2-yl)ethyl)-5,6,6a,7,9,10-hexahydro-[1,4]oxazino[3,4-h]pteridine

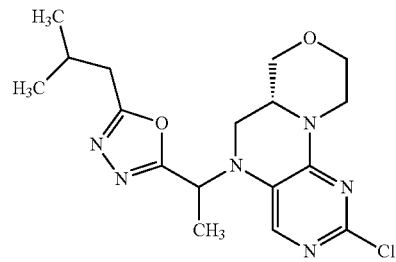 [SMILES: CC(C)Cc1nnc(C(C)N2C[C@@H]3COCCN3c3nc(Cl)ncc32)o1]

A TFA salt of the title compound was prepared in a manner similar to PREPARATION x56 using (R)-2-chloro-5,6,6a,7,9,10-hexahydro-[1,4]oxazino[3,4-h]pteridine (PREPARATION x2, 200 mg, 0.882 mmol) in DMSO (7 mL), sodium tert-butoxide (110 mg, 1.147 mmol) and 2-(1-chloroethyl)-5-ethyl-1,3,42-(1-chloroethyl)-5-isobutyl-1,3,4-oxadiazole (200 mg, 1.059 mmol) (260 mg, 78%). $^1$H NMR (400 MHz, DMSO-d$_6$) δ ppm 0.91 (td, J=6.57, 1.52 Hz, 6H), 1.48-1.62 (m, 3H), 1.95-2.07 (m, 1H), 2.56-2.65 (m, 1H), 2.72 (s, 2H), 2.89-3.06 (m, 2H), 3.06-3.19 (m, 1H), 3.35-3.56 (m, 2H), 3.56-3.69 (m, 1H), 3.81-3.99 (m, 1H), 4.22-4.33 (m, 1H), 5.34-5.47 (m, 1H), 7.63-7.77 (m, 1H); ESI-MS m/z [M+H]$^+$ calc'd for C$_{17}$H$_{23}$ClN$_6$O$_2$, 379.16. found 379.3.

Example 1

5-(5,6,6a,7,9,10-hexahydro-[1,4]oxazino[3,4-h]pteridin-2-yl)pyrimidin-2-amine

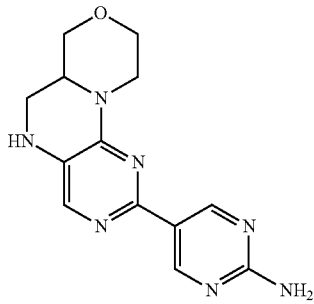 [SMILES: Nc1ncc(-c2ncc3c(n2)N2CCOCC2CN3)cn1]

A mixture of 2-chloro-5,6,6a,7,9,10-hexahydro-[1,4]oxazino[3,4-h]pteridine (PREPARATION x2, 308 mg, 1.359 mmol), 2-aminopyrimidin-5-ylboronic acid (378 mg, 2.72 mmol) and PdCl$_2$(dppf) (49.7 mg, 0.068 mmol) was partially dissolved in dioxane (8 mL) and aqueous saturated NaHCO$_3$ (1.6 mL). The resulting brown suspension was heated in a microwave on high absorbance at 120° C. for 2 hours. The reaction mixture was subsequently diluted with ethyl acetate and washed with brine (3×15 mL). The combined organic layers were dried over MgSO$_4$, filtered, and concentrated in vacuo. The product was purified by LC/MS using a gradient of 1-20% CH$_3$CN (with 0.035% TFA) in H$_2$O (with 0.05% TFA). The pure fractions were combined and lyophilized to afford a TFA salt of the title compound as an off-white solid (85.3 mg, 22%). $^1$H NMR (400 MHz, ACETONITRILE-d$_3$) δ 3.01 (dd, J=11.87, 8.34 Hz, 1H), 3.15-3.24 (m, 1H), 3.25-3.33 (m, 1H), 3.41 (dd, J=11.87, 4.29 Hz, 1H), 3.57 (d, J=2.78 Hz, 1H), 3.77-3.86 (m, 1H), 3.93-3.99 (m, 1H), 4.00-4.07 (m, 1H), 4.82-4.90 (m, 1H), 6.23-6.36 (br s, 1H), 7.56 (s, 1H), 8.99 (s, 2H). ESI-MS m/z [M+H]$^+$ calc'd for C$_{13}$H$_{15}$N$_7$O, 286.13. found 286.3.

Example 2

2-(1H-indol-4-yl)-5,6,6a,7,9,10-hexahydro-[1,4]oxazino[3,4-h]pteridine

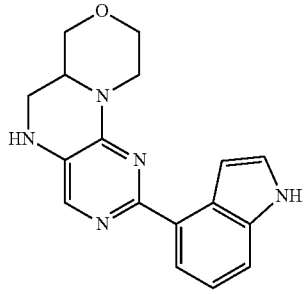 [SMILES: c1cc(-c2ncc3c(n2)N2CCOCC2CN3)c2cc[nH]c2c1]

A mixture of 2-chloro-5,6,6a,7,9,10-hexahydro-[1,4]oxazino[3,4-h]pteridine (PREPARATION x2, 308 mg, 1.359 mmol), 4-(4,4,5,5-tetramethyl-1,3,2-dioxaborolan-2-yl)-1H-indole (330 mg, 1.359 mmol) and PdCl$_2$(dppf) (49.7 mg, 0.068 mmol) were partially dissolved in dioxane (8 mL) and aqueous saturated NaHCO$_3$ (1.6 mL). The resulting brown suspension was heated in a microwave on high absorbance at 120° C. for 2 hours. The reaction mixture was subsequently diluted with ethyl acetate and washed with brine (3×15 mL). The combined organic layers were dried over MgSO$_4$, filtered, and concentrated in vacuo. The product was purified by LC/MS using a gradient of 20-35% CH$_3$CN (with 0.035% TFA) in H$_2$O (with 0.05% TFA). The pure fractions were combined and lyophilized to give a TFA salt of the title compound as an off-white solid (52.6 mg, 12.6%). $^1$H NMR (400 MHz, DMSO-d$_6$) δ 3.04 (dd, J=11.87, 8.34 Hz, 1H), 3.28 (t, J=11.12 Hz, 2H), 3.44-3.67 (m, 2H), 3.78-3.91 (m, 1H), 3.97-4.16 (m, 2H), 4.72 (d, J=12.13 Hz, 1H), 6.66-6.82 (br s, 1H), 6.99 (d, J=2.02 Hz, 1H), 7.29 (t, J=7.71 Hz, 1H), 7.49-7.74 (m, 4H), 11.58 (br s, 1H). ESI-MS m/z [M+H]$^+$ calc'd for C$_{17}$H$_{17}$N$_5$O, 308.14. found 308.3.

Example 3

5-(cyclopropylmethyl)-2-(1H-indol-4-yl)-5,6,6a,7,9,10-hexahydro-[1,4]oxazino[3,4-h]pteridine

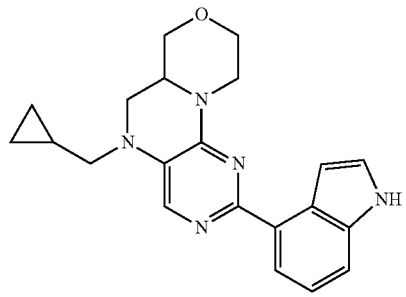 [SMILES: c1cc(-c2ncc3c(n2)N2CCOCC2CN3CC2CC2)c2cc[nH]c2c1]

A mixture of 2-chloro-5-(cyclopropylmethyl)-5,6,6a,7,9,10-hexahydro-[1,4]oxazino[3,4-h]pteridine (PREPARATION x5, 100 mg, 0.356 mmol), 4-(4,4,5,5-tetramethyl-1,3,2-dioxaborolan-2-yl)-1H-indole (173 mg, 0.712 mmol) and PdCl$_2$(dppf) (13.03 mg, 0.018 mmol) were partially dissolved in dioxane (2 mL) and aqueous saturated NaHCO$_3$ (0.4 mL). The resulting tan suspension was heated to 100° C. and stirred for 18 hours. The reaction mixture was subsequently diluted with ethyl acetate and washed with aqueous saturated NaHCO$_3$ (2×10 mL) and brine (2×10 mL). The combined organic layers were dried over MgSO$_4$, filtered, and concentrated in vacuo. The product was purified by LC/MS using a gradient of 20-40% CH$_3$CN (with 0.035% TFA) in H$_2$O (with 0.05% TFA). The pure fractions were combined and lyophilized to give a TFA salt of the title compound as a yellow solid (47 mg, 37%). $^1$H NMR (400 MHz, DMSO-d$_6$) δ 0.22-0.63 (m, 4H), 1.01-1.13 (m, 1H), 2.9-3.24 (m, 4H), 3.52-3.61 (m, 3H), 3.84-3.97 (m, 1H), 4.00-4.17 (m, 2H), 4.66-4.80 (m, 1H), 6.96-7.06 (m, 1H), 7.21-7.36 (m, 1H), 7.64 (d, J=1.77 Hz, 4H), 11.27-11.66 (m, 1H). ESI-MS m/z [M+H]$^+$ calc'd for C$_{21}$H$_{23}$N$_5$O, 362.19. found 362.4.

Example 4

5-(5-(4-(methylsulfonyl)benzyl)-5,6,6a,7,9,10-hexahydro-[1,4]oxazino[3,4-h]pteridin-2-yl)pyrimidin-2-amine

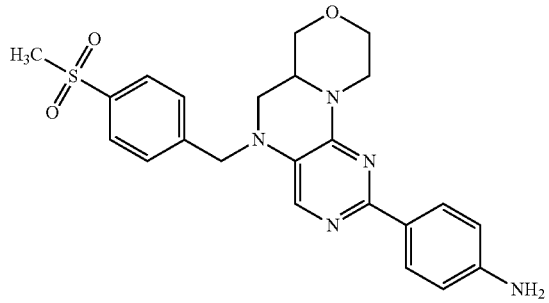 [SMILES: CS(=O)(=O)c1ccc(CN2CC3COCCN3c3nc(-c4ccc(N)cc4)ncc32)cc1]

To a solution of 5-(5,6,6a,7,9,10-hexahydro-[1,4]oxazino[3,4-h]pteridin-2-yl)pyrimidin-2-amine (EXAMPLE 1, 70.2 mg, 0.246 mmol) in DMSO (1.2 mL) was added sodium tert-butoxide (28.4 mg, 0.295 mmol). The resulting mixture was stirred at room temperature for 5 minutes after which 1-(bromomethyl)-4-(methylsulfonyl)benzene (0.5 mL, 0.271 mmol) was added dropwise. The resulting brown solution was stirred at room temperature for 2 hours. The reaction mixture was quenched with aqueous saturated NH$_4$Cl, diluted with ethyl acetate, and washed with aqueous saturated NH$_4$Cl (3×10 mL). The combined organic layers were dried over MgSO$_4$, filtered, and concentrated in vacuo. The product was purified by LC/MS and the pure fractions were combined and lyophilized to give a yellow solid (4.6 mg, 4%). The product's regiochemistry was confirmed by 2D NOESY. $^1$H NMR (400 MHz, DMSO-d$_6$) δ 3.16-3.25 (m, 7H), 3.44-3.46 (m, 1H), 3.53-3.57 (m, 1H), 3.80-3.97 (m, 1H), 3.98-4.03 (m, 1H), 4.65 (s, 2H), 4.76-4.80 (d, 1H), 7.37 (s, 1H), 7.42 (br s, 2H), 7.61-7.63 (d, J=8.0 Hz, 2H) 7.91-7.93 (d, J=8.0 Hz, 2H), 9.00 (s, 2H). ESI-MS m/z [M+H]$^+$ calc'd for C$_{21}$H$_{23}$N$_7$O$_3$S, 454.16. found 454.4.

Example 5

5-(2-chloro-4-(methylsulfonyl)benzyl)-2-(1H-indol-4-yl)-5,6,6a,7,9,10-hexahydro-[1,4]oxazino[3,4-h]pteridine

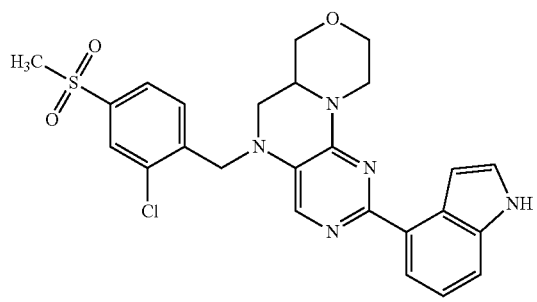

A mixture of 2-chloro-5-(2-chloro-4-(methylsulfonyl)benzyl)-5,6,6a,7,9,10-hexahydro-[1,4]oxazino[3,4-h]pteridine (PREPARATION x6, 143 mg, 0.333 mmol), 4-(4,4,5,5-tetramethyl-1,3,2-dioxaborolan-2-yl)-1H-indole (162 mg, 0.666 mmol) and PdCl$_2$(dppf) (12.19 mg, 0.017 mmol) were partially dissolved in dioxane (1.4 mL) and aqueous saturated NaHCO$_3$ (0.3 mL). The resulting tan suspension was heated in a microwave on high absorbance at 100° C. for 2 hours. The reaction mixture was subsequently diluted with ethyl acetate and washed with aqueous saturated NH$_4$Cl (3×15 mL). The combined organic layers were dried over MgSO$_4$, filtered, and concentrated in vacuo. The product was purified by LC/MS using a gradient of 20-45% CH$_3$CN (with 0.035% TFA) in H$_2$O (with 0.05% TFA). The pure fractions were combined and lyophilized to give a TFA salt of the title compound as a pale yellow solid (31 mg, 18%). $^1$H NMR (400 MHz, DMSO-d$_6$) δ 3.61-3.67 (m, 8H), 3.95-4.04 (m, 2H), 4.08-4.18 (m, 1H), 4.62-4.84 (m, 3H), 6.99-7.06 (m, 1H), 7.27 (s, 1H), 7.46-7.75 (m, 5H), 7.86 (d, J=1.77 Hz, 1H), 8.08 (d, J=1.77 Hz, 1H), 11.33-11.73 (m, 1H). ESI-MS m/z [M+H]$^+$ calc'd for C$_{25}$H$_{24}$ClN$_5$O$_3$S, 510.13. found 510.4.

Example 6

1-(4-(5-(2-chloro-4-(methylsulfonyl)benzyl)-5,6,6a,7,9,10-hexahydro-[1,4]oxazino[3,4-h]pteridin-2-yl)phenyl)-3-methylurea

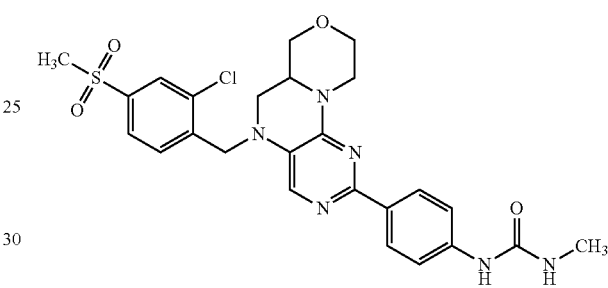

The title compound was prepared in a manner similar to EXAMPLE 5 using 2-chloro-5-(2-chloro-4-(methylsulfonyl)benzyl)-5,6,6a,7,9,10-hexahydro-[1,4]oxazino[3,4-h]pteridine (PREPARATION x6, 175 mg, 0.408 mmol), (1-methyl-3-(4-(4,4,5,5-tetramethyl-1,3,2-dioxaborolan-2-yl)phenyl)urea (225 mg, 0.815 mmol) and PdCl$_2$(dppf) (14.91 mg, 0.020 mmol) in dioxane (5 mL) and aqueous saturated NaHCO$_3$ (1 mL). $^1$H NMR (400 MHz, DMSO-d$_6$) δ 2.61-2.71 (m, 3H), 3.28-3.31 (m, 2H), 3.53-3.66 (m, 1H), 3.87-4.02 (m, 2H), 4.03-4.15 (m, 1H), 4.59-4.79 (m, 2H), 4.79-4.91 (m, 1H), 6.14-6.25 (m, 1H), 7.32-7.38 (m, 1H), 7.53-7.62 (m, 2H), 7.63-7.71 (m, 1H), 7.81-7.90 (m, 1H), 7.99-8.12 (m, 3H), 8.91-9.05 (m, 1H). ESI-MS m/z [M+H]$^+$ calc'd for C$_{25}$H$_{27}$ClN$_6$O$_4$S, 543.15. found 543.5.

Example 7

5-(5-(2-chloro-4-(methylsulfonyl)benzyl)-5,6,6a,7,9,10-hexahydro-[1,4]oxazin[3,4-h]pteridin-2-yl)pyrimidin-2-amine

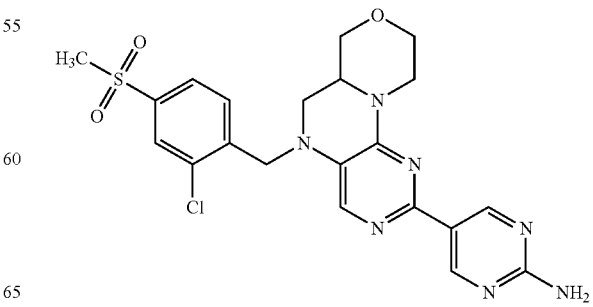

The title compound was prepared in a manner similar to EXAMPLE 5 using 2-chloro-5-(2-chloro-4-(methylsulfonyl)benzyl)-5,6,6a,7,9,10-hexahydro-[1,4]oxazino[3,4-h]pteridine (PREPARATION x6, 175 mg, 0.408 mmol), 2-aminopyrimidin-5-ylboronic acid (113 mg, 0.815 mmol), and PdCl$_2$(dppf) (23.86 mg, 0.033 mmol) in dioxane (2.3 mL) and aqueous saturated NaHCO$_3$ (0.5 mL). $^1$H NMR (400 MHz, DMSO-d$_6$) δ 3.20 3.35 (m, 7H), 3.77 4.12 (m, 4H), 4.59-4.89 (m, 3H), 7.32-7.56 (m, 3H), 7.64 (d, J=8.08 Hz, 1H), 7.85 (dd, J=8.08, 1.77 Hz, 1H), 8.06 (d, J=1.52 Hz, 1H), 8.96 (s, 2H). ESI-MS m/z [M+H]$^+$ calc'd for C$_{21}$H$_{22}$ClN$_7$O$_3$S, 488.12. found 488.4.

Example 8

2-(6-methoxy-1H-indol-3-yl)-5,6,6a,7,9,10-hexahydro-[1,4]oxazino[3,4-h]pteridine

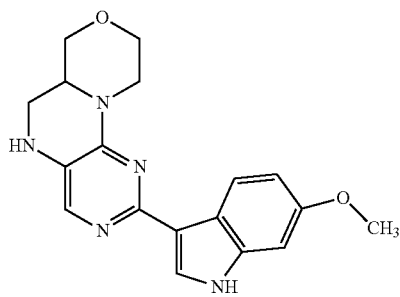 [SMILES: COc1ccc2c(-c3ncc4c(n3)N3CCOCC3CN4)c[nH]c2c1]

STEP A: tert-butyl 3-(5,6,6a,7,9,10-hexahydro-[1,4]oxazino[3,4-h]pteridin-2-yl)-6-methoxy-1H-indole-1-carboxylate The title compound was prepared in a manner similar to EXAMPLE 1 using 2-chloro-5,6,6a,7,9,10-hexahydro-[1,4]oxazino[3,4-h]pteridine (PREPARATION x2, 50 mg, 0.221 mmol), tert-butyl 6-methoxy-3-(4,4,5,5-tetramethyl-1,3,2-dioxaborolan-2-yl)-1H-indole-1-carboxylate (124 mg, 0.331 mmol) and PdCl$_2$(dppf) (12.91 mg, 0.018 mmol) in dioxane (1.9 mL) and aqueous saturated NaHCO$_3$ (0.4 mL).

STEP B: 2-(6-methoxy-1H-indol-3-yl)-5,6,6a,7,9,10-hexahydro-[1,4]oxazino[3,4-h]pteridine A solution of tert-Butyl 3-(5,6,6a,7,9,10-hexahydro-[1,4]oxazino[3,4-h]pteridin-2-yl)-6-methoxy-1H-indole-1-carboxylate (97 mg, 0.222 mmol) and CH$_2$Cl$_2$/TFA (1:1, 3 mL) was stirred at room temperature for 30 minutes. The reaction mixture was subsequently concentrated in vacuo and the crude product was purified by LC/MS using a gradient of 20-30% CH$_3$CN (with 0.035% TFA) in H$_2$O (with 0.05% TFA). The pure fractions were combined and lyophilized to give a TFA salt of the title compound as a pale yellow solid (26 mg, 35%). $^1$H NMR (400 MHz, DMSO-d$_6$) δ 2.92-3.03 (m, 1H), 3.33-3.35 (m, 3H), 3.55-3.68 (m, 1H), 3.80 (s, 3H), 3.82-3.88 (m, 1H), 3.94-4.18 (m, 2H), 4.70-4.81 (m, 1H), 6.33-6.46 (br s, 1H), 6.82-6.93 (m, 1H), 6.97-7.08 (m, 1H), 7.36-7.50 (m, 1H), 8.07-8.22 (m, 2H), 11.77-11.94 (m, 1H). ESI-MS m/z [M+H]$^+$ calc'd for C$_{18}$H$_{19}$N$_5$O$_2$S, 338.15. found 338.4.

Example 9

2-(7-methoxy-1H-indol-3-yl)-5,6,6a,7,9,10-hexahydro-[1,4]oxazino[3,4-h]pteridine

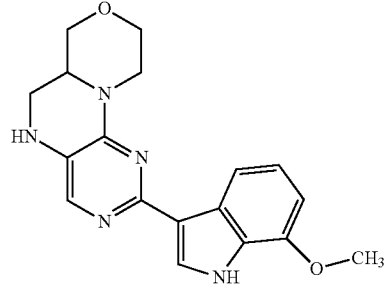 [SMILES: COc1cccc2c(-c3ncc4c(n3)N3CCOCC3CN4)c[nH]c12]

STEP A: tert-butyl 3-(5,6,6a,7,9,10-hexahydro-[1,4]oxazino[3,4-h]pteridin-2-yl)-7-methoxy-1H-indole-1-carboxylate The title compound was prepared in a manner similar to EXAMPLE 1 using 2-chloro-5,6,6a,7,9,10-hexahydro-[1,4]oxazino[3,4-h]pteridine (PREPARATION x2, 50 mg, 0.221 mmol), tert-butyl 6-methoxy-3-(4,4,5,5-tetramethyl-1,3,2-dioxaborolan-2-yl)-1H-indole-1-carboxylate (124 mg, 0.331 mmol) and PdCl$_2$(dppf) (12.91 mg, 0.018 mmol) in dioxane (1.9 mL) and aqueous saturated NaHCO$_3$ (0.4 mL).

STEP B: 2-(7-methoxy-1H-indol-3-yl)-5,6,6a,7,9,10-hexahydro-[1,4]oxazino[3,4-h]pteridine A TFA salt of the title compound was prepared in a manner similar to EXAMPLE 8 using tert-butyl 3-(5,6,6a,7,9,10-hexahydro-[1,4]oxazino[3,4-h]pteridin-2-yl)-7-methoxy-1H-indole-1-carboxylate (60 mg, 0.137 mmol) in CH$_2$Cl$_2$ and TFA. $^1$H NMR (400 MHz, DMSO-d$_6$) δ 2.92-3.05 (m, 1H), 3.27-3.30 (m, 1H), 3.53-3.66 (m, 1H), 3.76-3.90 (m, 1H), 3.91-3.98 (m, 5H), 3.97-4.06 (m, 1H), 4.08-4.18 (m, 1H), 4.68-4.84 (m, 1H), 6.33-6.45 (br s, 1H), 6.79-6.87 (m, 1H), 7.09-7.20 (m, 1H), 7.38-7.46 (m, 1H), 7.80-7.89 (m, 1H), 8.15-8.23 (m, 1H), 12.18-12.29 (m, 1H). ESI-MS m/z [M+H]$^+$ calc'd for C$_{18}$H$_{19}$N$_5$O$_2$S, 338.15. found 338.4.

Example 10

2-(1H-benzo[d]imidazol-4-yl)-5,6,6a,7,9,10-hexahydro-[1,4]oxazino[3,4-h]pteridine

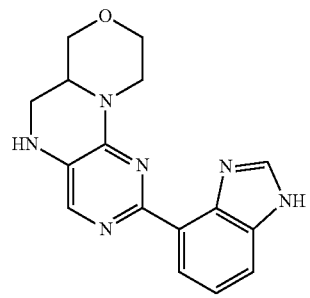

The title compound was prepared in a manner similar to EXAMPLE 1 using 2-chloro-5,6,6a,7,9,10-hexahydro-[1,4]oxazino[3,4-h]pteridine (PREPARATION x2, 50 mg, 0.221 mmol), 1H-benzo[d]imidazol-4-ylboronic acid (71.5 mg, 0.441 mmol) and PdCl$_2$(dppf) (12.91 mg, 0.018 mmol) in dioxane (2 mL) and aqueous saturated NaHCO$_3$ (0.4 mL). $^1$H NMR (400 MHz, DMSO-d$_6$) δ 3.03 (dd, J=11.87, 8.59 Hz, 1H), 3.33-3.75 (m, 5H), 3.98 (m, 2H), 4.74-4.84 (m, 1H), 6.49-7.07 (br s, 1H), 7.54 (t, J=7.83 Hz, 1H), 7.79-7.91 (m, 2H), 8.25-8.33 (m, 1H), 8.98 (s, 1H), 12.18-12.29 (m, 1H). ESI-MS m/z [M+H]$^+$ calc'd for C$_{16}$H$_{16}$N$_6$O, 309.14. found 309.3.

Example 11

2-(7-chloro-1H-indol-3-yl)-5,6,6a,7,9,10-hexahydro-[1,4]oxazino[3,4-h]pteridine

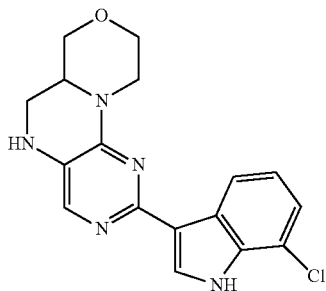 [SMILES: Clc1cccc2c(-c3ncc4c(n3)N3CCOCC3CN4)c[nH]c12]

STEP A: tert-butyl 7-chloro-3-(5,6,6a,7,9,10-hexahydro-[1,4]oxazino[3,4-h]pteridin-2-yl)-1H-indole-1-carboxylate The title compound was prepared in a manner similar to EXAMPLE 1 using 2-chloro-5,6,6a,7,9,10-hexahydro-[1,4] oxazino[3,4-h]pteridine (PREPARATION x2, 50 mg, 0.221 mmol), tert-butyl 7-chloro-3-(4,4,5,5-tetramethyl-1,3,2-dioxaborolan-2-yl)-1H-indole-1-carboxylate (125 mg, 0.331 mmol) and PdCl$_2$(dppf) (12.91 mg, 0.018 mmol) in dioxane (2 mL) and aqueous saturated NaHCO$_3$ (0.4 mL).

STEP B: 2-(7-chloro-1H-indol-3-yl)-5,6,6a,7,9,10-hexahydro-[1,4]oxazino[3,4-h]pteridine A mixture of tert-butyl 7-chloro-3-(5,6,6a,7,9,10-hexahydro-[1,4]oxazino[3,4-h]pteridin-2-yl)-1H-indole-1-carboxylate and CH$_2$Cl$_2$/TFA (1:1) was heated to 50° C. and stirred for 2 hours. The reaction mixture was subsequently concentrated in vacuo and the crude product purified by LC/MS using a gradient of 30-40% CH$_3$CN (with 0.035% TFA) in H$_2$O (with 0.05% TFA). The pure fractions were combined and lyophilized to give a TFA salt of the title compound as a tan solid (20 mg, 27%). $^1$H NMR (400 MHz, DMSO-d$_6$) δ 2.98-3.01 (m, 2H), 3.56-3.58 (m, 3H), 3.72-4.25 (m, 3H), 4.65-4.92 (m, 1H), 6.34-6.58 (br s, 1H), 7.12-7.59 (m, 3H), 8.12-8.52 (m, 2H), 12.27-12.56 (m, 1H). ESI-MS m/z [M+H]$^+$ calc'd for C$_{17}$H$_{16}$ClN$_5$O, 342.10. found 342.3.

Example 12

4-(5,6,6a,7,9,10-hexahydro-[1,4]oxazino[3,4-h]pteridin-2-yl)-1H-indol-2-ol

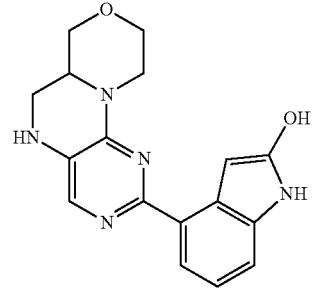 [SMILES: Oc1cc2c(-c3ncc4c(n3)N3CCOCC3CN4)cccc2[nH]1]

The title compound was prepared in a manner similar to EXAMPLE 1 using 2-chloro-5,6,6a,7,9,10-hexahydro-[1,4] oxazino[3,4-h]pteridine (PREPARATION x2, 50 mg, 0.221 mmol), 4-(4,4,5,5-tetramethyl-1,3,2-dioxaborolan-2-yl)-1H-indol-2-ol (30 mg, 0.116 mmol), and PdCl$_2$(dppf) (12.91 mg, 0.018 mmol) in dioxane (2 mL) and aqueous saturated NaHCO$_3$ (0.4 mL). $^1$H NMR (400 MHz, DMSO-d$_6$) δ 2.95-3.03 (m, 2H), 3.20-3.30 (m, 3H), 3.77-3.83 (m, 2H), 3.88-3.95 (m, 1H), 4.00-4.08 (m, 1H), 4.36-4.45 (m, 1H), 6.01-6.15 (m, 1H), 6.78-6.85 (m, 1H), 7.18-7.26 (m, 1H), 7.62-7.68 (m, 1H), 7.74-7.80 (m, 1H), 10.23-10.52 (m, 1H), 12.27-12.56 (m, 1H). ESI-MS m/z [M+H]$^+$ calc'd for C$_{17}$H$_{17}$N$_5$O$_2$, 323.14. found 324.3.

Example 13

2-(4-((2-(1H-indol-4-yl)-6a,7,9,10-tetrahydro-[1,4]oxazino[3,4-h]pteridin-5(6H)-yl)methyl)phenyl)propan-2-ol

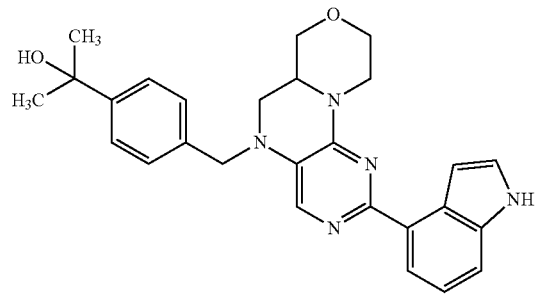 [SMILES: CC(C)(O)c1ccc(CN2CC3COCCN3c3nc(-c4cccc5[nH]ccc45)ncc32)cc1]

The title compound was prepared in a manner similar to EXAMPLE 2 using 2-(4-((2-chloro-6a,7,9,10-tetrahydro-[1,4]oxazin[3,4-h]pteridin-5(6H)-yl)methyl)phenyl)propan-2-ol (PREPARATION x8, 39 mg, 0.104 mmol), 4-(4,4,5,5-tetramethyl-1,3,2-dioxaborolan-2-yl)-1H-indole (50.6 mg, 0.208 mmol), and PdCl$_2$(dppf) (6.09 mg, 8.32 µmol) in dioxane (8 mL) and aqueous saturated NaHCO$_3$ (2 mL). $^1$H NMR (400 MHz, DMSO-d$_6$) δ 1.42 (s, 6H), 3.18 (m, 4H), 3.58-3.66 (m, 1H), 3.94-4.04 (m, 2H), 4.08-4.15 (m, 1H), 4.56 (s, 2H), 4.70-4.79 (m, 1H), 6.99-7.05 (m, 1H), 7.23-7.37 (m, 3H), 7.45-7.51 (m, 3H), 7.58 (s, 1H), 7.60-7.69 (m, 2H), 11.45-11.63 (m, 1H). ESI-MS m/z [M+H]$^+$ calc'd for C$_{27}$H$_{29}$N$_5$O$_2$, 456.23. found 456.5.

Example 14

2-(2-methoxypyridin-4-yl)-5,6,6a,7,9,10-hexahydro-[1,4]oxazino[3,4-h]pteridine

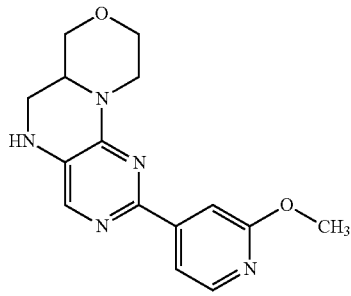 [SMILES: COc1cc(-c2ncc3c(n2)N2CCOCC2CN3)ccn1]

The title compound was prepared in a manner similar to EXAMPLE 1 using 2-methoxypyridin-4-ylboronic acid (270 mg, 1.765 mmol), 2-chloro-5,6,6a,7,9,10-hexahydro-[1,4]oxazino[3,4-h]pteridine (PREPARATION x2, 200 mg, 0.882 mmol), and PdCl$_2$(dppf) (51.7 mg, 0.071 mmol) in dioxane (5 mL) and aqueous saturated NaHCO$_3$ (1 mL). $^1$H NMR (400 MHz, DMSO-d$_6$) δ 3.01-3.23 (m, 7H), 3.89 (m, 3H), 3.92-3.97 (m, 1H), 3.99-4.06 (m, 1H), 4.53-4.62 (m, 1H), 7.47 (d, J=0.76 Hz, 1H), 7.62 (s, 1H), 7.68 (dd, J=5.31, 1.52 Hz, 1H), 8.24 (d, J=5.56 Hz, 1H). ESI-MS m/z [M+H]$^+$ calc'd for C$_{15}$H$_{17}$N$_5$O$_2$, 299.14. found 300.2.

Example 15

2-(1H-pyrrolo[2,3-b]pyridin-4-yl)-5,6,6a,7,9,10-hexahydro-[1,4]oxazino[3,4-h]pteridine

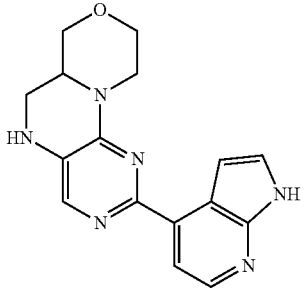

STEP A: 2-(1-tosyl-1H-pyrrolo[2,3-b]pyridin-4-yl)-5,6,6a,7,9,10-hexahydro-[1,4]oxazino[3,4-h]pteridine The title compound was prepared in a manner similar to EXAMPLE 2 using 4-(4,4,5,5-tetramethyl-1,3,2-dioxaborolan-2-yl)-1-tosyl-1H-pyrrolo[2,3-b]pyridine (PREPARATION x2, 527 mg, 1.324 mmol), 2-chloro-5,6,6a,7,9,10-hexahydro-[1,4]oxazino[3,4-h]pteridine (150 mg, 0.662 mmol), and PdCl$_2$(dppf) (38.7 mg, 0.053 mmol) in dioxane (3.5 mL) and aqueous saturated NaHCO$_3$ (0.8 mL).

STEP B: 2-(1H-pyrrolo[2,3-b]pyridin-4-yl)-5,6,6a,7,9,10-hexahydro-[1,4]oxazino[3,4-h]pteridine To a solution of 2-(1-tosyl-1H-pyrrolo[2,3-b]pyridin-4-yl)-5,6,6a,7,9,10-hexahydro-[1,4]oxazino[3,4-h]pteridine (171 mg, 0.370 mmol) in DMF (13 mL) was added KOH (0.555 mL, 1.109 mmol) in MeOH (5 mL) dropwise. Upon addition the solution turned orange/red and was stirred for 18 hours. The reaction mixture was subsequently diluted with ethyl acetate and washed with 1M HCl (2×5 mL) and brine (2×10 mL). The combined organic layers were dried over MgSO$_4$, filtered, and concentrated in vacuo. The product was purified by LC/MS using a gradient of 10-30% CH$_3$CN (with 0.035% TFA) in H$_2$O (with 0.05% TFA). The pure fractions were combined and lyophilized to give a TFA salt of the title compound as a yellow solid (55 mg, 48%). $^1$H NMR (400 MHz, DMSO-d$_6$) δ 2.97-3.11 (m, 1H), 3.16-3.31 (m, 2H), 3.39-3.50 (m, 1H), 3.90-4.18 (m, 3H), 4.41-4.72 (m, 2H), 7.07-7.32 (m, 1H), 7.70 (m, 3H), 8.28-8.42 (m, 1H), 11.79-12.19 (m, 1H). ESI-MS m/z [M+H]$^+$ calc'd for C$_{16}$H$_{16}$N$_5$O, 309.14. found 309.2.

Example 16

2-(7-fluoro-3-methyl-1H-indol-4-yl)-5-(4-(methylsulfonyl)benzyl)-5,6,6a,7,9,10-hexahydro-[1,4]oxazino[3,4-h]pteridine

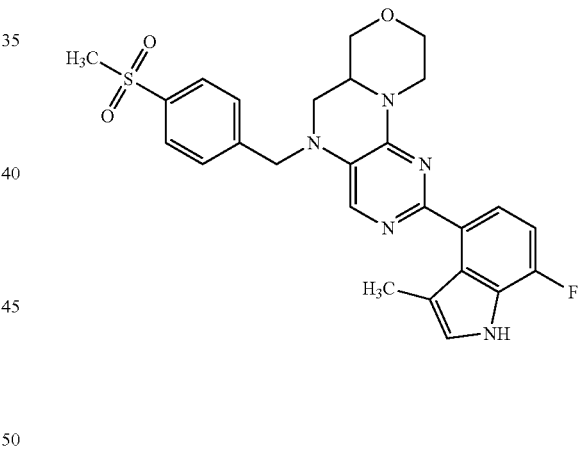

The title compound was prepared in a manner similar to EXAMPLE 2 using 2-chloro-5-(4-(methylsulfonyl)benzyl)-5,6,6a,7,9,10-hexahydro-[1,4]oxazino[3,4-h]pteridine (PREPARATION x9, 66.0 mg, 0.167 mmol), 7-fluoro-3-methyl-4-(4,4,5,5-tetramethyl-1,3,2-dioxaborolan-2-yl)-1H-indole (92 mg, 0.334 mmol) and PdCl$_2$(dppf) (9.79 mg, 0.013 mmol) in dioxane (1 mL) and aqueous saturated NaHCO$_3$ (0.2 mL). $^1$H NMR (400 MHz, DMSO-d$_6$) δ 1.93-2.07 (m, 3H), 2.89-2.99 (m, 1H), 3.21-3.34 (m, 6H), 3.47-3.49 (m, 1H), 3.67-3.72 (m, 1H), 3.86-3.99 (m, 2H), 4.35-4.44 (m, 1H), 4.57-4.64 (m, 2H), 6.83-6.91 (m, 1H), 7.02-7.08 (m, 1H), 7.11-7.17 (m, 1H), 7.58-7.66 (m, 3H), 7.87-7.96 (m, 2H), 11.23-11.30 (m, 1H). ESI-MS m/z [M+H]$^+$ calc'd for C$_{26}$H$_{26}$FN$_5$O$_3$S, 508.17. found 508.5.

Example 17

2-(7-fluoro-1H-indol-4-yl)-5-(4-(methylsulfonyl)benzyl)-5,6,6a,7,9,10-hexahydro-[1,4]oxazino[3,4-h]pteridine

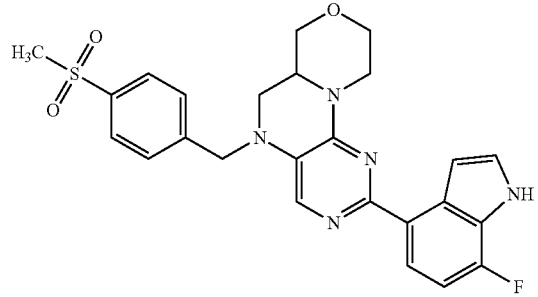 [SMILES: CS(=O)(=O)c1ccc(CN2CC3COCCN3c3nc(-c4ccc(F)c5[nH]ccc45)ncc32)cc1]

The title compound was prepared in a manner similar to EXAMPLE 2 using 2-chloro-5-(4-(methylsulfonyl)benzyl)-5,6,6a,7,9,10-hexahydro-[1,4]oxazino[3,4-h]pteridine (PREPARATION x9, 90 mg, 0.228 mmol), 7-fluoro-4-(4,4,5,5-tetramethyl-1,3,2-dioxaborolan-2-yl)-1H-indole (119 mg, 0.456 mmol) and PdCl$_2$(dppf) (8.34 mg, 0.011 mmol) in dioxane (2.5 mL) and aqueous saturated NaHCO$_3$ (0.5 mL). $^1$H NMR (400 MHz, DMSO-d$_6$) δ 3.22 (m, 3H), 3.24-3.36 (m, 2H), 3.39-3.75 (m, 3H), 3.88-4.06 (m, 2H), 4.06-4.16 (m, 1H), 4.62-4.77 (m, 2H), 7.05-7.21 (m, 2H), 7.45-7.53 (m, 1H), 7.55-7.62 (m, 1H), 7.62-7.72 (m, 3H), 7.90-7.97 (m, 2H), 11.85-12.09 (m, 1H). ESI-MS m/z [M+H]$^+$ calc'd for C$_{25}$H$_{24}$FN$_5$O$_3$S, 494.16. found 494.5.

Example 18

2-(1H-indol-4-yl)-5-tosyl-5,6,6a,7,9,10-hexahydro-[1,4]oxazino[3,4-h]pteridine

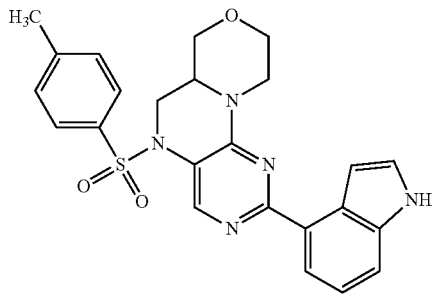 [SMILES: Cc1ccc(S(=O)(=O)N2CC3COCCN3c3nc(-c4cccc5[nH]ccc45)ncc32)cc1]

The title compound was prepared in a manner similar to EXAMPLE 3 using 2-chloro-5-tosyl-5,6,6a,7,9,10-hexahydro-[1,4]oxazino[3,4-h]pteridine (PREPARATION x11, 68 mg, 0.179 mmol), 4-(4,4,5,5-tetramethyl-1,3,2-dioxaborolan-2-yl)-1H-indole (87 mg, 0.357 mmol) and PdCl$_2$(dppf) (6.53 mg, 8.93 μmol) in dioxane (2 mL) and aqueous saturated NaHCO$_3$ (0.4 mL). $^1$H NMR (400 MHz, DMSO-d$_6$) δ 2.35-2.41 (m, 3H), 2.55-2.66 (m, 1H), 2.68-2.76 (m, 1H), 2.97-3.09 (m, 1H), 3.17-3.27 (m, 1H), 3.82-3.98 (m, 2H), 4.16-4.27 (m, 1H), 4.53-4.63 (m, 1H), 4.57-4.57 (m, 1H), 7.14-7.24 (m, 1H), 7.23-7.31 (m, 1H), 7.38-7.50 (m, 3H), 7.51-7.63 (m, 3H), 8.00-8.10 (m, 1H), 8.48-8.58 (m, 1H), 11.19-11.35 (m, 1H). ESI-MS m/z [M+H]$^+$ calc'd for C$_{24}$H$_{23}$N$_5$O$_3$S, 462.15. found 462.4.

Example 19

2-(1H-indol-4-yl)-5-(4-(methylsulfonyl)benzyl)-5,6,6a,7,9,10-hexahydro-[1,4]oxazino[3,4-h]pteridine

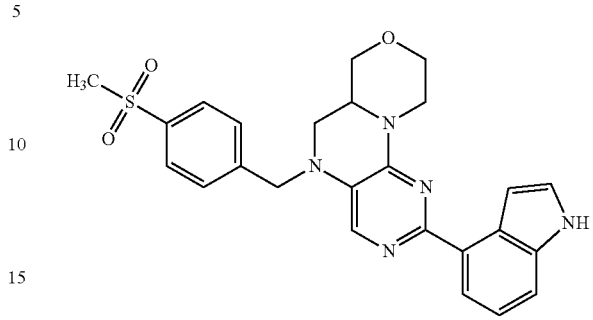

The title compound was prepared in a manner similar to EXAMPLE 3 using 2-chloro-5-(4-(methylsulfonyl)benzyl)-5,6,6a,7,9,10-hexahydro-[1,4]oxazino[3,4-h]pteridine (PREPARATION x9, 50 mg, 0.127 mmol), 4-(4,4,5,5-tetramethyl-1,3,2-dioxaborolan-2-yl)-1H-indole (61.6 mg, 0.253 mmol) and PdCl$_2$(dppf) (4.63 mg, 6.33 μmol) in dioxane (2 mL) and aqueous saturated NaHCO$_3$ (0.4 mL). $^1$H NMR (400 MHz, DMSO-d$_6$) δ 3.22 (m, 4H), 3.48-3.55 (m, 1H), 3.57-3.68 (m, 1H), 3.93-4.05 (m, 2H), 4.07-4.17 (m, 1H), 4.68-4.79 (m, 3H), 7.00-7.09 (m, 1H), 7.21-7.30 (m, 1H), 7.44-7.50 (m, 1H), 7.52-7.58 (m, 1H), 7.60-7.71 (m, 4H), 7.90-7.98 (m, 2H), 11.44-11.51 (m, 1H). ESI-MS m/z [M+H]$^+$ calc'd for C$_{25}$H$_{23}$N$_5$O$_3$S, 476.17. found 476.4.

Example 20

1-(2-(1H-indol-4-yl)-6a,7,9,10-tetrahydro-[1,4]oxazino[3,4-h]pteridin-5(6H)-yl)-2-(4-methoxyphenyl)ethanone

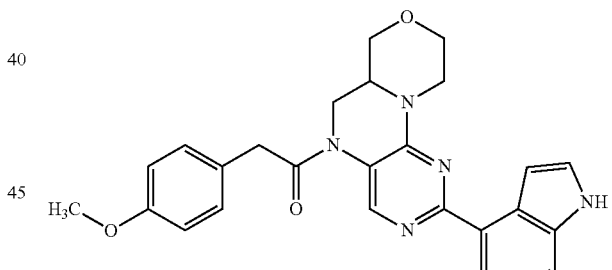

To 1-(2-(1-(tert-butyldimethylsilyl)-1H-indol-4-yl)-6a,7,9,10-tetrahydro-[1,4]oxazino[3,4-h]pteridin-5(6H)-yl)-2-(4-methoxyphenyl)ethanone (PREPARATION x13, 40 mg, 0.070 mmol) dissolved in THF (0.5 mL) was added tetrabutylammonium fluoride in THF (1M, 0.14 mL, 0.14 mmol). The resulting bright yellow solution was stirred for 5 hours at room temperature. The reaction mixture was subsequently diluted with ethyl acetate and washed with aqueous saturated NH$_4$Cl (3×10 mL). The combined organic layers were dried over MgSO$_4$, filtered, and concentrated in vacuo. The product was purified by LC/MS using a gradient of 20-45% CH$_3$CN (with 0.035% TFA) in H$_2$O (with 0.05% TFA). The pure fractions were combined and lyophilized to give a TFA salt of the title compound as a yellow solid (17 mg, 52%). $^1$H NMR (400 MHz, DMSO-d$_6$) δ 3.17-3.25 (m, 3H), 3.49-3.58 (m, 1H), 3.67-3.76 (m, 4H), 3.89-3.96 (m, 2H), 3.97-4.10 (m, 2H), 4.36-4.51 (m, 1H), 4.70-4.80 (m, 1H), 6.77-6.94 (m, 2H), 7.06-7.21 (m, 3H), 7.21-7.29 (m, 1H), 7.45-7.56 (m, 1H), 7.57-7.70 (m, 1H), 7.79-7.98 (m, 1H), 8.39-8.94 (m, 1H), 11.36-11.47 (m, 1H). ESI-MS m/z [M+H]+ calc'd for $C_{26}H_{25}N_5O_3$, 456.20. found 456.5.

Example 21

5-(4-(methylsulfonyl)benzyl)-2-(2-(trifluoromethyl)-1H-indol-4-yl)-5,6,6a,7,9,10-hexahydro-[1,4]oxazino[3,4-h]pteridine

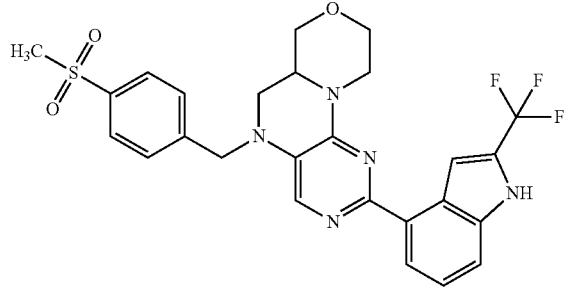

The title compound was prepared in a manner similar to EXAMPLE 3 using 2-chloro-5-(4-(methylsulfonyl)benzyl)-5,6,6a,7,9,10-hexahydro-[1,4]oxazino[3,4-h]pteridine (PREPARATION x9, 63.5 mg, 0.161 mmol), 4-(4,4,5,5-tetramethyl-1,3,2-dioxaborolan-2-yl)-2-(trifluoromethyl)-1H-indole (100 mg, 0.321 mmol) and PdCl₂(dppf) (5.88 mg, 8.04 mmol) in dioxane (2 mL) and aqueous saturated NaHCO₃ (0.4 mL). ¹H NMR (400 MHz, DMSO-d₆) δ 3.21 (m, 3H), 3.23-3.34 (m, 3H), 3.56-3.66 (m, 2H), 3.88-4.03 (m, 2H), 4.05-4.16 (m, 1H), 4.59-4.68 (m, 1H), 4.71 (s, 2H), 7.41-7.48 (m, 1H), 7.56 (s, 2H), 7.65 (d, J=8.34 Hz, 3H), 7.79-7.86 (m, 1H), 7.94 (d, J=8.34 Hz, 2H), 12.56-12.65 (m, 1H). ESI-MS m/z [M+H]+ calc'd for $C_{26}H_{24}F_3N_5O_3S$, 544.16. found 544.5.

Example 22

2-(1H-indazol-4-yl)-5-(4-(methylsulfonyl)benzyl)-5,6,6a,7,9,10-hexahydro-[1,4]oxazino[3,4-h]pteridine

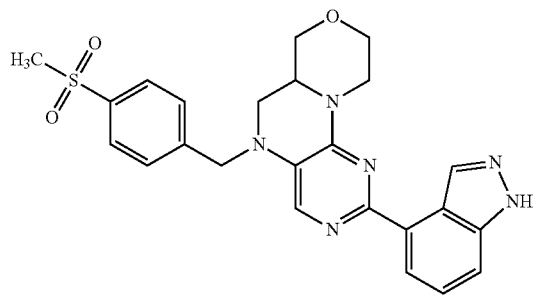 [SMILES: CS(=O)(=O)c1ccc(CN2CC3COCCN3c3nc(-c4cccc5[nH]ccc45)ncc32)cc1]

The title compound was prepared in a manner similar to EXAMPLE 3 using 2-chloro-5-(4-(methylsulfonyl)benzyl)-5,6,6a,7,9,10-hexahydro-[1,4]oxazino[3,4-h]pteridine (PREPARATION x9, 75 mg, 0.190 mmol), 1-(4-(4,4,5,5-tetramethyl-1,3,2-dioxaborolan-2-yl)-1H-indazol-1-yl)ethanone (109 mg, 0.381 mmol) and PdCl₂(dppf) (6.97 mg, 9.52 μmol) in dioxane (2 mL) and aqueous saturated NaHCO₃ (0.4 mL). ¹H NMR (400 MHz, DMSO-d₆) δ 3.18-3.38 (m, 5H), 3.88-4.05 (m, 3H), 4.09-4.19 (m, 2H), 4.73 (m, 4H), 7.49 (s, 1H), 7.56 (s, 1H), 7.65 (d, J=8.34 Hz, 2H), 7.72 (s, 1H), 7.84 (d, J=7.33 Hz, 1H), 7.94 (d, J=8.34 Hz, 2H), 8.61 (s, 1H), 13.00-13.68 (m, 1H). ESI-MS m/z [M+H]+ calc'd for $C_{24}H_{24}N_6O_3S$, 477.16. found 477.4.

Example 23

5-(4-(methylsulfonyl)benzyl)-2-(1H-pyrrolo[2,3-c]pyridin-4-yl)-5,6,6a,7,9,10-hexahydro-[1,4]oxazino[3,4-h]pteridine

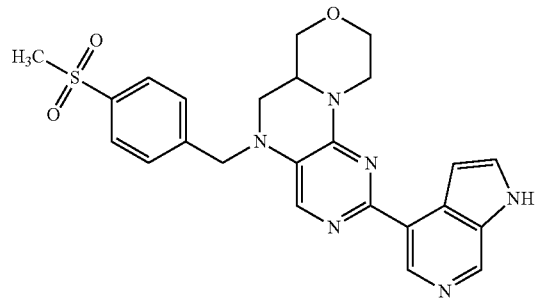 [SMILES: CS(=O)(=O)c1ccc(CN2CC3COCCN3c3nc(-c4cncc5[nH]ccc45)ncc32)cc1]

The title compound was prepared in a manner similar to EXAMPLE 3 using 2-chloro-5-(4-(methylsulfonyl)benzyl)-5,6,6a,7,9,10-hexahydro-[1,4]oxazino[3,4-h]pteridine (PREPARATION x9, 75 mg, 0.190 mmol), 1-acetyl-1H-pyrrolo[2,3-c]pyridin-4-ylboronic acid (77 mg, 0.380 mmol) and PdCl₂(dppf) (6.95 mg, 9.50 μmol) in dioxane (2 mL) and aqueous saturated NaHCO₃ (0.4 mL). ¹H NMR (400 MHz, DMSO-d₆) δ 3.08-3.19 (m, 1H), 3.21 (m, 2H), 3.23-3.34 (m, 2H), 3.47-3.56 (m, 1H), 3.57-3.67 (m, 1H), 3.70-3.81 (m, 1H), 3.93-4.01 (m, 2H), 4.06-4.15 (m, 1H), 4.49-4.58 (m, 1H), 4.64-4.80 (m, 2H), 7.55-7.68 (m, 3H), 7.69-7.75 (m, 1H), 7.88-7.98 (m, 2H), 8.28-8.37 (m, 1H), 8.86-8.96 (m, 1H), 9.05-9.15 (m, 1H), 12.85-12.97 (m, 1H). ESI-MS m/z [M+H]+ calc'd for $C_{24}H_{24}N_6O_3S$, 477.16. found 477.5.

Example 24

5-(4-(methylsulfonyl)benzyl)-2-(1H-pyrrolo[3,2-b]pyridin-6-yl)-5,6,6a,7,9,10-hexahydro-[1,4]oxazino[3,4-h]pteridine

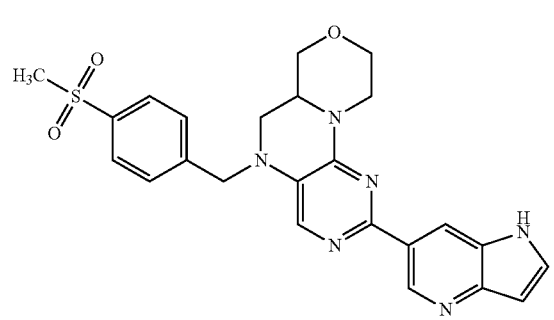 [SMILES: CS(=O)(=O)c1ccc(CN2CC3COCCN3c3nc(-c4cnc5cc[nH]c5c4)ncc32)cc1]

The title compound was prepared in a manner similar to EXAMPLE 3 using 2-chloro-5-(4-(methylsulfonyl)benzyl)-5,6,6a,7,9,10-hexahydro-[1,4]oxazino[3,4-h]pteridine (PREPARATION x9, 50 mg, 0.127 mmol), 6-(4,4,5,5-tetramethyl-1,3,2-dioxaborolan-2-yl)-1H-pyrrolo[3,2-b]pyridine (61.8 mg, 0.253 mmol) and PdCl₂(dppf) (4.63 mg, 6.33 μmol) in dioxane (2 mL) and aqueous saturated NaHCO₃ (0.4 mL). ¹H NMR (400 MHz, DMSO-d₆) δ 3.03-3.18 (m, 1H), 3.18-3.30 (m, 5H), 3.73-3.87 (m, 2H), 3.92-4.19 (m, 3H), 4.59-

4.81 (m, 3H), 6.76-6.97 (m, 1H), 7.53-7.77 (m, 2H), 7.86-8.08 (m, 2H), 8.14-8.33 (m, 1H), 8.96-9.20 (m, 1H), 9.26-9.42 (m, 1H), 12.40-12.69 (m, 1H). ESI-MS m/z [M+H]+ calc'd for $C_{24}H_{24}N_6O_3S$, 477.16. found 477.2.

Example 25

5-(4-(methylsulfonyl)benzyl)-2-(1H-pyrrolo[2,3-b]pyridin-5-yl)-5,6,6a,7,9,10-hexahydro-[1,4]oxazino[3,4-h]pteridine

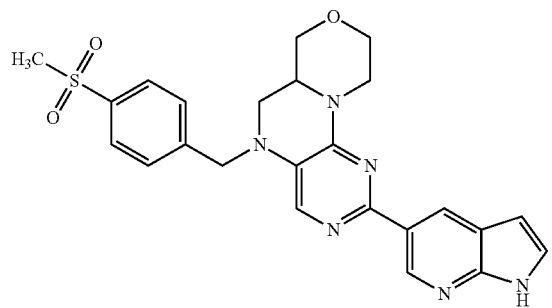 [SMILES: CS(=O)(=O)c1ccc(CN2CC3COCCN3c3nc(-c4cnc5[nH]ccc5c4)ncc32)cc1]

The title compound was prepared in a manner similar to EXAMPLE 3 using 2-chloro-5-(4-(methylsulfonyl)benzyl)-5,6,6a,7,9,10-hexahydro-[1,4]oxazino[3,4-h]pteridine (PREPARATION x9, 50 mg, 0.127 mmol), 5-(4,4,5,5-tetramethyl-1,3,2-dioxaborolan-2-yl)-1H-pyrrolo[2,3-b]pyridine (61.8 mg, 0.253 mmol) and PdCl₂(dppf) (4.63 mg, 6.33 µmol) in dioxane (2 mL) and aqueous saturated NaHCO₃ (0.4 mL). ¹H NMR (400 MHz, DMSO-d₆) δ 3.14-3.26 (m, 2H), 3.31-3.45 (m, 6H), 3.54-3.65 (m, 2H), 3.93-4.03 (m, 1H), 4.03-4.13 (m, 1H), 4.62-4.72 (m, 2H), 6.51-6.61 (m, 1H), 7.44-7.53 (m, 1H), 7.53-7.60 (m, 1H), 7.60-7.68 (m, 2H), 7.89-7.96 (m, 2H), 8.67-8.73 (m, 1H), 8.99-9.07 (m, 1H), 11.76-12.07 (m, 1H). ESI-MS m/z [M+H]+ calc'd for $C_{24}H_{24}N_6O_3S$, 477.16. found 477.3.

Example 26

2-(1H-indol-4-yl)-4-methyl-5-(4-(methylsulfonyl)benzyl)-5,6,6a,7,9,10-hexahydro-[1,4]oxazino[3,4-h]pteridine

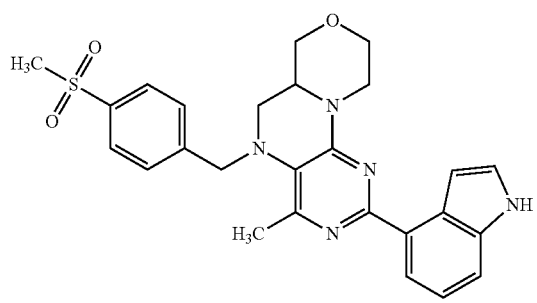 [SMILES: Cc1nc(-c2cccc3[nH]ccc23)nc2c1N(Cc1ccc(S(C)(=O)=O)cc1)CC1COCCN21]

To a 10 mL vial were added 2-chloro-4-methyl-5-(4-(methylsulfonyl)benzyl)-5,6,6a,7,9,10-hexahydro-[1,4]oxazino[3,4-h]pteridine (PREPARATION x21, 94 mg, 0.230 mmol), 1H-indol-4-ylboronic acid (74.0 mg, 0.460 mmol) and PdCl₂(dppf)-DCM (9.39 mg, 0.011 mmol) in dioxane (3615 µL) and aqueous saturated NaHCO₃ (723 µL). The reaction mixture was heated at 100° C. overnight. Additional 1H-indol-4-ylboronic acid (74.0 mg, 0.460 mmol) and PdCl₂(dppf)-DCM (9.39 mg, 0.011 mmol) were added and the reaction mixture was heated in a microwave at 100° C. for 1 hour. The mixture was subsequently filtered and the filtrate was purified by preparatory HPLC using a gradient of 20-45% CH₃CN (with 0.035% TFA) in H₂O (with 0.05% TFA). The pure fractions were combined and lyophilized to give a TFA salt of the title compound as a yellow solid (16 mg, 14%). ¹H NMR (400 MHz, DMSO-d₆) δ 2.53 (s, 3H), 2.74 (dd, J=14.16, 10.25 Hz, 1H), 3.03 (d, J=11.23 Hz, 1H), 3.13-3.19 (m, 1H), 3.24 (s, 3H), 3.28-3.37 (m, 1H), 3.59 (td, J=12.08, 2.68 Hz, 2H), 3.94 (d, J=10.74 Hz, 1H), 4.11 (dd, J=11.72, 3.42 Hz, 1H), 4.18-4.29 (m, 2H), 4.77 (d, J=12.20 Hz, 1H), 7.03 (dd, J=8.05, 7.08 Hz, 1H), 7.27-7.36 (m, 1H), 7.59 (br s, 1H), 7.67-7.84 (m, 4H), 7.96-8.02 (m, 2H), 11.56 (br s, 1H). ESI-MS m/z [M+H]+ calc'd for $C_{26}H_{27}N_5O_3S$, 490.18. found 490.6.

Example 27

5-(cyclopropylmethyl)-2-(1H-indol-4-yl)-4-methyl-5,6,6a,7,9,10-hexahydro-[1,4]oxazino[3,4-h]pteridine

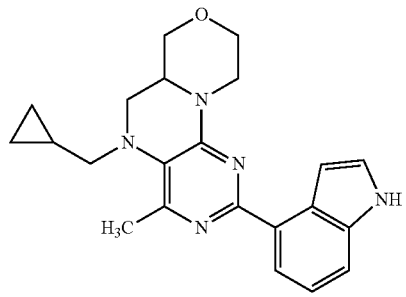 [SMILES: Cc1nc(-c2cccc3[nH]ccc23)nc2c1N(CC1CC1)CC1COCCN21]

To a 10 mL vial were added 2-chloro-5-(cyclopropylmethyl)-4-methyl-5,6,6a,7,9,10-hexahydro-[1,4]oxazino[3,4-h]pteridine (PREPARATION x22, 56 mg, 0.190 mmol), 1H-indol-4-ylboronic acid (61.2 mg, 0.380 mmol) and PdCl₂(dppf)-DCM (7.76 mg, 9.50 µmol) in dioxane (3.0 mL) and aqueous saturated NaHCO₃ (0.60 mL). The reaction mixture was heated in a microwave at 100° C. for 1 hour. The mixture was subsequently filtered and the filtrate was purified by preparatory HPLC using a gradient of 20-45% CH₃CN (with 0.035% TFA) in H₂O (with 0.05% TFA). The pure fractions were combined and lyophilized to give a TFA salt of the title compound as a yellow solid (30 mg, 42%). ¹H NMR (400 MHz, DMSO-d₆) δ 0.17-0.23 (m, 1H), 0.31 (dt, J=9.28, 4.64 Hz, 1H), 0.47-0.60 (m, 2H), 1.06-1.13 (m, 1H), 2.69-2.75 (m, 2H), 2.79-2.85 (m, 1H), 3.20 (t, J=10.98 Hz, 1H), 3.51 (br s, 3H), 3.58 (td, J=11.96, 2.93 Hz, 3H), 3.85 (br s, 1H), 4.03 (dd, J=11.23, 3.42 Hz, 1H), 4.09 (dd, J=11.47, 3.66 Hz, 1H), 4.75 (d, J=12.69 Hz, 1H), 6.99 (br s, 1H), 7.30 (t, J=7.81 Hz, 1H), 7.58 (br s, 1H), 7.71 (br s, 2H), 11.55 (br s, 1H). ESI-MS m/z [M+H]+ calc'd for $C_{22}H_{25}N_5O$, 376.21. found 376.6.

Example 28

(S)-2-(1H-indol-4-yl)-5-(4-(methylsulfonyl)benzyl)-5,6,6a,7,9,10-hexahydro-[1,4]oxazino[3,4-h]pteridine

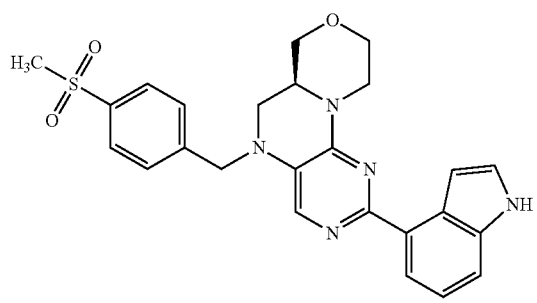

To a 2 mL microwave vial were added (S)-2-chloro-5-(4-(methylsulfonyl)benzyl)-5,6,6a,7,9,10-hexahydro-[1,4]oxazino[3,4-h]pteridine (90 mg, 0.228 mmol), indole-4-boronic acid (36.7 mg, 0.228 mmol) and [1,1'-bis(diphenylphosphino)ferrocene]-dichloropalladium(II) (9.38 mg, 0.011 mmol). The vial was evacuated, filled with nitrogen, and sealed. Dioxane (1.6 mL) and aqueous saturated NaHCO$_3$ (0.4 mL) were added and the mixture was heated in a microwave to 120° C. for 45 minutes. After the reaction mixture was cooled to room temperature, DMF (2 mL) was added and the solids were removed by passing the mixture through a syringe filter. The crude product was purified by preparatory HPLC using a gradient of 20-40% CH$_3$CN (with 0.035% TFA) in H$_2$O (with 0.05% TFA). The collected fractions were lyophilized to give a TFA salt of the title compound as a yellow powder (31 mg, 24% yield). $^1$H NMR (DMSO-d$_6$) δ 3.19-3.25 (m, 3H), 3.53-3.62 (m, 4H), 4.00 (d, J=8.8 Hz, 2H), 4.04-4.15 (m, 1H), 4.12 (dd, J=11.6, 3.5 Hz, 1H), 4.66-4.80 (m, 3H), 7.04 (br s, 1H), 7.26 (t, J=7.8 Hz, 1H), 7.48 (s, 1H), 7.56 (t, J=2.5 Hz, 1H), 7.60-7.73 (m, 4H), 7.94 (d, J=8.6 Hz, 2H), 11.52 (br s, 1H). ESI-MS m/z [M+H]$^+$ calc'd for C$_{25}$H$_{25}$N$_5$O$_3$S, 476.17. found 476.4.

Example 29

(R)-2-(1H-indol-4-yl)-5-(4-(methylsulfonyl)benzyl)-5,6,6a,7,9,10-hexahydro-[1,4]oxazino[3,4-h]pteridine

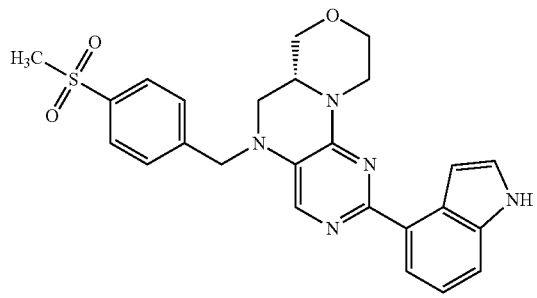

To a 2 mL microwave vial were added (R)-2-chloro-5-(4-(methylsulfonyl)benzyl)-5,6,6a,7,9,10-hexahydro-[1,4]oxazino[3,4-h]pteridine (PREPARATION x3, 110 mg, 0.279 mmol), indole-4-boronic acid (44.8 mg, 0.279 mmol) and [1,1'-bis(diphenylphosphino)ferrocene]-dichloropalladium(II) (11.46 mg, 0.014 mmol). The vial was evacuated, filled with nitrogen, and sealed. Dioxane (1.6 mL) and aqueous saturated NaHCO$_3$ (0.4 mL) were added and the reaction mixture was heated in a microwave to 120° C. for 45 minutes. After the reaction mixture was cooled to room temperature, DMF (2 mL) was added and the solids were removed by passing the mixture through a syringe filter. The crude product was purified by preparatory HPLC using a gradient of 20-40% CH$_3$CN (with 0.035% TFA) in H$_2$O (with 0.05% TFA). The collected fractions were lyophilized to give a TFA salt of the title compound as a yellow solid (28 mg, 21%). $^1$H NMR (DMSO-d$_6$) δ 3.23 (s, 3H), 3.25-3.40 (m, 3H), 3.53-3.64 (m, 3H), 4.00 (d, J=8.8 Hz, 2H), 4.12 (dd, J=11.4, 3.0 Hz, 1H), 4.66-4.79 (m, 2H), 7.04 (br s, 1H), 7.26 (t, J=7.8 Hz, 1H), 7.48 (s, 1H), 7.56 (d, J=2.5 Hz, 1H), 7.66 (d, J=8.3 Hz, 3H), 7.95 (s, 2H), 11.53 (br s, 1H). ESI-MS m/z [M+H]$^+$ calc'd for C$_{25}$H$_{25}$N$_5$O$_3$S, 476.17. found 476.4.

Example 30

(R)-5-(4-(methylsulfonyl)benzyl)-2-(1H-pyrrolo[2,3-c]pyridin-4-yl)-5,6,6a,7,9,10-hexahydro-[1,4]oxazino[3,4-h]pteridine

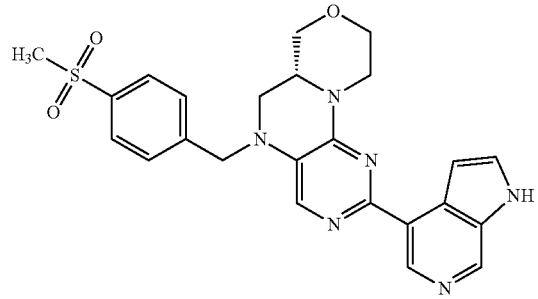 [SMILES: CS(=O)(=O)c1ccc(CN2C[C@@H]3COCCN3c3nc(-c4cncc5[nH]ccc45)ncc32)cc1]

To a 2 mL microwave vial were added (R)-2-chloro-5-(4-(methylsulfonyl)benzyl)-5,6,6a,7,9,10-hexahydro-[1,4]oxazino[3,4-h]pteridine (PREPARATION x3, 100 mg, 0.253 mmol), 1-acetyl-1H-pyrrolo[2,3-c]pyridin-4-ylboronic acid (67.2 mg, 0.329 mmol) and [1,1'-bis(diphenylphosphino)ferrocene]-dichloropalladium(II) (10.42 mg, 0.013 mmol). The vial was evacuated, filled with nitrogen, and sealed. Dioxane (1.6 mL) and aqueous saturated NaHCO$_3$ (0.4 mL) were added and the reaction mixture was heated in a microwave to 120° C. for 45 minutes. After the reaction mixture was cooled to room temperature, DMF (2 mL) was added and the solids were removed by passing the mixture through a syringe filter. The crude product was purified by preparatory HPLC, eluting with a gradient of 20-40% CH$_3$CN (with 0.035% TFA) in H$_2$O (with 0.05% TFA). The collected fractions were lyophilized to give a TFA salt of the title compound (15 mg, 10%). $^1$H NMR (DMSO-d$_6$) δ 3.21 (s, 3H), 4.10 (dd, J=11.4, 3.3 Hz, 1H), 4.54 (d, J=11.9 Hz, 1H), 4.63-4.81 (m, 2H), 7.58-7.72 (m, 4H), 7.93 (d, J=8.6 Hz, 2H), 8.33 (t, J=2.8 Hz, 1H), 8.93 (s, 1H), 9.06-9.14 (m, 1H), 12.93 (br s, 1H).

Example 31

(R)-5-((5-ethyl-1,3,4-oxadiazol-2-yl)methyl)-2-(1H-indol-4-yl)-5,6,6a,7,9,10-hexahydro-[1,4]oxazino[3,4-h]pteridine

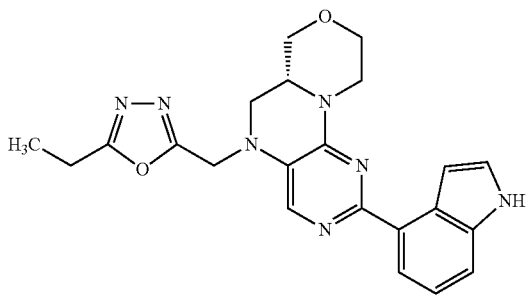 [SMILES: CCc1nnc(CN2C[C@@H]3COCCN3c3nc(-c4cccc5[nH]ccc45)ncc32)o1]

(R)-2-Chloro-5-((5-ethyl-1,3,4-oxadiazol-2-yl)methyl)-5,6,6a,7,9,10-hexahydro-[1,4]oxazino[3,4-h]pteridine (PREPARATION x19, 165 mg, 0.490 mmol), 1H-indol-4-ylboronic acid (158 mg, 0.980 mmol) and PdCl$_2$(dppf) (17.92 mg, 0.024 mmol) were suspended in dioxane (3 mL) and aqueous saturated NaHCO$_3$ (0.6 mL) then heated to 100° C. and stirred overnight. The reaction mixture was subsequently diluted with ethyl acetate and washed with aqueous saturated NH$_4$Cl (3×10 mL). The combined organic layers were dried over MgSO$_4$, filtered, and concentrated in vacuo. The product was purified by LC/MS, eluting with a CH$_3$CN (15-40%)/H$_2$O (0.035% TFA. The pure fractions were combined and lyophilized to give a TFA salt of the title compound as a yellow solid (136 mg, 66%). $^1$H NMR (400 MHz, DMSO-d$_6$) δ 1.26 (t, J=7.58 Hz, 3H), 2.86 (q, J=7.58 Hz, 2H), 3.31 (m, 3H), 3.59 (td, J=12.25, 3.03 Hz, 2H), 3.90-4.16 (m, 3H), 4.80 (d, J=16.93 Hz, 2H), 5.07 (d, J=16.93 Hz, 1H), 7.01 (br s, 1H), 7.28 (s, 1H), 7.53-7.60 (m, 1H), 7.66 (t, J=6.82 Hz, 2H), 7.78 (s, 1H), 11.50-11.62 (m, 1H). ESI-MS m/z [M+H]$^+$ calc'd for C$_{22}$H$_{23}$N$_7$O$_2$S, 418.19. found 418.3.

The compounds of EXAMPLES 32 through 45, below, were prepared as shown in Scheme G, following the procedures described in PREPARATION x5 for the (i) alkylation and PREPARATION x9 for the (ii) Suzuki coupling.

Scheme G

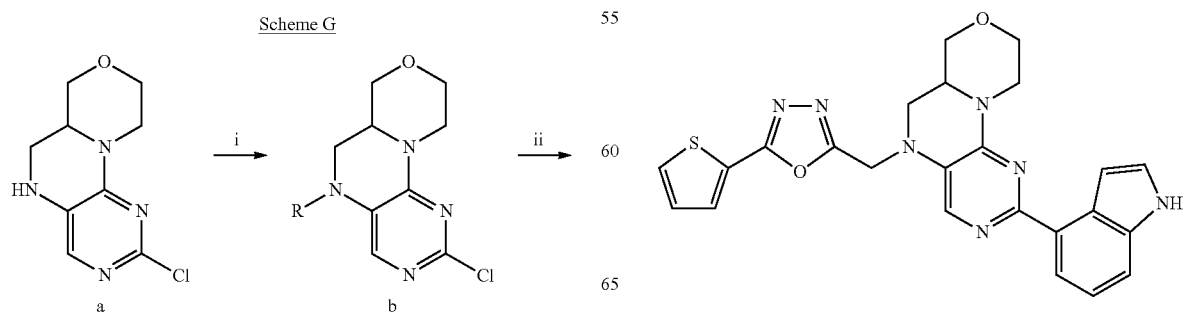

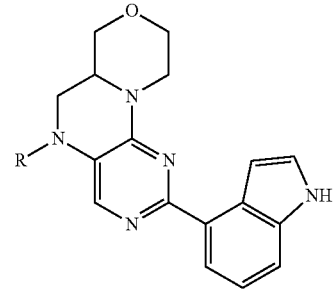

Reaction conditions: (i) starting material (a) (75 mg, 0.331 mmol) in DMSO (2 mL), R—X (0.364 mmol), and sodium tert-butoxide (38.2 mg, 0.397 mmol) at room temperature for ~18 h; (ii) (b) (1 equivalent), 4-(4,4,5,5-tetramethyl-1,32-dioxaborolan-2-yl)-1H-indole (2 equivalents), and PdCl$_2$ (dppf) (0.05 equivalents) in a 5:1 mixture of dioxane and aqueous saturated NaHCO$_3$ (0.042 M of b) at 100° C. for 18 hours. The title compounds were isolated as TFA salts.

Example 32

2-(1H-indol-4-yl)-5-(2-phenoxyethyl)-5,6,6a,7,9,10-hexahydro-[1,4]oxazino[3,4-h]pteridine

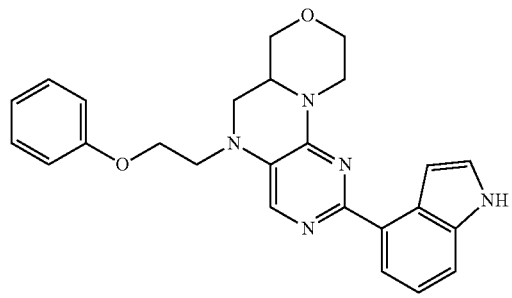 [SMILES: c1ccc(OCCN2CC3COCCN3c3nc(-c4cccc5[nH]ccc45)ncc32)cc1]

$^1$H NMR (400 MHz, DMSO-d$_6$) δ 3.25-3.39 (m, 4H), 3.54-3.65 (m, 2H), 3.67-3.78 (m, 1H), 3.80-3.93 (m, 2H), 3.97-4.16 (m, 2H), 4.20-4.34 (m, 2H), 4.64-4.75 (m, 1H), 6.90-6.99 (m, 3H), 7.00-7.05 (m, 1H), 7.23-7.34 (m, 3H), 7.53-7.58 (m, 1H), 7.61-7.69 (m, 2H), 7.73-7.79 (m, 1H), 11.40-11.53 (m, 1H). ESI-MS m/z [M+H]$^+$ calc'd for C$_{25}$H$_{25}$N$_5$O$_2$, 428.20. found 428.5.

Example 33

2-(1H-indol-4-yl)-5-((5-(thiophen-2-yl)-1,3,4-oxadiazol-2-yl)methyl)-5,6,6a,7,9,10-hexahydro-[1,4]oxazino[3,4-h]pteridine ¹H NMR (400 MHz, DMSO-d₆) δ 3.26-3.33 (m, 2H), 3.54-3.65 (m, 2H), 3.87-4.15 (m, 4H), 4.65-4.77 (m, 1H), 4.84-4.94 (m, 1H), 5.10-5.19 (m, 1H), 7.01-7.10 (m, 1H), 7.22-7.33 (m, 2H), 7.51-7.58 (m, 1H), 7.59-7.67 (m, 1H), 7.67-7.75 (m, 1H), 7.80-7.84 (m, 1H), 7.85-7.89 (m, 1H), 7.94-7.99 (m, 1H), 11.42-11.54 (m, 1H). ESI-MS m/z [M+H]⁺ calc'd for $C_{24}H_{21}N_7O_2S$, 472.15. found 472.4.

Example 34

3-(2-(1H-indol-4-yl)-6a,7,9,10-tetrahydro-[1,4]oxazino[3,4-h]pteridin-5(6H)-yl)-N-(furan-2-ylmethyl)propanamide

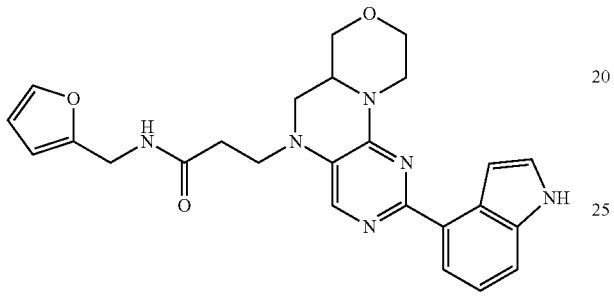

¹H NMR (400 MHz, DMSO-d₆) δ 2.99-3.11 (m, 1H), 3.17-3.25 (m, 2H), 3.33-3.40 (m, 3H), 3.50-3.70 (m, 3H), 3.72-3.85 (m, 1H), 3.92-4.02 (m, 1H), 4.04-4.14 (m, 1H), 4.22-4.31 (m, 2H), 4.60-4.74 (m, 1H), 6.16-6.26 (m, 1H), 6.28-6.39 (m, 1H), 6.93-7.12 (m, 1H), 7.18-7.35 (m, 1H), 7.46-7.77 (m, 4H), 8.41-8.57 (m, 1H), 11.39-11.59 (m, 1H). ESI-MS m/z [M+H]⁺ calc'd for $C_{25}H_{26}N_6O_3$, 459.21. found 459.5.

Example 35

5-((5-ethyl-1,3,4-oxadiazol-2-yl)methyl)-2-(1H-indol-4-yl)-5,6,6a,7,9,10-hexahydro-[1,4]oxazino[3,4-h]pteridine

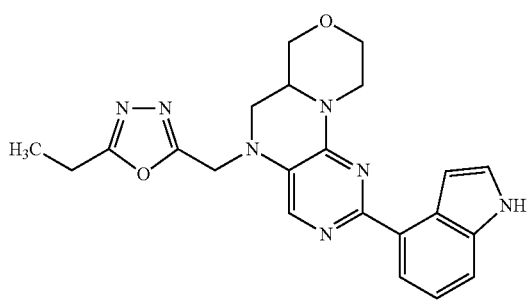

¹H NMR (400 MHz, DMSO-d₆) δ 1.15-1.34 (m, 3H), 2.80-2.92 (m, 2H), 3.18-3.28 (m, 3H), 3.51-3.66 (m, 2H), 3.85-4.14 (m, 3H), 4.64-4.84 (m, 2H), 5.00-5.11 (m, 1H), 6.98-7.11 (m, 1H), 7.20-7.32 (m, 1H), 7.50-7.58 (m, 1H), 7.59-7.76 (m, 1H), 7.76-7.84 (m, 2H), 11.41-11.56 (m, 1H). ESI-MS m/z [M+H]⁺ calc'd for $C_{22}H_{23}N_7O_2$, 418.19. found 418.5.

Example 36

5-((1-cyclopropyl-1H-tetrazol-5-yl)methyl)-2-(1H-indol-4-yl)-5,6,6a,7,9,10-hexahydro-[1,4]oxazino[3,4-h]pteridine

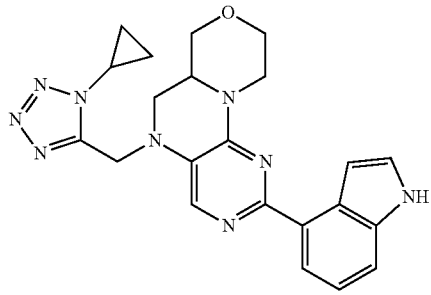 [SMILES: c1cc(-c2ncc3c(n2)N2CCOCC2CN3Cc2nnnn2C2CC2)c2cc[nH]c2c1]

¹H NMR (400 MHz, DMSO-d₆) δ 1.18-1.36 (m, 4H), 3.31-3.37 (m, 2H), 3.49-3.67 (m, 3H), 3.81-3.90 (m, 1H), 3.90-4.04 (m, 2H), 4.05-4.16 (m, 1H), 4.67-4.79 (m, 1H), 4.92-5.13 (m, 2H), 6.93-7.14 (m, 1H), 7.17-7.34 (m, 1H), 7.43-7.91 (m, 4H), 11.33-11.65 (m, 1H). ESI-MS m/z [M+H]⁺ calc'd for $C_{22}H_{23}N_9O$, 430.20. found 430.4.

Example 37

2-(1H-indol-4-yl)-5-((2-phenyloxazol-4-yl)methyl)-5,6,6a,7,9,10-hexahydro-[1,4]oxazino[3,4-h]pteridine

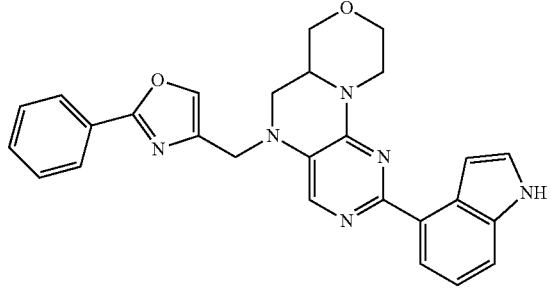 [SMILES: c1ccc(-c2nc(CN3CC4COCCN4c4nc(-c5cccc6[nH]ccc56)ncc43)co2)cc1]

¹H NMR (400 MHz, DMSO-d₆) δ 3.35-3.45 (m, 4H), 3.50-3.67 (m, 2H), 3.96-4.16 (m, 2H), 4.42-4.58 (m, 1H), 4.60-4.78 (m, 2H), 6.42-6.60 (m, 1H), 6.94-7.14 (m, 1H), 7.17-7.33 (m, 1H), 7.47-7.59 (m, 5H), 7.81-7.89 (m, 1H), 7.93-8.02 (m, 2H), 8.25-8.30 (m, 1H), 11.33-11.65 (m, 1H). ESI-MS m/z [M+H]⁺ calc'd for $C_{27}H_{24}N_6O$, 465.20. found 465.4.

Example 38

2-(1H-indol-4-yl)-5-((5-phenyl-1,3,4-oxadiazol-2-yl)methyl)-5,6,6a,7,9,10-hexahydro-[1,4]oxazino[3,4-h]pteridine

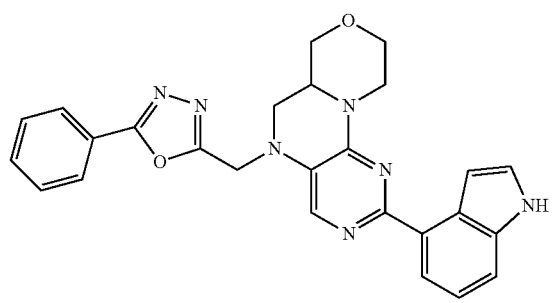 [SMILES: c1ccc(-c2nnc(CN3CC4COCCN4c4nc(-c5cccc6[nH]ccc56)ncc43)o2)cc1]

$^1$H NMR (400 MHz, DMSO-d$_6$) δ 3.30-3.40 (m, 3H), 3.54-3.69 (m, 2H), 3.87-4.17 (m, 3H), 4.62-4.81 (m, 1H), 4.83-5.23 (m, 2H), 6.98-7.13 (m, 1H), 7.16-7.32 (m, 1H), 7.44-7.77 (m, 6H), 7.81-7.92 (m, 1H), 7.96-8.06 (m, 2H), 11.33-11.65 (m, 1H). ESI-MS m/z [M+H]$^+$ calc'd for C$_{26}$H$_{23}$N$_7$O$_2$, 466.19. found 466.4.

Example 39

2-(1H-indol-4-yl)-5-(oxazol-2-ylmethyl)-5,6,6a,7,9,10-hexahydro-[1,4]oxazino[3,4-h]pteridine

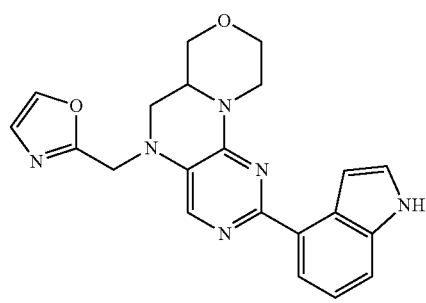 [SMILES: c1cc(-c2ncc3c(n2)N2CCOCC2CN3Cc2ncco2)c2cc[nH]c2c1]

$^1$H NMR (400 MHz, DMSO-d$_6$) δ 3.11-3.24 (m, 3H), 3.45-3.60 (m, 2H), 3.77-4.06 (m, 3H), 4.55-4.96 (m, 3H), 6.91-7.03 (m, 1H), 7.12-7.26 (m, 2H), 7.43-7.52 (m, 1H), 7.53-7.64 (m, 2H), 7.65-7.73 (m, 1H), 8.03-8.15 (m, 1H), 11.33-11.56 (m, 1H). ESI-MS m/z [M+H]$^+$ calc'd for C$_{21}$H$_{20}$N$_6$O$_2$, 389.16. found 389.3.

Example 40

2-(1H-indol-4-O-5-((1-phenyl-1H-1,2,3-triazol-4-yl)methyl)-5,6,6a,7,9,10-hexahydro-[1,4]oxazino[3,4-h]pteridine

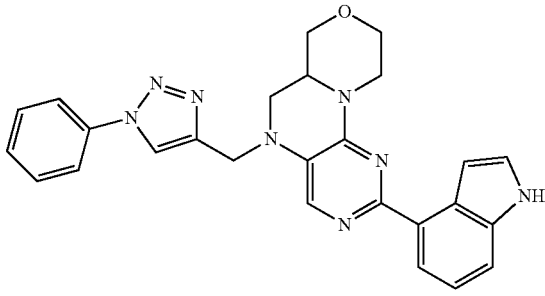 [SMILES: c1ccc(-n2cc(CN3CC4COCCN4c4nc(-c5cccc6[nH]ccc56)ncc43)nn2)cc1]

$^1$H NMR (400 MHz, DMSO-d$_6$) δ 2.30-2.41 (m, 3H), 2.65-2.76 (m, 2H), 3.04-3.28 (m, 3H), 3.74-4.06 (m, 3H), 6.05-6.22 (m, 1H), 6.32-6.46 (m, 1H), 6.56-6.87 (m, 6H), 6.89-7.10 (m, 3H), 7.94-8.05 (m, 1H), 10.55-10.76 (m, 1H). ESI-MS m/z [M+H]$^+$ calc'd for C$_{26}$H$_{24}$N$_8$O, 465.21. found 465.4.

Example 41

2-(2-(1H-indol-4-yl)-6a,7,9,10-tetrahydro-[1,4]oxazino[3,4-h]pteridin-5(6H)-yl)-N-(2-methylbenzyl)acetamide

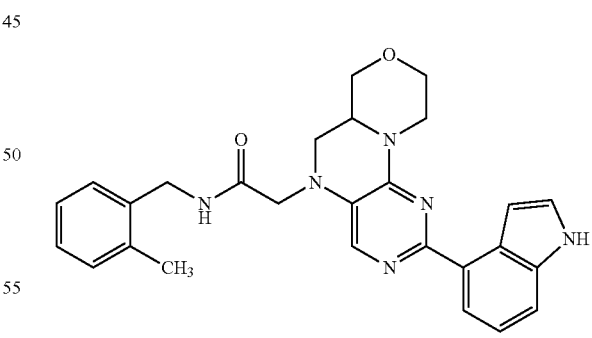

$^1$H NMR (400 MHz, DMSO-d$_6$) δ 2.26-2.29 (m, 3H), 3.30-3.40 (m, 4H), 3.43-3.54 (m, 1H), 3.54-3.68 (m, 3H), 3.87-4.15 (m, 1H), 4.18-4.36 (m, 3H), 4.63-4.79 (m, 1H), 6.90-7.36 (m, 3H), 7.40-7.81 (m, 6H), 8.46-8.57 (m, 1H), 11.39-11.66 (m, 1H). ESI-MS m/z [M+H]$^+$ calc'd for C$_{27}$H$_{28}$N$_6$O$_2$, 469.23. found 469.4.

Example 42

2-(2-(1H-indol-4-yl)-6a,7,9,10-tetrahydro-[1,4]ox-azino[3,4-h]pteridin-5(6H)-yl)-N-isopropylacetamide

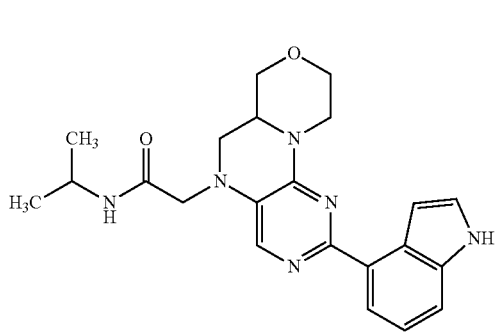 [SMILES: CC(C)NC(=O)CN1CC2COCCN2c2nc(-c3cccc4[nH]ccc34)ncc21]

$^1$H NMR (400 MHz, DMSO-d$_6$) δ 1.10 (d, J=6.57 Hz, 6H), 3.24-3.34 (m, 4H), 3.56-3.68 (m, 1H), 3.83-4.05 (m, 4H), 4.06-4.21 (m, 2H), 4.67-4.78 (m, 1H), 6.94-7.08 (m, 1H), 7.22-7.34 (m, 1H), 7.36-7.49 (m, 1H), 7.52-7.75 (m, 3H), 7.97-8.13 (m, 1H), 11.44-11.65 (m, 1H). ESI-MS m/z [M+H]$^+$ calc'd for C$_{22}$H$_{26}$N$_6$O$_2$, 407.21. found 407.3.

Example 43

2-(2-(1H-indol-4-yl)-6a,7,9,10-tetrahydro-[1,4]ox-azino[3,4-h]pteridin-5(6H)-yl)-N,N-dimethylacetamide

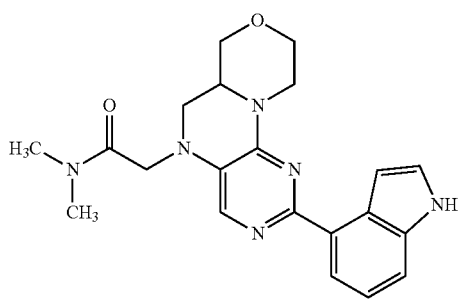 [SMILES: CN(C)C(=O)CN1CC2COCCN2c2nc(-c3cccc4[nH]ccc34)ncc21]

$^1$H NMR (400 MHz, DMSO-d$_6$) δ 2.86 (s, 3H), 3.02 (s, 3H), 3.22-3.32 (m, 2H), 3.57-3.69 (m, 1H), 3.86-4.04 (m, 2H), 4.06-4.15 (m, 1H), 4.16-4.27 (m, 1H), 4.53-4.63 (m, 1H), 4.66-4.81 (m, 1H), 6.90-7.08 (m, 1H), 7.24-7.35 (m, 1H), 7.47-7.53 (m, 1H), 7.55-7.74 (m, 3H), 11.47-11.64 (m, 1H). ESI-MS m/z [M+H]$^+$ calc'd for C$_{21}$H$_{24}$N$_6$O$_2$, 393.20. found 393.3

Example 44

2-(2-(1H-indol-4-yl)-6a,7,9,10-tetrahydro-[1,4]ox-azino[3,4-h]pteridin-5(6H)-yl)-N-isopropyl-N-methylacetamide

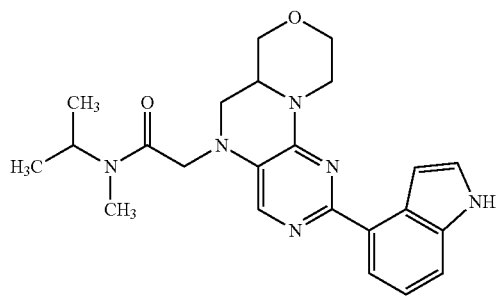 [SMILES: CC(C)N(C)C(=O)CN1CC2COCCN2c2nc(-c3cccc4[nH]ccc34)ncc21]

$^1$H NMR (400 MHz, DMSO-d$_6$) δ 0.99-1.12 (m, 6H), 1.14-1.29 (m, 3H), 2.68-2.73 (m, 1H), 2.80-2.88 (m, 2H), 3.56-3.68 (m, 1H), 3.84-4.29 (m, 5H), 4.46-4.57 (m, 1H), 4.58-4.79 (m, 2H), 6.92-7.09 (m, 1H), 7.22-7.35 (m, 1H), 7.37-7.49 (m, 1H), 7.52-7.77 (m, 3H), 11.40-11.66 (m, 1H). ESI-MS m/z [M+H]$^+$ calc'd for C$_{23}$H$_{28}$N$_6$O$_2$, 421.23. found 421.3.

Example 45

2-((2-(1H-indol-4-yl)-6a,7,9,10-tetrahydro-[1,4]ox-azino[3,4-h]pteridin-5(6H)-yl)methyl)benzonitrile

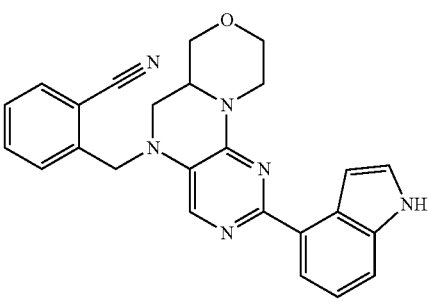 [SMILES: N#Cc1ccccc1CN1CC2COCCN2c2nc(-c3cccc4[nH]ccc34)ncc21]

$^1$H NMR (400 MHz, DMSO-d$_6$) δ 3.14-3.44 (m, 4H), 3.55-3.67 (m, 1H), 3.92-4.05 (m, 2H), 4.07-4.16 (m, 1H), 4.65-4.89 (m, 3H), 6.97-7.08 (m, 1H), 7.21-7.33 (m, 1H), 7.58 (s, 7H), 7.88-7.99 (m, 1H), 11.46-11.62 (m, 1H). ESI-MS m/z [M+H]$^+$ calc'd for C$_{25}$H$_{22}$N$_6$O, 423.19. found 423.3.

Example 46

2-((2-(1H-indol-4-yl)-6a,7,9,10-tetrahydro-[1,4]oxazino[3,4-h]pteridin-5(6H)-yl)methyl)-4-fluorobenzonitrile

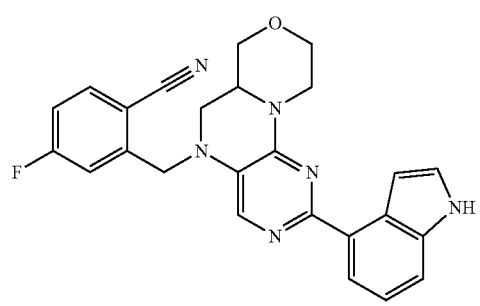 [SMILES: N#Cc1ccc(F)cc1CN1CC2COCCN2c2nc(-c3cccc4[nH]ccc34)ncc21]

$^1$H NMR (400 MHz, DMSO-d$_6$) δ 3.18-3.27 (m, 2H), 3.44-3.51 (m, 2H), 3.55-3.66 (m, 1H), 3.93-4.07 (m, 2H), 4.07-4.17 (m, 1H), 4.65-4.79 (m, 2H), 4.79-4.89 (m, 1H), 6.97-7.13 (m, 1H), 7.18-7.32 (m, 1H), 7.34-7.60 (m, 4H), 7.60-7.77 (m, 2H), 7.99-8.10 (m, 1H), 11.41-11.61 (m, 1H). ESI-MS m/z [M+H]$^+$ calc'd for C$_{25}$H$_{21}$FN$_6$O, 440.18. found 440.3.

Example 47

4-((2-(1H-indol-4-yl)-6a,7,9,10-tetrahydro-[1,4]oxazino[3,4-h]pteridin-5(6H)-yl)methyl)-3-methoxybenzonitrile

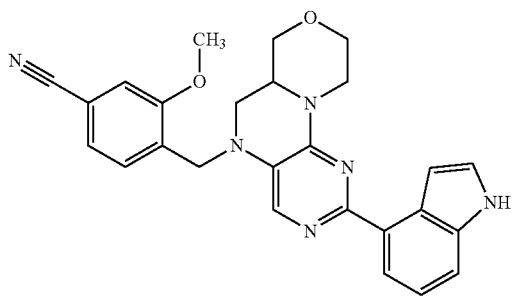 [SMILES: COc1cc(C#N)ccc1CN1CC2COCCN2c2nc(-c3cccc4[nH]ccc34)ncc21]

$^1$H NMR (400 MHz, DMSO-d$_6$) δ 3.18-3.27 (m, 2H), 3.44-3.54 (m, 2H), 3.55-3.66 (m, 1H), 3.87-3.96 (m, 4H), 3.96-4.04 (m, 1H), 4.07-4.16 (m, 1H), 4.48-4.63 (m, 2H), 4.64-4.76 (m, 1H), 6.95-7.08 (m, 1H), 7.18-7.30 (m, 1H), 7.34-7.76 (m, 7H), 11.40-11.60 (m, 1H). ESI-MS m/z [M+H]$^+$ calc'd for C$_{26}$H$_{24}$N$_6$O$_2$, 452.20. found 452.3.

The compounds of EXAMPLES 48 through 54, below, were prepared as shown in Scheme H, following the procedures described in PREPARATION x13 for the (i) acylation and PREPARATION x9 for the (ii) Suzuki coupling.

Scheme H

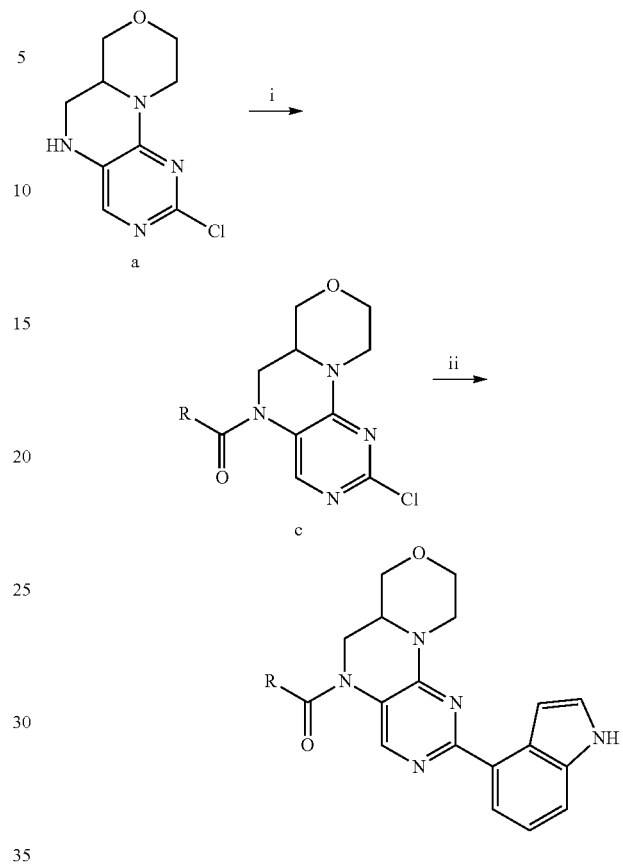

Reaction conditions: (i) starting material (a) (75 mg, 0.331 mmol), triethylamine (0.092 mL, 0.662 mmol), and RC(O)Cl (0.397 mmol) in CH$_2$Cl$_2$ (2 mL) at room temperature for 18 hours; (ii) (c) (1 equivalent), 1H-indol-4-ylboronic acid (2 equivalents), and PdCl$_2$(dppf) (0.05 equivalent) in a 5:1 mixture of dioxane and aqueous saturated NaHCO$_3$ (0.13 M of c) at 100° C. for 18 hours. The title compounds were isolated as TFA salts.

Example 48

1-(2-(1H-indol-4-yl)-6a,7,9,10-tetrahydro-[1,4]oxazino[3,4-h]pteridin-5(6H)-yl)-2-phenylethanone

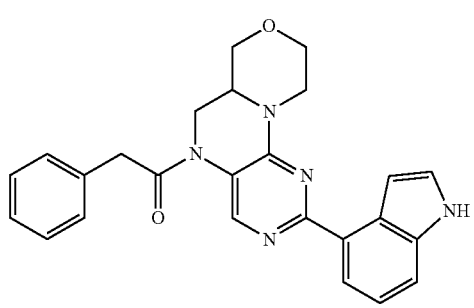 [SMILES: O=C(Cc1ccccc1)N1CC2COCCN2c2nc(-c3cccc4[nH]ccc34)ncc21]

$^1$H NMR (400 MHz, DMSO-d$_6$), δ 3.17-3.29 (m, 3H), 3.60-3.74 (m, 2H), 4.03 (m, 4H), 4.38-4.51 (m, 1H), 4.71-4.81 (m, 1H), 7.04-7.18 (m, 1H), 7.18-7.45 (m, 6H), 7.51-

7.59 (m, 1H), 7.62-7.73 (m, 1H), 7.78-7.93 (m, 1H), 8.58-9.02 (m, 1H), 11.41-11.60 (m, 1H). ESI-MS m/z [M+H]+ calc'd for C25H23N5O2, 426.19. found 426.4.

Example 49

1-(2-(1H-indol-4-yl)-6a,7,9,10-tetrahydro-[1,4]ox-azino[3,4-h]pteridin-5(6H)-yl)-2-(thiophen-2-yl) ethanone

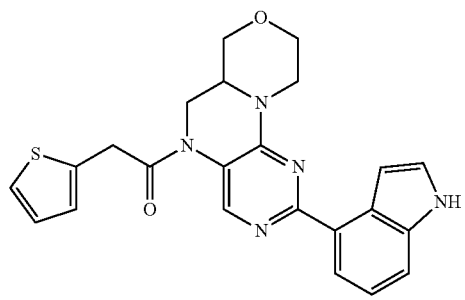 [SMILES: O=C(Cc1cccs1)N1CC2COCCN2c2nc(-c3cccc4[nH]ccc34)ncc21]

1H NMR (400 MHz, DMSO-d6) δ 3.16-3.28 (m, 3H), 3.67-3.83 (m, 2H), 3.96-4.12 (m, 2H), 4.21-4.34 (m, 2H), 4.38-4.54 (m, 1H), 4.70-4.82 (m, 1H), 6.78-7.09 (m, 3H), 7.12-7.32 (m, 2H), 7.35-7.49 (m, 1H), 7.49-7.56 (m, 1H), 7.57-7.70 (m, 1H), 7.81-8.05 (m, 1H), 11.32-11.59 (m, 1H). ESI-MS m/z [M+H]+ calc'd for C23H21N5O2S, 432.14. found 432.3.

Example 50

1-(2-(1H-indol-4-yl)-6a,7,9,10-tetrahydro-[1,4]ox-azino[3,4-h]pteridin-5(6H)-yl)-2-(3-methoxyphenyl) ethanone

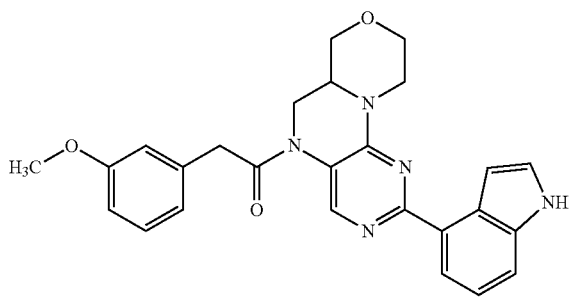 [SMILES: COc1cccc(CC(=O)N2CC3COCCN3c3nc(-c4cccc5[nH]ccc45)ncc32)c1]

1H NMR (400 MHz, DMSO-d6) δ 3.12-3.28 (m, 2H), 3.30-3.45 (m, 4H), 3.64-3.85 (m, 2H), 3.95-4.11 (m, 4H), 4.36-4.52 (m, 1H), 4.70-4.81 (m, 1H), 6.60-7.00 (m, 3H), 7.06-7.36 (m, 3H), 7.48-7.73 (m, 2H), 7.78-7.98 (m, 1H), 8.54-8.93 (m, 1H), 11.39-11.60 (m, 1H). ESI-MS m/z [M+H]+ calc'd for C26H25N5O3, 456.20. found 456.4.

Example 51

1-(2-(1H-indol-4-yl)-6a,7,9,10-tetrahydro-[1,4]ox-azino[3,4-h]pteridin-5(6H)-yl)-2-(thiophen-3-yl) ethanone

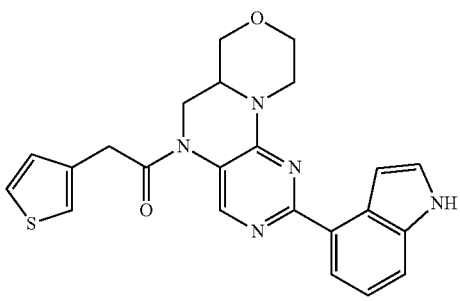 [SMILES: O=C(Cc1ccsc1)N1CC2COCCN2c2nc(-c3cccc4[nH]ccc34)ncc21]

1H NMR (400 MHz, DMSO-d6) δ 3.14-3.31 (m, 2H), 3.69-3.80 (m, 3H), 4.03 (m, 4H), 4.33-4.55 (m, 1H), 4.70-4.82 (m, 1H), 6.88-7.09 (m, 1H), 7.09-7.21 (m, 1H), 7.21-7.40 (m, 2H), 7.42-7.61 (m, 2H), 7.61-7.72 (m, 1H), 7.78-8.00 (m, 1H), 8.58-8.96 (m, 1H), 11.34-11.65 (m, 1H). ESI-MS m/z [M+H]+ calc'd for C23H21N5O2S, 432.14. found 432.3.

Example 52

1-(2-(1H-indol-4-yl)-6a,7,9,10-tetrahydro-[1,4]ox-azino[3,4-h]pteridin-5(6H)-yl)-2-(benzofuran-3-yl) ethanone

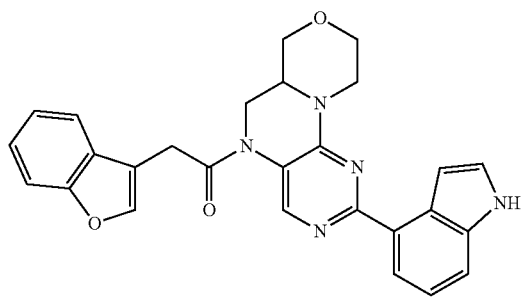 [SMILES: O=C(Cc1coc2ccccc12)N1CC2COCCN2c2nc(-c3cccc4[nH]ccc34)ncc21]

1H NMR (400 MHz, DMSO-d6) δ 3.31-3.38 (m, 3H), 3.47-3.65 (m, 1H), 3.78-3.95 (m, 1H), 3.99-4.26 (m, 4H), 4.43-4.60 (m, 1H), 4.70-4.84 (m, 1H), 7.05-7.39 (m, 4H), 7.43-7.72 (m, 4H), 7.75-8.07 (m, 2H), 8.52-8.91 (m, 1H), 11.31-11.59 (m, 1H). ESI-MS m/z [M+H]+ calc'd for C27H23N5O3, 466.18. found 466.3.

Example 53 benzyl 2-(1H-indol-4-yl)-6a,7,9,10-tetrahydro-[1,4]oxazino[3,4-h]pteridine-5(6H)-carboxylate

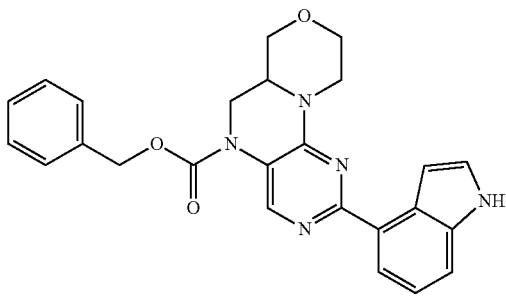 [SMILES: O=C(OCc1ccccc1)N1CC2COCCN2c2nc(-c3cccc4[nH]ccc34)ncc21]

$^1$H NMR (400 MHz, DMSO-d$_6$) δ 3.08-3.27 (m, 3H), 3.47-3.59 (m, 1H), 3.60-3.69 (m, 1H), 3.98-4.08 (m, 2H), 4.30-4.37 (m, 1H), 4.64-4.74 (m, 1H), 5.25 (s, 2H), 7.09-7.21 (m, 1H), 7.41 (m, 8H), 7.95-8.07 (m, 1H), 8.58-8.79 (m, 1H), 11.19-11.27 (m, 1H). ESI-MS m/z [M+H]$^+$ calc'd for C$_{25}$H$_{23}$N$_5$O$_3$, 442.18. found 442.3.

Example 54

2-(2,6-difluorophenyl)-1-(2-(indolin-4-yl)-6a,7,9,10-tetrahydro-[1,4]oxazino[3,4-h]pteridin-5(6H)-yl)ethanone

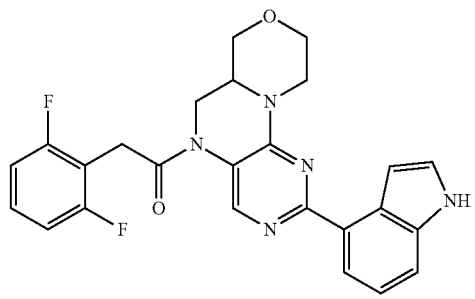 [SMILES: O=C(Cc1c(F)cccc1F)N1CC2COCCN2c2nc(-c3cccc4[nH]ccc34)ncc21]

$^1$H NMR (400 MHz, DMSO-d$_6$) δ 3.30-3.52 (m, 5H), 3.99-4.16 (m, 3H), 4.16-4.28 (m, 1H), 4.43-4.60 (m, 1H), 4.72-4.86 (m, 1H), 6.91-7.32 (m, 4H), 7.32-7.49 (m, 1H), 7.49-7.73 (m, 2H), 7.77-8.06 (m, 1H), 8.55-8.90 (m, 1H), 11.29-11.58 (m, 1H). ESI-MS m/z [M+H]$^+$ calc'd for C$_{25}$H$_{21}$F$_2$N$_5$O$_2$, 462.17. found 462.3.

Example 55

1-(2-(2-(difluoromethyl)-1H-benzo[c]imidazol-1-yl)-6a,7,9,10-tetrahydro-[1,4]oxazino[3,4-h]pteridin-5(6H)-yl)ethanone

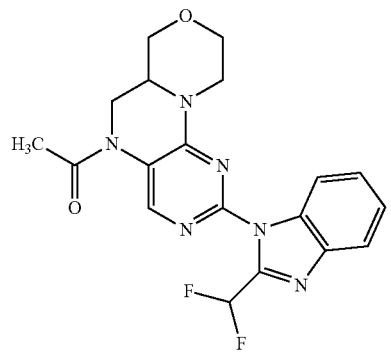 [SMILES: CC(=O)N1CC2COCCN2c2nc(-n3c(C(F)F)nc4ccccc43)ncc21]

To a 5 mL microwave vial equipped with a magnetic stirbar were added 1-(2-chloro-6a,7,9,10-tetrahydro-[1,4]oxazino[3,4-h]pteridin-5(6H)-yl)ethanone (300 mg, 1.116 mmol), 2-(difluoromethyl)-1H-benzo[d]imidazole (179 mg, 1.063 mmol), tris(dibenzylideneacetone)dipalladium(0) (38.9 mg, 0.043 mmol) and cesium carbonate (520 mg, 1.595 mmol). The vial was evacuated and filled with nitrogen four times and then sealed. DMF (2.1 mL) was added to give an orange suspension, which was heated to 140° C. for 45 minutes. The reaction mixture was heated for an additional 30 minutes, was subsequently diluted with ACN (3 mL), and was passed through a syringe filter. The filtrate was directly purified by preparatory HPLC using a gradient of 40-60% CH$_3$CN (with 0.035% TFA) in H$_2$O (with 0.05% TFA). Lyophilization of the collected fractions gave a TFA salt of the title compound (135 mg, 31.7%). ESI-MS m/z [M+H]$^+$ calc'd for C$_{19}$H$_{18}$F$_2$N$_6$O$_2$, 401.15. found 401.3.

Example 56

1-(2-(2-methyl-1H-benzo[d]imidazol-1-yl)-6a,7,9,10-tetrahydro-[1,4]oxazino[3,4-h]pteridin-5(6H)-yl)ethanone

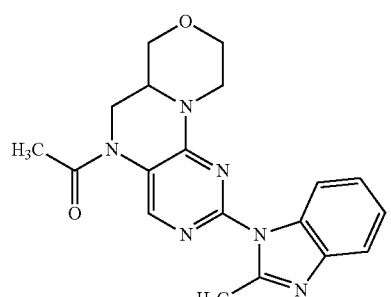

To a 5 mL microwave vial were added tris(dibenzylideneacetone)dipalladium(0) (38.9 mg, 0.043 mmol), 2-dicyclohexylphosphino-2',4',6'-triisopropyl-1,1'-biphenyl (40.6 mg, 0.085 mmol), 1-(2-chloro-6a,7,9,10-tetrahydro-[1,4]oxazino[3,4-h]pteridin-5(6H)-yl)ethanone (300 mg, 1.116 mmol), 2-methyl-1H-benzo[d]imidazole (141 mg, 1.063 mmol) and cesium carbonate (520 mg, 1.595 mmol). The vial was evacuated, filled with nitrogen, and sealed. DMF (2.1 mL) was added to give a dark brown suspension, which was heated in a microwave at 130° C. for 45 minutes. After cooling, DMF (2 mL) and ACN (4 mL) were added to the mixture, which was subsequently passed through a syringe filter. The crude product was purified by preparatory HPLC using a gradient of 15-40% $CH_3CN$ (with 0.035% TFA) in $H_2O$ (with 0.05% TFA). Lyophilization of the collected fractions gave a TFA salt of the title compound (241 mg, 47.4%). $^1H$ NMR (DMSO-$d_6$) δ 2.22 (s, 3H), 2.80-2.89 (m, 3H), 3.07-3.21 (m, 2H), 3.39-3.51 (m, 1H), 3.66 (br s, 1H), 3.96 (ddd, J=19.8, 11.4, 3.2 Hz, 2H), 4.09-4.56 (m, 2H), 7.26-7.39 (m, 2H), 7.62-7.69 (m, 1H), 8.06-8.14 (m, 1H), 8.26-8.92 (m, 1H). ESI-MS m/z [M+H]$^+$ calc'd for $C_{19}H_{20}N_6O_2$, 365.16. found 365.3.

Example 57 tert-butyl ((1r,4r)-4-((2-(1H-indol-4-yl)-6a,7,9,10-tetrahydro-[1,4]oxazino[3,4-h]pteridin-5(6H)-yl)methyl)cyclohexyl)carbamate

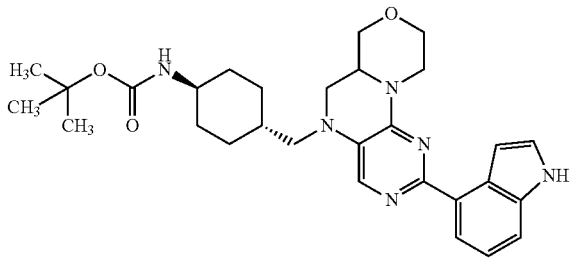 [SMILES: CC(C)(C)OC(=O)N[C@H]1CC[C@H](CN2CC3COCCN3c3nc(-c4cccc5[nH]ccc45)ncc32)CC1]

To a microwave vial were added tert-butyl (1r,4r)-4-((2-chloro-6a,7,9,10-tetrahydro-[1,4]oxazino[3,4-h]pteridin-5(6H)-yl)methyl)cyclohexylcarbamate (PREPARATION x23, 31 mg, 0.071 mmol), 1H-indol-4-ylboronic acid (22.79 mg, 0.142 mmol) and $PdCl_2$(dppf)-DCM (2.89 mg, 3.54 μmol) in dioxane (1.1 mL) and aqueous saturated $NaHCO_3$ (0.223 mL). The reaction mixture was heated in microwave at 100° C. for 1 hour. The mixture was subsequently filtered and the filtrate was purified by preparatory HPLC using a gradient of 65-90% ACN in $H_2O$ with 10 mmol $NH_4HCO_3$. The pure fractions were combined and lyophilized to give the title compound as a yellow solid (2 mg, 5.4%). $^1H$ NMR (500 MHz, DMSO-$d_6$) δ 1.00-1.18 (m, 4H), 1.37 (s, 9H), 1.66 (d, J=10.25 Hz, 1H), 1.76 (d, J=6.83 Hz, 5H), 2.98-3.08 (m, 2H), 3.09-3.14 (m, 2H), 3.16-3.21 (m, 2H), 3.49-3.60 (m, 2H), 3.93 (dd, J=10.98, 3.17 Hz, 1H), 4.05 (dd, J=11.23, 3.42 Hz, 1H), 4.47-4.52 (m, 1H), 6.70 (d, J=8.30 Hz, 1H), 7.11 (t, J=7.81 Hz, 1H), 7.32-7.34 (m, 1H), 7.35-7.36 (m, 1H), 7.37-7.40 (m, 1H), 7.76 (s, 1H), 7.92 (dd, J=7.32, 0.98 Hz, 1H), 11.08 (s, 1H). ESI-MS m/z [M+H]$^+$ calc'd for $C_{29}H_{38}N_6O_3$, 519.3. found 519.5.

Example 58

(1r,4r)-4-((2-(1H-indol-4-yl)-6a,7,9,10-tetrahydro-[1,4]oxazino[3,4-h]pteridin-5(6H)-yl)methyl)cyclohexanamine

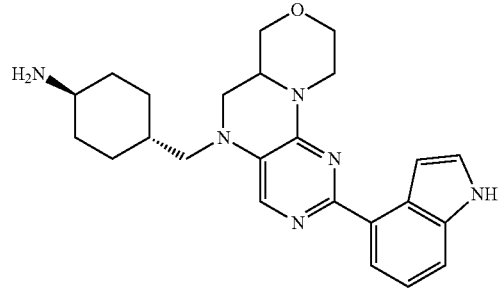 [SMILES: N[C@H]1CC[C@H](CN2CC3COCCN3c3nc(-c4cccc5[nH]ccc45)ncc32)CC1]

To a solution of tert-butyl (1r,4r)-4-((2-(1H-indol-4-yl)-6a,7,9,10-tetrahydro-[1,4]oxazino[3,4-h]pteridin-5(6H)-yl)methyl)cyclohexylcarbamate (EXAMPLE 57, 10 mg, 0.019 mmol) in DCM (1 mL) was added TFA (1 mL, 12.98 mmol) at ambient temperature under nitrogen. The reaction mixture was stirred for 1 hour and then concentrated in vacuo. The crude material was purified by preparatory HPLC using a gradient of 15-40% $CH_3CN$ (with 0.035% TFA) in $H_2O$ (with 0.05% TFA). The fractions were collected and concentrated in vacuo to give a TFA salt of the title compound as a yellow solid (6 mg, 74%). $^1H$ NMR (500 MHz, $CD_3OD$) δ 1.20-1.30 (m, 2H), 1.33 (t, J=7.32 Hz, 1H), 1.37-1.40 (m, 1H), 1.41-1.50 (m, 2H), 1.87 (ddd, J=11.23, 7.81, 3.91 Hz, 1H), 1.99 (d, J=11.23 Hz, 2H), 2.09-2.15 (m, 2H), 3.08-3.16 (m, 2H), 3.18-3.28 (m, 3H), 3.37-3.44 (m, 2H), 3.53 (dd, J=12.20, 4.39 Hz, 1H), 3.72 (td, J=11.96, 2.93 Hz, 1H), 3.97-4.03 (m, 1H), 4.09 (dd, J=11.23, 3.42 Hz, 1H), 4.16 (dd, J=11.72, 3.91 Hz, 1H), 4.94-4.99 (m, 1H), 7.04 (dd, J=2.93, 0.98 Hz, 1H), 7.32 (t, J=7.81 Hz, 1H), 7.46 (s, 1H), 7.50 (d, J=3.42 Hz, 1H), 7.59-7.62 (m, 1H), 7.70 (d, J=7.81 Hz, 1H). ESI-MS m/z [M+H]$^+$ calc'd for $C_{24}H_{30}N_6O$, 419.25. found 419.6.

Example 59

3-((2-(1H-indol-4-yl)-6a,7,9,10-tetrahydro-[1,4]oxazino[3,4-h]pteridin-5(6H)-yl)methyl)benzonitrile

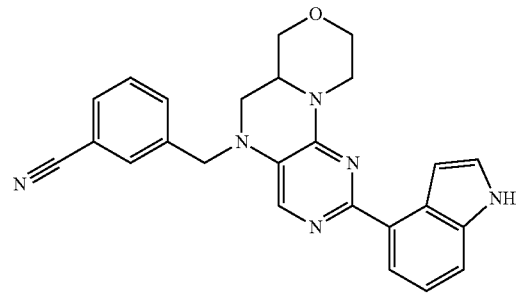 [SMILES: N#Cc1cccc(CN2CC3COCCN3c3nc(-c4cccc5[nH]ccc45)ncc32)c1]

The title compound was prepared in a manner similar to EXAMPLE 3 using 3-((2-chloro-6a,7,9,10-tetrahydro-[1,4]oxazino[3,4-h]pteridin-5(6H)-yl)methyl)benzonitrile (PREPARATION x14, 59 mg, 0.173 mmol), $PdCl_2$(dppf) (6.32 mg, 8.63 μmol) and 1H-indol-4-ylboronic acid (55.6 mg, 0.345 mmol) in dioxane (2 mL) and aqueous saturated NaHCO$_3$ (0.4 mL). $^1$H NMR (400 MHz, DMSO-d$_6$) δ 3.16-3.32 (m, 3H), 3.55-3.66 (m, 2H), 3.92-4.06 (m, 2H), 4.07-4.16 (m, 1H), 4.57-4.78 (m, 3H), 6.96-7.07 (m, 1H), 7.20-7.32 (m, 1H), 7.40-7.48 (m, 1H), 7.52-7.69 (m, 4H), 7.71-7.84 (m, 2H), 7.85-7.93 (m, 1H), 11.45-11.59 (m, 1H). ESI-MS m/z [M+H]$^+$ calc'd for C$_{25}$H$_{22}$N$_6$O, 423.19. found 423.3.

Example 60

3-((2-(1H-indol-4-yl)-6a,7,9,10-tetrahydro-[1,4]oxazino[3,4-h]pteridin-5(6H)-yl)methyl)-4-fluorobenzonitrile

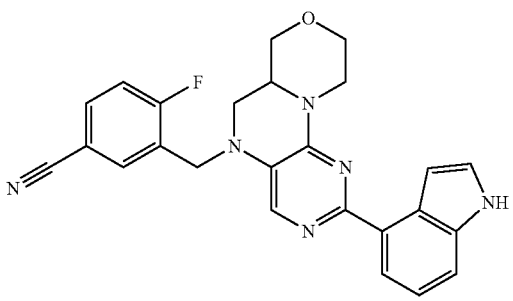 [SMILES: N#Cc1ccc(F)c(CN2CC3COCCN3c3nc(-c4cccc5[nH]ccc45)ncc32)c1]

The title compound was prepared in a manner similar to EXAMPLE 3 using 3-((2-chloro-6a,7,9,10-tetrahydro-[1,4]oxazino[3,4-h]pteridin-5(6H)-yl)methyl)-4-fluorobenzonitrile (PREPARATION x15, 73 mg, 0.203 mmol), PdCl$_2$(dppf) (7.42 mg, 10.14 μmol) and 1H-indol-4-ylboronic acid (65.3 mg, 0.406 mmol) in dioxane (2 mL) and aqueous saturated NaHCO$_3$ (0.4 mL). $^1$H NMR (400 MHz, DMSO-d$_6$) δ 3.18-3.30 (m, 3H), 3.46-3.53 (m, 1H), 3.56-3.67 (m, 1H), 3.92-4.05 (m, 2H), 4.07-4.17 (m, 1H), 4.58-4.78 (m, 3H), 6.98-7.08 (m, 1H), 7.22-7.32 (m, 1H), 7.48-7.60 (m, 3H), 7.60-7.70 (m, 2H), 7.89-8.03 (m, 2H), 11.47-11.58 (m, 1H). ESI-MS m/z [M+H]$^+$ calc'd for C$_{25}$H$_{21}$FN$_6$O, 441.18. found 441.3.

Example 61

1-(4-(5-benzyl-5,6,6a,7,9,10-hexahydro-[1,4]oxazino[3,4-h]pteridin-2-yl)phenyl)-3-methylurea

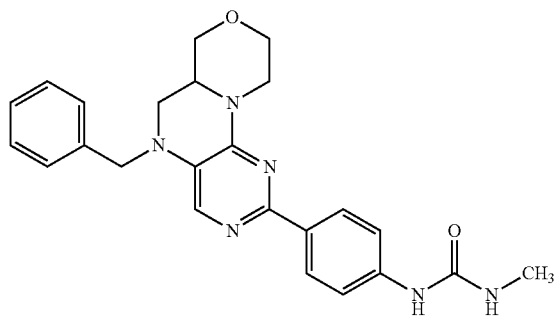 [SMILES: CNC(=O)Nc1ccc(-c2ncc3c(n2)N2CCOCC2CN3Cc2ccccc2)cc1]

5-Benzyl-2-chloro-5,6,6a,7,9,10-hexahydro-[1,4]oxazino[3,4-h]pteridine (PREPARATION x16, 55 mg, 0.174 mmol), 1-methyl-3-(4-(4,4,5,5-tetramethyl-1,3,2-dioxaborolan-2-yl)phenyl)urea (96 mg, 0.347 mmol) and PdCl$_2$(dppf) (6.35 mg, 8.68 μmol) were partially dissolved in dioxane (1.5 mL) and aqueous saturated NaHCO$_3$ (0.3 mL). The resulting brown suspension was heated to 100° C. and stirred overnight. The reaction mixture was subsequently diluted with ethyl acetate and washed with aqueous saturated NH$_4$Cl (3×15 mL). The combined organic layers were dried over MgSO$_4$, filtered, and concentrated in vacuo. The product was purified by LC/MS using a gradient of 25-50% CH$_3$CN (with 0.035% TFA) in H$_2$O (with 0.05% TFA). The pure fractions were combined and lyophilized to afford a TFA salt of the title compound as an off-white solid (4 mg, 5%). $^1$H NMR (400 MHz, DMSO-d$_6$) δ 2.59-2.73 (m, 3H), 3.04-3.21 (m, 3H), 3.48-3.66 (m, 2H), 3.78-4.14 (m, 3H), 4.41-4.62 (m, 2H), 4.69-4.87 (m, 1H), 6.06-6.27 (m, 1H), 7.37 (m, 6H), 7.49-7.64 (m, 2H), 7.91-8.13 (m, 2H), 8.80-9.02 (m, 1H). ESI-MS m/z [M+H]$^+$ calc'd for C$_{24}$H$_{26}$N$_6$O$_2$, 431.21. found 431.5.

The compounds of EXAMPLES 62 through 64, below, were prepared as shown in Scheme I, following the procedures described in PREPARATION x16 for the (i) alkylation and EXAMPLE 61 for the (ii) Suzuki coupling.

Scheme I

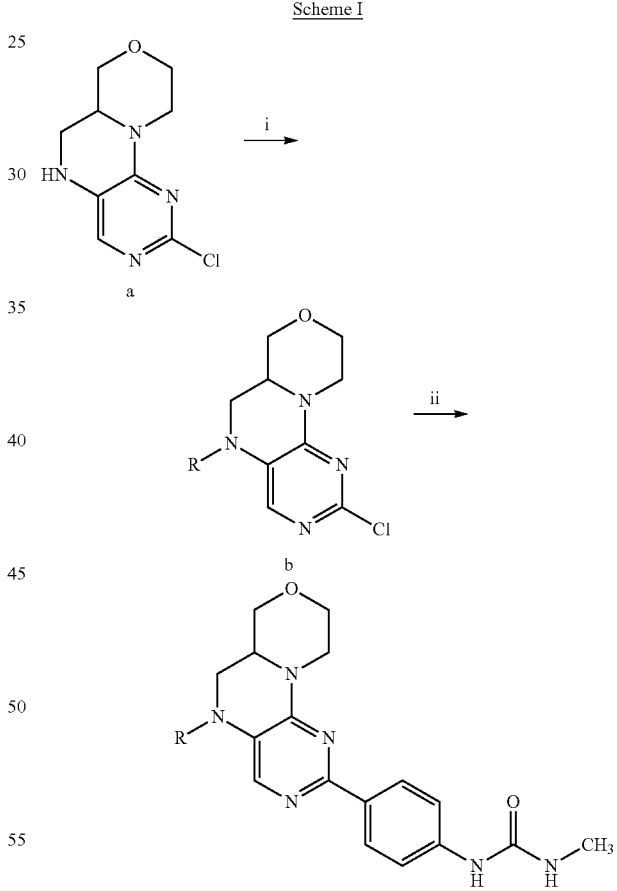

Reaction conditions: (i) starting material (a) (82 mg, 0.36 mmol), R—Br (0.39 mmol) and N,N-diisopropylethylamine (0.08 mL, 0.43 mmol) in DMF (2 mL) at room temperature for 48 hours; (ii) (b) (1.0 equivalent), 1-methyl-3-(4-(4,4,5,5-tetramethyl-1,3,2-dioxaborolan-2-yl)phenyl)urea (2.0 equivalents), and PdCl$_2$(dppf) (0.051 equivalents) in a 5:1 mixture of dioxane and aqueous saturated NaHCO$_3$ (0.094 M of b) at 100° C. for 18 hours. The title compounds were isolated as TFA salts.

Example 62

1-methyl-3-(4-(5-(4-methylbenzyl)-5,6,6a,7,9,10-hexahydro-[1,4]oxazino[3,4-h]pteridin-2-yl)phenyl)urea

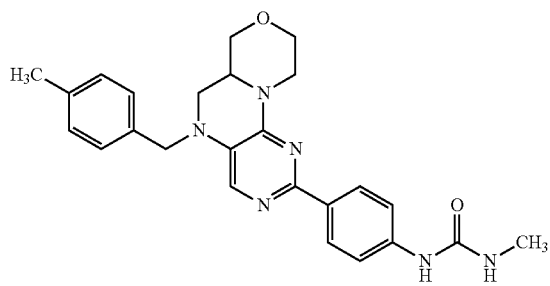

$^1$H NMR (400 MHz, DMSO-$d_6$) δ 2.29 (s, 3H), 2.62-2.69 (d, 3H), 3.04-3.15 (m, 1H), 3.31-3.45 (m, 3H), 3.51-3.63 (m, 1H), 3.92-4.11 (m, 3H), 4.40-4.58 (m, 2H), 4.77-4.89 (m, 1H), 6.16-6.29 (m, 1H), 7.13-7.31 (m, 4H), 7.33-7.41 (m, 1H), 7.54-7.63 (m, 2H), 7.97-8.08 (m, 2H), 8.93-9.04 (m, 1H). ESI-MS m/z [M+H]$^+$ calc'd for $C_{25}H_{28}N_6O_2$, 445.23. found 445.5.

Example 63

1-(4-(5-(4-chlorobenzyl)-5,6,6a,7,9,10-hexahydro-[1,4]oxazino[3,4-h]pteridin-2-yl)phenyl)-3-methylurea

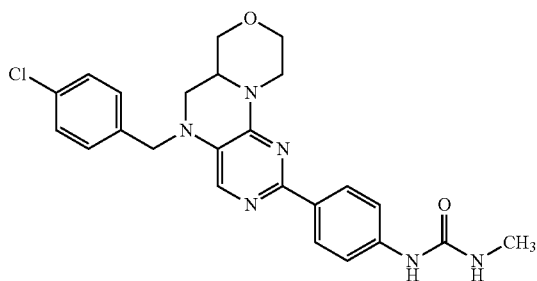 [SMILES: CNC(=O)Nc1ccc(-c2ncc3c(n2)N2CCOCC2CN3Cc2ccc(Cl)cc2)cc1]

$^1$H NMR (400 MHz, DMSO-$d_6$) δ 2.62-2.69 (m, 3H), 3.05-3.16 (m, 1H), 3.31-3.45 (m, 3H), 3.50-3.62 (m, 1H), 3.83-4.11 (m, 3H), 4.45-4.60 (m, 2H), 4.75-4.86 (m, 1H), 6.11-6.23 (m, 1H), 7.33-7.50 (m, 5H), 7.50-7.62 (m, 2H), 7.97-8.09 (m, 2H), 8.84-9.01 (br s, 1H). ESI-MS m/z [M+H]$^+$ calc'd for $C_{24}H_{25}ClN_6O_2$, 465.17. found 465.4.

Example 64

1-(4-(5-(cyclopropylmethyl)-5,6,6a,7,9,10-hexahydro-[1,4]oxazino[3,4-h]pteridin-2-yl)phenyl)-3-methylurea

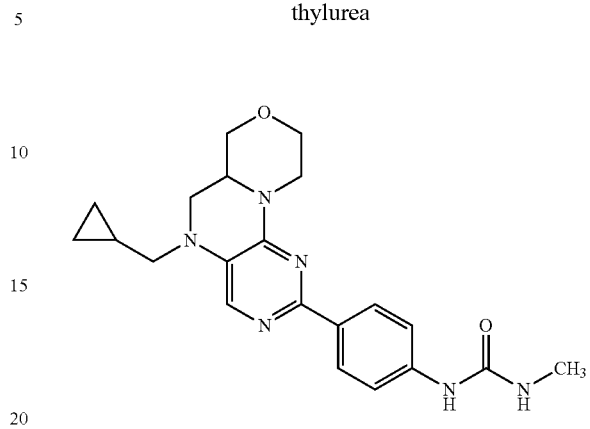

$^1$H NMR (400 MHz, DMSO-$d_6$) δ 0.23-0.35 (m, 2H), 0.51-0.60 (m, 2H), 0.98-1.10 (m, 1H), 2.66 (d, J=4.55 Hz, 3H), 2.97-3.14 (m, 2H), 3.16-3.35 (m, 3H), 3.49-3.61 (m, 3H), 3.82-3.92 (m, 2H), 3.97-4.10 (m, 2H), 4.77-4.87 (m, 1H), 6.18-6.27 (m, 1H), 7.51 (s, 1H), 7.58 (d, J=9.09 Hz, 2H), 8.05 (d, J=8.84 Hz, 2H), 8.94-9.04 (m, 1H). ESI-MS m/z [M+H]$^+$ calc'd for $C_{21}H_{26}N_6O_2$, 395.21. found 395.4.

Example 65

2-(1H-pyrrolo[2,3-b]pyridin-3-yl)-5,6,6a,7,9,10-hexahydro-[1,4]oxazino[3,4-h]pteridine

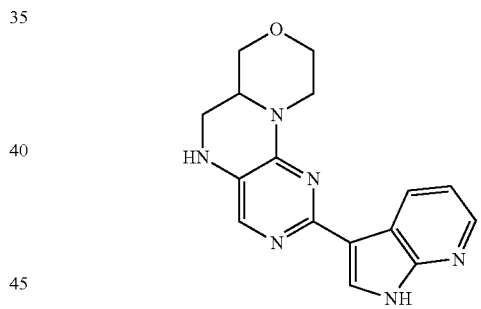

A mixture of 2-chloro-5,6,6a,7,9,10-hexahydro-[1,4]oxazino[3,4-h]pteridine (PREPARATION x2, 50 mg, 0.221 mmol), tert-butyl 3-(4,4,5,5-tetramethyl-1,3,2-dioxaborolan-2-yl)-1H-pyrrolo[2,3-b]pyridine-1-carboxylate (114 mg, 0.331 mmol) and PdCl$_2$(dppf) (8.07 mg, 0.011 mmol) were partially dissolved in dioxane (2 mL) and aqueous saturated NaHCO$_3$ (0.4 mL). The resulting brown suspension was stirred overnight at 100° C. By the following day, the coupling reaction was complete and the BOC group had also been removed. The reaction mixture was subsequently diluted with ethyl acetate and washed with brine (3×10 mL). The combined organic layers were dried over MgSO$_4$, filtered, and concentrated in vacuo. The product was first purified by LC/MS using a gradient of 0-30% CH$_3$CN (with 0.035% TFA) in H$_2$O (with 0.05% TFA). The product and the starting material co-eluted, yielding no pure fractions. The fractions which contained product were concentrated and lyophilized to give a yellow solid, which was re-purified via LC/MS using a 15-40% gradient of CH$_3$CN in H$_2$O with 10 mmol NH$_4$HCO$_3$. The pure fractions were combined and lyophilized to give the title compound as a white solid (10 mg, 15%). ¹H NMR (400 MHz, DMSO-d₆) δ 2.89-3.08 (m, 2H), 3.12-3.26 (m, 1H), 3.39-3.52 (m, 2H), 3.52-3.67 (m, 1H), 3.83-4.14 (m, 2H), 4.45-4.63 (m, 1H), 5.60-5.80 (m, 1H), 7.04-7.23 (m, 1H), 7.53-7.68 (m, 1H), 7.91-8.03 (m, 1H), 8.13-8.30 (m, 1H), 8.59-8.78 (m, 1H), 11.70-11.88 (m, 1H). ESI-MS m/z [M+H]⁺ calc'd for $C_{16}H_{16}N_6O$, 309.14. found 309.3.

Example 66

2-(benzo[c/][1,3]dioxol-4-yl)-5,6,6a,7,9,10-hexahydro-[1,4]oxazino[3,4-h]pteridine

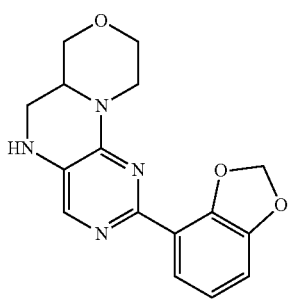 [SMILES: c1cc2c(c(-c3ncc4c(n3)N3CCOCC3CN4)c1)OCO2]

A mixture of 2-chloro-5,6,6a,7,9,10-hexahydro-[1,4]oxazino[3,4-h]pteridine (PREPARATION x2, 50 mg, 0.221 mmol), benzo[c/][1,3]dioxol-4-ylboronic acid (54.9 mg, 0.331 mmol) (54.9 mg, 0.331 mmol) and PdCl₂(dppf) (8.07 mg, 0.011 mmol) were partially dissolved in dioxane (2 mL) and aqueous saturated NaHCO₃ (0.4 mL). The resulting brown suspension was stirred overnight at 100° C. The reaction mixture was subsequently diluted with ethyl acetate and washed with aqueous saturated NH₄Cl (3×5 mL). The combined organic layers were dried over MgSO₄, filtered, and concentrated in vacuo. The product was purified by LC/MS using a gradient of 15-45% CH₃CN (with 0.035% TFA) in H₂O (with 0.05% TFA). Product containing fractions were pooled, concentrated, and repurified by column chromatography using a gradient of 25-55% CH₃CN in H₂O (10 mM (NH₄)₂CO₃). The pure fractions were combined and lyophilized to afford the title compound as a white solid (3.4 mg, 5%). ¹H NMR (400 MHz, DMSO-d₆) δ 2.84-3.02 (m, 2H), 3.10-3.20 (m, 1H), 3.37-3.59 (m, 5H), 3.85-4.04 (m, 2H), 4.40-4.53 (m, 1H), 5.95-6.08 (m, 3H), 6.78-6.93 (m, 2H), 7.52-7.60 (m, 1H), 7.60-7.66 (m, 1H). ESI-MS m/z [M+H]⁺ calc'd for $C_{16}H_{16}N_4O_3$, 313.12. found 313.3.

Example 67

(R)-2-(2-(difluoromethyl)-1H-benzo[d]imidazol-1-yl)-5-(4-(methylsulfonyl)benzyl)-5,6,6a,7,9,10-hexahydro-[1,4]oxazino[3,4-h]pteridine

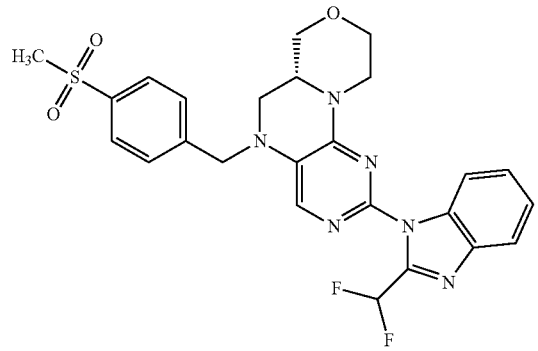 [SMILES: CS(=O)(=O)c1ccc(CN2C[C@@H]3COCCN3c3nc(-n4c(C(F)F)nc5ccccc54)ncc32)cc1]

A mixture of (R)-2-chloro-5-(4-(methylsulfonyl)benzyl)-5,6,6a,7,9,10-hexahydro-[1,4]oxazino[3,4-h]pteridine (PREPARATION x10 50 mg, 0.127 mmol), 2-(difluoromethyl)-1H-benzo[d]imidazole (21.29 mg, 0.127 mmol), cesium carbonate (61.9 mg, 0.190 mmol), tris(dibenzylideneacetone)dipalladium(0) (4.64 mg, 5.06 μmol) and 2-dicyclohexylphosphino-2',4',6'-triisopropyl-1,1'-biphenyl (4.83 mg, 10.13 μmol) in DMF 253 μL was heated to 130° C. in a microwave for 40 minutes. Additional tris(dibenzylideneacetone)dipalladium(0) (4.64 mg, 5.06 μmol) and 2-dicyclohexylphosphino-2',4',6'-triisopropyl-1,1'-biphenyl (4.83 mg, 10.13 μmol) were added, and the reaction mixture was heated to 130° C. in a microwave for 1 hour. EtOAc and water were added and the mixture was filtered through Celite and extracted with EtOAc (2×). The combined extracts were washed with brine, dried over Na₂SO₄, filtered, and concentrated in vacuo. The residue was purified by column chromatography (SiO₂—NH₂, 30-100% EtOAc/hexane gradient) to afford the title compound as a yellow solid (14.3 mg, 21.4%). ¹H NMR (400 MHz, CDCl₃) δ 3.08 (s, 3H), 3.19-3.38 (m, 4H), 3.68 (td, J=12.00, 2.78 Hz, 1H), 3.83-3.92 (m, 1H), 3.94-4.02 (m, 1H), 4.11-4.20 (m, 1H), 4.44-4.63 (m, 3H), 7.36-7.75 (m, 6H), 7.93-8.01 (m, 3H), 8.17-8.23 (m, 1H). ESI-MS m/z [M+H]⁺ calc'd for $C_{25}H_{24}F_2N_6O_3S$, 527.16. found 527.3.

Example 68

(R)-tert-butyl 2-(2-(1H-indol-4-yl)-6a,7,9,10-tetrahydro-[1,4]oxazino[3,4-h]pteridin-5(6H)-yl)acetate

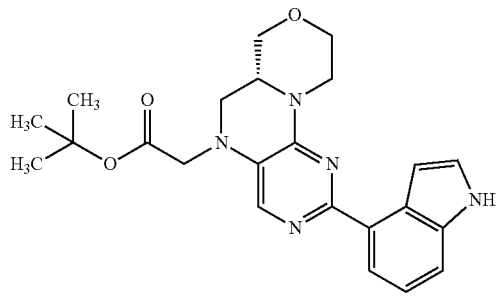 [SMILES: CC(C)(C)OC(=O)CN1C[C@@H]2COCCN2c2nc(-c3cccc4[nH]ccc34)ncc21]

A mixture of (R)-tert-butyl 2-(2-chloro-6a,7,9,10-tetrahydro-[1,4]oxazino[3,4-h]pteridin-5(6H)-yl)acetate (PREPARATION x24, 100 mg, 0.293 mmol), indole-4-boronic acid (70.8 mg, 0.440 mmol), tetrakis(triphenylphosphine)palladium(0) (33.9 mg, 0.029 mmol) and sodium carbonate (62.2 mg, 0.587 mmol) in 1,4-dioxane (1 mL) and water (0.5 mL) was heated to 120° C. for 30 minutes in a microwave. After cooling to room temperature, the reaction mixture was diluted with EtOAc, filtered through Celite, washed with water and brine, dried over $Na_2SO_4$, filtered, and concentrated in vacuo. The residue was purified by column chromatography ($SiO_2$, 20-80% EtOAc/hexane gradient) to afford the title compound as an off-white solid (110 mg, 89%). $^1$H NMR (400 MHz, $CDCl_3$) δ 1.48 (s, 9H), 3.07-3.36 (m, 3H), 3.42-3.51 (m, 1H), 3.62-3.79 (m, 3H), 3.93 (dd, J=10.86, 3.28 Hz, 1H), 4.01-4.16 (m, 2H), 4.77 (dd, J=13.39, 2.02 Hz, 1H), 7.22-7.31 (m, 2H), 7.39-7.46 (m, 2H), 7.66 (s, 1H), 8.01 (dd, J=7.45, 0.88 Hz, 1H), 8.26 (br s, 1H). ESI-MS m/z [M+H]$^+$ calc'd for $C_{23}H_{27}N_5O_3$, 422.21. found 422.3.

Example 69

(R)-2-(2-(1H-indol-4-yl)-6a,7,9,10-tetrahydro-[1,4]oxazino[3,4-h]pteridin-5(6H)-yl)acetic acid

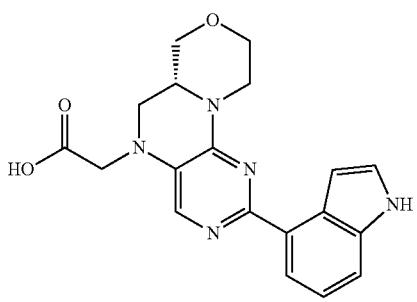 [SMILES: O=C(O)CN1C[C@@H]2COCCN2c2nc(-c3cccc4[nH]ccc34)ncc21]

A mixture of (R)-tert-butyl 2-(2-(1H-indol-4-yl)-6a,7,9,10-tetrahydro-[1,4]oxazino[3,4-h]pteridin-5(6H)-yl)acetate (250 mg, 0.593 mmol), HCl (4M in 1,4-dioxane) (10 mL, 40.0 mmol) and 1 N hydrochloric acid (2 mL, 2 mmol) was stirred at 70° C. for 1 hour. The mixture was subsequently concentrated in vacuo to give an HCl salt of the title compound as a brown solid (245 mg, 103%). $^1$H NMR (400 MHz, DMSO-$d_6$) δ 3.17-3.74 (m, 5H), 3.90-4.03 (m, 2H), 4.06-4.17 (m, 2H), 4.46 (d, J=18.19 Hz, 1H), 4.73 (d, J=12.13 Hz, 1H), 7.00 (br s, 1H), 7.29 (t, J=7.83 Hz, 1H), 7.52-7.62 (m, 2H), 7.69 (d, J=7.83 Hz, 2H), 11.61 (br s, 1H), 13.14 (br s, 1H) 14.22 (br s, 1H). ESI-MS m/z [M+H]$^+$ calc'd for $C_{19}H_{19}N_5O_3$, 366.15. found 366.2.

Example 70

(R)-2-(2-(1H-indol-4-yl)-6a,7,9,10-tetrahydro-[1,4]oxazino[3,4-h]pteridin-5(6H)-yl)-N-(cyclopropylmethyl)acetamide

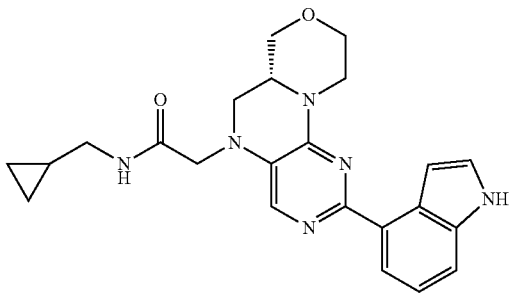 [SMILES: O=C(CN1C[C@@H]2COCCN2c2nc(-c3cccc4[nH]ccc34)ncc21)NCC1CC1]

To a mixture of (R)-2-(2-(1H-indol-4-yl)-6a,7,9,10-tetrahydro-[1,4]oxazino[3,4-h]pteridin-5(6H)-yl)acetic acid, HCl (60 mg, 0.149 mmol), cyclopropanemethylamine (0.019 mL, 0.224 mmol) and $Et_3N$ (0.062 mL, 0.448 mmol) in DMF (1 mL) was added HATU (73.8 mg, 0.194 mmol) at room temperature. The resulting mixture was stirred at room temperature for 1 hour, diluted with EtOAc, washed with aqueous saturated $NaHCO_3$ and brine, dried over $Na_2SO_4$, filtered, and concentrated in vacuo. The residue was purified by column chromatography ($SiO_2$—NH, 0-10% MeOH/$CHCl_3$ gradient) and recrystallized from MeOH/EtOAc to give the title compound as a white solid (6 mg, 9.6%). $^1$H NMR (400 MHz, DMSO-$d_6$) δ 0.13-0.20 (m, 2H), 0.37-0.44 (m, 2H), 0.93 (s, 1H), 2.93-3.10 (m, 3H), 3.15-3.37 (m, 3H), 3.53-3.69 (m, 2H), 3.79 (d, J=17.18 Hz, 1H), 3.91 (s, 1H), 4.00-4.11 (m, 2H), 4.55 (d, J=13.39 Hz, 1H), 7.11 (t, J=7.83 Hz, 1H), 7.28-7.43 (m, 3H), 7.58 (s, 1H), 7.92 (d, J=7.33 Hz, 1H), 8.16 (t, J=5.81 Hz, 1H), 11.11 (br s, 1H). ESI-MS m/z [M+H]$^+$ calc'd for $C_{23}H_{26}N_6O_2$, 419.21. found 419.3.

Example 71

(R)-2-(2-(1H-indol-4-yl)-6a,7,9,10-tetrahydro-[1,4]oxazino[3,4-h]pteridin-5(6H)-yl)-N-(2-hydroxy-2-methylpropyl)acetamide

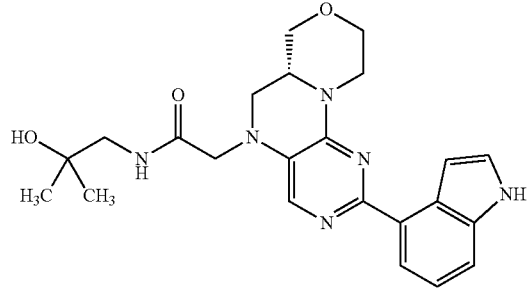 [SMILES: CC(C)(O)CNC(=O)CN1C[C@@H]2COCCN2c2nc(-c3cccc4[nH]ccc34)ncc21]

To a mixture of (R)-2-(2-(1H-indol-4-yl)-6a,7,9,10-tetrahydro-[1,4]oxazino[3,4-h]pteridin-5(6H)-yl)acetic acid, HCl (60 mg, 0.149 mmol), 1-amino-2-methyl-propan-2-ol (19.96 mg, 0.224 mmol) and $Et_3N$ (0.062 mL, 0.448 mmol) in DMF (1 mL) was added HATU (73.8 mg, 0.194 mmol) at room temperature. The resulting mixture was stirred at room temperature for 1 hour, diluted with EtOAc, washed with aqueous saturated $NaHCO_3$ and brine, dried over $Na_2SO_4$, filtered, and concentrated in vacuo. The residue was purified by column chromatography ($SIO_2$—NH, 0-10% MeOH/$CHCl_3$ gradient) to give the title compound as an off-white solid (23.3 mg, 35.7%). $^1$H NMR (400 MHz, DMSO-$d_6$) δ 1.06 (s, 6H), 3.07 (t, J=5.81 Hz, 3H), 3.20 (t, J=10.86 Hz, 1H), 3.35 (d, J=6.32 Hz, 2H), 3.51-3.66 (m, 2H), 3.83 (d, J=16.93 Hz, 1H), 3.91 (dd, J=11.12, 3.28 Hz, 1H), 4.03-4.17 (m, 2H), 4.49-4.59 (m, 2H), 7.11 (t, J=7.71 Hz, 1H), 7.27-7.43 (m, 3H), 7.59-7.67 (m, 1H), 7.87-7.98 (m, 2H), 11.11 (br s, 1H). ESI-MS m/z [M+H]$^+$ calc'd for $C_{23}H_{28}N_6O_3$, 437.22. found 437.4.

Example 72

(R)-2-(2-(1H-indol-4-yl)-6a,7,9,10-tetrahydro-[1,4]oxazino[3,4-h]pteridin-5(6H)-yl)-N-((1H-pyrazol-3-yl)methyl)acetamide

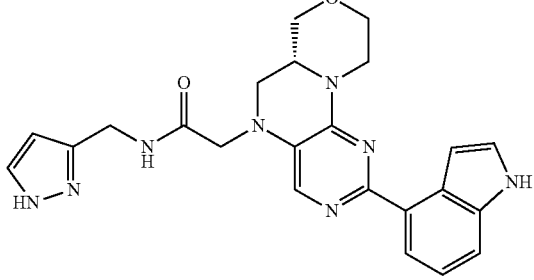

To a mixture of (R)-2-(2-(1H-indol-4-yl)-6a,7,9,10-tetrahydro-[1,4]oxazino[3,4-h]pteridin-5(6H)-yl)acetic acid, HCl (60 mg, 0.149 mmol), 1H-pyrazol-3-ylmethylamine (21.75 mg, 0.224 mmol) and Et$_3$N (0.062 mL, 0.448 mmol) in DMF (1 mL) was added HATU (73.8 mg, 0.194 mmol) at room temperature. The resulting mixture was stirred at room temperature for 1 hour and was subsequently diluted with EtOAc, washed with aqueous saturated NaHCO$_3$ and brine, dried over Na$_2$SO$_4$, filtered, and concentrated in vacuo. The residue was purified by column chromatography (SiO$_2$—NH, 0-10% MeOH/CHCl$_3$ gradient) to give the title compound as an off-white solid (34.9 mg, 52.6% yield). $^1$H NMR (400 MHz, DMSO-d$_6$) δ 3.02 (s, 1H), 3.14-3.42 (m, 3H), 3.51-3.72 (m, 2H), 3.80-3.95 (m, 2H), 4.02-4.14 (m, 2H), 4.31 (m, J=5.05 Hz, 2H), 4.49-4.59 (m, 1H), 6.14 (br s, 1H), 7.12 (t, J=7.83 Hz, 1H), 7.30-7.32 (m, 1H), 7.35-7.43 (m, 2H), 7.56-7.69 (m, 2H), 7.92 (dd, J=7.45, 0.88 Hz, 1H), 8.47 (br s, 1H), 11.12 (br s, 1H), 12.55-12.72 (m, 1H). ESI-MS m/z [M+H]$^+$ calc'd for C$_{23}$H$_{24}$N$_8$O$_2$, 445.20. found 445.3.

Example 73

(R)-2-(2-(1H-indol-4-yl)-6a,7,9,10-tetrahydro-[1,4]oxazino[3,4-h]pteridin-5(6H)-yl)-N-((tetrahydro-2H-pyran-4-yl)methyl)acetamide

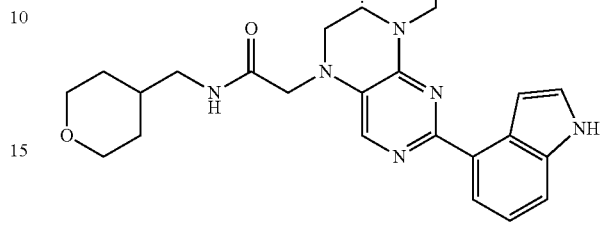

To a mixture of (R)-2-(2-(1H-indol-4-yl)-6a,7,9,10-tetrahydro-[1,4]oxazino[3,4-h]pteridin-5(6H)-yl)acetic acid, HCl (60 mg, 0.149 mmol), 4-aminomethyltetrahydropyran (25.8 mg, 0.224 mmol) and Et$_3$N (0.062 mL, 0.448 mmol) in DMF (1 mL) was added HATU (73.8 mg, 0.194 mmol) at room temperature. The resulting mixture was stirred at room temperature for 1 hour, diluted with EtOAc, washed with aqueous saturated NaHCO$_3$ and brine, dried over Na$_2$SO$_4$, filtered, and concentrated in vacuo. The residue was purified by column chromatography (SiO$_2$—NH, 0-10% MeOH/CHCl$_3$ gradient) to give the title compound as an off-white solid (14.5 mg, 21%). $^1$H NMR (400 MHz, DMSO-d$_6$) δ 1.07-1.22 (m, 2H), 1.50-1.74 (m, 3H), 2.93-3.09 (m, 3H), 3.15-3.37 (m, 5H), 3.53-3.69 (m, 2H), 3.76-3.86 (m, 3H), 3.91 (dd, J=11.12, 3.28 Hz, 1H), 3.99-4.12 (m, 2H), 4.54 (m, J=11.37 Hz, 1H), 7.11 (t, J=7.71 Hz, 1H), 7.30 (t, J=2.15 Hz, 1H), 7.34-7.42 (m, 2H), 7.58 (s, 1H), 7.91 (dd, J=7.45, 0.88 Hz, 1H), 8.10 (t, J=5.94 Hz, 1H), 11.11 (br s, 1H). ESI-MS m/z [M+H]$^+$ calc'd for C$_{25}$H$_{30}$N$_6$O$_3$, 463.24. found 463.4.

The compounds of EXAMPLES 74 through 79, below, were prepared as shown in Scheme J, following the procedures described in PREPARATION x9 for the (i) alkylation, PREPARATION x18 for (ii) conversion of the nitrile to the amide, and EXAMPLE 61 for the (iii) Suzuki coupling. The title compounds were isolated as TFA salts.

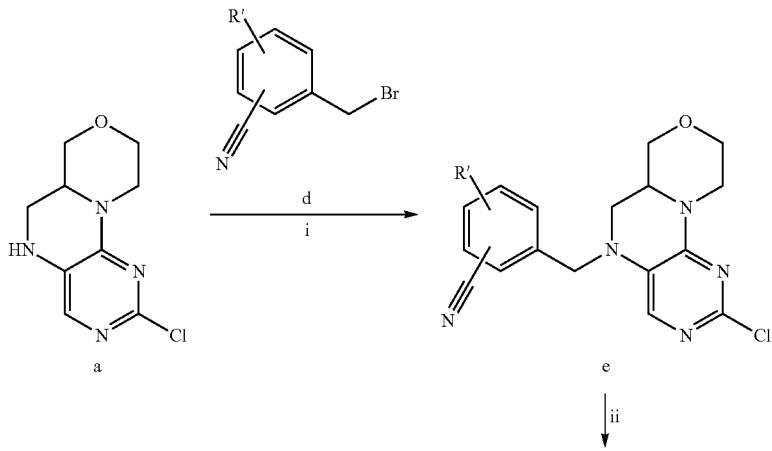

Scheme J

119

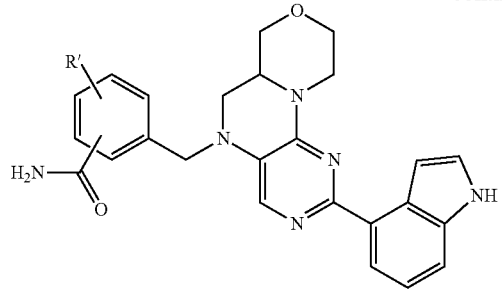

-continued

120

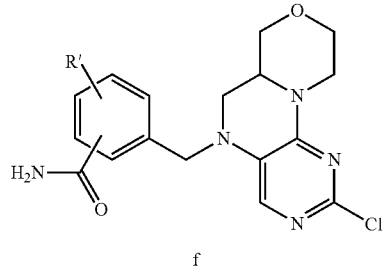

Reaction conditions: (i) starting material (a) (100 mg, 0.441 mmol), (d) (0.485 mmol), and sodium tert-butoxide (50.9 mg, 0.529 mmol) in DMSO (2.5 mL) at room temperature for 18 hours; (ii) (e) (1.0 equivalents) in concentrated H$_2$SO$_4$ (0.1 M of e) at room temperature for 18 hours; and (iii) (f) (1.0 equivalents), 1H-indol-4-ylboronic acid (2.0 equivalents), PdCl$_2$(dppf) (0.05 equivalents) in 5:1 mixture of dioxane and aqueous saturated NaHCO$_3$ (0.13 M of f) at 100° C. for 18 hours.

Example 74

2-((2-(1H-indol-4-yl)-6a,7,9,10-tetrahydro-[1,4]ox-azino[3,4-h]pteridin-5(6H)-yl)methyl)benzamide

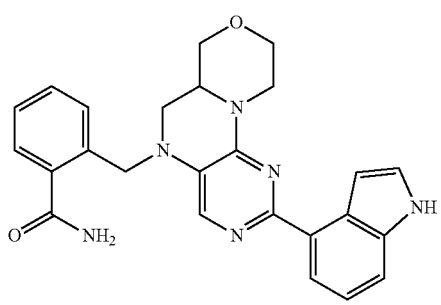 [SMILES: NC(=O)c1ccccc1CN1CC2COCCN2c2nc(-c3cccc4[nH]ccc34)ncc21]

$^1$H NMR (400 MHz, DMSO-d$_6$) δ 3.11-3.20 (m, 2H), 3.30-3.40 (m, 1H), 3.55-3.66 (m, 2H), 3.92-4.04 (m, 2H), 4.08-4.16 (m, 1H), 4.50-4.59 (m, 1H), 4.70-4.83 (m, 2H), 6.94-7.08 (m, 1H), 7.21-7.31 (m, 1H), 7.34-7.51 (m, 5H), 7.51-7.72 (m, 4H), 7.83-7.94 (m, 1H), 11.45-11.60 (m, 1H). ESI-MS m/z [M+H]$^+$ calc'd for C$_{25}$H$_{24}$N$_6$O$_2$, 440.20. found 440.3.

Example 75

2-((2-(1H-indol-4-yl)-6a,7,9,10-tetrahydro-[1,4]ox-azino[3,4-h]pteridin-5(6H)-yl)methyl)-4-fluorobenzamide

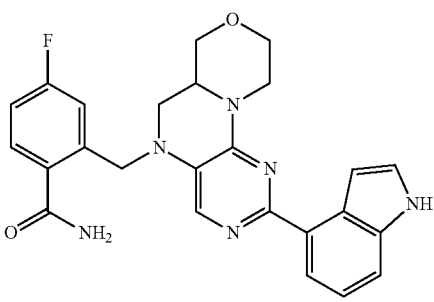 [SMILES: NC(=O)c1ccc(F)cc1CN1CC2COCCN2c2nc(-c3cccc4[nH]ccc34)ncc21]

$^1$H NMR (400 MHz, DMSO-d$_6$) δ 3.14-3.24 (m, 1H), 3.30-3.40 (m, 3H), 3.56-3.67 (m, 1H), 3.92-4.18 (m, 3H), 4.49-4.65 (m, 1H), 4.67-4.87 (m, 2H), 6.97-7.11 (m, 1H), 7.17-7.31 (m, 2H), 7.31-7.41 (m, 1H), 7.41-7.48 (m, 1H), 7.50-7.73 (m, 5H), 7.81-8.00 (m, 1H), 11.42-11.64 (m, 1H). ESI-MS m/z [M+H]$^+$ calc'd for C$_{25}$H$_{23}$FN$_6$O$_2$, 458.19. found 458.3.

Example 76

3-((2-(1H-indol-4-yl)-6a,7,9,10-tetrahydro-[1,4]ox-azino[3,4-h]pteridin-5(6H)-yl)methyl)benzamide

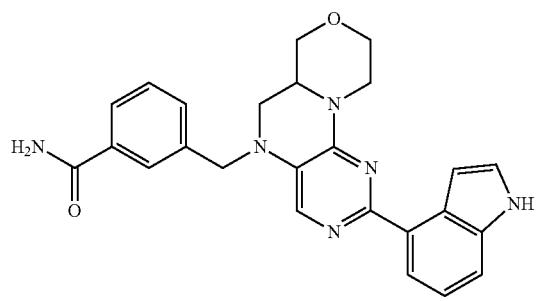 [SMILES: NC(=O)c1cccc(CN2CC3COCCN3c3nc(-c4cccc5[nH]ccc45)ncc32)c1]

$^1$H NMR (400 MHz, DMSO-d$_6$) δ 3.16-3.25 (m, 1H), 3.30-3.40 (m, 3H), 3.57-3.67 (m, 1H), 3.91-4.06 (m, 2H), 4.06-4.15 (m, 1H), 4.55-4.69 (m, 2H), 4.69-4.79 (m, 1H), 6.99-7.10 (m, 1H), 7.20-7.31 (m, 1H), 7.38-7.71 (m, 7H), 7.78-7.91 (m, 2H), 7.96-8.06 (m, 1H), 11.42-11.59 (m, 1H). ESI-MS m/z [M+H]$^+$ calc'd for C$_{25}$H$_{24}$N$_6$O$_2$, 440.20. found 440.3.

Example 77

3-((2-(1H-indol-4-yl)-6a,7,9,10-tetrahydro-[1,4]oxazino[3,4-h]pteridin-5(6H)-yl)methyl)-4-fluorobenzamide

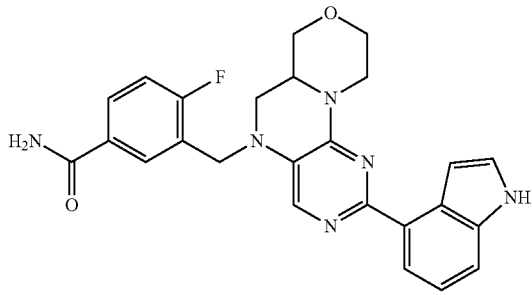 [SMILES: NC(=O)c1ccc(F)c(CN2CC3COCCN3c3nc(-c4cccc5[nH]ccc45)ncc32)c1]

$^1$H NMR (400 MHz, DMSO-d$_6$) δ 3.13-3.22 (m, 1H), 3.28 (m, 2H), 3.57-3.65 (m, 2H), 3.88-4.16 (m, 3H), 4.54-4.79 (m, 3H), 7.04 (br s, 1H), 7.26 (s, 1H), 7.38 (s, 1H), 7.43-7.74 (m, 5H), 7.86-7.99 (m, 2H), 7.99-8.12 (m, 1H), 11.45-11.62 (m, 1H). ESI-MS m/z [M+H]$^+$ calc'd for C$_{25}$H$_{23}$FN$_6$O$_2$, 458.19. found 458.3.

Example 78

4-((2-(1H-indol-4-yl)-6a,7,9,10-tetrahydro-[1,4]oxazino[3,4-h]pteridin-5(6H)-yl)methyl)benzamide

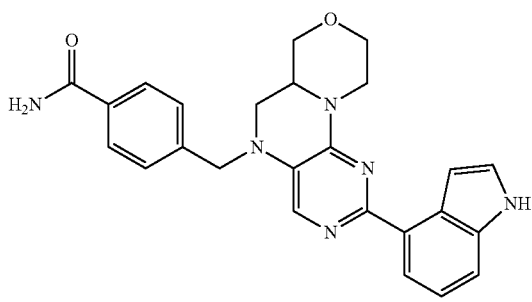 [SMILES: NC(=O)c1ccc(CN2CC3COCCN3c3nc(-c4cccc5[nH]ccc45)ncc32)cc1]

$^1$H NMR (400 MHz, DMSO-d$_6$) δ 3.15-3.25 (m, 1H), 3.30-3.40 (m, 3H), 3.56-3.66 (m, 1H), 3.92-4.05 (m, 2H), 4.07-4.16 (m, 1H), 4.57-4.70 (m, 2H), 4.70-4.78 (m, 1H), 6.98-7.08 (m, 1H), 7.19-7.31 (m, 1H), 7.33-7.42 (m, 1H), 7.45 (s, 3H), 7.53-7.60 (m, 1H), 7.60-7.71 (m, 2H), 7.88 (s, 2H), 7.93-8.05 (m, 1H), 11.44-11.61 (m, 1H). ESI-MS m/z [M+H]$^+$ calc'd for C$_{25}$H$_{24}$N$_6$O$_2$, 440.20. found 440.3.

Example 79

4-((2-(1H-indol-4-yl)-6a,7,9,10-tetrahydro-[1,4]oxazino[3,4-h]pteridin-5(6H)-yl)methyl)-3-methoxybenzamide

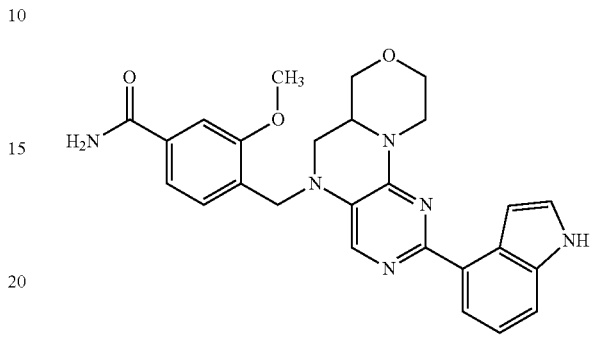

$^1$H NMR (400 MHz, DMSO-d$_6$) δ 3.25-3.30 (m, 1H), 3.31-3.40 (m, 4H), 3.55-3.70 (m, 1H), 3.75 (s, 3H), 3.95-4.06 (m, 1H), 4.05-4.16 (m, 1H), 4.43-4.62 (m, 2H), 4.64-4.79 (m, 1H), 6.94-7.09 (m, 1H), 7.20-7.31 (m, 1H), 7.32-7.76 (m, 8H), 7.94-8.13 (m, 1H), 11.38-11.63 (m, 1H). ESI-MS m/z [M+H]$^+$ calc'd for C$_{26}$H$_{26}$N$_6$O$_3$, 470.21. found 471.3.

Example 80

2-(1H-indol-4-yl)-5-((6-methylpyridin-2-yl)methyl)-5,6,6a,7,9,10-hexahydro-[1,4]oxazino[3,4-h]pteridine

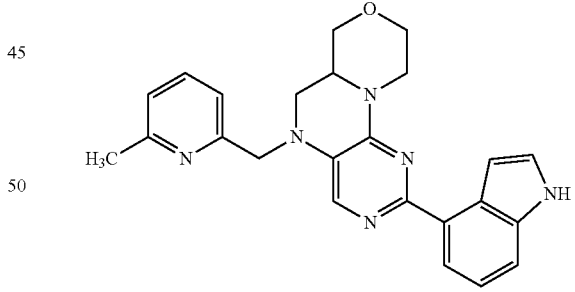

The title compound was prepared in a manner similar to EXAMPLE 3 using 2-chloro-5-((6-methylpyridin-2-yl)methyl)-5,6,6a,7,9,10-hexahydro-[1,4]oxazino[3,4-h]pteridine (PREPARATION x28, 36 mg, 0.108 mmol), 1H-indol-4-ylboronic acid (34.9 mg, 0.217 mmol) and PdCl$_2$(dppf) (7.94 mg, 10.85 μmol) in dioxane (2 mL) and aqueous saturated NaHCO$_3$ (0.4 mL). $^1$H NMR (400 MHz, DMSO-d$_6$) δ 2.50 (s, 3H), 3.26-3.44 (m, 3H), 3.54-3.68 (m, 2H), 3.95-4.06 (m, 1H), 4.06-4.17 (m, 1H), 4.55-4.81 (m, 4H), 6.93-7.05 (m, 1H), 7.20-7.37 (m, 3H), 7.54-7.64 (m, 3H), 7.64-7.70 (m, 1H), 7.70-7.81 (m, 1H), 11.47-11.66 (m, 1H). ESI-MS m/z [M+H]$^+$ calc'd for C$_{24}$H$_{24}$N$_6$O, 412.20. found 412.3.

Example 81

5-((5-cyclopropyl-1,3,4-oxadiazol-2-yl)methyl)-2-(1H-indol-4-yl)-5,6,6a,7,9,10-hexahydro-[1,4]oxazino[3,4-h]pteridine

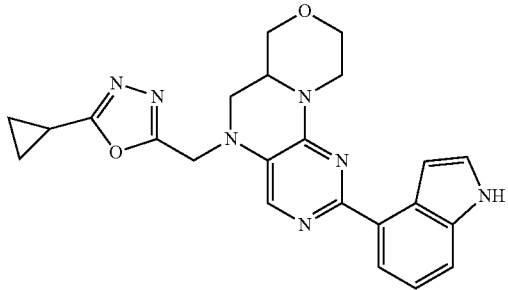 [SMILES: c1cc(-c2ncc3c(n2)N2CCOCC2CN3Cc2nnc(C3CC3)o2)c2cc[nH]c2c1]

The title compound was prepared in a manner similar to EXAMPLE 3 using 2-chloro-5-((6-methylpyridin-2-yl)methyl)-5,6,6a,7,9,10-hexahydro-[1,4]oxazino[3,4-h]pteridine (PREPARATION x29, 36 mg, 0.108 mmol), 1H-indol-4-ylboronic acid (34.9 mg, 0.217 mmol) and PdCl$_2$(dppf) (7.94 mg, 10.85 μmol) in dioxane (2 mL) and aqueous saturated NaHCO$_3$ (0.4 mL). $^1$H NMR (400 MHz, DMSO-d$_6$) δ 0.95-1.04 (m, 2H), 1.09-1.20 (m, 2H), 2.18-2.29 (m, 1H), 3.15-3.40 (m, 3H), 3.51-3.64 (m, 2H), 3.89-4.15 (m, 3H), 4.67-4.82 (m, 2H), 5.01 (d, J=16.93 Hz, 1H), 7.02 (br s, 1H), 7.27 (t, J=7.83 Hz, 1H), 7.57 (t, J=2.78 Hz, 2H), 7.66 (d, J=7.58 Hz, 5H), 7.77 (s, 1H), 11.54 (br s, 1H). ESI-MS m/z [M+H]$^+$ calc'd for C$_{23}$H$_{23}$N$_7$O$_2$, 429.19. found 429.3.

Example 82

(R)-2-(2-(3-(hydroxymethyl)phenyl)-6a,7,9,10-tetrahydro-[1,4]oxazino[3,4-h]pteridin-5(6H)-yl)-N-((tetrahydro-2H-pyran-4-yl)methyl)acetamide

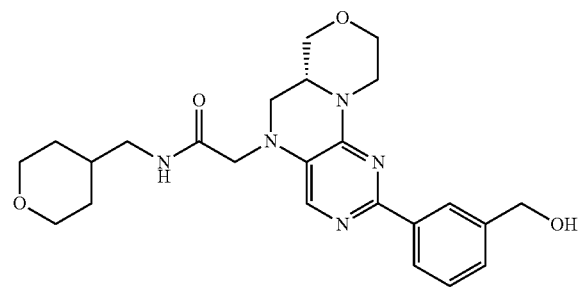 [SMILES: O=C(CN1C[C@@H]2COCCN2c2nc(-c3cccc(CO)c3)ncc21)NCC1CCOCC1]

A mixture of (R)-2-(2-chloro-6a,7,9,10-tetrahydro-[1,4]oxazino[3,4-h]pteridin-5(6H)-yl)-N-((tetrahydro-2H-pyran-4-yl)methyl)acetamide (PREPARATION x26, 50 mg, 0.131 mmol), 3-(hydroxymethyl)phenylboronic acid (29.8 mg, 0.196 mmol), tetrakis(triphenylphospine)palladium(0) (15.13 mg, 0.013 mmol) and sodium carbonate (27.8 mg, 0.262 mmol) in 1,4-dioxane (0.5 mL) and H$_2$O (0.25 mL) was heated to 120° C. in a microwave for 1 hour. After cooling to room temperature, the reaction mixture was diluted with EtOAc, washed with water and brine, dried over Na$_2$SO$_4$, filtered, and concentrated in vacuo. The residue was purified by column chromatography (amine-functionalized silica, 0-10% MeOH gradient in CHCl$_3$) to afford the title compound as an off-white solid (47.2 mg, 0.104 mmol, 79%). $^1$H NMR (400 MHz, DMSO-d$_6$) δ 1.06-1.24 (m, 2H), 1.47-1.71 (m, 3H), 2.92-3.03 (m, 3H), 3.12-3.37 (m, 5H), 3.50-3.67 (m, 2H), 3.73-3.93 (m, 4H), 3.98-4.07 (m, 2H), 4.50-4.60 (m, 3H), 5.21 (t, J=5.81 Hz, 1H), 7.26-7.38 (m, 2H), 7.50 (s, 1H), 8.06-8.11 (m, 2H), 8.18 (s, 1H). ESI-MS m/z [M+H]$^+$ calc'd for C$_{24}$H$_{31}$N$_5$O$_4$, 453.24. found 454.4.

Example 83

(R)-2-(2-(3-(2-hydroxypropan-2-yl)phenyl)-6a,7,9,10-tetrahydro-[1,4]oxazino[3,4-h]pteridin-5(6H)-yl)-N-((tetrahydro-2H-pyran-4-yl)methyl)acetamide

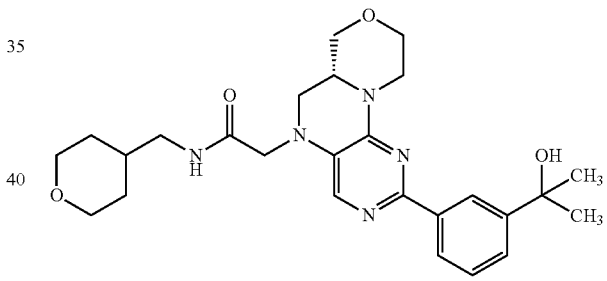

A mixture of (R)-2-(2-chloro-6a,7,9,10-tetrahydro-[1,4]oxazino[3,4-h]pteridin-5(6H)-yl)-N-((tetrahydro-2H-pyran-4-yl)methyl)acetamide (PREPARATION x26, 50 mg, 0.131 mmol), 2-(3-(4,4,5,5-tetramethyl-1,3,2-dioxaborolan-2-yl)phenyl)propan-2-ol (51.5 mg, 0.196 mmol), tetrakis(triphenylphospine)palladium (0) (15.13 mg, 0.013 mmol) and sodium carbonate (27.8 mg, 0.262 mmol) in 1,4-dioxane (0.5 mL) and H$_2$O (0.25 mL) was heated to 120° C. in a microwave for 1 hour. After cooling to room temperature, the reaction mixture was diluted with EtOAc, washed with water and brine, dried over Na$_2$SO$_4$, filtered, and concentrated in vacuo. The residue was purified by column chromatography (amine-functionalized silica, 0-10% MeOH gradient in CHCl$_3$) to afford the title compound as an off-white solid (43.4 mg, 0.090 mmol, 68.8%). $^1$H NMR (400 MHz, DMSO-d$_6$) δ 1.06-1.26 (m, 2H), 1.45 (s, 6H), 1.48-1.71 (m, 3H), 2.91-3.05 (m, 3H), 3.11-3.36 (m, 5H), 3.50-3.67 (m, 2H), 3.73-3.93 (m, 4H), 3.96-4.09 (m, 2H), 4.56 (d, J=11.87 Hz, 1H), 5.04 (s, 1H), 7.31 (t, J=7.71 Hz, 1H), 7.40-7.47 (m, 1H), 7.51 (s, 1H), 7.99-8.12 (m, 2H), 8.34 (s, 1H). ESI-MS m/z [M+H]$^+$ calc'd for C$_{26}$H$_{35}$N$_5$O$_4$, 481.27. found 482.4.

Example 84

1-(4-(5-((R)-1-(4-chlorophenyl)ethyl)-6-oxo-5,6,6a,7,9,10-hexahydro-[1,4]oxazino[3,4-h]pteridin-2-yl)phenyl)-3-methylurea

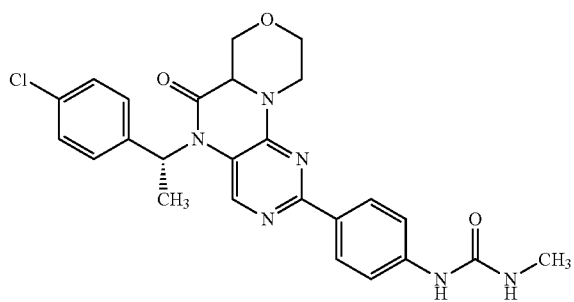 [SMILES: CNC(=O)Nc1ccc(-c2ncc3c(n2)N2CCOCC2C(=O)N3[C@H](C)c2ccc(Cl)cc2)cc1]

(R)-2-Chloro-5-(1-(4-chlorophenyl)ethyl)-6a,7,9,10-tetrahydro-[1,4]oxazino[3,4-h]pteridin-6(5H)-one (PREPARATION x34, 58 mg, 0.153 mmol), 1-methyl-3-(4-(4,4,5,5-tetramethyl-1,3,2-dioxaborolan-2-yl)phenyl)urea (84 mg, 0.306 mmol) and PdCl$_2$(dppf) (5.60 mg, 7.65 µmol) were suspended in dioxane (1.5 mL) and aqueous saturated NaHCO$_3$ (0.3 mL). The resulting brown suspension was heated to 100° C. and stirred for 18 hours. The reaction mixture was subsequently cooled to room temperature, H$_2$O (3 mL) was added, and the solids were collected by vacuum filtration. The resulting gray solid was dried under vacuum for several hours and the crude product was purified by LC/MS using a gradient of 25-50% CH$_3$CN (with 0.035% TFA) in H$_2$O (with 0.05% TFA). The pure fractions were combined and lyophilized to afford a TFA salt of the title compound as an off-white solid (27 mg, 36%). $^1$H NMR (400 MHz, DMSO-d$_6$) δ 1.71-1.85 (m, 3H), 2.62-2.69 (m, 3H), 2.96-3.08 (m, 1H), 3.56-3.78 (m, 2H), 3.96-4.07 (m, 1H), 4.18-4.29 (m, 1H), 4.39-4.57 (m, 2H), 6.03-6.29 (m, 2H), 7.32-7.51 (m, 7H), 8.05-8.15 (m, 2H), 8.73-8.78 (m, 1H). ESI-MS m/z [M+H]$^+$ calc'd for C$_{25}$H$_{25}$ClN$_6$O$_3$, 493.17. found 493.4.

Example 85

1-(4-(5-((S)-1-(4-chlorophenyl)ethyl)-6-oxo-5,6,6a,7,9,10-hexahydro-[1,4]oxazino[3,4-h]pteridin-2-yl)phenyl)-3-methylurea

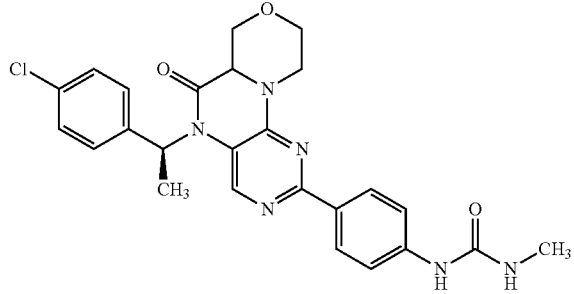 [SMILES: CNC(=O)Nc1ccc(-c2ncc3c(n2)N2CCOCC2C(=O)N3[C@@H](C)c2ccc(Cl)cc2)cc1]

To a 2 mL microwave vial were added 2-chloro-5-((S)-1-(4-chlorophenyl)ethyl)-6a,7,9,10-tetrahydro-[1,4]oxazino[3,4-h]pteridin-6(5H)-one (PREPARATION x51, 100 mg, 0.264 mmol), 1-methyl-3-(4-(4,4,5,5-tetramethyl-1,3,2-dioxaborolan-2-yl)phenyl)urea (146 mg, 0.527 mmol) and [1,1'-bis(diphenylphosphino)ferrocene]-dichloropalladium (II) (10.85 mg, 0.013 mmol). After the vial was sealed, dioxane (1.5 mL) and aqueous saturated NaHCO$_3$ (0.38 mL) were added, and the mixture was degassed by bubbling nitrogen through a syringe needle for 10 minutes. The mixture was then heated in a microwave to 120° C. for 30 minutes. The reaction mixture was partitioned between brine and ethyl acetate. The aqueous layer was extracted with ethyl acetate and the combined organic layers were dried over MgSO$_4$, filtered, and concentrated. The crude product was purified by normal phase column chromatography (SiO$_2$, 50-100% EtOAc/hexanes in 20 minutes) to give the title compound (single diastereomer, 21 mg, 16%). $^1$H NMR (400 MHz, DMSO-d$_6$) δ 1.75 (d, J=7.1 Hz, 1H), 1.83 (d, J=7.1 Hz, 3H), 2.65 (d, J=4.5 Hz, 3H), 2.95-3.07 (m, 1H), 3.55-3.73 (m, 2H), 4.02 (dd, J=11.6, 3.0 Hz, 1H), 4.25 (dd, J=11.2, 3.7 Hz, 1H), 4.40 (dd, J=10.6, 3.8 Hz, 1H), 4.45-4.54 (m, 1H), 6.02-6.09 (m, 1H), 6.14 (d, J=7.1 Hz, 1H), 7.33-7.50 (m, 7H), 7.60 (s, 1H), 7.76 (s, 1H), 8.07-8.16 (m, 2H), 8.70 (s, 1H). ESI-MS m/z [M+H]$^+$ calc'd for C$_{25}$H$_{25}$ClN$_6$O$_3$, 493.17. found 493.4.

Example 86 & 87

1-methyl-3-(4-((S)-6-oxo-5-((S)-1-(p-tolyl)ethyl)-5,6,6a,7,9,10-hexahydro-[1,4]oxazino[3,4-h]pteridin-2-yl)phenyl)urea and 1-methyl-3-(4-((R)-6-oxo-5-((S)-1-(p-tolyl)ethyl)-5,6,6a,7,9,10-hexahydro-[1,4]oxazino[3,4-h]pteridin-2-yl)phenyl)urea

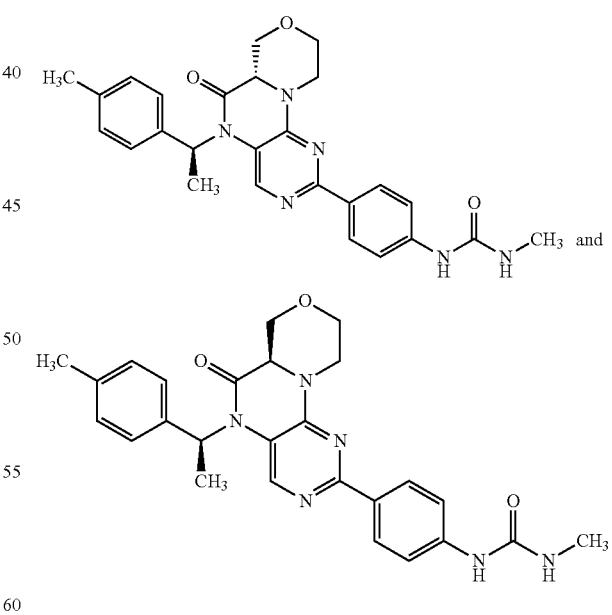

The title compounds were prepared in a manner similar to EXAMPLE 84 using 1-methyl-3-(4-(4,4,5,5-tetramethyl-1,3,2-dioxaborolan-2-yl)phenyl)urea (46.2 mg, 0.167 mmol), PdCl$_2$(dppf) (3.06 mg, 4.18 µmol) and either Diastereomer 1 (PREPARATION x35, 30 mg, 0.084 mmol) or Diastereomer 2 (PREPARATION x35, 30 mg, 0.084 mmol) of 2-chloro-5-

((S)-1-p-tolylethyl)-6a,7,9,10-tetrahydro-[1,4]oxazino[3,4-h]pteridin-6(5H)-one, in dioxane (1.5 mL) and aqueous saturated NaHCO$_3$ (0.3 mL). Relative stereo-configuration of the two compounds was not assigned.

EXAMPLE 86 (Diastereomer 1): $^1$H NMR (400 MHz, DMSO-d$_6$) δ 1.68-1.76 (m, 3H), 2.28-2.32 (s, 3H), 2.61-2.66 (m, 3H), 2.96-3.08 (m, 1H), 3.55-3.68 (m, 1H), 3.97-4.08 (m, 1H), 4.22-4.31 (m, 1H), 4.46-4.57 (m, 2H), 6.02-6.12 (m, 1H), 6.23-6.33 (m, 1H), 7.17-7.30 (m, 4H), 7.42-7.49 (m, 3H), 7.50-7.55 (m, 1H), 8.05-8.12 (m, 2H), 8.69-8.77 (m, 1H). ESI-MS m/z [M+H]$^+$ calc'd for C$_{26}$H$_{28}$N$_6$O, 473.22. found 473.4.

EXAMPLE 87 (Diastereomer 2): $^1$H NMR (400 MHz, DMSO-d$_6$) δ 1.75-1.85 (m, 3H), 2.23-2.29 (m, 3H), 2.61-2.66 (m, 3H), 2.96-3.08 (m, 1H), 3.56-3.74 (m, 1H), 3.94-4.07 (m, 1H), 4.21-4.31 (m, 1H), 4.37-4.46 (m, 1H), 4.46-4.57 (m, 1H), 6.01-6.11 (m, 1H), 6.11-6.22 (m, 1H), 7.13-7.26 (m, 4H), 7.40-7.49 (m, 3H), 7.64-7.72 (m, 1H), 8.02-8.10 (m, 2H), 8.68-8.75 (m, 1H). ESI-MS m/z [M+H]$^+$ calc'd for C$_{26}$H$_{28}$N$_6$O, 473.22. found 473.4.

The compounds of EXAMPLES 88 through 95 were prepared as shown in Scheme K.

Scheme K

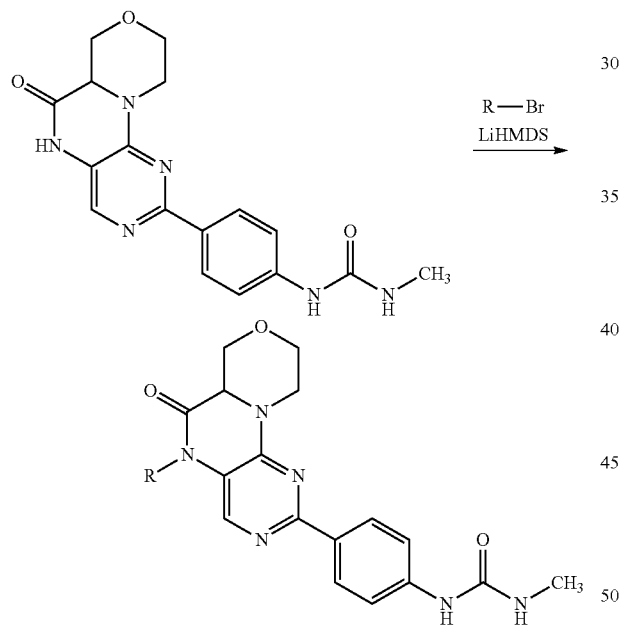

Reaction conditions: To mixtures of 1-methyl-3-(4-(6-oxo-5,6,6a,7,9,10-hexahydro-[1,4]oxazino[3,4-h]pteridin-2-yl)phenyl)urea (PREPARATION x37, 20 mg, 0.056 mmol) and R—Br (0.062 mmol) in DMF (1 mL) were added 1M lithium bis(trimethylsilyl)amide in hexanes solution (62 μL, 0.062 mmol). Each reaction mixture was agitated at room temperature overnight, then diluted with dioxane (1 mL) and purified by LC/MS using a gradient of 25-55% CH$_3$CN (with 0.035% TFA) in H$_2$O (with 0.05% TFA). The pure fractions were combined and lyophilized to afford TFA salts of the title compounds, below.

Example 88 methyl 4-((2-(4-(3-methylureido)phenyl)-6-oxo-6a,7,9,10-tetrahydro-[1,4]oxazino[3,4-h]pteridin-5(6H)-yl)methyl)benzoate

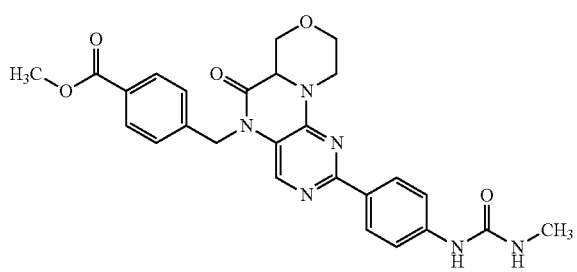

ESI-MS m/z [M+H]$^+$ calc'd for C$_{26}$H$_{26}$N$_6$O$_5$, 503.20. found 503.4.

Example 89

1-(4-(5-(4-chlorobenzyl)-6-oxo-5,6,6a,7,9,10-hexahydro-[1,4]oxazino[3,4-h]pteridin-2-yl)phenyl)-3-methylurea

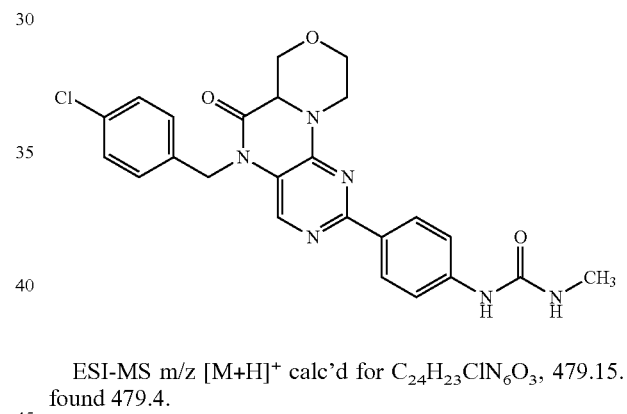

ESI-MS m/z [M+H]$^+$ calc'd for C$_{24}$H$_{23}$ClN$_6$O$_3$, 479.15. found 479.4.

Example 90

1-(4-(5-(3-(1H-pyrrol-1-yl)benzyl)-6-oxo-5,6,6a,7,9,10-hexahydro-[1,4]oxazino[3,4-h]pteridin-2-yl)phenyl)-3-methylurea

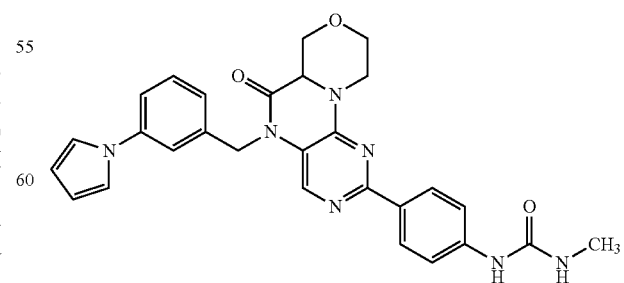

ESI-MS m/z [M+H]$^+$ calc'd for C$_{28}$H$_{27}$N$_7$O$_3$, 510.22. found 510.5.

Example 91

1-methyl-3-(4-(5-(4-(methylsulfonyl)benzyl)-6-oxo-5,6,6a,7,9,10-hexahydro-[1,4]oxazino[3,4-h]pteridin-2-yl)phenyl)urea

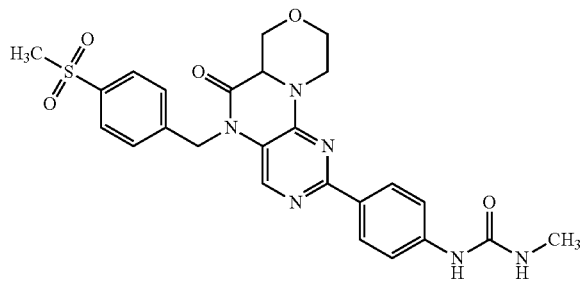

$^1$H NMR (400 MHz, DMSO-$d_6$) δ 2.61-2.66 (m, 3H), 2.99-3.12 (m, 1H), 3.55-3.65 (m, 2H), 3.65-3.74 (m, 2H), 3.98-4.07 (m, 1H), 4.21-4.32 (m, 1H), 4.54-4.65 (m, 2H), 5.18-5.38 (m, 2H), 6.02-6.12 (m, 1H), 7.42-7.51 (m, 2H), 7.55-7.63 (m, 2H), 7.87-7.95 (m, 3H), 8.09-8.18 (m, 2H), 8.70-8.76 (m, 1H). ESI-MS m/z [M+H]$^+$ calc'd for $C_{25}H_{26}N_6O_5S$, 523.17. found 523.4.

Example 92

1-(4-(5-(4-(1H-1,2,4-triazol-1-yl)benzyl)-6-oxo-5,6,6a,7,9,10-hexahydro-[1,4]oxazino[3,4-h]pteridin-2-yl)phenyl)-3-methylurea

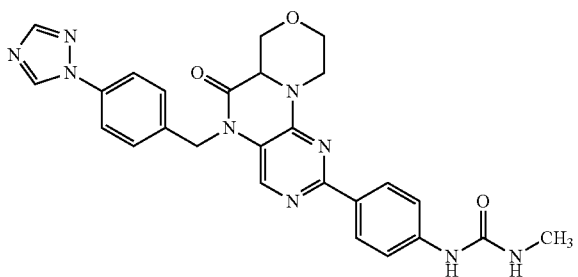 [SMILES: CNC(=O)Nc1ccc(-c2ncc3c(n2)N2CCOCC2C(=O)N3Cc2ccc(-n3cncn3)cc2)cc1]

$^1$H NMR (400 MHz, DMSO-$d_6$) δ 2.61-2.66 (m, 3H), 2.99-3.12 (m, 1H), 3.55-3.65 (m, 1H), 3.65-3.74 (m, 1H), 3.98-4.07 (m, 1H), 4.21-4.32 (m, 1H), 4.54-4.65 (m, 2H), 5.18-5.38 (m, 2H), 6.02-6.12 (m, 1H), 7.42-7.51 (m, 4H), 7.55-7.63 (m, 2H), 7.87-7.95 (m, 1H), 8.09-8.18 (m, 2H), 8.20-8.23 (m, 1H), 8.70-8.76 (m, 1H), 9.24 (s, 1H). ESI-MS m/z [M+H]$^+$ calc'd for $C_{26}H_{25}N_9O_3$, 512.21. found 512.4.

Example 93

1-(4-(5-((2,2-difluorocyclopropyl)methyl)-6-oxo-5,6,6a,7,9,10-hexahydro-[1,4]oxazino[3,4-h]pteridin-2-yl)phenyl)-3-methylurea

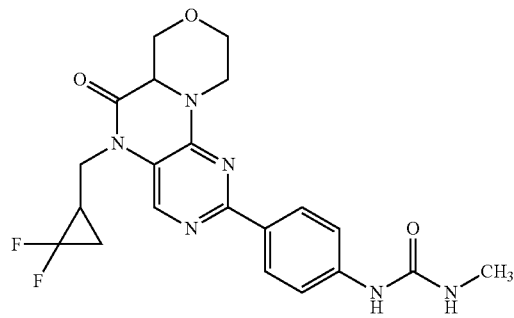 [SMILES: CNC(=O)Nc1ccc(-c2ncc3c(n2)N2CCOCC2C(=O)N3CC2CC2(F)F)cc1]

ESI-MS m/z [M+H]$^+$ calc'd for $C_{21}H_{22}F_2N_6O_3$, 445.17. found 445.4.

Example 94

1-(4-(5-(2-(3,5-dimethyl-1H-pyrazol-4-yl)ethyl)-6-oxo-5,6,6a,7,9,10-hexahydro-[1,4]oxazino[3,4-h]pteridin-2-yl)phenyl)-3-methylurea

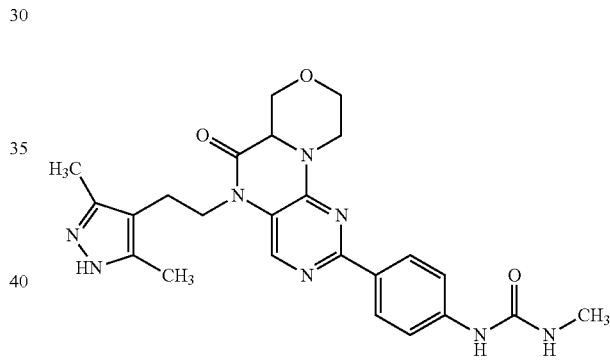

ESI-MS m/z [M+H]$^+$ calc'd for $C_{24}H_{28}N_8O_3$, 477.23. found 477.5.

Example 95

1-(4-(5-(2-chloro-4-(methylsulfonyl)benzyl)-6-oxo-5,6,6a,7,9,10-hexahydro-[1,4]oxazino[3,4-h]pteridin-2-yl)phenyl)-3-methylurea

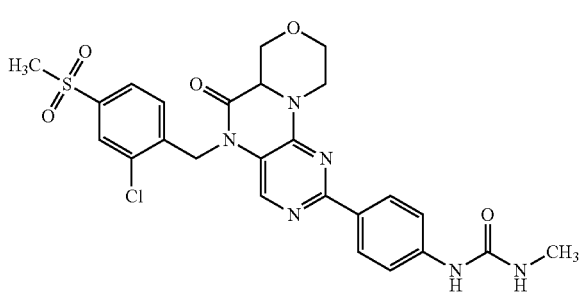

$^1$H NMR (400 MHz, DMSO-d$_6$) δ 2.61-2.67 (d, 2H), 2.99-3.15 (m, 2H), 3.30-3.38 (m, 3H), 3.55-3.74 (m, 2H), 3.98-4.10 (m, 1H), 4.18-4.28 (m, 1H), 4.55-4.67 (m, 2H), 5.08-5.39 (m, 2H), 6.01-6.13 (m, 1H), 7.42-7.51 (m, 3H), 7.76-7.84 (m, 2H), 8.03-8.10 (m, 1H), 8.10-8.18 (m, 2H), 8.70-8.76 (m, 1H). ESI-MS m/z [M+H]$^+$ calc'd for C$_{25}$H$_{25}$ClN$_6$O$_5$S, 557.13. found 557.4.

Example 96

5-((S)-2,3-dihydro-1H-inden-1-yl)-2-(1H-pyrazol-4-yl)-6a,7,9,10-tetrahydro-[1,4]oxazino[3,4-h]pteridin-6(5H)-one

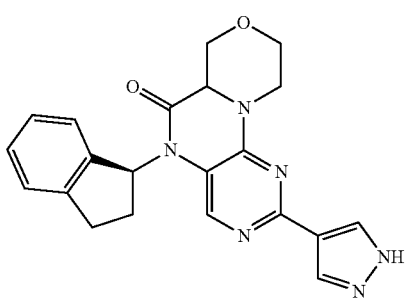 [SMILES: O=C1C2COCCN2c2nc(-c3cn[nH]c3)ncc2N1[C@H]1CCc2ccccc21]

To a 2 mL microwave vial were added (S)-2-chloro-5-(2,3-dihydro-1H-inden-1-yl)-6a,7,9,10-tetrahydro-[1,4]oxazino[3,4-h]pteridin-6(5H)-one (PREPARATION x49, 45 mg, 0.126 mmol), pyrazole-4-boronic acid pinacol cyclic ester (48.9 mg, 0.252 mmol) and [1,1'-bis(diphenylphosphino)ferrocene]-dichloropalladium(II) (5.19 mg, 6.31 μmol). After the vial was sealed, dioxane (0.6 mL) and aqueous saturated NaHCO$_3$ (0.15 mL) were added, and the mixture was degassed by bubbling nitrogen through a syringe needle for 10 minutes. The mixture was then heated in a microwave to 120° C. for 60 minutes. Since the reaction was only half complete, another 0.025 equivalents of palladium catalyst and 1 equivalent of boronic ester were added. The mixture was heated in the microwave to 130° C. for another 30 minutes. DMF (1 mL) was added and the mixture was filtered by syringe filter. The crude product was purified by preparatory HPLC, eluting with a gradient of 25-35% CH$_3$CN (with 0.035% TFA) in H$_2$O (with 0.05% TFA). Lyophilization of the collected fractions gave a diastereomeric mixture of the title compound (TFA salt) as a white powder (15 mg, 24%). $^1$H NMR (400 MHz, DMSO-d$_6$) δ 1.68 (d, J=7.1 Hz, 3H), 1.75 (d, J=7.3 Hz, 4H), 2.26 (t, J=1.8 Hz, 1H), 2.60, (t, J=1.8 Hz, 1H), 2.94 (br s, 3H), 3.46-3.73 (m, 11H), 3.90-3.99 (m, 4H), 4.18 (dt, J=11.4, 3.6 Hz, 4H), 4.40-4.66 (m, 7H), 6.13 (d, J=6.8 Hz, 1H), 6.24 (d, J=7.1 Hz, 1H), 6.72 (br s, 3H), 7.17-7.38 (m, 14H), 7.40 (br s, 1H), 7.55 (d, J=18.4 Hz, 4H). ESI-MS m/z [M+H]$^+$ calc'd for C$_{21}$H$_{20}$N$_6$O$_2$, 389.16. found 389.4.

Example 97

5-((S)-1-phenylethyl)-2-(1H-pyrazol-3-yl)-6a,7,9,10-tetrahydro-[1,4]oxazino[3,4-h]pteridin-6(5H)-one

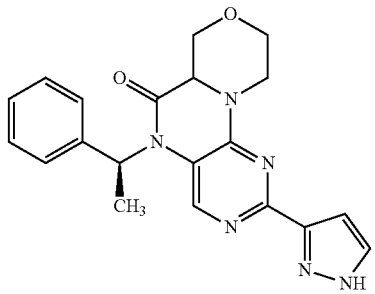 [SMILES: C[C@@H](c1ccccc1)N1C(=O)C2COCCN2c2nc(-c3cc[nH]n3)ncc21]

To a 2 mL microwave vial were added (S)-2-chloro-5-(1-phenylethyl)-6a,7,9,10-tetrahydro-[1,4]oxazino[3,4-h]pteridin-6(5H)-one (PREPARATION x47, 36 mg, 0.104 mmol), 3-(4,4,5,5-tetramethyl-1,3,2-dioxabolone)-pyrrazole (40.5 mg, 0.209 mmol) and [1,1'-bis(diphenylphosphino)ferrocene]-dichloropalladium(II) (4.29 mg, 5.22 μmol). After the vial was sealed, dioxane (0.6 mL) and aqueous saturated NaHCO$_3$ (0.15 mL) were added, and the mixture was degassed by bubbling nitrogen through a syringe needle for 10 minutes. The mixture was then heated in a microwave to 120° C. for 60 minutes. Another 2 equivalents of boronic ester and 0.05 equivalents of palladium catalyst were added, and the mixture was heated in the microwave for another 60 minutes. DMF (1 mL) was added and the mixture was filtered by syringe filter. The crude product was purified by preparatory HPLC, eluting with a gradient of 25-30% CH$_3$CN (with 0.035% TFA) in H$_2$O (with 0.05% TFA). Lyophilization of the collected fractions gave a diastereomeric mixture of the title compound (TFA salt) as a white solid (7 mg, 14%). $^1$H NMR (400 MHz, DMSO-d$_6$) δ 1.68 (d, J=7.1 Hz, 3H), 1.75 (d, J=7.3 Hz, 4H), 2.26 (t, J=1.8 Hz, 1H), 2.60, (t, J=1.8 Hz, 1H), 2.94 (br s, 3H), 3.46-3.73 (m, 11H), 3.90-3.99 (m, 4H), 4.18 (dt, J=11.4, 3.6 Hz, 4H), 4.40-4.66 (m, 7H), 6.13 (d, J=6.8 Hz, 1H), 6.24 (d, J=7.1 Hz, 1H), 6.72 (br s, 3H), 7.17-7.38 (m, 14H), 7.40 (br s, 1H), 7.55 (d, J=18.4 Hz, 4H). ESI-MS m/z [M+H]$^+$ calc'd for C$_{20}$H$_{20}$N$_6$O$_2$, 377.16. found 377.4.

Example 98

N-isopropyl-3-(5-(4-(methylsulfonyl)benzyl)-6-oxo-5,6,6a,7,9,10-hexahydro-[1,4]oxazino[3,4-h]pteridin-2-yl)benzenesulfonamide

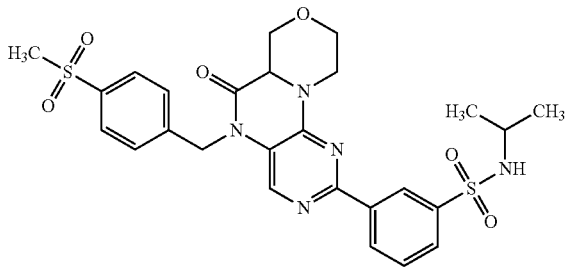 [SMILES: CC(C)NS(=O)(=O)c1cccc(-c2ncc3c(n2)N2CCOCC2C(=O)N3Cc2ccc(S(C)(=O)=O)cc2)c1]

2-Chloro-5-(4-(methylsulfonyl)benzyl)-6a,7,9,10-tetrahydro-[1,4]oxazino[3,4-h]pteridin-6(5H)-one (PREPARATION x38, 40 mg, 0.098 mmol), 3-(N-isopropylsulfamoyl)phenylboronic acid (47.6 mg, 0.196 mmol) and PdCl$_2$(dppf) (7.16 mg, 9.78 μmol) were suspended in dioxane (1 mL). The reaction mixture was heated to 100° C. and stirred for 18 hours, then diluted with ethyl acetate and washed with aqueous saturated NH$_4$Cl (3×2 mL) and brine (3×2 mL). The combined organic layers were dried over MgSO$_4$, filtered, and concentrated in vacuo to give a crude product, which was purified by LC/MS using a gradient of 35-60% CH$_3$CN (with 0.035% TFA) in H$_2$O (with 0.05% TFA). The pure fractions were combined and lyophilized to afford a TFA salt of the title compound as an off-white solid (27 mg, 36%). $^1$H NMR (400 MHz, DMSO-d$_6$) δ 0.83-1.02 (m, 6H), 3.03-3.13 (m, 1H), 3.16-3.25 (m, 6H), 3.56-3.78 (m, 1H), 3.98-4.09 (m, 1H), 4.23-4.34 (m, 1H), 4.52-4.68 (m, 1H), 5.18-5.44 (m, 2H), 7.55-7.63 (m, 2H), 7.64-7.75 (m, 2H), 7.83-7.95 (m, 3H), 7.99-8.04 (m, 1H), 8.45-8.52 (m, 1H), 8.65-8.70 (m, 1H). ESI-MS m/z [M+H]$^+$ calc'd for C$_{26}$H$_{29}$N$_5$O$_6$S$_2$, 572.16. found 572.5.

Example 99

1-(4-(5-(1-(4-chlorophenyl)cyclopropyl)-6-oxo-5,6,6a,7,9,10-hexahydro-[1,4]oxazino[3,4-h]pteridin-2-yl)phenyl)-3-methylurea

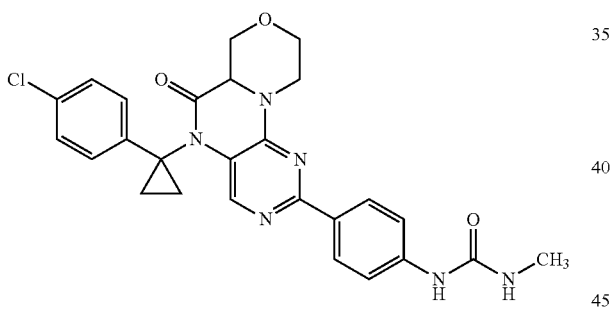

The title compound was prepared in a manner similar to EXAMPLE 84 using 2-chloro-5-(1-(4-chlorophenyl)cyclopropyl)-6a,7,9,10-tetrahydro-[1,4]oxazino[3,4-h]pteridin-6(5H)-one (PREPARATION x36, 100 mg, 0.256 mmol), 1-methyl-3-(4-(4,4,5,5-tetramethyl-1,3,2-dioxaborolan-2-yl)phenyl)urea (141 mg, 0.511 mmol), and PdCl$_2$(dppf) (18.70 mg, 0.026 mmol) in dioxane (2 mL) and aqueous saturated NaHCO$_3$ (0.4 mL). $^1$H NMR (400 MHz, DMSO-d$_6$) δ 1.10-1.24 (m, 2H), 1.46-1.60 (m, 2H), 2.54-2.60 (d, 3H), 2.84-3.03 (m, 1H), 3.46-3.57 (m, 2H), 3.91-4.00 (m, 1H), 4.08-4.20 (m, 1H), 4.33-4.55 (m, 2H), 5.98-6.07 (m, 1H), 7.01-7.17 (m, 2H), 7.23-7.34 (m, 2H), 7.36-7.46 (m, 2H), 7.68-7.73 (m, 1H), 8.02-8.13 (m, 2H), 8.61-8.70 (m, 1H). ESI-MS m/z [M+H]$^+$ calc'd for C$_{26}$H$_{25}$ClN$_6$O$_3$, 505.17. found 505.4.

The compounds of EXAMPLES 100 through 144 were prepared as shown in Scheme L.

Scheme L

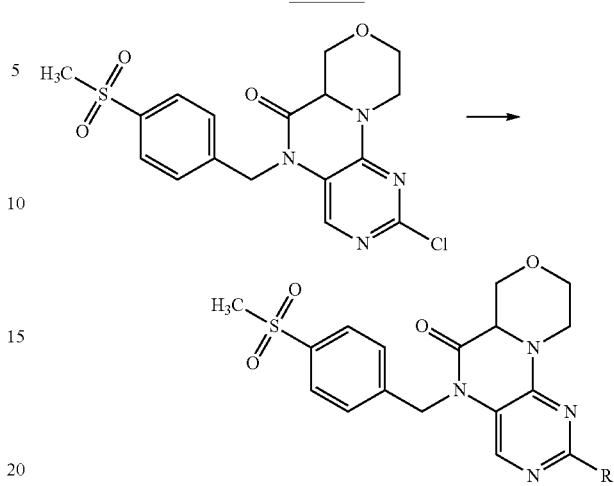

Reaction Conditions: 2-chloro-5-(4-(methylsulfonyl)benzyl)-6a,7,9,10-tetrahydro-[1,4]oxazino[3,4-h]pteridin-6(5H)-one (PREPARATION x38, 40 mg, 0.098 mmol), R-boronic acid (0.196 mmol) or R-boronic acid pinacol ester (0.196 mmol), and PdCl$_2$(dppf) (7.16 mg, 9.78 μmol) were suspended in dioxane (1 mL) and aqueous saturated NaHCO$_3$ (0.2 mL). Each of the reaction mixtures were heated to 100° C. and stirred for 18 hours, then purified by LC/MS using a gradient of 20-55% CH$_3$CN (with 0.035% TFA) in H$_2$O (with 0.05% TFA). The pure fractions were combined and lyophilized to afford TFA salts of the title compounds, below.

Example 100

2-(1H-indol-6-yl)-5-(4-(methylsulfonyl)benzyl)-6a,7,9,10-tetrahydro-[1,4]oxazino[3,4-h]pteridin-6(5H)-one

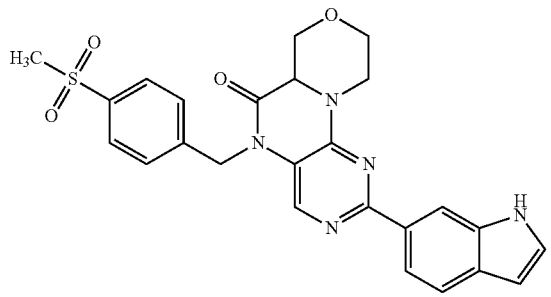 [SMILES: CS(=O)(=O)c1ccc(CN2C(=O)C3COCCN3c3nc(-c4ccc5cc[nH]c5c4)ncc32)cc1]

$^1$H NMR (400 MHz, DMSO-d$_6$) δ 3.06-3.17 (m, 1H), 3.17-3.23 (m, 2H), 3.65-3.76 (m, 4H), 4.01-4.11 (m, 1H), 4.23-4.33 (m, 1H), 4.55-4.70 (m, 1H), 5.12-5.52 (m, 2H), 6.39-6.52 (m, 1H), 7.34-7.67 (m, 4H), 7.81-8.05 (m, 4H), 8.21-8.50 (m, 1H), 11.14-11.36 (m, 1H). ESI-MS m/z [M+H]$^+$ calc'd for C$_{25}$H$_{23}$N$_5$O$_4$, 490.15. found 490.4

Example 101

N-(3-(5-(4-(methylsulfonyl)benzyl)-6-oxo-5,6,6a,7,9,10-hexahydro-[1,4]oxazino[3,4-h]pteridin-2-yl)phenyl)acetamide

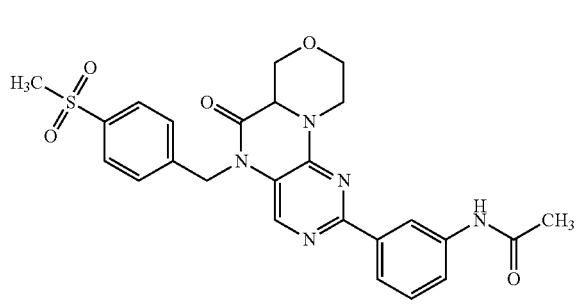 [SMILES: CC(=O)Nc1cccc(-c2ncc3c(n2)N2CCOCC2C(=O)N3Cc2ccc(S(C)(=O)=O)cc2)c1]

$^1$H NMR (400 MHz, DMSO-d$_6$) δ 3.00-3.13 (m, 1H), 3.19 (s, 3H), 3.60-3.70 (m, 5H), 4.00-4.08 (m, 1H), 4.22-4.31 (m, 1H), 4.52-4.65 (m, 2H), 5.18-5.41 (m, 2H), 7.30-7.39 (m, 1H), 7.55-7.63 (m, 2H), 7.68-7.75 (m, 1H), 7.86-8.03 (m, 4H), 8.41-8.50 (m, 1H), 9.97-10.04 (m, 1H). ESI-MS m/z [M+H]$^+$ calc'd for C$_{25}$H$_{25}$N$_5$O$_5$, 508.16. found 508.4.

Example 102

N-(4-(5-(4-(methylsulfonyl)benzyl)-6-oxo-5,6,6a,7,9,10-hexahydro-[1,4]oxazino[3,4-h]pteridin-2-yl)phenyl)methanesulfonamide

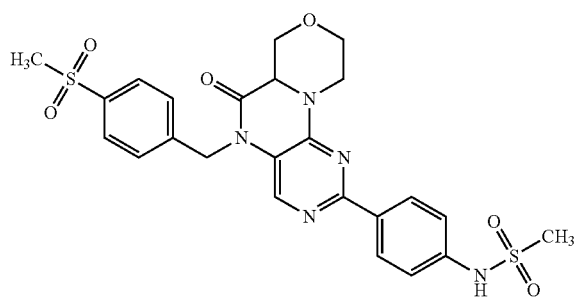

$^1$H NMR (400 MHz, DMSO-d$_6$) δ 3.00-3.11 (m, 3H), 3.19 (s, 3H), 3.51-3.63 (m, 2H), 4.02 (dd, J=12.00, 2.91 Hz, 2H), 4.26 (dd, J=11.37, 3.79 Hz, 1H), 4.60 (dd, J=10.61, 3.79 Hz, 2H), 5.19-5.39 (m, 2H), 7.26 (d, J=8.84 Hz, 2H), 7.60 (s, 2H), 7.93 (d, J=14.91 Hz, 3H), 8.13-8.29 (m, 2H), 9.99 (s, 1H). ESI-MS m/z [M+H]$^+$ calc'd for C$_{24}$H$_{25}$N$_5$O$_6$S$_2$, 545.12. found 544.4.

Example 103

2-(3-aminophenyl)-5-(4-(methylsulfonyl)benzyl)-6a,7,9,10-tetrahydro-[1,4]oxazino[3,4-h]pteridin-6(5H)-one

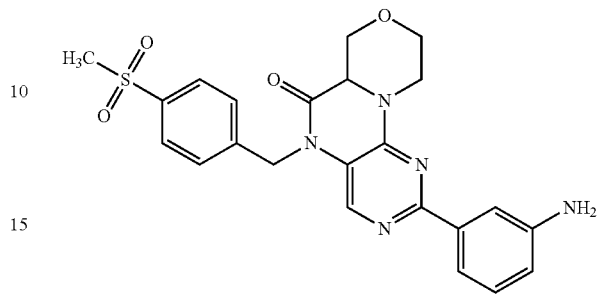

ESI-MS m/z [M+H]$^+$ calc'd for C$_{23}$H$_{23}$N$_5$O$_4$S, 466.15. found 466.4.

Example 104

N-(2-(5-(4-(methylsulfonyl)benzyl)-6-oxo-5,6,6a,7,9,10-hexahydro-[1,4]oxazino[3,4-h]pteridin-2-yl)phenyl)acetamide

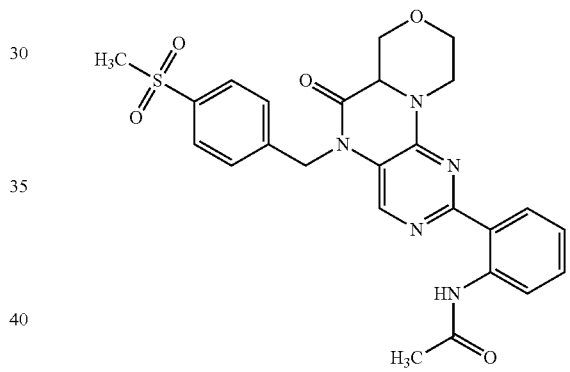

ESI-MS m/z [M+H]$^+$ calc'd for C$_{25}$H$_{25}$N$_5$O$_5$S, 508.16. found 508.2.

Example 105 ethyl 5-(5-(4-(methylsulfonyl)benzyl)-6-oxo-5,6,6a,7,9,10-hexahydro-[1,4]oxazino[3,4-h]pteridin-2-yl)nicotinate

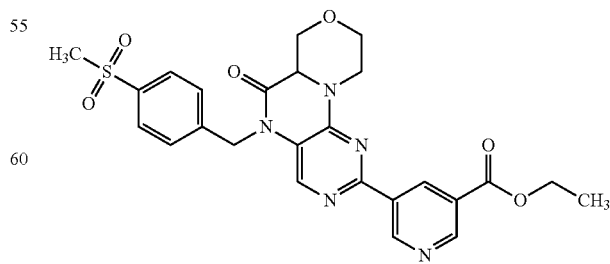

ESI-MS m/z [M+H]$^+$ calc'd for C$_{25}$H$_{25}$N$_5$O$_6$S, 524.15. found 524.5.

Example 106

2-(6-aminopyridin-3-yl)-5-(4-(methylsulfonyl)benzyl)-6a,7,9,10-tetrahydro-[1,4]oxazino[3,4-h]pteridin-6(5H)-one

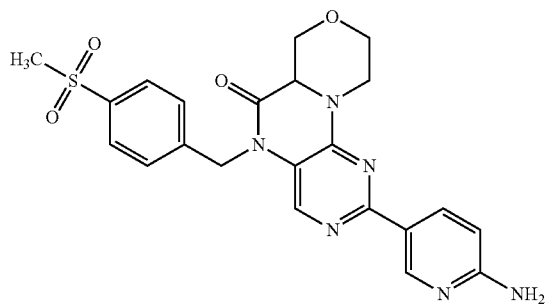

$^1$H NMR (400 MHz, DMSO-d$_6$) δ 3.01-3.10 (m, 1H), 3.19 (s, 3H), 3.52-3.66 (m, 3H), 3.97-4.07 (m, 1H), 4.23-4.34 (m, 1H), 4.57-4.65 (m, 1H), 5.20-5.37 (m, 2H), 6.95-7.04 (m, 2H), 7.53-7.62 (m, 2H), 7.87-7.92 (m, 2H), 8.55-8.62 (m, 1H), 8.64-8.71 (m, 1H). ESI-MS m/z [M+H]$^+$ calc'd for C$_{22}$H$_{22}$N$_6$O$_4$S, 467.14. found 467.4.

Example 107

4-(5-(4-(methylsulfonyl)benzyl)-6-oxo-5,6,6a,7,9,10-hexahydro-[1,4]oxazino[3,4-h]pteridin-2-yl)benzamide

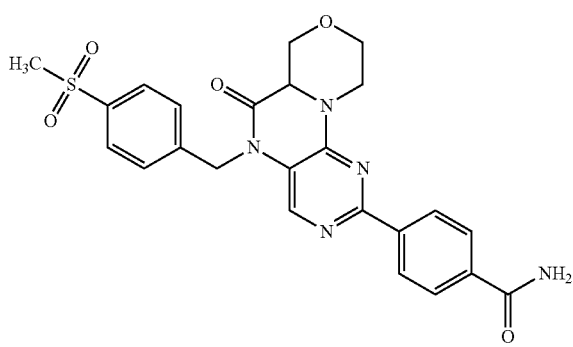 [SMILES: CS(=O)(=O)c1ccc(CN2C(=O)C3COCCN3c3nc(-c4ccc(C(N)=O)cc4)ncc32)cc1]

ESI-MS m/z [M+H]$^+$ calc'd for C$_{24}$H$_{23}$N$_5$O$_5$S, 494.14. found 494.4.

Example 108

5-(4-(methylsulfonyl)benzyl)-2-(1H-pyrrolo[2,3-b]pyridin-5-yl)-6a,7,9,10-tetrahydro-[1,4]oxazino[3,4-h]pteridin-6(5H)-one

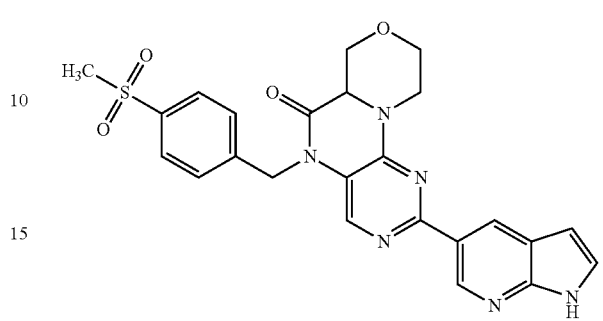

ESI-MS m/z [M+H]$^+$ calc'd for C$_{24}$H$_{22}$N$_6$O$_4$S, 491.14. found 491.4.

Example 109

N-methyl-5-(5-(4-(methylsulfonyl)benzyl)-6-oxo-5,6,6a,7,9,10-hexahydro-[1,4]oxazino[3,4-h]pteridin-2-yl)picolinamide

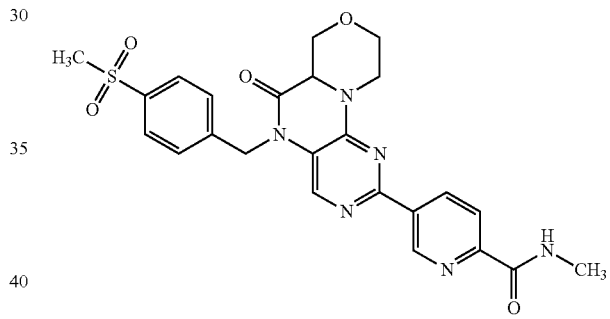

ESI-MS m/z [M+H]$^+$ calc'd for C$_{24}$H$_{24}$N$_6$O$_5$S, 509.15. found 509.4.

Example 110

2-(3-(1H-pyrazol-3-yl)phenyl)-5-(4-(methylsulfonyl)benzyl)-6a,7,9,10-tetrahydro-[1,4]oxazino[3,4-h]pteridin-6(5H)-one

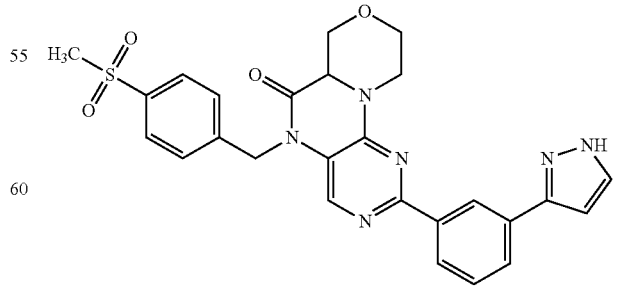

ESI-MS m/z [M+H]$^+$ calc'd for C$_{26}$H$_{24}$N$_6$O$_4$S, 517.16. found 517.5.

Example 111

N-methyl-3-(5-(4-(methylsulfonyl)benzyl)-6-oxo-5,6,6a,7,9,10-hexahydro-[1,4]oxazino[3,4-h]pteridin-2-yl)benzenesulfonamide

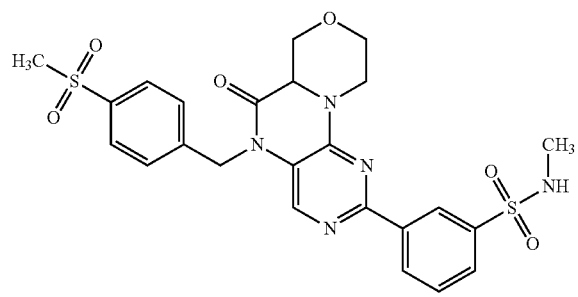

ESI-MS m/z [M+H]$^+$ calc'd for $C_{24}H_{25}N_5O_6S_2$, 544.12. found 544.4.

Example 112

N-(4-(5-(4-(methylsulfonyl)benzyl)-6-oxo-5,6,6a,7,9,10-hexahydro-[1,4]oxazino[3,4-h]pteridin-2-yl)phenyl)acetamide

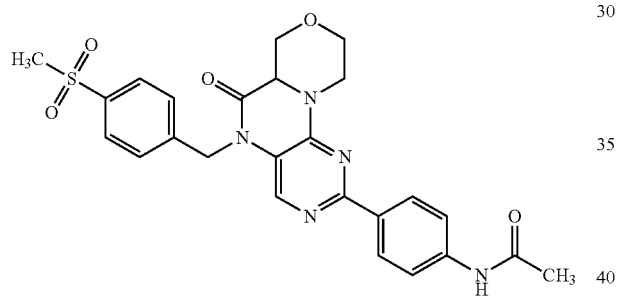

ESI-MS m/z [M+H]$^+$ calc'd for $C_{25}H_{25}N_5O_5S$, 508.16. found 508.4.

Example 113

3-(5-(4-(methylsulfonyl)benzyl)-6-oxo-5,6,6a,7,9,10-hexahydro-[1,4]oxazino[3,4-h]pteridin-2-yl)benzamide

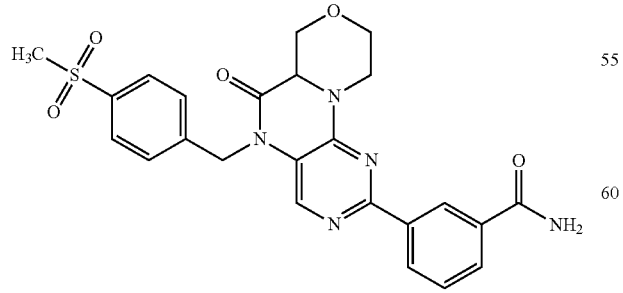

ESI-MS m/z [M+H]$^+$ calc'd for $C_{24}H_{23}N_5O_5S$, 494.14. found 494.4.

Example 114

2-(1H-indazol-5-yl)-5-(4-(methylsulfonyl)benzyl)-6a,7,9,10-tetrahydro-[1,4]oxazino[3,4-h]pteridin-6(5H)-one

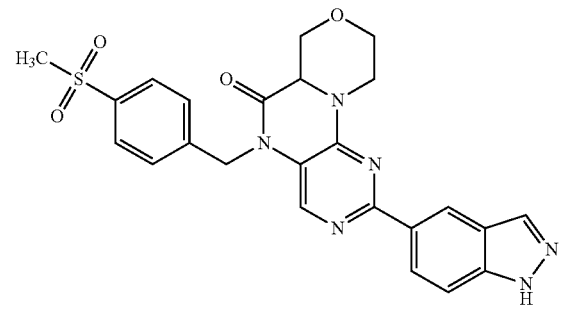 [SMILES: CS(=O)(=O)c1ccc(CN2C(=O)C3COCCN3c3nc(-c4ccc5[nH]ncc5c4)ncc32)cc1]

ESI-MS m/z [M+H]$^+$ calc'd for $C_{24}H_{22}N_6O_4S$, 491.14. found 491.4.

Example 115

3-(5-(4-(methylsulfonyl)benzyl)-6-oxo-5,6,6a,7,9,10-hexahydro-[1,4]oxazino[3,4-h]pteridin-2-yl)benzenesulfonamide

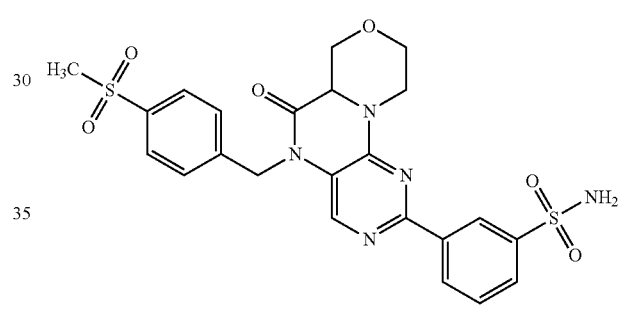

ESI-MS m/z [M+H]$^+$ calc'd for $C_{23}H_{23}N_5O_6S_2$, 530.11. found 530.4.

Example 116

N-cyclopropyl-3-(5-(4-(methylsulfonyl)benzyl)-6-oxo-5,6,6a,7,9,10-hexahydro-[1,4]oxazino[3,4-h]pteridin-2-yl)benzenesulfonamide

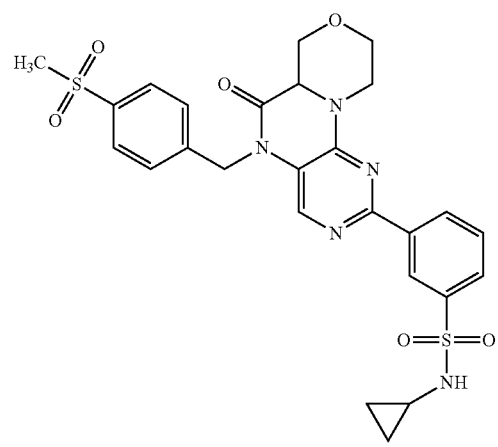 [SMILES: CS(=O)(=O)c1ccc(CN2C(=O)C3COCCN3c3nc(-c4cccc(S(=O)(=O)NC5CC5)c4)ncc32)cc1]

ESI-MS m/z [M+H]$^+$ calc'd for $C_{26}H_{27}H_5O_6S_2$, 570.14. found 570.5.

Example 117

N-(3-(5-(4-(methylsulfonyl)benzyl)-6-oxo-5,6,6a,7,9,10-hexahydro-[1,4]oxazino[3,4-h]pteridin-2-yl)phenyl)methanesulfonamide

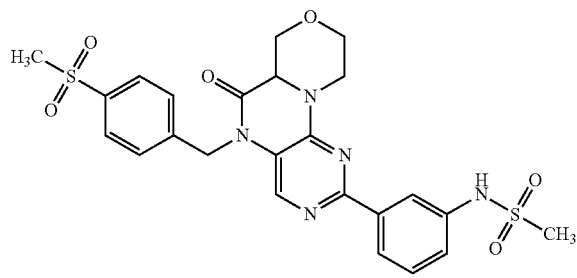

ESI-MS m/z [M+H]$^+$ calc'd for $C_{24}H_{25}N_5O_6S_2$, 544.12. found 544.4.

Example 118

N-(5-(5-(4-(methylsulfonyl)benzyl)-6-oxo-5,6,6a,7,9,10-hexahydro-[1,4]oxazino[3,4-h]pteridin-2-yl)pyridin-2-yl)acetamide

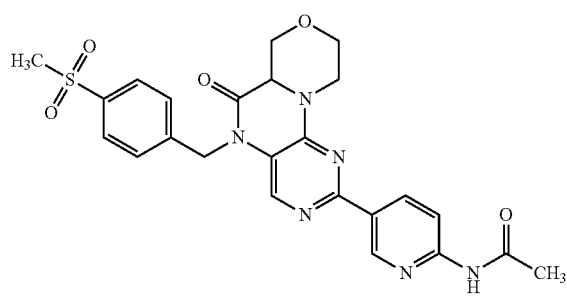

ESI-MS m/z [M+H]$^+$ calc'd for $C_{24}H_{24}N_6O_5S$, 509.15. found 509.4.

Example 119

5-(4-(methylsulfonyl)benzyl)-2-(2-oxo-2,3-dihydro-1H-benzo[d]imidazol-5-yl)-6a,7,9,10-tetrahydro-[1,4]oxazino[3,4-h]pteridin-6(5H)-one

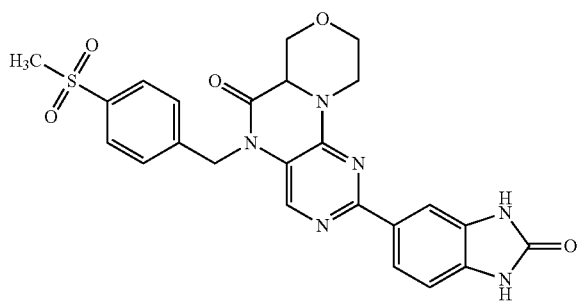 [SMILES: CS(=O)(=O)c1ccc(CN2C(=O)C3COCCN3c3nc(-c4ccc5[nH]c(=O)[nH]c5c4)ncc32)cc1]

ESI-MS m/z [M+H]$^+$ calc'd for $C_{24}H_{22}N_6O_5S$, 507.14. found 507.4.

Example 120

N-(3-(5-(4-(methylsulfonyl)benzyl)-6-oxo-5,6,6a,7,9,10-hexahydro-[1,4]oxazino[3,4-h]pteridin-2-yl)phenyl)cyclopropanesulfonamide

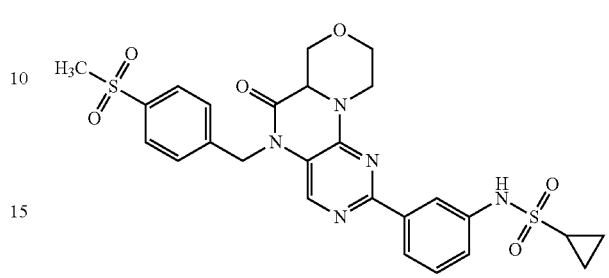

ESI-MS m/z [M+H]$^+$ calc'd for $C_{26}H_{27}N_5O_6S_2$, 570.14. found 570.5.

Example 121

5-(4-(methylsulfonyl)benzyl)-2-(1H-pyrrolo[3,2-b]pyridin-6-yl)-6a,7,9,10-tetrahydro-[1,4]oxazino[3,4-h]pteridin-6(5H)-one

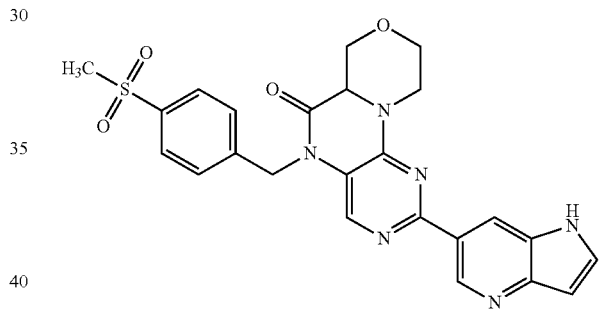

ESI-MS m/z [M+H]$^+$ calc'd for $C_{24}H_{22}N_6O_5S$, 491.14. found 491.5.

Example 122

N-methyl-3-(5-(4-(methylsulfonyl)benzyl)-6-oxo-5,6,6a,7,9,10-hexahydro-[1,4]oxazino[3,4-h]pteridin-2-yl)benzamide

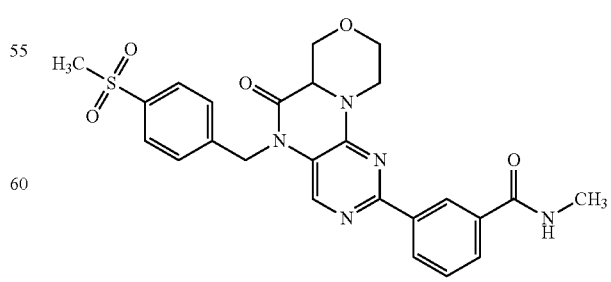

ESI-MS m/z [M+H]$^+$ calc'd for $C_{25}H_{25}N_5O_5S$, 508.16. found 508.4.

Example 123

2-(1H-indol-4-yl)-5-(4-(methylsulfonyl)benzyl)-6a,7,9,10-tetrahydro-[1,4]oxazino[3,4-h]pteridin-6(5H)-one

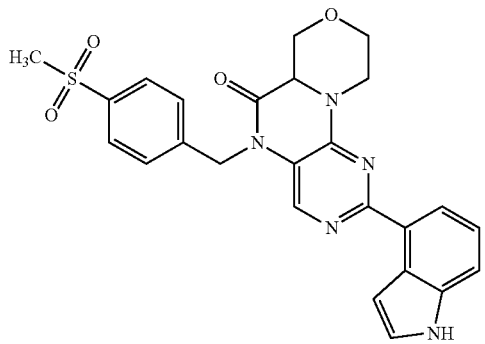 [SMILES: CS(=O)(=O)c1ccc(CN2C(=O)C3COCCN3c3nc(-c4cccc5[nH]ccc45)ncc32)cc1]

$^1$H NMR (400 MHz, DMSO-d$_6$) δ 3.10-3.42 (m, 4H), 3.59-3.77 (m, 2H), 4.08 (dd, J=11.87, 3.28 Hz, 1H), 4.29 (dd, J=11.49, 3.92 Hz, 1H), 4.53-4.68 (m, 2H), 5.21-5.43 (m, 2H), 7.16 (t, J=7.83 Hz, 1H), 7.29 (br s, 1H), 7.43 (t, J=2.78 Hz, 1H), 7.51 (d, J=8.08 Hz, 1H), 7.62 (d, J=8.34 Hz, 2H), 7.92 (d, J=8.59 Hz, 2H), 8.00 (d, J=6.82 Hz, 1H), 8.04 (s, 1H), 11.24 (br s, 1H). ESI-MS m/z [M+H]$^+$ calc'd for C$_{25}$H$_{23}$N$_5$O$_4$S, 490.15. found 490.4.

Example 124

2-(1H-indazol-6-yl)-5-(4-(methylsulfonyl)benzyl)-6a,7,9,10-tetrahydro-[1,4]oxazino[3,4-h]pteridin-6(5H)-one

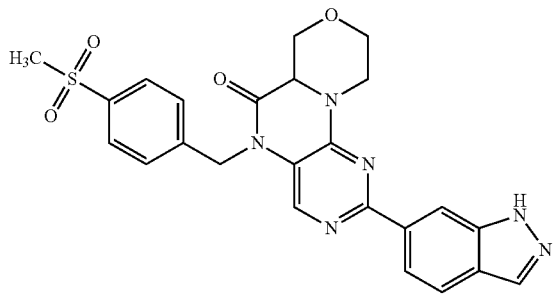 [SMILES: CS(=O)(=O)c1ccc(CN2C(=O)C3COCCN3c3nc(-c4ccc5cn[nH]c5c4)ncc32)cc1]

ESI-MS m/z [M+H]$^+$ calc'd for C$_{24}$H$_{24}$N$_6$O$_4$S, 491.14. found 491.4.

Example 125

2-(2-aminopyrimidin-5-yl)-5-(4-(methylsulfonyl)benzyl)-6a,7,9,10-tetrahydro-[1,4]oxazino[3,4-h]pteridin-6(5H)-one

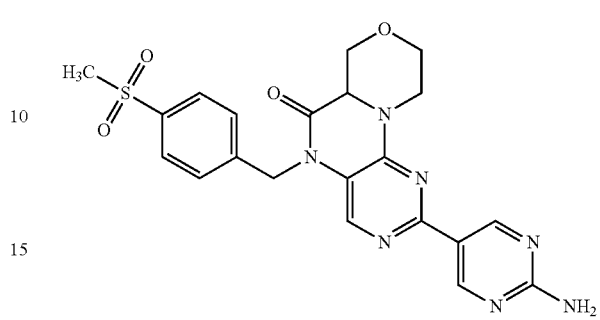

ESI-MS m/z [M+H]$^+$ calc'd for C$_{21}$H$_{21}$N$_7$O$_4$S, 468.14. found 468.4.

Example 126

2-(1-methyl-1H-pyrazol-5-yl)-5-(4-(methylsulfonyl)benzyl)-6a,7,9,10-tetrahydro-[1,4]oxazino[3,4-h]pteridin-6(5H)-one

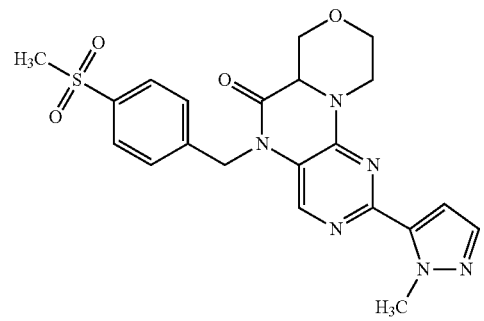 [SMILES: Cn1nccc1-c1ncc2c(n1)N1CCOCC1C(=O)N2Cc1ccc(S(C)(=O)=O)cc1]

$^1$H NMR (400 MHz, DMSO-d$_6$) δ 3.01-3.11 (m, 1H), 3.18-3.22 (m, 3H), 3.62-3.68 (m, 2H), 3.98-4.05 (m, 1H), 4.15-4.20 (m, 3H), 4.23-4.30 (m, 1H), 4.40-4.48 (m, 1H), 4.58-4.64 (m, 1H), 5.10-5.42 (m, 2H), 6.79-6.87 (m, 1H), 7.41-7.45 (m, 1H), 7.56-7.62 (m, 2H), 7.85-7.98 (m, 3H). ESI-MS m/z [M+H]$^+$ calc'd for C$_{21}$H$_{22}$N$_6$O$_4$S, 455.14. found 455.4.

Example 127

2-(1H-indol-5-yl)-5-(4-(methylsulfonyl)benzyl)-6a,7,9,10-tetrahydro-[1,4]oxazino[3,4-h]pteridin-6(5H)-one

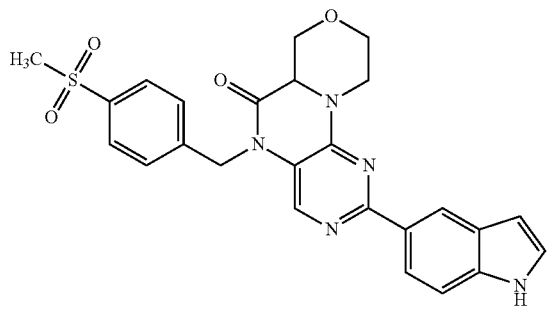 [SMILES: CS(=O)(=O)c1ccc(CN2C(=O)C3COCCN3c3nc(-c4ccc5[nH]ccc5c4)ncc32)cc1]

¹H NMR (400 MHz, DMSO-d₆) δ 3.08-3.22 (m, 1H), 3.23 (s, 3H), 3.67-3.73 (m, 2H), 3.91-3.94 (m, 1H), 4.25-4.31 (m, 1H), 4.59-4.75 (m, 2H), 5.20-5.43 (m, 2H), 6.47-6.58 (m, 1H), 7.35-7.48 (m, 2H), 7.61 (d, J=8.34 Hz, 2H), 7.86-7.95 (m, 3H), 8.02-8.09 (m, 1H), 8.52 (s, 1H), 11.21-11.33 (m, 1H). ESI-MS m/z [M+H]⁺ calc'd for $C_{25}H_{23}N_5O_4S$, 490.15. found 490.4.

Example 128

2-(3-(1H-pyrazol-1-yl)phenyl)-5-(4-(methylsulfonyl)benzyl)-6a,7,9,10-tetrahydro-[1,4]oxazino[3,4-h]pteridin-6(5H)-one

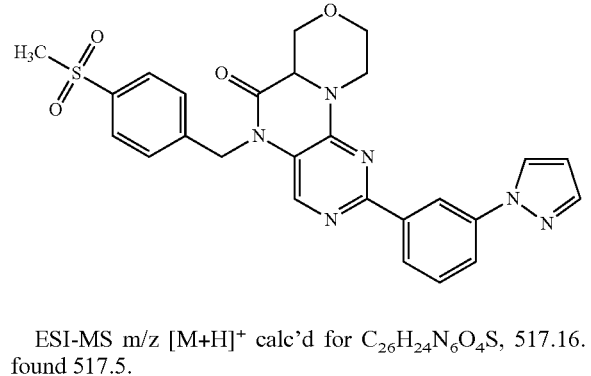

ESI-MS m/z [M+H]⁺ calc'd for $C_{26}H_{24}N_6O_4S$, 517.16. found 517.5.

Example 129

2-(3-(ethylamino)phenyl)-5-(4-(methylsulfonyl)benzyl)-6a,7,9,10-tetrahydro-[1,4]oxazino[3,4-h]pteridin-6(5H)-one

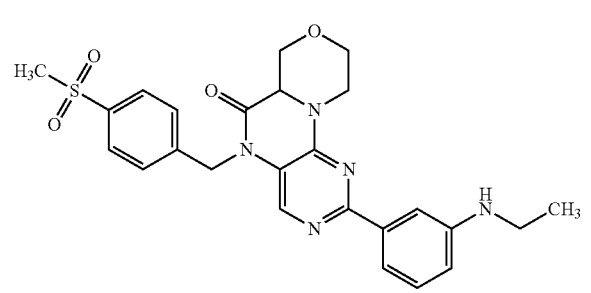 [SMILES: CCNc1cccc(-c2ncc3c(n2)N2CCOCC2C(=O)N3Cc2ccc(S(C)(=O)=O)cc2)c1]

ESI-MS m/z [M+H]⁺ calc'd for $C_{25}H_{27}N_5O_4S$, 494.18. found 494.4.

Example 130

2-(3-methyl-1H-pyrazol-4-yl)-5-(4-(methylsulfonyl)benzyl)-5,6,6a,7,9,10-hexahydro-[1,4]oxazino[3,4-h]pteridine

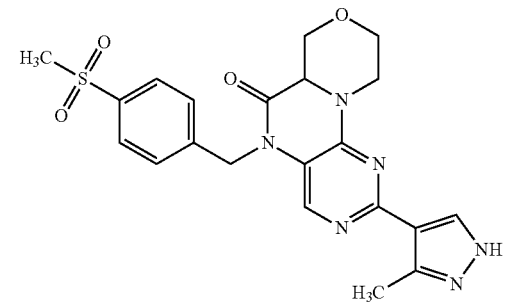 [SMILES: Cc1n[nH]cc1-c1ncc2c(n1)N1CCOCC1C(=O)N2Cc1ccc(S(C)(=O)=O)cc1]

ESI-MS m/z [M+H]⁺ calc'd for $C_{21}H_{22}N_6O_4S$, 455.14. found 455.4.

Example 131

2-(3,4-diaminophenyl)-5-(4-(methylsulfonyl)benzyl)-6a,7,9,10-tetrahydro-[1,4]oxazino[3,4-h]pteridin-6(5H)-one

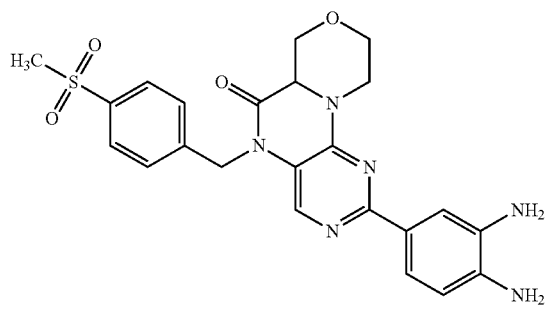 [SMILES: CS(=O)(=O)c1ccc(CN2C(=O)C3COCCN3c3nc(-c4ccc(N)c(N)c4)ncc32)cc1]

ESI-MS m/z [M+H]⁺ calc'd for $C_{23}H_{24}N_6O_4S$, 481.16. found 481.4.

Example 132

2-(3-(1,1-dioxidoisothiazolidin-2-yl)phenyl)-5-(4-(methylsulfonyl)benzyl)-6a,7,9,10-tetrahydro-[1,4]oxazino[3,4-h]pteridin-6(5H)-one

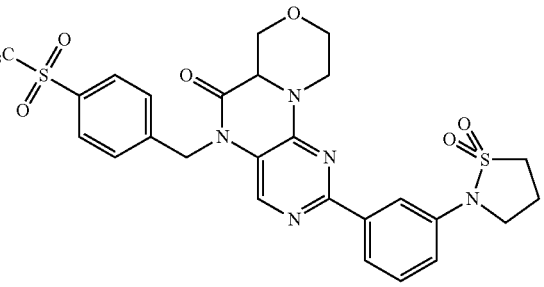

ESI-MS m/z [M+H]⁺ calc'd for $C_{26}H_{27}N_5O_6S_2$, 570.14. found 570.4.

Example 133

2-(2-aminophenyl)-5-(4-(methylsulfonyl)benzyl)-6a,7,9,10-tetrahydro-[1,4]oxazino[3,4-h]pteridin-6(5H)-one

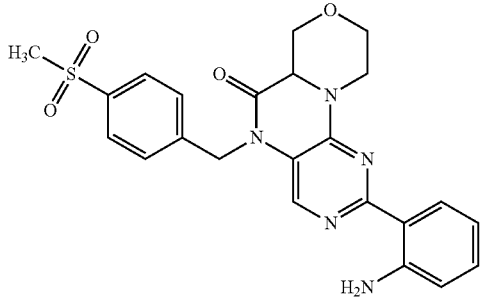 [SMILES: CS(=O)(=O)c1ccc(CN2C(=O)C3COCCN3c3nc(-c4ccccc4N)ncc32)cc1]

ESI-MS m/z [M+H]+ calc'd for $C_{23}H_{23}N_5O_4S$, 466.15. found 466.4.

Example 134

2-(7-chloro-1H-indol-3-yl)-5-(4-(methylsulfonyl)benzyl)-6a,7,9,10-tetrahydro-[1,4]oxazino[3,4-h]pteridin-6(5H)-one

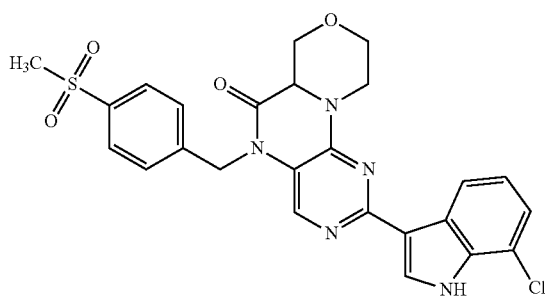 [SMILES: CS(=O)(=O)c1ccc(CN2C(=O)C3COCCN3c3nc(-c4c[nH]c5c(Cl)cccc45)ncc32)cc1]

$^1$H NMR (400 MHz, DMSO-d$_6$) δ 3.20 (s, 3H), 3.60-3.79 (m, 3H), 4.03-4.13 (m, 1H), 4.24-4.33 (m, 1H), 4.60-4.71 (m, 2H), 5.20-5.40 (m, 2H), 7.13-7.21 (m, 1H), 7.25-7.31 (m, 1H), 7.57-7.64 (m, 2H), 7.85-7.95 (m, 3H), 8.17-8.24 (m, 1H), 8.32-8.38 (m, 1H), 12.06-12.23 (m, 1H). ESI-MS m/z [M+H]+ calc'd for $C_{25}H_{22}ClN_5O_4S$, 524.11. found 524.4.

Example 135

2-(2-hydroxy-1H-indol-4-yl)-5-(4-(methylsulfonyl)benzyl)-6a,7,9,10-tetrahydro-[1,4]oxazino[3,4-h]pteridin-6(5H)-one

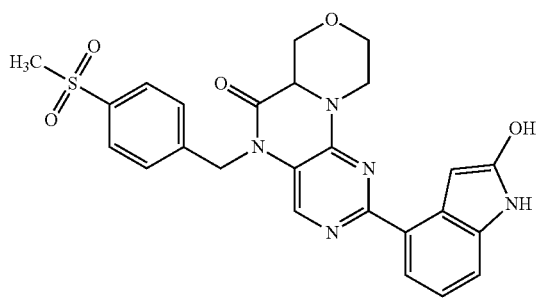 [SMILES: CS(=O)(=O)c1ccc(CN2C(=O)C3COCCN3c3nc(-c4cccc5[nH]c(O)cc45)ncc32)cc1]

$^1$H NMR (400 MHz, DMSO-d$_6$) δ 3.06-3.12 (m, 1H), 3.19 (s, 3H), 3.56-3.74 (m, 1H), 3.75-3.92 (m, 2H), 4.04-4.15 (m, 1H), 4.21-4.36 (m, 1H), 4.43-4.55 (m, 1H), 4.55-4.67 (m, 1H), 5.18-5.43 (m, 2H), 6.82-6.96 (m, 1H), 7.19-7.35 (m, 1H), 7.54-7.68 (m, 2H), 7.78-7.97 (m, 4H), 7.97-8.08 (m, 1H), 10.41-10.53 (m, 1H). ESI-MS m/z [M+H]+ calc'd for $C_{25}H_{23}N_5O_5S$, 506.14. found 506.4.

Example 136

2-(6-methoxy-1H-indol-3-yl)-5-(4-(methylsulfonyl)benzyl)-6a,7,9,10-tetrahydro-[1,4]oxazino[3,4-h]pteridin-6(5H)-one

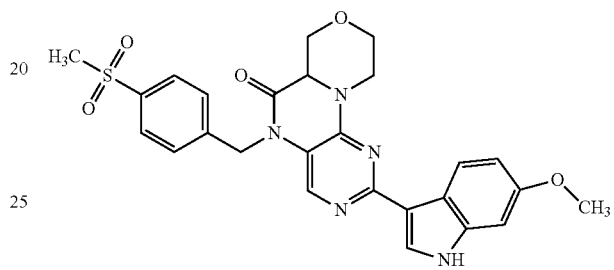

$^1$H NMR (400 MHz, DMSO-d$_6$) δ 3.20 (s, 3H), 3.61-3.67 (m, 3H), 3.75-3.82 (s, 3H), 4.04-4.15 (m, 1H), 4.23-4.34 (m, 1H), 4.58-4.76 (m, 2H), 5.19-5.41 (m, 2H), 6.77-6.87 (m, 1H), 6.93-6.99 (m, 1H), 7.58-7.65 (m, 2H), 7.75-7.85 (m, 1H), 7.88-7.95 (m, 2H), 8.02-8.16 (m, 1H), 8.18-8.24 (m, 1H). ESI-MS m/z [M+H]+ calc'd for $C_{26}H_{25}N_5O_5S$, 520.16. found 520.4.

Example 137

5-(4-(methylsulfonyl)benzyl)-2-(1H-pyrrolo[2,3-b]pyridin-3-yl)-6a,7,9,10-tetrahydro-[1,4]oxazino[3,4-h]pteridin-6(5H)-one

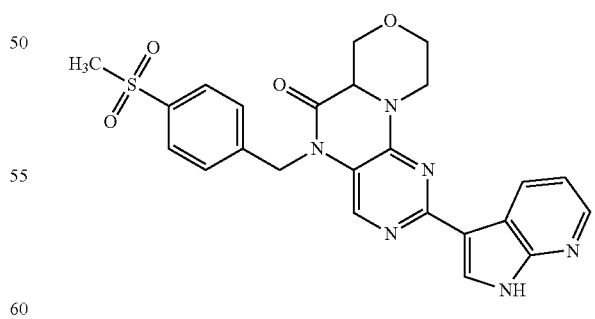

$^1$H NMR (400 MHz, DMSO-d$_6$) δ 3.12 (s, 3H), 3.51-3.69 (m, 3H), 4.01-4.13 (m, 1H), 4.23-4.33 (m, 1H), 4.57-4.71 (m, 2H), 5.18-5.43 (m, 2H), 7.15-7.27 (m, 1H), 7.60 (d, J=8.34 Hz, 2H), 7.83-7.96 (m, 3H), 8.21-8.35 (m, 2H), 8.61-8.75 (m, 1H), 12.09-12.45 (m, 1H). ESI-MS m/z [M+H]+ calc'd for $C_{24}H_{22}N_6O_4S$, 491.14. found 491.4.

Example 138

2-(7-methoxy-1H-indol-3-yl)-5-(4-(methylsulfonyl)benzyl)-6a,7,9,10-tetrahydro-[1,4]oxazino[3,4-h]pteridin-6(5H)-one

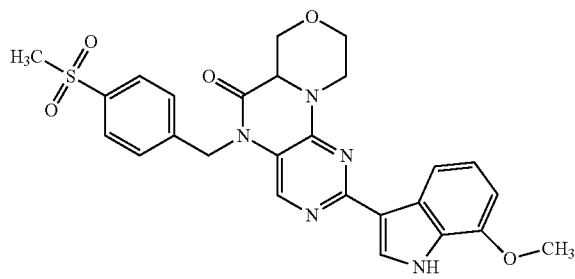

$^1$H NMR (400 MHz, DMSO-d$_6$) δ 3.21 (s, 3H), 3.61-3.72 (m, 2H), 3.73-3.83 (m, 1H), 3.94 (s, 3H), 4.05-4.15 (m, 1H), 4.24-4.33 (m, 1H), 4.64-4.81 (m, 2H), 5.20-5.41 (m, 2H), 6.75-6.84 (m, 1H), 7.07-7.17 (m, 1H), 7.63 (d, 2H), 7.74-7.83 (m, 1H), 7.91 (m, 3H), 8.08-8.23 (m, 1H), 12.01-12.24 (m, 1H). ESI-MS m/z [M+H]$^+$ calc'd for C$_{26}$H$_{23}$N$_5$O$_5$S, 520.16. found 520.4.

Example 139

2-(1H-benzo[d]imidazol-4-yl)-5-(4-(methylsulfonyl)benzyl)-6a,7,9,10-tetrahydro-[1,4]oxazino[3,4-h]pteridin-6(5H)-one

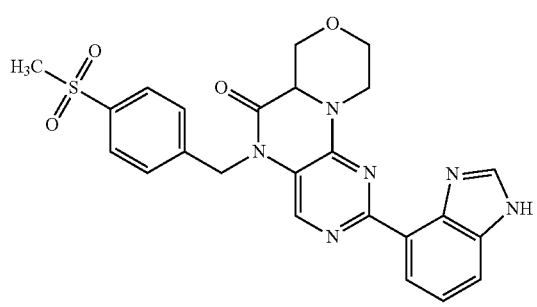 [SMILES: CS(=O)(=O)c1ccc(CN2C(=O)C3COCCN3c3nc(-c4cccc5[nH]cnc45)ncc32)cc1]

$^1$H NMR (400 MHz, DMSO-d$_6$) δ 3.12-3.19 (m, 1H), 3.20 (s, 3H), 3.51-3.69 (m, 2H), 4.03-4.09 (m, 1H), 4.25-4.34 (m, 1H), 4.64-4.76 (m, 2H), 5.17-5.29 (m, 1H), 5.40-5.51 (m, 1H), 7.53-7.67 (m, 3H), 7.84-7.97 (m, 4H), 8.36-8.43 (m, 1H), 8.98-9.23 (m, 1H). ESI-MS m/z [M+H]$^+$ calc'd for C$_{24}$H$_{22}$N$_6$O$_4$S, 491.14. found 491.4.

Example 140

2-(2-methoxypyridin-4-yl)-5-(4-(methylsulfonyl)benzyl)-6a,7,9,10-tetrahydro-[1,4]oxazino[3,4-h]pteridin-6(5H)-one

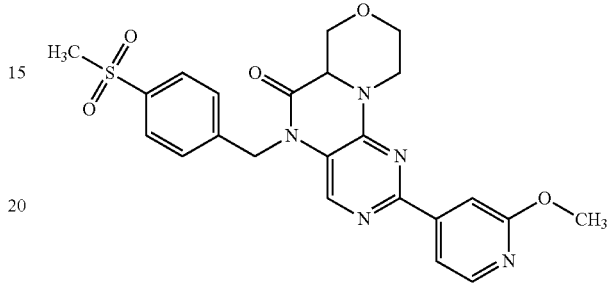

$^1$H NMR (400 MHz, DMSO-d$_6$) δ 3.02-3.13 (m, 1H), 3.18-3.21 (m, 3H), 3.56-3.66 (m, 1H), 3.67-3.77 (m, 1H), 3.86-3.92 (m, 3H), 4.00-4.07 (m, 1H), 4.24-4.31 (m, 1H), 4.58-4.68 (m, 2H), 5.19-5.42 (m, 2H), 7.52-7.56 (m, 1H), 7.57-7.64 (m, 2H), 7.73-7.77 (m, 1H), 7.88-7.94 (m, 2H), 7.99-8.04 (m, 1H), 8.23-8.28 (m, 1H). ESI-MS m/z [M+H]$^+$ calc'd for C$_{23}$H$_{23}$FN$_5$O$_5$S, 482.14. found 482.4.

Example 141

2-(4-aminopyridin-2-yl)-5-(4-(methylsulfonyl)benzyl)-6a,7,9,10-tetrahydro-[1,4]oxazino[3,4-h]pteridin-6(5H)-one

$^1$H NMR (400 MHz, DMSO-d$_6$) δ 3.06-3.17 (m, 1H), 3.18-3.21 (m, 3H), 3.56-3.61 (m, 1H), 3.70-3.81 (m, 1H), 3.98-4.07 (m, 1H), 4.22-4.30 (m, 1H), 4.61-4.77 (m, 2H), 5.21-5.40 (m, 2H), 6.46-6.53 (m, 1H), 6.88-6.98 (m, 2H), 7.55-7.64 (m, 2H), 7.91-7.93 (m, 1H), 8.70-8.82 (m, 1H), 9.08-9.17 (m, 2H). ESI-MS m/z [M+H]$^+$ calc'd for C$_{22}$H$_{22}$N$_6$O$_4$S, 467.14. found 467.5.

Example 142

2-(7-fluoro-1H-indol-4-yl)-5-(4-(methylsulfonyl) benzyl)-6a,7,9,10-tetrahydro-[1,4]oxazino[3,4-h] pteridin-6(5H)-one

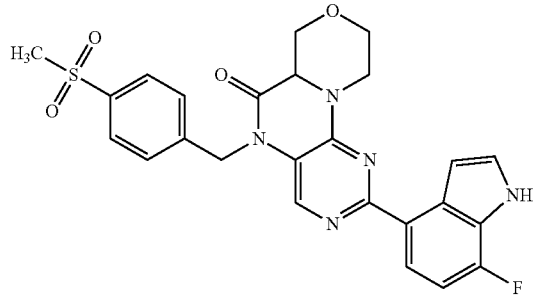 [SMILES: CS(=O)(=O)c1ccc(CN2C(=O)C3COCCN3c3nc(-c4ccc(F)c5[nH]ccc45)ncc32)cc1]

$^1$H NMR (400 MHz, DMSO-d$_6$) δ 3.19 (m, 4H), 3.59-3.66 (m, 1H), 3.66-3.76 (m, 1H), 4.03-4.13 (m, 1H), 4.24-4.34 (m, 1H), 4.51-4.68 (m, 2H), 5.19-5.44 (m, 2H), 6.94-7.06 (m, 1H), 7.33-7.40 (m, 1H), 7.46-7.52 (m, 1H), 7.58-7.66 (m, 2H), 7.88-7.96 (m, 2H), 7.97-8.06 (m, 2H), 11.72-11.78 (m, 1H). ESI-MS m/z [M+H]$^+$ calc'd for C$_{25}$H$_{22}$FN$_5$O$_4$S, 508.14. found 508.4.

Example 143

2-(7-fluoro-3-methyl-1H-indol-4-yl)-5-(4-(methylsulfonyl)benzyl)-6a,7,9,10-tetrahydro-[1,4]oxazino [3,4-h]pteridin-6(5H)-one

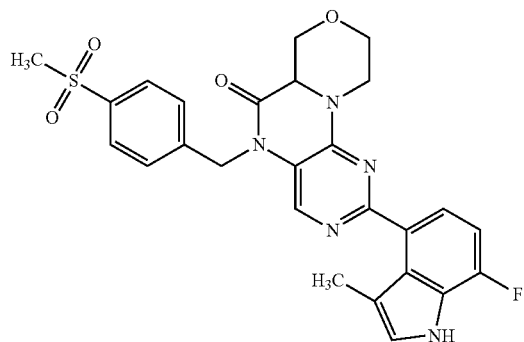 [SMILES: Cc1c[nH]c2c(F)ccc(-c3ncc4c(n3)N3CCOCC3C(=O)N4Cc3ccc(S(C)(=O)=O)cc3)c12]

$^1$H NMR (400 MHz, DMSO-d$_6$) δ 1.97-2.04 (m, 3H), 3.02-3.10 (m, 1H), 3.19 (s, 3H), 3.51-3.62 (m, 1H), 3.68-3.78 (m, 1H), 3.95-4.02 (m, 1H), 4.22-4.32 (m, 1H), 4.42-4.72 (m, 2H), 5.19-5.43 (m, 2H), 6.90-7.00 (m, 1H), 7.15-7.21 (m, 1H), 7.22-7.27 (m, 1H), 7.58-7.66 (m, 2H), 7.89-7.95 (m, 2H), 7.96-8.04 (m, 1H). ESI-MS m/z [M+H]$^+$ calc'd for C$_{26}$H$_{24}$FN$_5$O$_4$S, 522.15. found 522.5.

Example 144

5-(4-(methylsulfonyl)benzyl)-2-(1H-pyrrolo[2,3-c] pyridin-4-yl)-6a,7,9,10-tetrahydro-[1,4]oxazino[3,4-h]pteridin-6(5H)-one

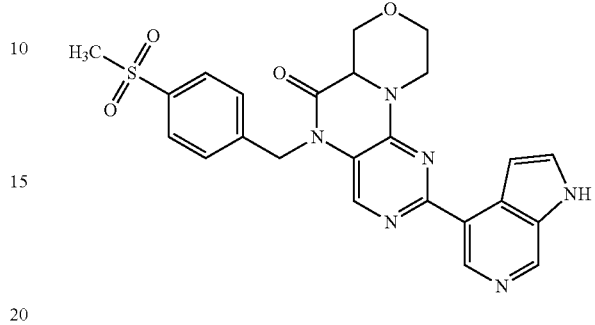

$^1$H NMR (400 MHz, DMSO-d$_6$) δ 3.12-3.19 (m, 1H), 3.19-3.23 (s, 3H), 3.60-3.80 (m, 2H), 4.04-4.14 (m, 1H), 4.25-4.35 (m, 1H), 4.55-4.64 (m, 1H), 4.65-4.73 (m, 1H), 5.23-5.46 (m, 2H), 7.55-7.68 (m, 3H), 7.87-7.98 (m, 2H), 8.06-8.15 (m, 1H), 8.27-8.38 (m, 1H), 8.98-9.07 (m, 1H), 9.11-9.19 (m, 1H), 12.82-12.99 (m, 1H). ESI-MS m/z [M+H]$^+$ calc'd for C$_{24}$H$_{24}$N$_6$O$_4$S, 491.14. found 491.4.

Example 145

5-benzyl-2-(1H-indol-4-yl)-6a,7,9,10-tetrahydro-[1,4]oxazino[3,4-h]pteridin-6(5H)-one

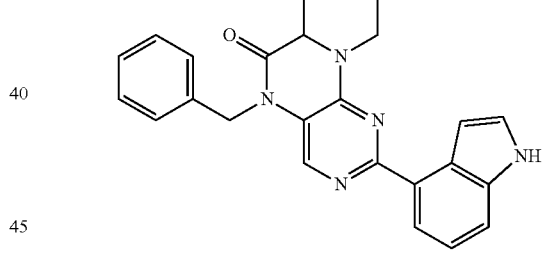

5-Benzyl-2-chloro-6a,7,9,10-tetrahydro-[1,4]oxazino[3,4-h]pteridin-6(5H)-one (PREPARATION x39, 200 mg, 0.605 mmol), 4-(4,4,5,5-tetramethyl-1,3,2-dioxaborolan-2-yl)-1H-indole (294 mg, 1.209 mmol), and PdCl$_2$(dppf) (22.12 mg, 0.030 mmol) was suspended in dioxane (3 mL) and aqueous saturated NaHCO$_3$ (0.6 mL). The resulting brown suspension was heated to 100° C. for 18 hours, then diluted with ethyl acetate and washed with aqueous saturated NH$_4$Cl (3×5 mL) and brine (3×5 mL). The combined organic layers were dried over MgSO$_4$, filtered, and concentrated in vacuo to give crude product, which was loaded onto an ISCO® silica gel cartridge (12 g) and eluted using an ethyl acetate/hexane gradient. The product was collected and concentrated in vacuo to afford the title compound as a white solid (80 mg, 32%). $^1$H NMR (400 MHz, DMSO-d$_6$) δ 3.06-3.19 (m, 1H), 3.58-3.74 (m, 2H), 4.01-4.12 (m, 1H), 4.25-4.34 (m, 1H), 4.49-4.63 (m, 2H), 5.12-5.31 (m, 2H), 7.11-7.18 (m, 1H), 7.24-7.40 (m, 6H), 7.40-7.44 (m, 1H), 7.46-7.51 (m, 1H), 7.99-8.03 (m, 1H), 8.04-8.07 (m, 1H), 11.20-11.26 (m, 1H). ESI-MS m/z [M+H]$^+$ calc'd for C$_{24}$H$_{21}$N$_5$O$_2$, 412.17. found 412.4.

Example 146

5-(6-chloro-2,3-dihydro-1H-inden-1-yl)-2-(1H-indol-4-yl)-6a,7,9,10-tetrahydro-[1,4]oxazino[3,4-h]pteridin-6(5H)-one

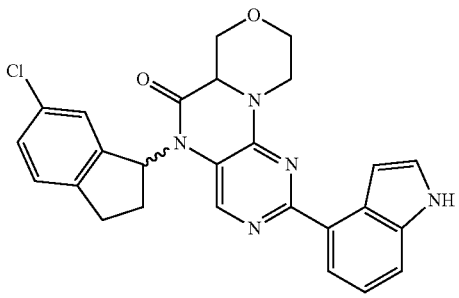 [SMILES: O=C1C2COCCN2c2nc(-c3cccc4[nH]ccc34)ncc2N1C1CCc2ccc(Cl)cc21]

2-Chloro-5-(6-chloro-2,3-dihydro-1H-inden-1-yl)-6a,7,9,10-tetrahydro-[1,4]oxazino[3,4-h]pteridin-6(5H)-one (PREPARATION x41, 90 mg, 0.230 mmol), 4-(4,4,5,5-tetramethyl-1,3,2-dioxaborolan-2-yl)-1H-indole (112 mg, 0.460 mmol) and PdCl$_2$(dppf) (8.42 mg, 0.012 mmol) were suspended in dioxane (2 mL) and aqueous saturated NaHCO$_3$ (0.4 mL). The resulting brown suspension was heated to 100° C. and stirred overnight. The reaction mixture was subsequently diluted with EtOAc and washed with aqueous saturated NH$_4$Cl (3×5 mL). The combined organic layers were dried over MgSO$_4$, filtered, and concentrated to give crude product, which was taken up in DMSO (1.5 mL) and purified by LC/MS using a gradient of 35-60% CH$_3$CN (with 0.035% TFA) in H$_2$O (with 0.05% TFA). The pure fractions were combined and lyophilized to give a TFA salt of the title compound as a bright yellow solid (20.2 mg, 18.6%). $^1$H NMR (400 MHz, DMSO-d$_6$) δ 2.42-2.49 (m, 2H), 2.93-3.24 (m, 4H), 3.60-3.72 (m, 2H), 3.98-4.15 (m, 1H), 4.15-4.35 (m, 1H), 4.43-4.66 (m, 2H), 7.12-7.49 (m, 7H), 7.50-7.59 (m, 1H), 7.89-7.98 (m, 1H), 11.27-11.36 (m, 1H). ESI-MS m/z [M+H]$^+$ calc'd for C$_{26}$H$_{22}$ClN$_5$O$_2$, 472.15. found 472.5.

Example 147

1-(4-(5-(6-chloro-2,3-dihydro-1H-inden-1-yl)-6-oxo-5,6,6a,7,9,10-hexahydro-[1,4]oxazino[3,4-h]pteridin-2-yl)phenyl)-3-methylurea

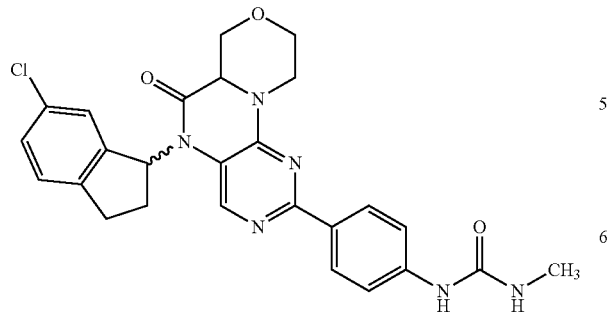

The title compound was prepared in a manner similar to EXAMPLE 84 using 2-chloro-5-(6-chloro-2,3-dihydro-1H-inden-1-yl)-6a,7,9,10-tetrahydro-[1,4]oxazino[3,4-h]pteridin-6(5H)-one (PREPARATION x41, 90 mg, 0.230 mmol), 1-methyl-3-(4-(4,4,5,5-tetramethyl-1,3,2-dioxaborolan-2-yl)phenyl)urea (127 mg, 0.460 mmol) and PdCl$_2$(dppf) (8.42 mg, 0.012 mmol) in dioxane (2 mL) and aqueous saturated NaHCO$_3$ (0.4 mL). $^1$H NMR (400 MHz, DMSO-d$_6$) δ 2.36-2.45 (m, 2H), 2.62-2.66 (d, 3H), 3.08-3.22 (m, 3H), 3.55-3.67 (m, 3H), 3.95-4.10 (m, 1H), 4.13-4.30 (m, 1H), 4.38-4.66 (m, 2H), 6.03-6.16 (m, 1H), 7.14-7.43 (m, 4H), 7.43-7.52 (d, 2H), 8.03-8.16 (d, 2H), 8.72-8.82 (m, 1H). ESI-MS m/z [M+H]$^+$ calc'd for C$_{26}$H$_{25}$ClN$_6$O$_3$, 505.17. found 505.4.

Example 148

1-(4-(5-(6-methoxy-2,3-dihydro-1H-inden-1-yl)-6-oxo-5,6,6a,7,9,10-hexahydro-[1,4]oxazino[3,4-h]pteridin-2-yl)phenyl)-3-methylurea

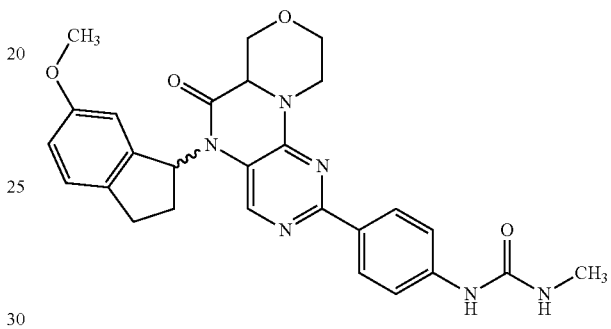

The title compound was prepared in a manner similar to EXAMPLE 84 using 2-chloro-5-(6-methoxy-2,3-dihydro-1H-inden-1-yl)-6a,7,9,10-tetrahydro-[1,4]oxazino[3,4-h]pteridin-6(5H)-one (PREPARATION x43, 70 mg, 0.181 mmol), 1-methyl-3-(4-(4,4,5,5-tetramethyl-1,3,2-dioxaborolan-2-yl)phenyl)urea (100 mg, 0.362 mmol) and PdCl$_2$(dppf) (6.62 mg, 9.05 μmol) in dioxane (3 mL) and aqueous saturated NaHCO$_3$ (0.6 mL). $^1$H NMR (400 MHz, DMSO-d$_6$) δ 2.23-2.45 (m, 3H), 2.60-2.66 (m, 3H), 2.87-3.17 (m, 4H), 3.55-3.72 (m, 4H), 3.95-4.10 (m, 1H), 4.16-4.34 (m, 1H), 4.38-4.64 (m, 2H), 6.04-6.15 (m, 1H), 6.49-6.91 (m, 3H), 7.23-7.34 (m, 1H), 7.41-7.50 (m, 2H), 8.04-8.14 (m, 2H), 8.72-8.81 (m, 1H). ESI-MS m/z [M+H]$^+$ calc'd for C$_{27}$H$_{28}$N$_6$O$_4$, 501.22. found 501.5.

Example 149 & 150

(R)-2-(1H-indol-4-yl)-6a,7,9,10-tetrahydro-[1,4]oxazino[3,4-h]pteridin-6(5H)-one and (S)-2-(1H-indol-4-yl)-6a,7,9,10-tetrahydro-[1,4]oxazino[3,4-h]pteridin-6(5H)-one

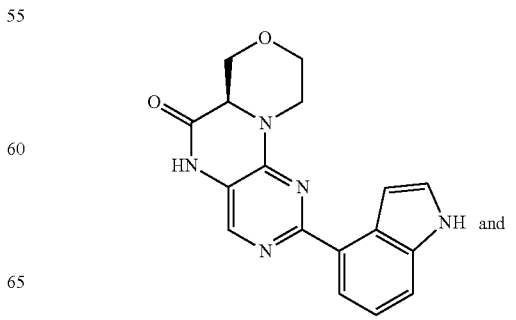

and

-continued

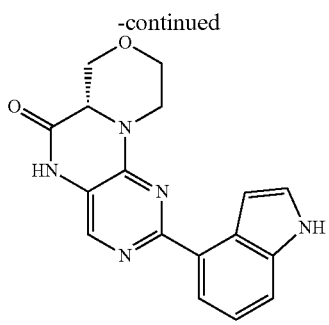

To a 2 mL microwave vial were added 2-chloro-6a,7,9,10-tetrahydro-[1,4]oxazino[3,4-h]pteridin-6(5H)-one (PREPARATION x1, 200 mg, 0.831 mmol), 4-(4,4,5,5-tetramethyl-1,3,2-dioxaborolan-2-yl)-1H-indole (303 mg, 1.247 mmol) and [1,1'-bis(diphenylphosphino)ferrocene]-dichloropalladium(II) (34.2 mg, 0.042 mmol). After the vial was sealed, dioxane (3.3 mL) and aqueous saturated NaHCO$_3$ (0.83 mL) were added, and the mixture was degassed by bubbling nitrogen through a syringe needle for 10 minutes. The mixture was then heated in a microwave to 120° C. for 60 minutes. Combined organic layers were dried over MgSO$_4$, filtered, and concentrated. DMF (1 mL) was added and the mixture was filtered by syringe filter. The crude product was purified by preparatory HPLC using a 10-25% gradient of CH$_3$CN (with 0.035% TFA) in H$_2$O (with 0.05% TFA). Lyophilization of the collected fractions gave a racemic mixture of the title compounds (TFA salt) (65 mg, 24.3%). $^1$H NMR (DMSO-d$_6$) δ 3.18 (td, J=12.6, 3.3 Hz, 1H), 3.55-3.71 (m, 2H), 4.04 (dd, J=11.6, 3.3 Hz, 1H), 4.19 (dd, J=11.4, 3.8 Hz, 1H), 4.50 (d, J=8.1 Hz, 1H), 4.63 (d, J=12.6 Hz, 1H), 7.18-7.27 (m, 2H), 7.51 (br s, 1H), 7.60 (d, J=8.1 Hz, 1H), 7.84 (s, 1H), 7.88 (d, J=7.3 Hz, 1H), 11.07 (br s, 1H), 11.41 (br s, 1H). ESI-MS m/z [M+H]$^+$ calc'd for C$_{17}$H$_{15}$N$_5$O$_2$, 322.12. found 322.3.

The racemic mixture was subsequently dissolved in MeOH (10 mL) and separated by supercritical fluid chromatography (SFC): Chiralcel OJ-H (5 μm, 20×150 mm), 40% MeOH in liquid CO$_2$ at 50 mL/min, 3.3 mL/injection. The fractions collected at ~5.8 and ~7.1 minutes were identified as the enantiomers of the title compound, but the absolute stereochemical configuration was not assigned. Lyophilization of each enantiomer gave TFA salts of the title compounds (EXAMPLE 149: 10 mg, shorter retention time; EXAMPLE 150: 11 mg, longer retention time).

Example 151

2-(benzo[d][1,3]dioxol-4-yl)-6a,7,9,10-tetrahydro-[1,4]oxazino[3,4-h]pteridin-6(5H)-one

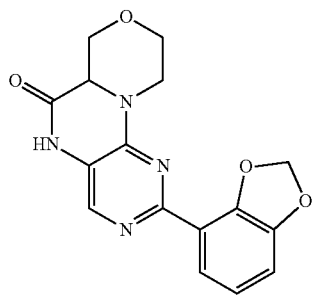 [SMILES: O=C1Nc2cnc(-c3cccc4c3OCO4)nc2N2CCOCC12]

The title compound was prepared in a manner similar to EXAMPLE 84 using 2-chloro-6a,7,9,10-tetrahydro-[1,4]oxazino[3,4-h]pteridin-6(5H)-one (PREPARATION x1, 50 mg, 0.208 mmol), benzo[d][1,3]dioxol-4-ylboronic acid (51.7 mg, 0.312 mmol) and PdCl$_2$(dppf) (7.60 mg, 10.39 μmol) in dioxane (2 mL) and aqueous saturated NaHCO$_3$ (0.4 mL). $^1$H NMR (400 MHz, DMSO-d$_6$) δ 2.96-3.09 (m, 1H), 3.62 (m, 2H), 3.93-4.01 (m, 1H), 4.11-4.20 (m, 1H), 4.36-4.46 (m, 1H), 4.52-4.62 (m, 1H), 6.12 (s, 2H), 6.94 (t, 1H), 7.02 (m, 1H), 7.58-7.65 (m, 1H), 7.83 (s, 1H), 10.98 (s, 1H). ESI-MS m/z [M+H]$^+$ calc'd for C$_{16}$H$_{14}$N$_4$O$_4$, 327.10. found 327.3.

Example 152

2-(1H-benzo[d]imidazol-4-yl)-6a,7,9,10-tetrahydro-[1,4]oxazino[3,4-h]pteridin-6(5H)-one

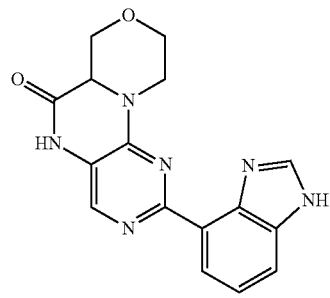 [SMILES: O=C1Nc2cnc(-c3cccc4[nH]cnc34)nc2N2CCOCC12]

The title compound was prepared in a manner similar to EXAMPLE 84 using 2-chloro-6a,7,9,10-tetrahydro-[1,4]oxazino[3,4-h]pteridin-6(5H)-one (PREPARATION x1, 50 mg, 0.208 mmol), 1H-benzo[d]imidazol-4-ylboronic acid (71.5 mg, 0.441 mmol), and PdCl$_2$(dppf) (7.60 mg, 10.39 μmol) in dioxane (2 mL) and aqueous saturated NaHCO$_3$ (0.4 mL). $^1$H NMR (400 MHz, DMSO-d$_6$) δ 3.10-3.19 (m, 1H), 3.50-3.59 (m, 2H), 3.99 (d, J=3.28 Hz, 1H), 4.18 (dd, J=11.24, 3.66 Hz, 1H), 4.43 (dd, J=10.61, 3.79 Hz, 1H), 4.59-4.71 (m, 1H), 7.49-7.67 (m, 1H), 7.90 (d, J=8.08 Hz, 1H), 8.03 (s, 1H), 8.39 (d, J=7.83 Hz, 1H), 9.23 (br s, 1H), 11.03 (s, 1H). ESI-MS m/z [M+H]$^+$ calc'd for C$_{16}$H$_{14}$N$_6$O$_2$, 323.12. found 323.2.

Example 153 & 154

(S)-2-(1H-indol-4-yl)-5-((S)-1-p-tolylethyl)-6a,7,9,10-tetrahydro-[1,4]oxazino[3,4-h]pteridin-6(5H)-one and (R)-2-(1H-indol-4-yl)-5-((S)-1-p-tolylethyl)-6a,7,9,10-tetrahydro-[1,4]oxazino[3,4-h]pteridin-6(5H)-one

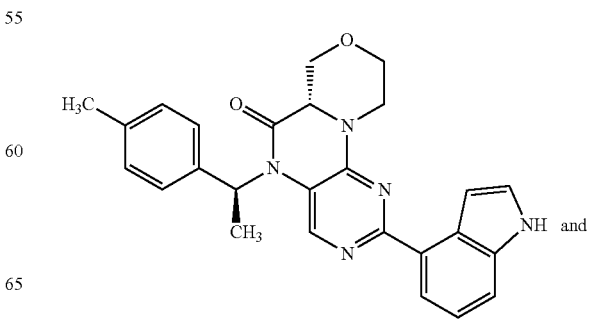

-continued

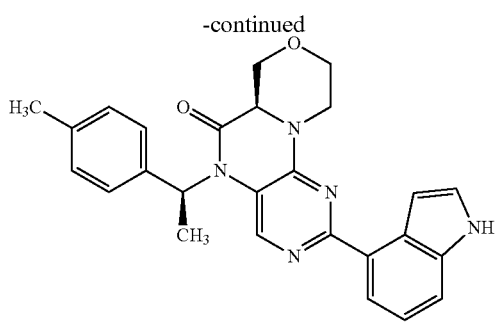

The title compounds were prepared in a manner similar to EXAMPLE 146 using 4-(4,4,5,5-tetramethyl-1,3,2-dioxaborolan-2-yl)-1H-indole (56.9 mg, 0.234 mmol), PdCl$_2$(dppf) (5.71 mg, 7.80 µmol), and either Diastereomer 1 (EXAMPLE 153) or Diastereomer 2 (EXAMPLE 154) of 2-chloro-5-((S)-1-p-tolylethyl)-6a,7,9,10-tetrahydro-[1,4]oxazino[3,4-h]pteridin-6(5H)-one (PREPARATION x35, 56 mg, 0.156 mmol) in dioxane (1.5 mL) and aqueous saturated NaHCO$_3$ (0.3 mL).

Example 153

$^1$H NMR (400 MHz, DMSO-d$_6$) δ 1.70-1.80 (m, 3H), 1.81-1.87 (m, 1H), 2.24-2.28 (m, 1H), 2.31 (s, 1H), 3.07-3.20 (m, 1H), 3.59-3.71 (m, 3H), 4.01-4.13 (m, 1H), 4.23-4.35 (m, 1H), 4.43-4.64 (m, 2H), 6.25-6.36 (m, 1H), 7.11-7.33 (m, 5H), 7.40-7.47 (m, 1H), 7.48-7.57 (m, 1H), 7.60-7.66 (m, 1H), 7.91-7.98 (m, 1H), 11.15-11.40 (m, 1H). ESI-MS m/z [M+H]$^+$ calc'd for C$_{26}$H$_{25}$N$_5$O$_2$, 440.20. found 440.5.

Example 154

$^1$H NMR (400 MHz, DMSO-d$_6$) δ 1.72-1.79 (m, 1H), 1.80-1.88 (m, 3H), 2.27 (s, 1H), 2.29-2.33 (m, 1H), 3.08-3.20 (m, 1H), 3.61-3.71 (m, 2H), 3.71-3.80 (m, 1H), 4.01-4.12 (m, 1H), 4.23-4.35 (m, 1H), 4.43-4.63 (m, 2H), 6.11-6.23 (m, 1H), 6.26-6.35 (m, 1H), 7.10-7.34 (m, 3H), 7.40-7.48 (m, 1H), 7.49-7.57 (m, 1H), 7.60-7.65 (m, 1H), 7.74-7.82 (m, 1H), 7.86-7.96 (m, 1H), 11.22-11.35 (m, 1H). ESI-MS m/z [M+H]$^+$ calc'd for C$_{26}$H$_{25}$N$_5$O$_2$, 440.20. found 440.5.

Example 155

5-(4-(methylsulfonyl)benzyl)-2-(1H-pyrrolo[2,3-b]pyridin-4-yl)-6a,7,9,10-tetrahydro-[1,4]oxazino[3,4-h]pteridin-6(5H)-one

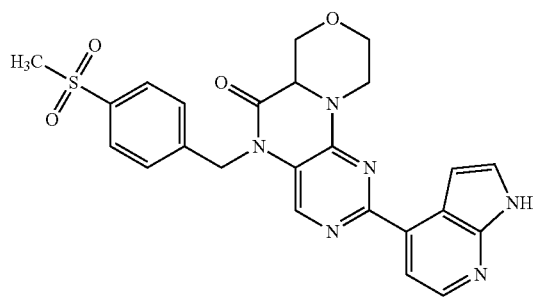 [SMILES: CS(=O)(=O)c1ccc(CN2C(=O)C3COCCN3c3nc(-c4ccnc5[nH]ccc45)ncc32)cc1]

5-(4-(Methylsulfonyl)benzyl)-2-(1-tosyl-1H-pyrrolo[2,3-b]pyridin-4-yl)-6a,7,9,10-tetrahydro-[1,4]oxazino[3,4-h]pteridin-6(5H)-one (PREPARATION x44, 130 mg, 0.202 mmol) was dissolved in DMF (7 mL). Potassium hydroxide (2M, 302 µL, 0.605 mmol) in methanol (3 mL) was added dropwise. The reaction was stirred at room temperature for 18 hours. The reaction mixture was subsequently diluted with CH$_2$Cl$_2$ (5 mL) and washed with 1M hydrochloric acid (3×3 mL) and brine (3×3 mL). The combined organic layers were dried over MgSO$_4$, filtered, and concentrated in vacuo to give crude product, which was purified by LC/MS using a gradient of 20-35% CH$_3$CN (with 0.035% TFA) in H$_2$O (with 0.05% TFA). The pure fractions were combined and lyophilized to afford a TFA salt of the title compound as an off-white solid (7 mg, 7%). $^1$H NMR (400 MHz, DMSO-d$_6$) δ 3.22 (s, 3H), 3.42-3.50 (m, 2H), 3.69-3.77 (m, 1H), 4.04-4.12 (m, 1H), 4.26-4.32 (m, 1H), 4.54-4.68 (m, 2H), 5.23-5.43 (m, 2H), 7.20-7.25 (m, 1H), 7.53-7.57 (m, 1H), 7.59-7.65 (m, 2H), 7.88-7.95 (m, 3H), 8.08-8.12 (m, 1H), 8.27-8.32 (m, 1H), 11.73-11.80 (m, 1H). ESI-MS m/z [M+H]$^+$ calc'd for C$_{24}$H$_{22}$N$_6$O$_4$S, 491.14. found 491.4.

Example 156

2-(2-methyl-1H-imidazol-1-yl)-5-(4-(methylsulfonyl)benzyl)-6a,7,9,10-tetrahydro-[1,4]oxazino[3,4-h]pteridin-6(5H)-one

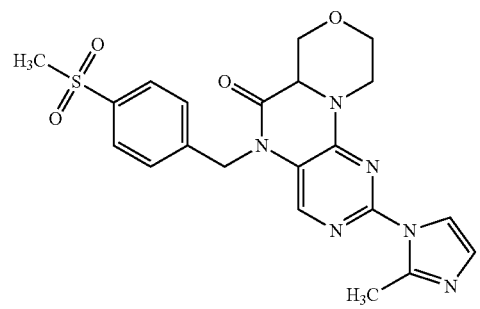 [SMILES: Cc1nccn1-c1ncc2c(n1)N1CCOCC1C(=O)N2Cc1ccc(S(C)(=O)=O)cc1]

STEP A: 4-(5-bromo-2-(2-methyl-1H-imidazol-1-yl)pyrimidin-4-yl)-N-(4-(methylsulfonyl)benzyl)morpholine-3-carboxamide

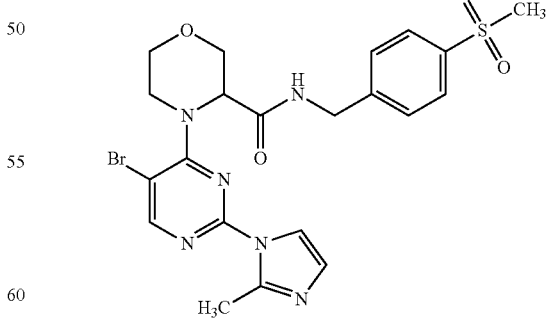

HATU (207 mg, 0.544 mmol) was added to a mixture of 4-(5-bromo-2-(2-methyl-1H-imidazol-1-yl)pyrimidin-4-yl)morpholine-3-carboxylic acid, HCl (PREPARATION x53, 200 mg, 0.494 mmol), 4-methanesulfonyl-benzylamine (101 mg, 0.544 mmol) and Et$_3$N (0.276 mL, 1.977 mmol) in DMF (4 mL) at 0° C. The resulting mixture was stirred at room temperature for 1 hour, then diluted with EtOAc and water, and extracted with EtOAc (2×). The extract was washed with brine, dried over Na$_2$SO$_4$, filtered, and concentrated in vacuo to give a residue, which was purified by column chromatography (SiO$_2$, 0-10% MeOH in CHCl$_3$ gradient) to give the title compound as a colorless amorphous solid (196 mg, 74.1%). $^1$H NMR (400 MHz, DMSO-d$_6$) δ 2.58 (s, 3H), 3.19 (s, 3H), 3.47-3.67 (m, 2H), 3.69-3.83 (m, 1H), 3.89-3.98 (m, 1H), 4.28-4.53 (m, 4H), 4.95 (br s, 1H), 6.86 (d, J=1.52 Hz, 1H), 7.47 (d, J=8.59 Hz, 2H), 7.71 (d, J=1.52 Hz, 1H), 7.78 (d, J=8.34 Hz, 2H), 8.60 (s, 1H), 8.81 (t, J=5.81 Hz, 1H).

STEP B: 2-(2-methyl-1H-imidazol-1-yl)-5-(4-(methylsulfonyl)benzyl)-6a,7,9,10-tetrahydro-[1,4]oxazino[3,4-h]pteridin-6(5H)-one A mixture of 4-(5-bromo-2-(2-methyl-1H-imidazol-1-yl)pyrimidin-4-yl)-N-(4-(methylsulfonyl)benzyl)morpholine-3-carboxamide (100 mg, 0.187 mmol), palladium(II) acetate (4.19 mg, 0.019 mmol), Xantphos (21.61 mg, 0.037 mmol), and potassium phosphate, tribasic (79 mg, 0.374 mmol) in 1,4-dioxane (1 mL) and tert-butanol 0.25 mL was heated to 100° C. in a microwave for 1 hour and then heated again to 100° C. in the microwave for 10 hours. Water was subsequently added to the reaction mixture, which formed a precipitate that was collected by filtration. The solids were washed with water and EtOAc to afford the title compound as an off-white solid (54.2 mg, 63.8%). $^1$H NMR (400 MHz, DMSO-d$_6$) δ 2.63 (s, 3H), 3.02-3.13 (m, 1H), 3.21 (s, 3H), 3.53-3.64 (m, 1H), 3.71 (t, J=10.99 Hz, 1H), 3.98-4.06 (m, 1H), 4.26 (dd, J=11.24, 3.92 Hz, 1H), 4.37-4.45 (m, 1H), 4.65 (dd, J=10.61, 3.79 Hz, 1H), 5.17-5.37 (m, 2H), 6.83 (d, J=1.52 Hz, 1H), 7.59 (d, J=8.34 Hz, 2H), 7.73 (d, J=1.52 Hz, 1H), 7.84-7.94 (m, 3H). ESI-MS m/z [M+H]$^+$ calc'd for C$_{21}$H$_{22}$N$_6$O$_4$S, 455.14. found 455.3.

Example 157

2-(2-(difluoromethyl)-1H-benzo[d]imidazol-1-yl)-5-((5-methyl-1,3,4-oxadiazol-2-yl)methyl)-6a,7,9,10-tetrahydro-[1,4]oxazino[3,4-h]pteridin-6(5H)-one

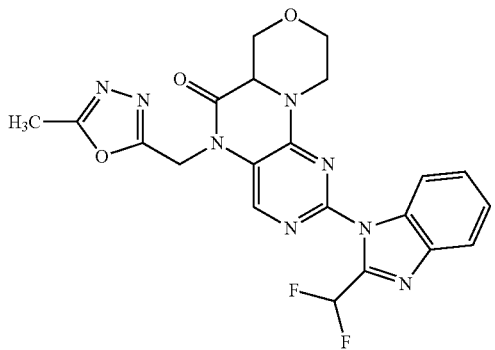 [SMILES: Cc1nnc(CN2C(=O)C3COCCN3c3nc(-n4c(C(F)F)nc5ccccc54)ncc32)o1]

STEP A: 4-(5-bromo-2-(2-(difluoromethyl)-1H-benzo[c/]imidazol-1-yl)pyrimidin-4-yl)-N-((5-methyl-1,3,4-oxadiazol-2-yl)methyl)morpholine-3-carboxamide

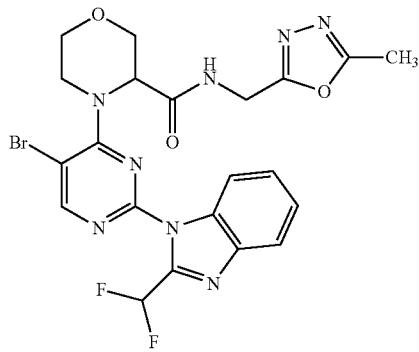 [SMILES: Cc1nnc(CNC(=O)C2COCCN2c2nc(-n3c(C(F)F)nc4ccccc43)ncc2Br)o1]

To a stirred solution of 4-(5-bromo-2-(2-(difluoromethyl)-1H-benzo[c/]imidazol-1-yl)pyrimidin-4-yl)morpholine-3-carboxylic acid (PREPARATION x45, 250 mg, 0.55 mmol) was added (5-methyl-1,3,4-oxadiazol-2-yl)methanamine (114 mg, 0.72 mmol), EDC (138 mg, 0.72 mmol), Et$_3$N (167 mg, 1.65 mmol) and HOBt (81 mg, 0.6 mmol). The reaction mixture was stirred overnight. Water was subsequently added and the resulting mixture was extracted with DCM (3×). The combined organic layers were washed with water, dried over sodium sulfate, and concentrated in vacuo. The crude product was purified by column chromatography (SiO$_2$, DCM:MeOH=18:1) to give the title compound (120 mg, 40%). $^1$H NMR (400 MHz, CDCl$_3$) δ 2.52 (s, 3H), 3.93-3.77 (m, 4H), 4.05-4.03 (m, 1H), 4.23-4.20 (m, 1H), 4.61-4.59 (m, 1H), 4.71-4.71 (m, 2H), 5.08 (s, 1H), 7.25 (d, J=8.0 Hz, 1H), 7.66-7.39 (m, 4H), 7.90 (d, J=7.2 Hz, 1H), 8.02 (s, 2H), 8.28 (d, J=8.0 Hz, 1H), 8.62 (s, 1H).

STEP B: 2-(2-(difluoromethyl)-1H-benzo[d]imidazol-1-yl)-5-((5-methyl-1,3,4-oxadiazol-2-yl)methyl)-6a,7,9,10-tetrahydro-[1,4]oxazino[3,4-h]pteridin-6(5H)-one A mixture of 4-(5-bromo-2-(2-(difluoromethyl)-1H-benzo[c/]imidazol-1-yl)pyrimidin-4-yl)-N-((5-methyl-1,3,4-oxadiazol-2-yl)methyl)morpholine-3-carboxamide (30 mg, 0.05 mmol), Pd(OAc)$_2$ (1 mg, 0.005 mmol), BINAP (2.5 mg, 0.05 mmol) and Cs$_2$CO$_3$ (33.0 mg, 0.10 mmol) in dioxane (5 mL) was stirred overnight at 100° C. under a blanket of nitrogen. The mixture was subsequently concentrated and the resulting residue was purified by column chromatography (SiO$_2$, DCM:MeOH=18:1) to give the title compound as a white solid (15 mg, 65%). $^1$H NMR (400 MHz, DMSO-d$_6$) δ 3.24 (td, J=12.8, 3.5 Hz, 1H), 3.39 (s, 3H), 3.62-3.78 (m, 2H), 4.10 (dd, J=11.5, 3.2 Hz, 1H), 4.31 (dd, J=11.5, 3.9 Hz, 1H), 4.45 (dd, J=13.3, 1.4 Hz, 1H), 4.67 (dd, J=10.6, 3.8 Hz, 1H), 5.45 (d, J=16.9 Hz, 1H), 5.56 (d, J=16.9 Hz, 1H), 7.49 (td, J=8.1, 1.3 Hz, 1H), 7.52-7.59 (m, 1H), 7.84 (t, J=53.1 Hz, 1H), 7.92 (d, J=7.6 Hz, 1H), 8.36-8.42 (m, 2H). ESI-MS m/z [M+H]$^+$ calc'd for C$_{21}$H$_{18}$F$_2$N$_8$O$_3$, 469.15. found 469.

Example 158

1-methyl-3-(4-(6-oxo-5-(tetrahydro-2H-pyran-4-yl)-5,6,6a,7,9,10-hexahydro-[1,4]oxazino[3,4-h]pteridin-2-yl)phenyl)urea

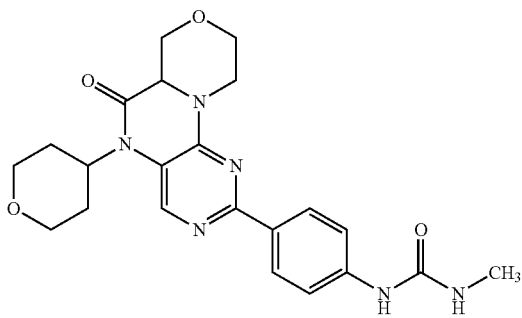

To a 5 mL microwave vial were added 2-chloro-5-(tetrahydro-2H-pyran-4-yl)-6a,7,9,10-tetrahydro-[1,4]oxazino[3,4-h]pteridin-6(5H)-one (PREPARATION x55, 190 mg, 0.585 mmol), 1-methyl-3-(4-(4,4,5,5-tetramethyl-1,3,2-dioxaborolan-2-yl)phenyl)urea (404 mg, 1.463 mmol) and [1,1'-bis(diphenylphosphino)ferrocene]-dichloropalladium(II) (24.07 mg, 0.029 mmol). After the vial was sealed, dioxane (2 mL) and aqueous saturated $NaHCO_3$ (0.500 mL) were added, and the mixture was degassed by bubbling nitrogen through a syringe needle for 10 minutes. The mixture was heated in a microwave to 120° C. for 60 minutes. Since the reaction was not complete, another 0.025 equivalents of palladium catalyst were added, and the mixture was heated in the microwave to 130° C. for another 60 minutes. DMF (1 mL) was added and the mixture was filtered by syringe filter. The crude product was purified by preparatory HPLC using a gradient of 15-25% $CH_3CN$ (with 0.035% TFA) in $H_2O$ (with 0.05% TFA). Lyophilization of the collected fractions gave the title compound as a white powder (21 mg, 8.2%). $^1H$ NMR (400 MHz, DMSO-$d_6$) δ 1.56-1.74 (m, 2H), 2.58-2.69 (m, 4H), 2.97 (td, J=12.8, 3.8 Hz, 1H), 3.41 (t, J=10.9 Hz, 1H), 3.47-3.63 (m, 3H), 3.88-4.05 (m, 3H), 4.14-4.24 (m, 2H), 4.39 (d, J=11.9 Hz, 2H), 6.05-6.15 (m, 1H), 7.45-7.55 (m, 2H), 8.15-8.23 (m, 2H), 8.46 (s, 1H), 8.75 (s, 1H). ESI-MS m/z $[M+H]^+$ calc'd for $C_{22}H_{26}N_6O_4$, 439.2. found 439.5.

Example 159

(R)-1-methyl-3-(4-(6-oxo-5-(tetrahydro-2H-pyran-4-yl)-5,6,6a,7,9,10-hexahydro-[1,4]oxazino[3,4-h]pteridin-2-yl)phenyl)urea

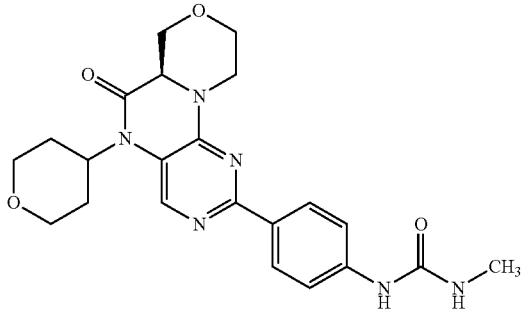 [SMILES: CNC(=O)Nc1ccc(-c2ncc3c(n2)N2CCOC[C@@H]2C(=O)N3C2CCOCC2)cc1]

An enantiomeric mixture of 1-methyl-3-(4-(6-oxo-5-(tetrahydro-2H-pyran-4-yl)-5,6,6a,7,9,10-hexahydro-[1,4]oxazino[3,4-h]pteridin-2-yl)phenyl)urea (EXAMPLE 158, 16 mg) was dissolved in 32 mL of EtOH+1% TFA and was separated by supercritical fluid chromatography (SFC): Chiralcel OJ-H (5 µm, 20×150 mm), 35% MeOH in liquid $CO_2$ at 50 mL/min, 2 mL/injection. The peak eluting at ~1.6 minutes was collected, concentrated, and lyophilized to give a TFA salt of the title compound as a white powder (3.0 mg). The stereochemical configuration was assigned based on comparison of retention time of an enantio-enriched sample synthesized in accordance with PREPARATIONS DD, −115 and −145 using optically pure (R)-morpholine-3-carboxylic acid.

Example 160

(S)-1-methyl-3-(4-(6-oxo-5-(tetrahydro-2H-pyran-4-yl)-5,6,6a,7,9,10-hexahydro-[1,4]oxazino[3,4-h]pteridin-2-yl)phenyl)urea

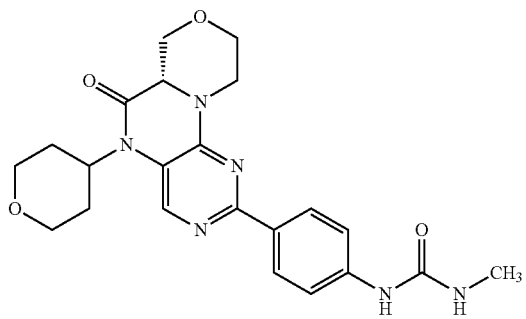 [SMILES: CNC(=O)Nc1ccc(-c2ncc3c(n2)N2CCOC[C@H]2C(=O)N3C2CCOCC2)cc1]

A TFA salt of the title compound was obtained as the peak eluting at ~2.5 minutes by chiral SFC chromatography in EXAMPLE 159.

Example 161

1-(4-(5-((S)-1-(4-chlorophenyl)ethyl)-6-oxo-5,6,6a,7,9,10-hexahydro-[1,4]oxazino[3,4-h]pteridin-2-yl)phenyl)-3-methylurea

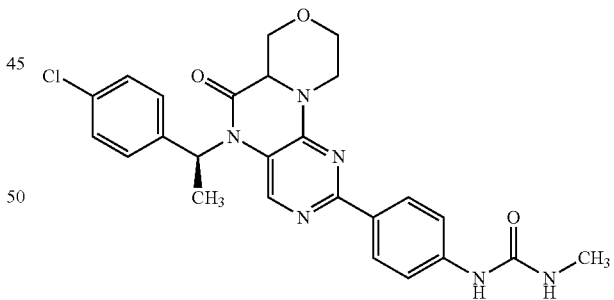

The title compound was prepared in a manner similar to EXAMPLE 85 using (S)-2-chloro-5-((S)-1-(4-chlorophenyl)ethyl)-6a,7,9,10-tetrahydro-[1,4]oxazino[3,4-h]pteridin-6(5H)-one (43 mg, 0.113 mmol), 1-methyl-3-(4-(4,4,5,5-tetramethyl-1,3,2-dioxaborolan-2-yl)phenyl)urea (62.6 mg, 0.227 mmol) and [1,1'-bis(diphenylphosphino)ferrocene]-dichloropalladium(II) (4.66 mg, 5.67 µmol). The crude product was purified by preparatory HPLC using a gradient of 25-40% $CH_3CN$ (with 0.035% TFA) in $H_2O$ (with 0.05% TFA). Lyophilization of the collected fractions gave a TFA salt of the title compound as a white powder (23 mg, 41%). Relative stereoconfiguration was not assigned. $^1H$ NMR (400

MHz, DMSO-d$_6$) δ 1.74 (d, J=7.3 Hz, 3H), 2.64 (d, J=4.5 Hz, 3H), 3.00 (td, J=12.9, 3.5 Hz, 1H), 3.55-3.64 (m, 3H), 4.02 (dd, J=11.2, 3.4 Hz, 1H), 4.24 (dd, J=11.2, 3.9 Hz, 1H), 4.45-4.53 (m, 2H), 6.04-6.10 (m, 1H), 6.25 (q, J=7.2 Hz, 1H), 7.44 (s, 8H), 7.58 (s, 1H), 8.11 (d, J=8.8 Hz, 2H), 8.71 (s, 1H). ESI-MS m/z [M+H]$^+$ calc'd for C$_{25}$H$_{25}$ClN$_6$O$_3$, 493.17. found 493.5.

Example 162

2-(2-aminopyrimidin-5-yl)-54(5)-1-(4-chlorophenyl) ethyl)-6a,7,9,10-tetrahydro-[1,4]oxazino[3,4-h]pteridin-6(5H)-one

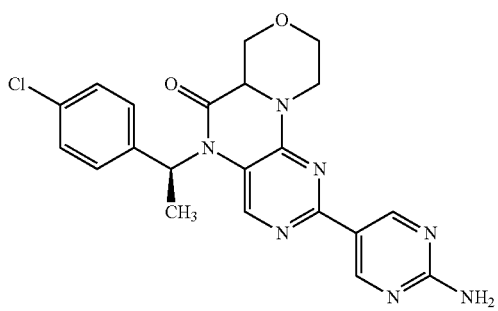 [SMILES: C[C@@H](c1ccc(Cl)cc1)N1C(=O)C2COCCN2c2nc(-c3cnc(N)nc3)ncc21]

The title compound was prepared in a manner similar to EXAMPLE 85 using (S)-2-chloro-5-((S)-1-(4-chlorophenyl) ethyl)-6a,7,9,10-tetrahydro-[1,4]oxazino[3,4-h]pteridin-6 (5H)-one (66 mg, 0.174 mmol), 5-(4,4,5,5-tetramethyl-1,3,2-dioxaborolan-2-yl)pyrimidin-2-amine (38.5 mg, 0.174 mmol) and [1,1'-bis(diphenylphosphino)ferrocene]-dichloropalladium(II) (7.16 mg, 8.70 μmol). The crude product was purified by preparatory HPLC using a gradient of 35-55% CH$_3$CN (with 0.035% TFA) in H$_2$O (with 0.05% TFA). Lyophilization of the collected fractions gave a diastereomeric mixture of the title compound (TFA salt) as a white solid (23 mg, 30.2%). ESI-MS m/z [M+H]$^+$ calc'd for C$_{21}$H$_{20}$ClN$_7$O$_2$, 438.14. found 438.4.

Example 163

5-((S)-1-(4-chlorophenyl)ethyl)-2-(1H-indol-4-yl)-6a,7,9,10-tetrahydro-[1,4]oxazino[3,4-h]pteridin-6 (5H)-one

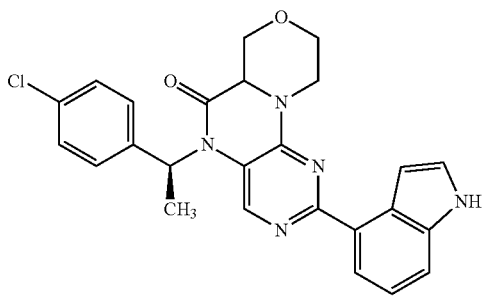 [SMILES: C[C@@H](c1ccc(Cl)cc1)N1C(=O)C2COCCN2c2nc(-c3cccc4[nH]ccc34)ncc21]

The title compound was prepared in a manner similar to EXAMPLE 85 using (S)-2-chloro-5-((S)-1-(4-chlorophenyl) ethyl)-6a,7,9,10-tetrahydro-[1,4]oxazino[3,4-h]pteridin-6 (5H)-one (43 mg, 0.113 mmol), 1H-indol-4-ylboronic acid (36.5 mg, 0.227 mmol) and [1,1'-bis(diphenylphosphino)ferrocene]-dichloropalladium(II) (4.66 mg, 5.67 μmol). The crude product was purified by preparatory HPLC using a gradient of 35-50% CH$_3$CN (with 0.035% TFA) in H$_2$O (with 0.05% TFA). Lyophilization of the collected fractions gave a diastereomeric mixture of title compound (TFA salt) as a yellow powder (23 mg, 44.1%). $^1$H NMR (400 MHz, DMSO-d$_6$) δ 1.74-1.81 (m, 2H), 1.82-1.89 (m, 1H), 11.20-11.34 (m, 1H), 3.07-3.18 (m, 1H), 3.58-3.77 (m, 3H), 4.03-4.12 (m, 2H), 4.23-4.31 (m, 2H), 4.41-4.60 (m, 3H), 6.32-6.08 (m, 1H), 7.12-7.19 (m, 1H), 7.22-7.30 (m, 1H), 7.35-7.55 (m, 6H), 7.81-7.73 (m, 1H), 7.91-8.01 (m, 1H). ESI-MS m/z [M+H]$^+$ calc'd for C$_{25}$H$_{22}$ClN$_5$O$_2$, 460.15. found 460.4.

Example 164

2-(1H-indol-4-yl)-5-(pyrimidin-2-ylmethyl)-5,6,6a,7,9,10-hexahydro-[1,4]oxazino[3,4-h]pteridine

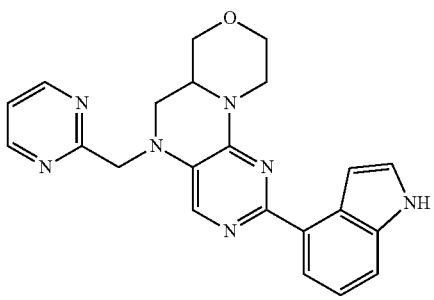 [SMILES: c1cnc(CN2CC3COCCN3c3nc(-c4cccc5[nH]ccc45)ncc32)nc1]

A TFA salt of the title compound was prepared in accordance with the method described for EXAMPLES 32 through 45. $^1$H NMR (400 MHz, DMSO-d$_6$) δ 3.42-3.49 (m, 3H), 3.58-3.71 (m, 2H), 3.89-4.17 (m, 3H), 4.67-4.79 (m, 2H), 4.97-5.10 (m, 1H), 6.95-7.08 (m, 1H), 7.19-7.33 (m, 1H), 7.43-7.50 (m, 1H), 7.51-7.73 (m, 4H), 8.77-8.90 (m, 2H), 11.47-11.63 (m, 1H). ESI-MS m/z [M+H]$^+$ calc'd for C$_{22}$H$_{21}$N$_7$O, 400.18. found 400.2.

Example 165

(R)-methyl 2-((2-(1H-indol-4-yl)-6a,7,9,10-tetrahydro-[1,4]oxazino[3,4-h]pteridin-5(6H)-yl)methyl)-4-methylbenzoate

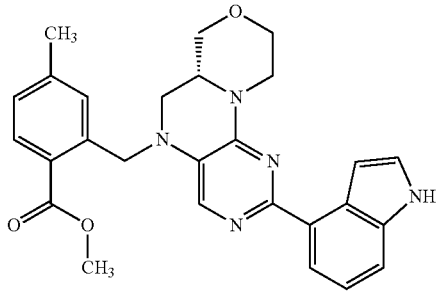 [SMILES: COC(=O)c1ccc(C)cc1CN1C[C@@H]2COCCN2c2nc(-c3cccc4[nH]ccc34)ncc21]

(R)-Methyl 2-((2-chloro-6a,7,9,10-tetrahydro-[1,4]oxazino[3,4-h]pteridin-5 (6H)-yl)methyl)-4-methylbenzoate (PREPARATION x57, 100 mg, 0.257 mmol), 1H-indol-4-ylboronic acid (83 mg, 0.514 mmol) and PdCl$_2$(dppf) (18.82 mg, 0.026 mmol) in dioxane (2 mL) and aqueous saturated NaHCO₃ (0.4 mL) were combined to give a brown suspension, which was heated to 100° C. and stirred overnight. The reaction mixture was subsequently diluted with ethyl acetate and washed with aqueous saturated NH₄Cl (3×10 mL). The combined organic layers were dried over MgSO₄, filtered, and concentrated in vacuo. The crude product was then loaded onto an ISCO® silica gel cartridge (4 g) and eluted using an ethyl acetate/hexane gradient. The product was collected and concentrated in vacuo to afford a TFA salt of the title compound as a yellow solid (75 mg, 62%). ¹H NMR (400 MHz, DMSO-d₆) δ ppm 2.22-2.32 (m, 3H), 3.11-3.26 (m, 4H), 3.50-3.63 (m, 1H), 3.76 (s, 3H), 3.80-3.98 (m, 2H), 4.00-4.11 (m, 1H), 4.59-4.92 (m, 3H), 6.91-7.08 (m, 1H), 7.11-7.28 (m, 3H), 7.28-7.39 (m, 1H), 7.42-7.70 (m, 3H), 7.72-7.85 (m, 1H), 11.30-11.54 (m, 1H); ESI-MS m/z [M+H]⁺ calc'd for C₂₇H₂₇N₅O₃, 470.22. found 470.3.

Example 166

(R)-(2-((2-(1H-indol-4-yl)-6a,7,9,10-tetrahydro-[1,4]oxazino[3,4-h]pteridin-5(6H)-yl)methyl)-4-methylphenyl)methanol

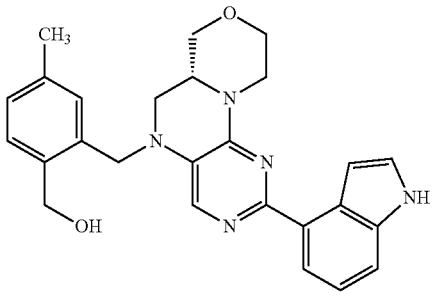 [SMILES: Cc1ccc(CO)c(CN2C[C@@H]3COCCN3c3nc(-c4cccc5[nH]ccc45)ncc32)c1]

(R)-Methyl 2-((2-(1H-indol-4-yl)-6a,7,9,10-tetrahydro-[1,4]oxazino[3,4-h]pteridin-5(6H)-yl)methyl)-4-methylbenzoate (EXAMPLE 165, 55 mg, 0.117 mmol) in THF (2 mL) was cooled to 0° C. LiAlH₄ in THF (2M, 0.088 mL, 0.176 mmol) was then added and the reaction mixture was allowed to slowly warm to room temperature. The reaction mixture was stirred overnight and was quenched with saturated NH₄Cl, diluted with ethyl acetate, and washed with aqueous saturated NH₄Cl (3×10 mL). The combined organic layers were dried over MgSO₄, filtered, and concentrated in vacuo. The product was purified by LC/MS using a 20-35% CH₃CN gradient in H₂O with 0.035% TFA. The pure fractions were combined and lyophilized to afford a TFA salt of the title compound as a yellow solid (13.6 mg, 26.3%). ¹H NMR (400 MHz, DMSO-d₆) δ ppm 3.08-3.20 (m, 1H), 3.23-3.41 (m, 5H), 3.57-3.67 (m, 2H), 3.87-4.03 (m, 2H), 4.05-4.16 (m, 1H), 4.36-4.47 (m, 1H), 4.51-4.60 (m, 2H), 4.61-4.79 (m, 2H), 6.96-7.16 (m, 3H), 7.18-7.39 (m, 2H), 7.42-7.51 (m, 1H), 7.51-7.76 (m, 3H), 11.37-11.64 (m, 1H); ESI-MS m/z [M+H]⁺ calc'd for C₂₆H₂₇N₅O₂, 442.22. found 442.3.

Example 167

(R)-5-((5-ethyl-1,3,4-oxadiazol-2-yl)methyl)-2-(1H-pyrrolo[2,3-c]pyridin-4-yl)-5,6,6a,7,9,10-hexahydro-[1,4]oxazino[3,4-h]pteridine

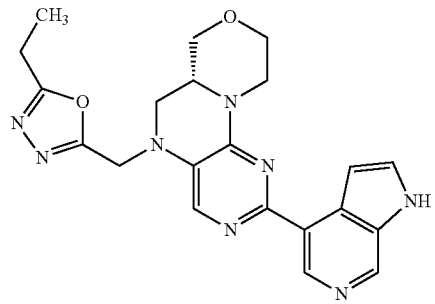 [SMILES: CCc1nnc(CN2C[C@@H]3COCCN3c3nc(-c4cncc5[nH]ccc45)ncc32)o1]

A TFA salt of the title compound was prepared in a manner similar to Example 2 using (R)-2-chloro-5-((5-ethyl-1,3,4-oxadiazol-2-yl)methyl)-5,6,6a,7,9,10-hexahydro-[1,4]oxazino[3,4-h]pteridine (PREPARATION x19, 70 mg, 0.208 mmol), 1-acetyl-1H-pyrrolo[2,3-c]pyridin-4-ylboronic acid (85 mg, 0.416 mmol), and PdCl₂(dppf) (7.60 mg, 10.39 μmol) in dioxane (2 mL) and aqueous saturated NaHCO₃ (0.4 mL) (8.3 mg, 9.5%). ¹H NMR (400 MHz, DMSO-d₆) δ ppm 1.22-1.28 (m, 3H), 2.80-2.91 (m, 2H), 3.13-3.31 (m, 2H), 3.52-3.63 (m, 1H), 3.76-3.87 (m, 2H), 3.95-4.14 (m, 1H), 4.57-4.68 (m, 1H), 4.73-4.83 (m, 1H), 5.04-5.14 (m, 1H), 7.00-7.08 (m, 1H), 7.85-7.94 (m, 1H), 8.16-8.24 (m, 1H), 8.41-8.50 (m, 1H), 9.29-9.39 (m, 1H), 10.03-10.12 (m, 1H), 12.83-12.95 (m, 1H); ESI-MS m/z [M+H]⁺ calc'd for C₂₁H₂₂N₈O₂, 419.19. found 419.3.

Example 168

(R)-5-(5-((5-ethyl-1,3,4-oxadiazol-2-yl)methyl)-5,6,6a,7,9,10-hexahydro-[1,4]oxazino[3,4-h]pteridin-2-yl)pyridin-2-ol

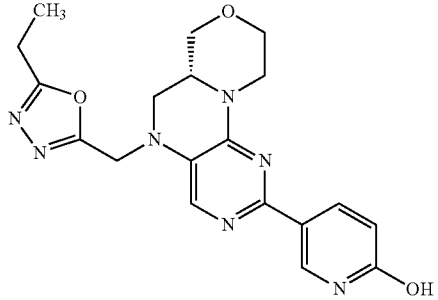 [SMILES: CCc1nnc(CN2C[C@@H]3COCCN3c3nc(-c4ccc(O)nc4)ncc32)o1]

A TFA salt of the title compound was prepared in a manner similar to Example 2 using (R)-2-chloro-5-((5-ethyl-1,3,4-oxadiazol-2-yl)methyl)-5,6,6a,7,9,10-hexahydro-[1,4]oxazino[3,4-h]pteridine (PREPARATION x19, 75 mg, 0.223 mmol), 5-(4,4,5,5-tetramethyl-1,3,2-dioxaborolan-2-yl)pyridin-2-ol (98 mg, 0.445 mmol), and PdCl₂(dppf) (8.15 mg, 0.011 mmol) in dioxane (2 mL) and aqueous saturated NaHCO₃ (0.4 mL) (8.4 mg, 9.5%). ¹H NMR (400 MHz, DMSO-d₆) δ ppm 1.24 (t, J=7.45 Hz, 3H), 2.84 (d, J=7.58 Hz, 2H), 3.05-3.28 (m, 5H), 3.75-3.88 (m, 1H), 3.92-4.07 (m, 2H), 4.62-4.77 (m, 2H), 4.90-5.03 (m, 1H), 6.40-6.50 (m, 1H), 7.67 (s, 1H), 8.10-8.20 (m, 1H), 8.20-8.30 (m, 1H), 11.95-12.33 (m, 1H); ESI-MS m/z [M+H]+ calc'd for C20H21N8O2, 396.18. found 396.3.

Example 169

(R)-4-(2-(1H-indol-4-yl)-6a,7,9,10-tetrahydro-[1,4]oxazino[3,4-h]pteridin-5(6H)-yl)-2-methylbutan-2-ol

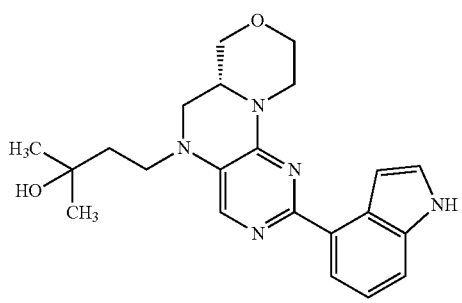 [SMILES: CC(C)(O)CCN1C[C@@H]2COCCN2c2nc(-c3cccc4[nH]ccc34)ncc21]

A TFA salt of the title compound was prepared in a manner similar to Example 2 using (R)-4-(2-chloro-6a,7,9,10-tetrahydro-[1,4]oxazino[3,4-h]pteridin-5(6H)-yl)-2-methylbutan-2-ol (PREPARATION x58, 70 mg, 0.224 mmol), 1H-indol-4-ylboronic acid (72.0 mg, 0.448 mmol), and PdCl2(dppf) (8.19 mg, 0.011 mmol) in dioxane (2 mL) and aqueous saturated NaHCO3 (0.4 mL) (7 mg, 8%). 1H NMR (400 MHz, DMSO-d6) δ ppm 1.10-1.21 (m, 6H), 1.59-1.75 (m, 2H), 3.01-3.15 (m, 1H), 3.22-3.28 (m, 2H), 3.42-3.54 (m, 3H), 3.54-3.66 (m, 1H), 3.81-3.97 (m, 1H), 3.97-4.16 (m, 2H), 4.48-4.65 (m, 1H), 4.65-4.76 (m, 1H), 6.97-7.09 (m, 1H), 7.36-7.46 (m, 1H), 7.46-7.60 (m, 2H), 7.60-7.72 (m, 1H), 11.42-11.60 (m, 1H); ESI-MS m/z [M+H]+ calc'd for C22H27N5O2, 394.22. found 394.3.

Example 170

(R)-4-(2-(1H-pyrrolo[2,3-c]pyridin-4-yl)-6a,7,9,10-tetrahydro-[1,4]oxazino[3,4-h]pteridin-5(6H)-yl)-2-methylbutan-2-ol

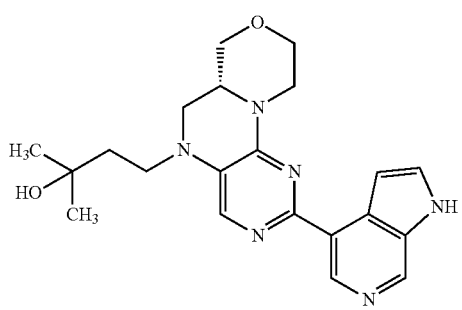 [SMILES: CC(C)(O)CCN1C[C@@H]2COCCN2c2nc(-c3cncc4[nH]ccc34)ncc21]

A TFA salt of the title compound was prepared in a manner similar to Example 2 using (R)-4-(2-chloro-6a,7,9,10-tetrahydro-[1,4]oxazino[3,4-h]pteridin-5(6H)-yl)-2-methylbutan-2-ol (PREPARATION x58, 70 mg, 0.224 mmol), 1-acetyl-1H-pyrrolo[2,3-c]pyridin-4-ylboronic acid (91 mg, 0.448 mmol), PdCl2(dppf) (8.19 mg, 0.011 mmol) in dioxane (2 mL) and aqueous saturated NaHCO3 (0.4 mL) (2 mg, 2%). 1H NMR (400 MHz, CD3CN) δ ppm 1.23 (d, J=2.02 Hz, 6H), 3.05-3.43 (m, 7H), 3.47-3.71 (m, 4H), 3.90-3.99 (m, 1H), 4.03-4.12 (m, 1H), 4.49-4.63 (m, 1H), 7.71-7.79 (m, 1H), 7.79-7.84 (m, 1H), 8.05-8.10 (m, 1H), 8.95-9.07 (m, 2H), 11.16-11.30 (m, 1H); ESI-MS m/z [M+H]+ calc'd for C21H26N6O2, 395.22. found 395.3.

Example 171

(R)-4-(2-(3-(hydroxymethyl)phenyl)-6a,7,9,10-tetrahydro-[1,4]oxazino[3,4-h]pteridin-5(6H)-yl)-2-methylbutan-2-ol

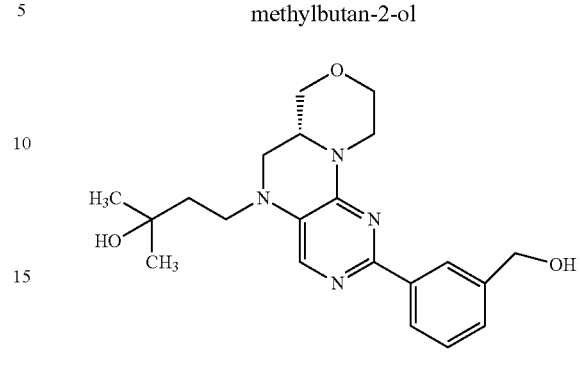

A TFA salt of the title compound was prepared in a manner similar to Example 2 using (R)-4-(2-chloro-6a,7,9,10-tetrahydro-[1,4]oxazino[3,4-h]pteridin-5(6H)-yl)-2-methylbutan-2-ol (PREPARATION x58, 70 mg, 0.224 mmol), 3-(hydroxymethyl)phenylboronic acid (68.0 mg, 0.448 mmol), PdCl2(dppf) (8.19 mg, 0.011 mmol) in dioxane (2 mL) and aqueous saturated NaHCO3 (0.4 mL) (6.6 mg, 7.7%). 1H NMR (400 MHz, DMSO-d6) δ ppm 1.16 (d, J=2.02 Hz, 6H), 1.58-1.72 (m, 2H), 2.08 (s, 1H), 2.98-3.12 (m, 1H), 3.14-3.38 (m, 2H), 3.37-3.63 (m, 4H), 3.76-3.90 (m, 2H), 3.94-4.13 (m, 3H), 4.59 (s, 2H), 4.70-4.84 (m, 1H), 7.43-7.60 (m, 2H), 7.97-8.08 (m, 1H), 8.09-8.17 (m, 1H); ESI-MS m/z [M+H]+ calc'd for C21H26N4O3, 385.22. found 385.3.

Example 172

(R)-(3-(5-((5-ethyl-1,3,4-oxadiazol-2-yl)methyl)-5,6,6a,7,9,10-hexahydro-[1,4]oxazino[3,4-h]pteridin-2-yl)phenyl)methanol

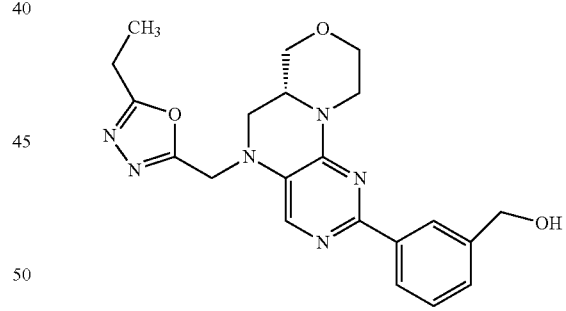

A TFA salt of the title compound was prepared in a manner similar to Example 2 using (R)-2-chloro-5-((5-ethyl-1,3,4-oxadiazol-2-yl)methyl)-5,6,6a,7,9,10-hexahydro-[1,4]oxazino[3,4-h]pteridine (PREPARATION x19, 70 mg, 0.208 mmol), 3-(hydroxymethyl)phenylboronic acid (63.2 mg, 0.416 mmol), and PdCl2(dppf) (7.60 mg, 10.39 μmol) in dioxane (2 mL) and aqueous saturated NaHCO3 (0.4 mL) (13 mg, 15%). 1H NMR (400 MHz, DMSO-d6) δ ppm 0.69 (t, J=7.58 Hz, 3H), 2.29 (d, J=7.58 Hz, 2H), 2.57-2.76 (m, 3H), 2.92-3.05 (m, 2H), 3.25-3.37 (m, 2H), 3.39-3.56 (m, 2H), 4.02 (s, 2H), 4.14-4.29 (m, 2H), 4.42-4.54 (m, 1H), 6.89-6.99 (m, 2H), 7.16-7.23 (m, 1H), 7.44-7.53 (m, 1H), 7.54-7.61 (m, 1H); ESI-MS m/z [M+H]+ calc'd for C21H24N6O3, 409.20. found 409.3.

Example 173

(R)-2-(2-(1H-indol-4-yl)-6a,7,9,10-tetrahydro-[1,4]oxazino[3,4-h]pteridin-5(6H)-yl)ethanol

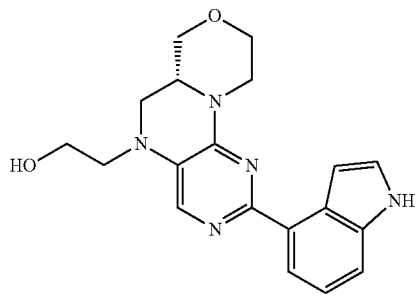 [SMILES: OCCN1C[C@@H]2COCCN2c2nc(-c3cccc4[nH]ccc34)ncc21]

A TFA salt of the title compound was prepared in a manner similar to Example 2 using (R)-2-(2-chloro-6a,7,9,10-tetrahydro-[1,4]oxazino[3,4-h]pteridin-5(6H)-yl)ethanol (PREPARATION x59, 79 mg, 0.292 mmol), 1H-indol-4-ylboronic acid (94 mg, 0.584 mmol), and PdCl$_2$(dppf) (10.68 mg, 0.015 mmol) in dioxane (2 mL) and aqueous saturated NaHCO$_3$ (0.4 mL) (27 mg, 26%). $^1$H NMR (400 MHz, DMSO-d$_6$) δ ppm 2.29 (s, 3H), 3.21-3.29 (m, 4H), 3.54-3.63 (m, 4H), 4.01-4.16 (m, 2H), 4.64-4.87 (m, 1H), 7.05-7.32 (m, 2H), 7.48-7.59 (m, 1H), 7.60-7.75 (m, 1H), 7.77-8.06 (m, 1H), 8.69-8.99 (m, 1H), 11.40-11.56 (m, 1H); ESI-MS m/z [M+H]$^+$ calc'd for C$_{19}$H$_{21}$N$_5$O$_2$, 352.18. found 352.3.

Example 174

(R)-2-(2-(1H-pyrrolo[2,3-c]pyridin-4-yl)-6a,7,9,10-tetrahydro-[1,4]oxazino[3,4-h]pteridin-5(6H)-yl)-N-((tetrahydro-2H-pyran-4-yl)methyl)acetamide

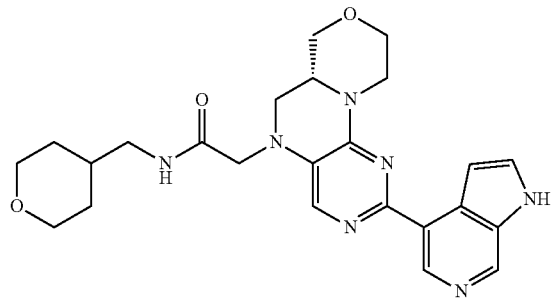 [SMILES: O=C(CN1C[C@@H]2COCCN2c2nc(-c3cncc4[nH]ccc34)ncc21)NCC1CCOCC1]

A TFA salt of the title compound was prepared in a manner similar to Example 2 using (R)-2-(2-chloro-6a,7,9,10-tetrahydro-[1,4]oxazino[3,4-h]pteridin-5 (6H)-yl)-N-((tetrahydro-2H-pyran-4-yl)methyl)acetamide (PREPARATION x26, 50 mg, 0.131 mmol), 1-acetyl-1H-pyrrolo[2,3-c]pyridin-4-ylboronic acid (53.4 mg, 0.262 mmol), PdCl$_2$(dppf) (4.79 mg, 6.55 µmol) in dioxane (2 mL) and aqueous saturated NaHCO$_3$ (0.4 mL) (2 mg, 3%). $^1$H NMR (400 MHz, CD$_3$CN) δ ppm 1.08-1.27 (m, 6H), 1.50-1.61 (m, 4H), 1.62-1.75 (m, 1H), 3.00-3.20 (m, 4H), 3.21-3.39 (m, 2H), 3.60-3.70 (m, 1H), 3.70-3.90 (m, 2H), 3.90-4.04 (m, 2H), 4.04-4.14 (m, 1H), 4.57-4.69 (m, 1H), 6.78-6.92 (m, 1H), 7.56-7.67 (m, 1H), 7.70-7.79 (m, 1H), 8.06-8.16 (m, 1H), 8.94-9.05 (m, 1H); ESI-MS m/z [M+H]$^+$ calc'd for C$_{24}$H$_{29}$N$_7$O$_3$, 464.24. found 464.3.

Example 175

(6aR)-2-(1H-indol-4-yl)-5-(1-(5-isobutyl-1,3,4-oxadiazol-2-yl)ethyl)-5,6,6a,7,9,10-hexahydro-[1,4]oxazino[3,4-h]pteridine

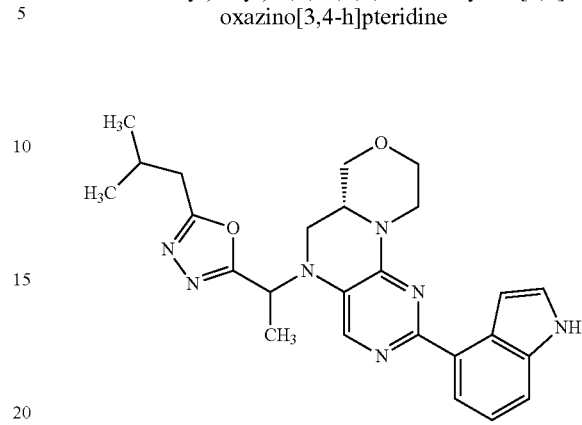

A TFA salt of the title compound was prepared in a manner similar to Example 2 using (6aR)-2-chloro-5-(1-(5-isobutyl-1,3,4-oxadiazol-2-yl)ethyl)-5,6,6a,7,9,10-hexahydro-[1,4]oxazino[3,4-h]pteridine (PREPARATION x85, 75 mg, 0.198 mmol), 1H-indol-4-ylboronic acid (63.7 mg, 0.396 mmol), and PdCl$_2$(dppf) (14.49 mg, 0.020 mmol) in dioxane (2 mL) and aqueous saturated NaHCO$_3$ (0.4 mL) (51 mg, 56%). $^1$H NMR (400 MHz, DMSO-d$_6$) δ ppm 0.94 (ddd, J=6.57, 5.43, 2.40 Hz, 6H), 1.64 (dd, J=17.94, 6.82 Hz, 3H), 2.05 (d, J=6.82 Hz, 1H), 2.75 (t, J=6.95 Hz, 2H), 3.07-3.21 (m, 1H), 3.27 (d, J=9.60 Hz, 3H), 3.65-3.72 (m, 1H), 3.76-4.15 (m, 2H), 4.69-4.82 (m, 1H), 5.52-5.65 (m, 1H), 7.01 (br s, 1H), 7.28 (d, J=2.02 Hz, 1H), 7.57 (t, J=2.78 Hz, 1H), 7.63-7.72 (m, 2H), 7.89 (d, J=8.59 Hz, 1H), 11.55 (br s, 1H); ESI-MS m/z [M+H]$^+$ calc'd for C$_{25}$H$_{29}$N$_7$O$_2$, 460.24. found 460.4.

Example 176

(3-46aR)-5-(1-(5-isobutyl-1,3,4-oxadiazol-2-yl)ethyl)-5,6,6a,7,9,10-hexahydro-[1,4]oxazino[3,4-h]pteridin-2-yl)phenyl)methanol

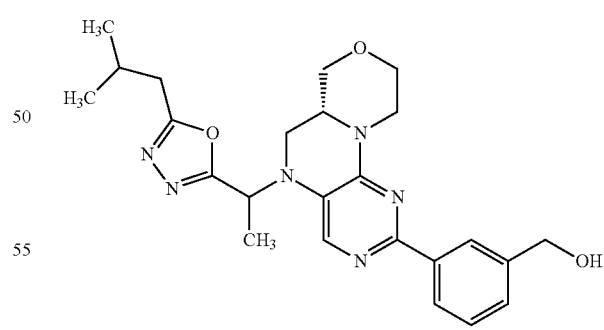

A TFA salt of the title compound was prepared in a manner similar to Example 2 using (6aR)-2-chloro-5-(1-(5-isobutyl-1,3,4-oxadiazol-2-yl)ethyl)-5,6,6a,7,9,10-hexahydro-[1,4]oxazino[3,4-h]pteridine (PREPARATION x85, 75 mg, 0.198 mmol), 3-(hydroxymethyl)phenylboronic acid (60.2 mg, 0.396 mmol), and PdCl$_2$(dppf) (14.49 mg, 0.020 mmol) in dioxane (2 mL) and aqueous saturated NaHCO$_3$ (0.4 mL) (37 mg, 42%). $^1$H NMR (400 MHz, DMSO-d$_6$) δ ppm 1.55-1.70

(m, 3H), 1.96-2.11 (m, 1H), 2.69-2.78 (m, 2H), 3.03-3.14 (m, 1H), 3.15-3.27 (m, 6H), 3.30-3.49 (m, 5H), 3.59-3.73 (m, 2H), 3.87-4.12 (m, 2H), 4.53-4.63 (m, 2H), 4.72-4.85 (m, 1H), 5.50-5.62 (m, 1H), 7.42-7.56 (m, 2H), 7.84-7.91 (m, 1H), 8.01-8.10 (m, 1H), 8.12-8.18 (m, 1H); ESI-MS m/z [M+H]$^+$ calc'd for $C_{24}H_{30}N_6O_3$, 451.24. found 451.4.

Example 177

(3-((6aR)-5-(1-(5-ethyl-1,3,4-oxadiazol-2-yl)ethyl)-5,6,6a,7,9,10-hexahydro-[1,4]oxazino[3,4-h]pteridin-2-yl)phenyl)methanol

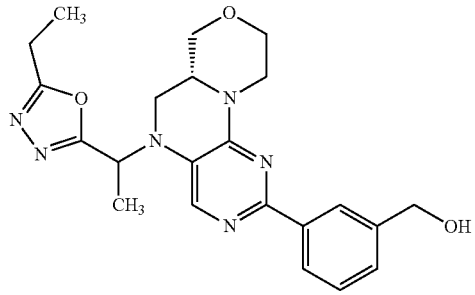 [SMILES: CCc1nnc(C(C)N2C[C@@H]3COCCN3c3nc(-c4cccc(CO)c4)ncc32)o1]

A TFA salt of the title compound was prepared in a manner similar to Example 2 using (6aR)-2-chloro-5-(1-(5-ethyl-1,3,4-oxadiazol-2-yl)ethyl)-5,6,6a,7,9,10-hexahydro-[1,4]oxazino[3,4-h]pteridine (PREPARATION x19, 55 mg, 0.157 mmol), 3-(hydroxymethyl)phenylboronic acid (47.6 mg, 0.314 mmol), and PdCl$_2$(dppf) (11.47 mg, 0.016 mmol)) in dioxane (2 mL) and aqueous saturated NaHCO$_3$ (0.4 mL) (13 mg, 20%). $^1$H NMR (400 MHz, DMSO-d$_6$) δ ppm 1.25 (d, J=9.09 Hz, 3H), 1.53-1.68 (m, 3H), 2.71-2.80 (m, 1H), 2.80-2.91 (m, 3H), 3.10-3.27 (m, 4H), 3.46-3.68 (m, 1H), 3.92-4.09 (m, 2H), 4.52-4.64 (m, 2H), 4.72-4.85 (m, 1H), 5.49-5.61 (m, 1H), 7.41-7.55 (m, 2H), 7.82-7.93 (m, 1H), 8.01-8.11 (m, 1H), 8.12-8.19 (m, 1H); ESI-MS m/z [M+H]$^+$ calc'd for $C_{22}H_{26}N_6O_3$, 423.21. found 423.4.

Example 178

(6aR)-5-(1-(5-ethyl-1,3,4-oxadiazol-2-yl)ethyl)-2-(1H-indol-4-yl)-5,6,6a,7,9,10-hexahydro-[1,4]oxazino[3,4-h]pteridine

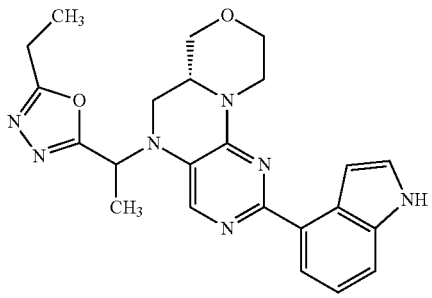 [SMILES: CCc1nnc(C(C)N2C[C@@H]3COCCN3c3nc(-c4cccc5[nH]ccc45)ncc32)o1]

A TFA salt of the title compound was prepared in a manner similar to Example 2 using (6aR)-2-chloro-5-(1-(5-ethyl-1,3,4-oxadiazol-2-yl)ethyl)-5,6,6a,7,9,10-hexahydro-[1,4]oxazino[3,4-h]pteridine (PREPARATION x19, 55 mg, 0.157 mmol), 1H-indol-4-ylboronic acid (50.5 mg, 0.314 mmol), and PdCl$_2$(dppf) (11.47 mg, 0.016 mmol) in dioxane (2 mL) and aqueous saturated NaHCO$_3$ (0.4 mL) (17 mg, 25%). $^1$H NMR (400 MHz, DMSO-d$_6$) δ ppm 1.21-1.32 (m, 3H), 1.57-

1.70 (m, 3H), 2.76-2.92 (m, 3H), 3.05-3.23 (m, 1H), 3.23-3.29 (m, 2H), 3.51-3.63 (m, 1H), 3.63-3.72 (m, 1H), 3.76-3.97 (m, 1H), 3.97-4.14 (m, 1H), 4.69-4.82 (m, 1H), 5.49-5.63 (m, 1H), 6.97-7.07 (m, 1H), 7.21-7.34 (m, 1H), 7.51-7.61 (m, 1H), 7.61-7.74 (m, 2H), 7.83-7.94 (m, 1H), 11.45-11.60 (m, 1H); ESI-MS m/z [M+H]$^+$ calc'd for $C_{23}H_{25}N_7O_2$, 432.21. found 432.4.

Example 179

(R)-(3-(5-((5-ethyl-1,3,4-oxadiazol-2-yl)methyl)-5,6,6a,7,9,10-hexahydro-[1,4]oxazino[3,4-h]pteridin-2-yl)-4-fluorophenyl)methanol

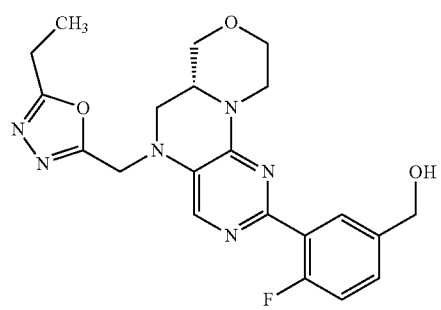 [SMILES: CCc1nnc(CN2C[C@@H]3COCCN3c3nc(-c4cc(CO)ccc4F)ncc32)o1]

A TFA salt of the title compound was prepared in a manner similar to Example 2 using (R)-2-chloro-5-((5-ethyl-1,3,4-oxadiazol-2-yl)methyl)-5,6,6a,7,9,10-hexahydro-[1,4]oxazino[3,4-h]pteridine (PREPARATION x19, 75 mg, 0.223 mmol), 2-fluoro-5-(hydroxymethyl)phenylboronic acid (76 mg, 0.445 mmol) and PdCl$_2$(dppf) (8.15 mg, 0.011 mmol) in dioxane (2 mL) and aqueous saturated NaHCO$_3$ (0.4 mL) (45 mg, 47%). $^1$H NMR (400 MHz, DMSO-d$_6$) δ ppm 1.26 (t, J=7.58 Hz, 3H), 2.85 (q, J=7.58 Hz, 2H), 3.11-3.33 (m, 3H), 3.55 (dd, J=11.62, 3.79 Hz, 2H), 3.88 (d, J=4.29 Hz, 2H), 3.94-4.07 (m, 2H), 4.54 (s, 2H), 4.59-4.71 (m, 1H), 4.77 (d, J=17.18 Hz, 1H), 5.03 (d, J=16.93 Hz, 1H), 7.35 (m, 1H), 7.48-7.60 (m, 1H), 7.78-7.88 (m, 2H); ESI-MS m/z [M+H]$^+$ calc'd for $C_{21}H_{23}FN_6O_3$, 427.19. found 427.3.

Example 180

(R)-5-((5-ethyl-1,3,4-oxadiazol-2-yl)methyl)-2-(1H-pyrrolo[3,2-c]pyridin-1-yl)-5,6,6a,7,9,10-hexahydro-[1,4]oxazino[3,4-h]pteridine

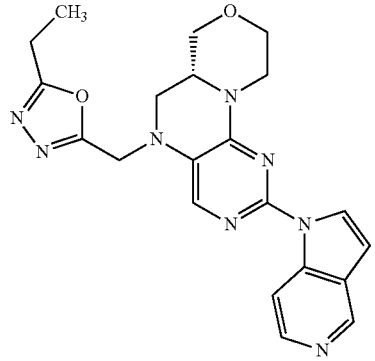 [SMILES: CCc1nnc(CN2C[C@@H]3COCCN3c3nc(-n4ccc5cnccc54)ncc32)o1]

To an oven dried vial were added (R)-2-chloro-5-((5-ethyl-1,3,4-oxadiazol-2-yl)methyl)-5,6,6a,7,9,10-hexahydro-[1,4]oxazino[3,4-h]pteridine (PREPARATION x19, 45 mg, 0.134 mmol), 1-tosyl-1H-pyrrolo[3,2-c]pyridine 5-oxide (116 mg, 0.401 mmol), cesium carbonate (87 mg, 0.267 mmol), pivalic acid (4.09 mg, 0.040 mmol), dicyclohexyl(2',4',6'-triisopropylbiphenyl-2-yl)phosphine (9.55 mg, 0.020 mmol) and palladium (II)acetate (1.5 mg, 6.68 μmol) in dioxane (1 mL). The resulting tan suspension was degassed for 5 minutes with N$_2$, then sealed and heated to 110° C. and stirred for 48 hours. The mixture was subsequently diluted with EtOAc and washed with aqueous saturated NH$_4$Cl (3×5 mL). The combined organic layers were dried over MgSO$_4$, filtered, and concentrated in vacuo. The product was purified by LC/MS using a 15-40% CH$_3$CN gradient in H$_2$O (with 0.035% TFA). The pure fractions were combined and lyophilized to afford a TFA salt of the title compound as a yellow solid (6 mg, 11%). $^1$H NMR (400 MHz, DMSO-d$_6$) δ ppm 1.25 (t, J=7.45 Hz, 3H), 2.86 (q, J=7.58 Hz, 2H), 3.11-3.31 (m, 3H), 3.45-3.65 (m, 2H), 3.73-3.84 (m, 1H), 3.94-4.10 (m, 2H), 4.55 (d, J=11.62 Hz, 1H), 4.67-5.08 (m, 2H), 7.22 (dd, J=3.66, 0.63 Hz, 1H), 7.83 (s, 1H), 8.59 (d, J=6.82 Hz, 1H), 8.65 (d, J=3.79 Hz, 1H), 8.94 (d, J=6.82 Hz, 1H), 9.35 (s, 1H); ESI-MS m/z [M+H]$^+$ calc'd for C$_{21}$H$_{22}$N$_8$O$_2$, 419.19. found 419.3.

Example 181

2-(1H-indol-4-yl)-5-phenyl-5,6,6a,7,9,10-hexahydro-[1,4]oxazino[3,4-h]pteridine

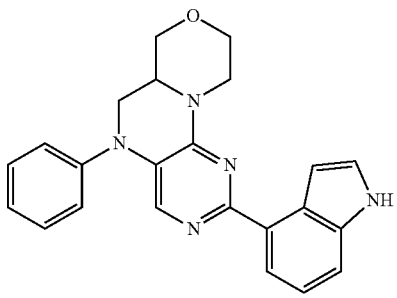 [SMILES: c1ccc(N2CC3COCCN3c3nc(-c4cccc5[nH]ccc45)ncc32)cc1]

To an oven dried vial were added 2-(1-(tert-butylmethyllsilyl)-1H-indol-4-yl)-5,6,6a,7,9,10-hexahydro-[1,4]oxazino[3,4-h]pteridine (PREPARATION x12, 75 mg, 0.137 mmol), cesium carbonate (90 mg, 0.275 mmol), palladium (II)acetate (1.543 mg, 6.87 μmol), dicyclohexyl(2',4',6'-triisopropylbiphenyl-2-yl)phosphine (9.83 mg, 0.021 mmol) and bromobenzene (0.043 mL, 0.412 mmol) in dioxane (5 mL). The resulting brown suspension was purged with N$_2$ for 5 minutes, then heated to 110° C., and stirred overnight. The reaction mixture was subsequently diluted with EtOAc and washed with aqueous saturated NH$_4$Cl (3×5 mL). The combined organic layers were dried over MgSO$_4$, filtered, and concentrated in vacuo. The product was purified by LC/MS using a 25-50% CH$_3$CN gradient in H$_2$O (with 0.035% TFA). The pure fractions were combined and lyophilized to afford a TFA salt of the title compound as a yellow solid (8 mg, 15%). $^1$H NMR (400 MHz, DMSO-d$_6$) δ ppm 3.40-3.50 (m, 1H), 3.50-3.63 (m, 1H), 3.66-3.82 (m, 2H), 3.92-3.99 (m, 1H), 3.99-4.11 (m, 1H), 4.60-4.78 (m, 1H), 7.03-7.23 (m, 3H), 7.23-7.33 (m, 3H), 7.34-7.64 (m, 4H), 7.71-7.87 (m, 1H), 11.17-11.36 (m, 1H); ESI-MS m/z [M+H]$^+$ calc'd for C$_{23}$H$_{21}$N$_5$O, 384.18. found 384.3.

Example 182

(R)-2-(1H-indol-4-yl)-5-((1-methyl-1H-pyrazol-4-yl)methyl)-5,6,6a,7,9,10-hexahydro-[1,4]oxazino[3,4-h]pteridine

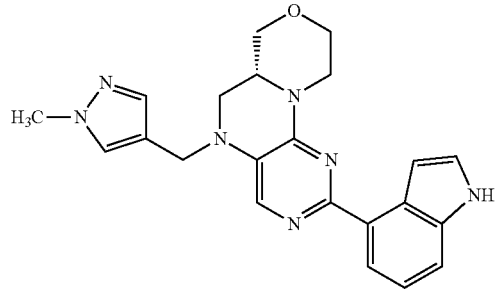 [SMILES: Cn1cc(CN2C[C@@H]3COCCN3c3nc(-c4cccc5[nH]ccc45)ncc32)cn1]

A TFA salt of the title compound was prepared in a manner similar to Example 2 using (R)-2-chloro-5-((1-methyl-1H-pyrazol-4-yl)methyl)-5,6,6a,7,9,10-hexahydro-[1,4]oxazino[3,4-h]pteridine (PREPARATION x60, 113 mg, 0.705 mmol), 1H-indol-4-ylboronic acid (113 mg, 0.705 mmol), and PdCl$_2$(dppf) (25.8 mg, 0.035 mmol) in dioxane (4 mL) and aqueous saturated NaHCO$_3$ (0.8 mL) (95 mg, 67%). $^1$H NMR (400 MHz, DMSO-d$_6$) δ ppm 2.98-3.09 (m, 1H), 3.28 (m, 2H), 3.45 (d, J=4.04 Hz, 2H), 3.57 (d, J=2.53 Hz, 2H), 3.80 (s, 3H), 3.89-4.05 (m, 1H), 4.05-4.13 (m, 1H), 4.31-4.54 (m, 2H), 4.67-4.76 (m, 1H), 6.99 (br s, 1H), 7.23-7.33 (m, 1H), 7.48 (d, J=0.51 Hz, 1H), 7.57 (t, J=2.78 Hz, 1H), 7.60-7.71 (m, 3H), 7.76 (s, 1H), 11.48-11.61 (m, 1H); ESI-MS m/z [M+H]$^+$ calc'd for C$_{22}$H$_{23}$N$_7$O, 402.20. found 402.3.

Example 183

(R)-5-(3-ethylphenyl)-2-(1H-indol-4-yl)-5,6,6a,7,9,10-hexahydro-[1,4]oxazino[3,4-h]pteridine

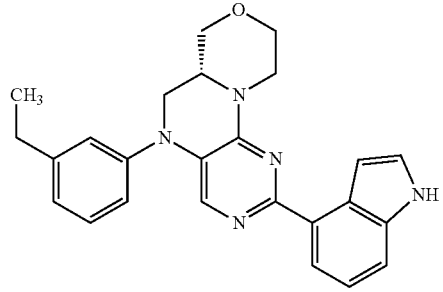 [SMILES: CCc1cccc(N2C[C@@H]3COCCN3c3nc(-c4cccc5[nH]ccc45)ncc32)c1]

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 100 mg, 0.237 mmol), cesium carbonate (155 mg, 0.474 mmol), palladium (II)acetate (2.66 mg, 0.012 mmol), dicyclohexyl(2',4',6'-triisopropylbiphenyl-2-yl)phosphine (113 mg, 0.237 mmol), and 1-bromo-3-ethylbenzene (132 mg, 0.712 mmol) in dioxane (2 mL) (10 mg, 10.3%). $^1$H NMR (400 MHz, DMSO-d$_6$) δ ppm 1.22 (m, 3H), 2.60-2.70 (m, 2H), 3.52-3.70 (m, 4H), 3.79-3.88 (m, 1H), 3.95-4.09 (m, 2H), 4.09-4.19 (m, 1H), 4.76-4.86 (m, 1H), 7.05-7.10 (m, 1H), 7.11-7.17 (m, 1H), 7.19-7.31 (m, 3H), 7.35-7.45 (m, 2H), 7.56-7.60 (m, 1H), 7.63-7.71 (m, 2H), 11.45-11.62 (m, 1H); ESI-MS m/z [M+H]$^+$ calc'd for C$_{25}$H$_{25}$N$_5$O, 412.21. found 412.3.

Example 184

(R)-5-(2-ethyl-phenyl)-2-(1H-indol-4-yl)-5,6,6a,7,9,10-hexahydro-[1,4]oxazino[3,4-h]pteridine

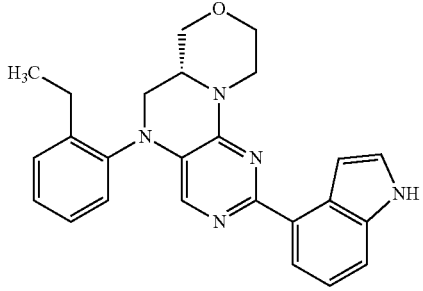 [SMILES: CCc1ccccc1N1C[C@@H]2COCCN2c2nc(-c3cccc4[nH]ccc34)ncc21]

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 90 mg, 0.213 mmol), cesium carbonate (139 mg, 0.427 mmol), palladium (II)acetate (2.66 mg, 0.012 mmol), dicyclohexyl(2',4',6'-triisopropylbiphenyl-2-yl)phosphine (113 mg, 0.237 mmol), and 1-bromo-2-ethylbenzene (0.087 mL, 0.640 mmol) in dioxane (2 mL) (15 mg, 17%). $^1$H NMR (400 MHz, DMSO-$d_6$) δ ppm 1.09-1.22 (m, 3H), 2.52-2.65 (m, 2H), 3.50-3.59 (m, 3H), 3.59-3.72 (m, 2H), 4.00-4.22 (m, 3H), 4.69-4.88 (m, 1H), 6.52-6.70 (m, 1H), 7.01-7.12 (m, 1H), 7.21-7.31 (m, 1H), 7.36-7.54 (m, 4H), 7.54-7.60 (m, 1H), 7.60-7.71 (m, 2H), 11.43-11.62 (m, 1H); ESI-MS m/z [M+H]$^+$ calc'd for $C_{25}H_{25}N_5O$, 412.21. found 412.3.

Example 185

(R)-2-(1H-indol-4-yl)-5-(oxazol-5-ylmethyl)-5,6,6a,7,9,10-hexahydro-[1,4]oxazino[3,4-h]pteridine

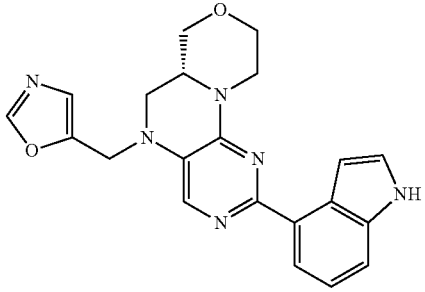 [SMILES: c1cc(-c2ncc3c(n2)N2CCOC[C@H]2CN3Cc2cnco2)c2cc[nH]c2c1]

A TFA salt of the title compound was prepared in a manner similar to Example 2 using (R)-2-chloro-5-(oxazol-5-ylmethyl)-5,6,6a,7,9,10-hexahydro-[1,4]oxazino[3,4-h]pteridine (PREPARATION x61, 171 mg, 0.556 mmol), 1H-indol-4-ylboronic acid (179 mg, 1.111 mmol), and PdCl$_2$(dppf) (40.7 mg, 0.056 mmol) in dioxane (5 mL) and aqueous saturated NaHCO$_3$ (1 mL) (121 mg, 56%). $^1$H NMR (400 MHz, DMSO-$d_6$) δ ppm 3.03-3.16 (m, 1H), 3.22-3.41 (m, 2H), 3.45-3.64 (m, 2H), 3.89-4.18 (m, 3H), 4.55-4.93 (m, 3H), 6.93-7.07 (m, 1H), 7.22-7.36 (m, 2H), 7.54-7.71 (m, 3H), 7.80 (s, 1H), 8.41 (s, 1H), 11.46-11.64 (m, 1H); ESI-MS m/z [M+H]$^+$ calc'd for $C_{21}H_{20}N_6O_2$, 389.17. found 389.3.

Example 186

(R)-2-(2-(1H-indol-4-yl)-6a,7,9,10-tetrahydro-[1,4]oxazino[3,4-h]pteridin-5(6H)-yl)benzonitrile

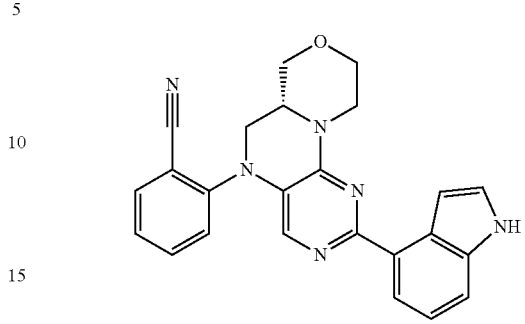

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 90 mg, 0.213 mmol), cesium carbonate (139 mg, 0.427 mmol), palladium (II)acetate (2.66 mg, 0.012 mmol), dicyclohexyl(2',4',6'-triisopropylbiphenyl-2-yl)phosphine (113 mg, 0.237 mmol), and 2-bromobenzonitrile (117 mg, 0.640 mmol) in dioxane (2 mL) (34 mg, 39%). $^1$H NMR (400 MHz, DMSO-$d_6$) δ ppm 3.32-3.42 (m, 2H), 3.61 (dd, J=11.24, 2.91 Hz, 2H), 3.82-3.91 (m, 1H), 3.91-4.01 (m, 1H), 4.01-4.18 (m, 2H), 4.75-4.85 (m, 1H), 7.06-7.16 (m, 1H), 7.20-7.31 (m, 1H), 7.41 (s, 1H), 7.47-7.58 (m, 2H), 7.59-7.72 (m, 2H), 7.72-7.81 (m, 1H), 7.81-7.90 (m, 1H), 7.94-8.03 (m, 1H), 11.41-11.59 (m, 1H); ESI-MS m/z [M+H]$^+$ calc'd for $C_{24}H_{20}N_6O$, 409.18. found 409.3.

Example 187

(R)-2-(1H-indol-4-yl)-5-(o-tolyl)-5,6,6a,7,9,10-hexahydro-[1,4]oxazino[3,4-h]pteridine

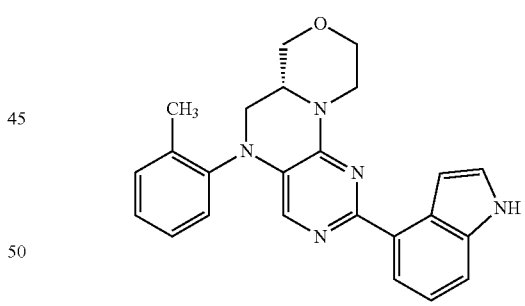

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 90 mg, 0.213 mmol), cesium carbonate (139 mg, 0.427 mmol), palladium (II)acetate (2.66 mg, 0.012 mmol), dicyclohexyl(2',4',6'-triisopropylbiphenyl-2-yl)phosphine (113 mg, 0.237 mmol), and 1-iodo-2-methylbenzene (140 mg, 0.640 mmol) in dioxane (2 mL) (19 mg, 22%). $^1$H NMR (400 MHz, DMSO-$d_6$) δ ppm 2.23 (s, 3H), 3.55-3.72 (m, 5H), 4.00-4.22 (m, 3H), 4.71-4.85 (m, 1H), 6.57-6.72 (m, 1H), 7.04-7.11 (m, 1H), 7.21-7.31 (m, 1H), 7.32-7.49 (m, 4H), 7.53-7.60 (m, 1H), 7.61-7.70 (m, 2H), 11.46-11.59 (m, 1H); ESI-MS m/z [M+H]$^+$ calc'd for $C_{24}H_{23}N_5O$, 398.20. found 398.3.

Example 188

(R)-5-((3-ethylisoxazol-5-yl)methyl)-2-(1H-indol-4-yl)-5,6,6a,7,9,10-hexahydro-[1,4]oxazino[3,4-h]pteridine

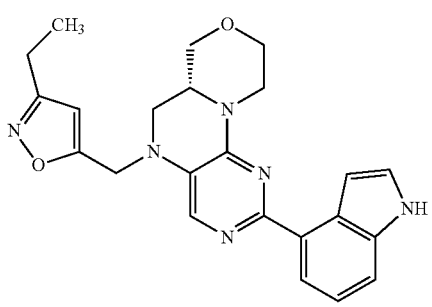 [SMILES: CCc1cc(CN2C[C@@H]3COCCN3c3nc(-c4cccc5[nH]ccc45)ncc32)on1]

A TFA salt of the title compound was prepared in a manner similar to Example 2 using (R)-2-chloro-5-((3-ethylisoxazol-5-yl)methyl)-5,6,6a,7,9,10-hexahydro-[1,4]oxazino[3,4-h]pteridine (PREPARATION x62, 75 mg, 0.223 mmol), 1H-indol-4-ylboronic acid (71.9 mg, 0.447 mmol), and PdCl$_2$(dppf) (8.17 mg, 0.011 mmol) in dioxane (2 mL) and aqueous saturated NaHCO$_3$ (0.4 mL) (18 mg, 19%). $^1$H NMR (400 MHz, DMSO-d$_6$) δ ppm 1.05-1.28 (m, 3H), 2.55-2.71 (m, 2H), 3.05-3.23 (m, 2H), 3.47-3.67 (m, 4H), 3.84-4.17 (m, 3H), 4.59-4.99 (m, 3H), 6.43-6.56 (m, 1H), 6.96-7.15 (m, 1H), 7.18-7.37 (m, 1H), 7.47-7.87 (m, 3H), 11.36-11.62 (m, 1H); ESI-MS m/z [M+H]$^+$ calc'd for C$_{23}$H$_{24}$N$_6$O$_2$, 417.20. found 417.4.

Example 189

(R)-4-(2-(1H-indol-4-yl)-6a,7,9,10-tetrahydro-[1,4]oxazino[3,4-h]pteridin-5(6H)-yl)cyclohexanol

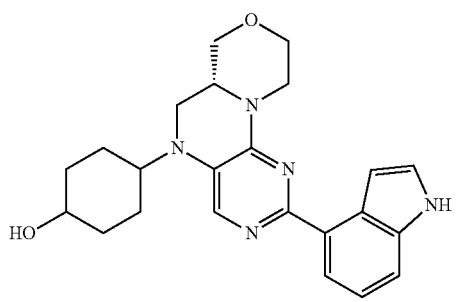 [SMILES: OC1CCC(N2C[C@@H]3COCCN3c3nc(-c4cccc5[nH]ccc45)ncc32)CC1]

The title compound was prepared in a manner similar to Example 2 using (R)-4-(2-chloro-6a,7,9,10-tetrahydro-[1,4]oxazino[3,4-h]pteridin-5(6H)-yl)cyclohexanol (PREPARATION x63, 30 mg, 0.092 mmol), 1H-indol-4-ylboronic acid (71.9 mg, 0.447 mmol) and PdCl$_2$(dppf) (8.17 mg, 0.011 mmol) in dioxane (2 mL) and aqueous saturated NaHCO$_3$ (0.4 mL) (2 mg, 5%). $^1$H NMR (400 MHz, DMSO-d$_6$) δ ppm 1.32-1.85 (m, 6H), 2.78-2.93 (m, 1H), 2.96-3.11 (m, 1H), 3.50-3.75 (m, 6H), 3.81-3.90 (m, 2H), 3.94-4.10 (m, 1H), 4.36-4.45 (m, 1H), 4.49-4.60 (m, 1H), 6.51-6.62 (m, 1H), 7.02-7.19 (m, 1H), 7.27-7.45 (m, 3H), 7.80-7.98 (m, 2H), 11.04-11.16 (m, 1H); ESI-MS m/z [M+H]$^+$ calc'd for C$_{23}$H$_{27}$N$_5$O$_2$, 406.22. found 406.4.

Example 190

(R)-ethyl 3-(2-(1H-indol-4-yl)-6a,7,9,10-tetrahydro-[1,4]oxazino[3,4-h]pteridin-5(6H)-yl)benzoate

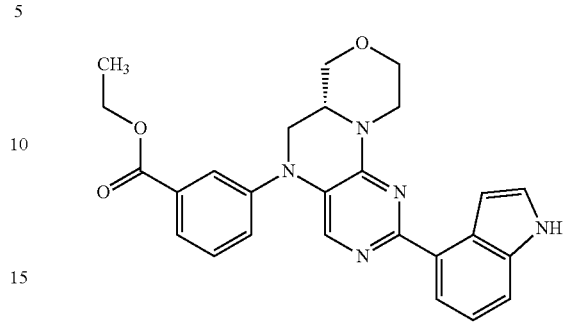

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 32.6 mg, 0.142 mmol), cesium carbonate (93 mg, 0.285 mmol), palladium (II)acetate (1.59 mg, 0.007 mmol), dicyclohexyl(2',4',6'-triisopropylbiphenyl-2-yl)phosphine (10.2 mg, 0.021 mmol), and ethyl 3-bromobenzoate (32.6 mg, 0.142 mmol) in dioxane (2 mL) (8 mg, 12%). $^1$H NMR (400 MHz, DMSO-d$_6$) δ ppm 1.23-1.40 (m, 3H), 3.52-3.72 (m, 5H), 3.79-3.98 (m, 2H), 3.98-4.19 (m, 2H), 4.22-4.44 (m, 1H), 4.71-4.87 (m, 1H), 7.08-7.20 (m, 1H), 7.20-7.32 (m, 1H), 7.48-7.72 (m, 5H), 7.72-7.85 (m, 2H), 7.84-7.94 (m, 1H), 11.34-11.57 (m, 1H); ESI-MS m/z [M+H]$^+$ calc'd for C$_{26}$H$_{25}$N$_5$O$_3$, 456.20. found 456.4.

Example 191

(R)-2-(1H-indol-4-yl)-5-(3-(methylsulfonyl)phenyl)-5,6,6a,7,9,10-hexahydro-[1,4]oxazino[3,4-h]pteridine

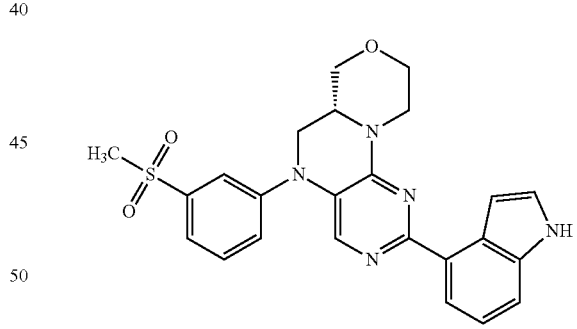

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 100 mg, 0.427 mmol), cesium carbonate (93 mg, 0.285 mmol), palladium (II)acetate (1.59 mg, 0.007 mmol), dicyclohexyl(2',4',6'-triisopropylbiphenyl-2-yl)phosphine (10.2 mg, 0.021 mmol), and 1-bromo-3-(methylsulfonyl)benzene (100 mg, 0.427 mmol) in dioxane (2 mL) (8 mg, 12%). $^1$H NMR (400 MHz, DMSO-d$_6$) δ ppm 3.25 (s, 3H), 3.51-3.71 (m, 5H), 3.81-4.07 (m, 4H), 4.07-4.20 (m, 1H), 4.69-4.87 (m, 1H), 7.09-7.34 (m, 2H), 7.47-7.77 (m, 5H), 7.77-7.98 (m, 3H), 11.32-11.57 (m, 1H); ESI-MS m/z [M+H]$^+$ calc'd for C$_{24}$H$_{23}$N$_5$O$_3$S, 462.16. found 462.3.

Example 192

(R)-2-(1H-indol-4-yl)-5-(tetrahydro-2H-pyran-4-yl)-5,6,6a,7,9,10-hexahydro-[1,4]oxazino[3,4-h]pteridine

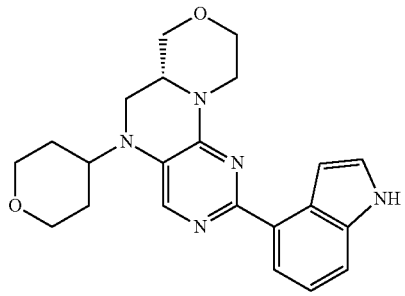 [SMILES: c1cc(-c2ncc3c(n2)N2CCOC[C@H]2CN3C2CCOCC2)c2cc[nH]c2c1]

A TFA salt of the title compound was prepared in a manner similar to Example 2 using (R)-2-chloro-5-(tetrahydro-2H-pyran-4-yl)-5,6,6a,7,9,10-hexahydro-[1,4]oxazino[3,4-h]pteridine (PREPARATION x64, 10 mg, 0.032 mmol), 1H-indol-4-ylboronic acid (10.4 mg, 0.064 mmol) and PdCl$_2$(dppf) (1.17 mg, 0.002 mmol) in dioxane 1 mL and aqueous saturated NaHCO$_3$ 0.2 mL (2 mg, 16%). $^1$H NMR (400 MHz, CD$_3$CN) δ ppm 1.58-1.83 (m, 5H), 2.84-2.94 (m, 1H), 3.25-3.37 (m, 2H), 3.46-3.57 (m, 3H), 3.57-3.68 (m, 1H), 3.71-3.90 (m, 2H), 3.96-4.12 (m, 4H), 4.77-4.91 (m, 1H), 7.04-7.12 (m, 1H), 7.25-7.34 (m, 1H), 7.42-7.50 (m, 1H), 7.64-7.76 (m, 3H), 9.68-9.85 (m, 1H); ESI-MS m/z [M+H]$^+$ calc'd for C$_{22}$H$_{25}$N$_5$O$_3$, 392.21. found 392.3.

Example 193

(R)-2,5-di(1H-indol-4-yl)-5,6,6a,7,9,10-hexahydro-[1,4]oxazino[3,4-h]pteridine

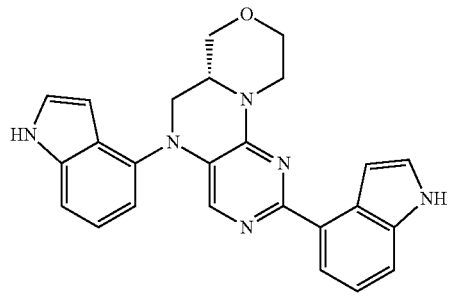 [SMILES: c1cc(-c2ncc3c(n2)N2CCOC[C@H]2CN3c2cccc3[nH]ccc23)c2cc[nH]c2c1]

(R)-tert-Butyl 4-(2-(1H-indol-4-yl)-6a,7,9,10-tetrahydro-[1,4]oxazino[3,4-h]pteridin-5(6H)-yl)-1H-indole-1-carboxylate (PREPARATION x65, 9 mg, 0.017 mmol) was dissolved in CH$_2$Cl$_2$ (1 mL) and trifluoroacetic acid (1 mL) and the mixture was stirred at room temperature for 30 minutes. The material was then concentrated in vacuo and the product was purified by LC/MS using a 20-45% CH$_3$CN gradient in H$_2$O (with 0.035% TFA). The pure fractions were combined and lyophilized to afford a TFA salt of the title compound as a yellow solid (2 mg, 28%). $^1$H NMR (400 MHz, CD$_3$CN) δ ppm 3.36-3.61 (m, 3H), 3.68-3.87 (m, 2H), 3.97-4.07 (m, 1H), 4.07-4.20 (m, 2H), 4.91-5.00 (m, 1H), 6.28-6.38 (m, 1H), 6.98-7.09 (m, 1H), 7.12-7.17 (m, 1H), 7.22-7.35 (m, 3H), 7.44-7.51 (m, 2H), 7.65-7.75 (m, 2H), 9.57-9.67 (m, 1H), 9.67-9.81 (m, 1H); ESI-MS m/z [M+H]$^+$ calc'd for C$_{25}$H$_{22}$N$_6$O, 423.19. found 423.3.

Example 194

(R)-5-(2-(1,3-dioxolan-2-yl)ethyl)-2-(1H-indol-4-yl)-5,6,6a,7,9,10-hexahydro-[1,4]oxazino[3,4-h]pteridine

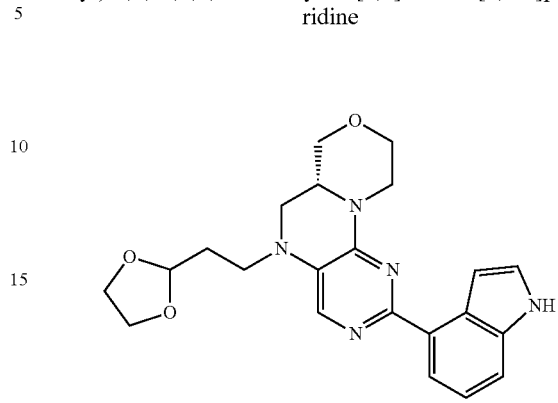

A TFA salt of the title compound was prepared in a manner similar to Example 2 using (R)-5-(2-(1,3-dioxolan-2-yl)ethyl)-2-chloro-5,6,6a,7,9,10-hexahydro-[1,4]oxazino[3,4-h]pteridine (PREPARATION x66, 25 mg, 0.077 mmol), 1H-indol-4-ylboronic acid (25 mg, 0.153 mmol), and PdCl$_2$(dppf) (2.80 mg, 0.004 mmol) in dioxane (1 mL) and aqueous saturated NaHCO$_3$ (0.2 mL) (5 mg, 16%). $^1$H NMR (400 MHz, CD$_3$CN) δ ppm 3.06-3.15 (m, 1H), 3.26-3.49 (m, 7H), 3.57-3.68 (m, 1H), 3.81-3.93 (m, 3H), 3.94-4.12 (m, 4H), 4.79-4.88 (m, 1H), 4.91-4.97 (m, 1H), 7.04-7.12 (m, 1H), 7.26-7.36 (m, 1H), 7.43-7.50 (m, 1H), 7.50-7.56 (m, 1H), 7.64-7.74 (m, 2H), 9.68-9.83 (m, 1H); ESI-MS m/z [M+H]$^+$ calc'd for C$_{22}$H$_{25}$N$_5$O$_3$, 408.20. found 408.3.

Example 195

(R)-methyl 4-(2-(1H-indol-4-yl)-6a,7,9,10-tetrahydro-[1,4]oxazino[3,4-h]pteridin-5(6H)-yl)butanoate

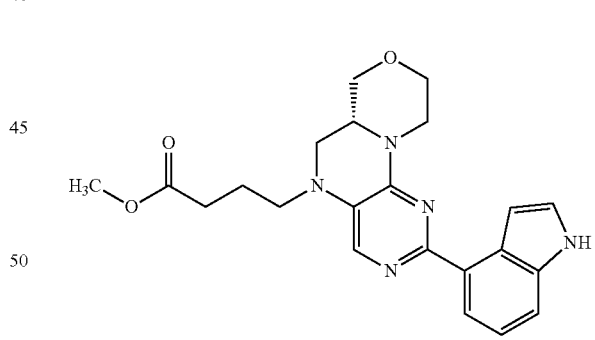

A TFA salt of the title compound was prepared in a manner similar to Example 2 using (R)-methyl 4-(2-chloro-6a,7,9,10-tetrahydro-[1,4]oxazino[3,4-h]pteridin-5(6H)-yl)butanoate (PREPARATION x67, 90 mg, 0.275 mmol), 1H-indol-4-ylboronic acid (89 mg, 0.551 mmol), and PdCl$_2$(dppf) (10.1 mg, 0.014 mmol) in dioxane (3 mL) and aqueous saturated NaHCO$_3$ (0.6 mL) (28 mg, 25%). $^1$H NMR (400 MHz, DMSO-d$_6$) δ ppm 1.75-1.93 (m, 2H), 2.42 (m, 2H), 2.94-3.11 (m, 2H), 3.14-3.31 (m, 4H), 3.60 (m, 5H), 3.88-3.97 (m, 1H), 4.02-4.10 (m, 1H), 4.48-4.57 (m, 1H), 7.11 (m, 1H), 7.37 (m, 3H), 7.84 (s, 1H), 7.90-7.98 (m, 1H), 11.04-11.16 (m, 1H); ESI-MS m/z [M+H]$^+$ calc'd for C$_{22}$H$_{25}$N$_5$O$_3$, 408.20. found 408.3.

Example 196

(R)-4-(2-(1H-indol-4-yl)-6a,7,9,10-tetrahydro-[1,4]oxazino[3,4-h]pteridin-5(6H)-yl)butanoic acid

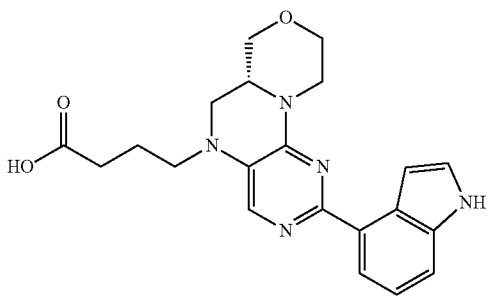 [SMILES: O=C(O)CCCN1C[C@@H]2COCCN2c2nc(-c3cccc4[nH]ccc34)ncc21]

(R)-Methyl 4-(2-(1H-indol-4-yl)-6a,7,9,10-tetrahydro-[1,4]oxazino[3,4-h]pteridin-5(6H)-yl)butanoate (EXAMPLE 195, 17 mg, 0.042 mmol) was dissolved in THF (1 mL). Sodium hydroxide (1M, 0.083 mL, 0.083 mmol) was added to give a green solution, which was stirred at ambient temperature for 4 hours. The reaction mixture was acidified to about pH 1 with 1M HCl. The material was then concentrated in vacuo. The product was purified by LC/MS using a 25-40% $CH_3CN$ gradient in $H_2O$ (with 0.035% TFA). The pure fractions were combined and lyophilized to afford a TFA salt of the title compound as a yellow solid (10 mg, 61%). $^1H$ NMR (400 MHz, DMSO-$d_6$) δ ppm 1.70-1.89 (m, 2H), 2.29-2.40 (m, 2H), 3.05-3.17 (m, 1H), 3.22-3.29 (m, 3H), 3.42-3.48 (m, 3H), 3.52-3.66 (m, 1H), 3.81-3.94 (m, 1H), 3.97-4.14 (m, 2H), 4.64-4.75 (m, 1H), 6.96-7.07 (m, 1H), 7.22-7.33 (m, 1H), 7.51-7.60 (m, 1H), 7.60-7.72 (m, 3H), 11.42-11.59 (m, 1H); ESI-MS m/z $[M+H]^+$ calc'd for $C_{21}H_{23}N_5O_3$, 394.19. found 394.4.

Example 197

(1R,4r)-4-4(R)-2-(1H-indol-4-yl)-6a,7,9,10-tetrahydro-[1,4]oxazino[3,4-h]pteridin-5(6H)-yl)methyl)cyclohexanamine

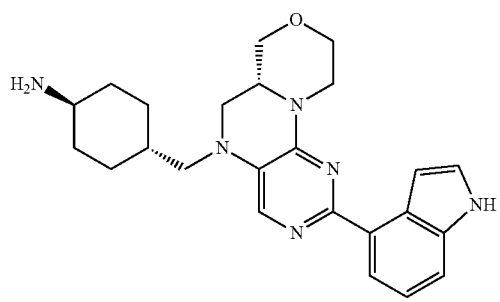 [SMILES: N[C@H]1CC[C@H](CN2C[C@@H]3COCCN3c3nc(-c4cccc5[nH]ccc45)ncc32)CC1]

To a round bottom flask was added benzyl ((1R,4r)-4-4(R)-2-(1H-indol-4-yl)-6a,7,9,10-tetrahydro-[1,4]oxazino[3,4-h]pteridin-5(6H)-yl)methyl)cyclohexyl)carbamate (PREPARATION x69, 30 mg, 0.054 mmol) in ethanol (0.5 mL) and ethyl acetate (0.5 mL). Palladium on barium sulfate (0.922 mg, 2.71 µmol) was then added. The flask was evacuated and hydrogen gas was introduced via a balloon. The reaction mixture was stirred for 2 hours at ambient temperature under a hydrogen atmosphere. The reaction mixture was subsequently diluted with EtOAc and Pd was filtered over a pad of Celite®. The product was then concentrated in vacuo and was purified by LC/MS using a 20-35% $CH_3CN$ gradient in $H_2O$ (with 0.035% TFA). The pure fractions were combined and lyophilized to afford the title compound as a yellow solid (12 mg, 53%). $^1H$ NMR (400 MHz, $CD_3CN$) δ ppm 1.00-1.18 (m, 2H), 1.32-1.51 (m, 2H), 1.68-1.82 (m, 2H), 1.82-1.91 (m, 2H), 2.02-2.10 (m, 2H), 2.94-3.17 (m, 4H), 3.22-3.42 (m, 3H), 3.57-3.69 (m, 1H), 3.78-3.91 (m, 1H), 3.93-4.13 (m, 2H), 4.73-4.84 (m, 1H), 7.05-7.12 (m, 1H), 7.24-7.31 (m, 1H), 7.43-7.49 (m, 2H), 7.54 (s, 1H), 7.64-7.73 (m, 2H), 9.78-9.90 (m, 1H); ESI-MS m/z $[M+H]^+$ calc'd for $C_{24}H_{30}N_6O$, 419.25. found 419.5.

Example 198

(R)-ethyl 5-(2-(1H-indol-4-yl)-6a,7,9,10-tetrahydro-[1,4]oxazino[3,4-h]pteridin-5(6H)-yl)nicotinate

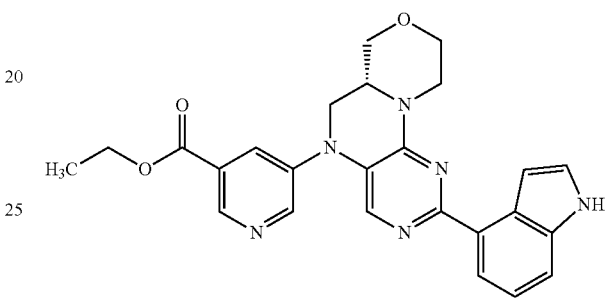

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 75 mg, 0.178 mmol), cesium carbonate (116 mg, 0.356 mmol), palladium (II)acetate (1.997 mg, 0.027 mmol), dicyclohexyl(2',4',6'-triisopropylbiphenyl-2-yl)phosphine (12.72 mg, 0.027 mmol), and ethyl 5-bromonicotinate (123 mg, 0.534 mmol) in dioxane (2 mL) (25 mg, 31%). $^1H$ NMR (400 MHz, DMSO-$d_6$) δ ppm 1.34 (t, 3H), 3.55-3.69 (m, 4H), 3.89-4.07 (m, 3H), 4.08-4.18 (m, 1H), 4.30-4.45 (m, 2H), 4.74-4.88 (m, 1H), 7.06-7.17 (m, 1H), 7.22-7.32 (m, 1H), 7.51-7.61 (m, 1H), 7.61-7.70 (m, 1H), 7.70-7.87 (m, 2H), 8.14-8.24 (m, 1H), 8.80-8.95 (m, 2H), 11.41-11.58 (m, 1H); ESI-MS m/z $[M+H]^+$ calc'd for $C_{25}H_{24}N_6O_3$, 457.20. found 457.4.

Example 199

(R)-methyl 5-(2-(1H-indol-4-yl)-6a,7,9,10-tetrahydro-[1,4]oxazino[3,4-h]pteridin-5(6H)-yl)nicotinate

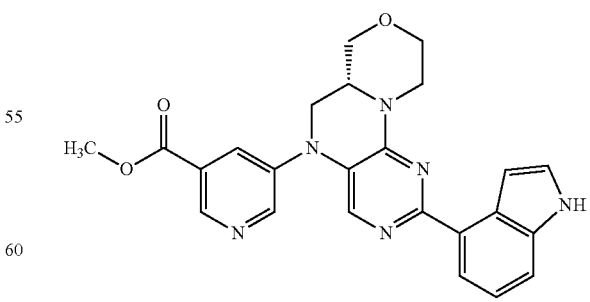

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 75 mg, 0.178 mmol), cesium carbonate (116 mg, 0.356 mmol), palladium (II)acetate (1.997 mg, 0.009 mmol), dicyclohexyl(2',4',6'-triisopropylbiphenyl-2-yl)phosphine (12.72 mg, 0.027 mmol), and methyl 4-bromopicolinate (115 mg, 0.534 mmol) in dioxane (2 mL) (6 mg, 7.6%). $^1$H NMR (400 MHz, CD$_3$CN) δ ppm 3.03-3.12 (m, 1H), 3.27-3.40 (m, 2H), 3.42-3.53 (m, 1H), 3.60-3.72 (m, 1H), 3.78-3.94 (m, 1H), 3.94-3.98 (m, 3H), 3.98-4.13 (m, 3H), 4.74-4.86 (m, 1H), 7.39-7.43 (m, 1H), 7.44-7.50 (m, 1H), 7.60-7.64 (m, 1H), 7.76-7.85 (m, 3H), 7.94-8.01 (m, 1H), 8.27-8.32 (m, 1H), 8.82-8.87 (m, 1H); ESI-MS m/z [M+H]$^+$ calc'd for C$_{24}$H$_{22}$N$_6$O$_3$, 443.18. found 443.3.

Example 200

(R)-methyl 2-(2-(1H-indol-4-yl)-6a,7,9,10-tetrahydro-[1,4]oxazino[3,4-h]pteridin-5(6H)-yl)isonicotinate

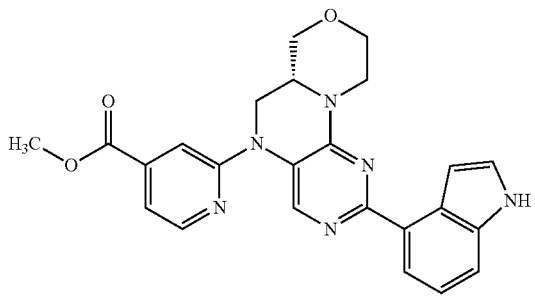 [SMILES: COC(=O)c1ccnc(N2C[C@@H]3COCCN3c3nc(-c4cccc5[nH]ccc45)ncc32)c1]

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 75 mg, 0.178 mmol), cesium carbonate (116 mg, 0.356 mmol), palladium (II)acetate (1.997 mg, 0.009 mmol), dicyclohexyl(2',4',6'-triisopropylbiphenyl-2-yl)phosphine (12.72 mg, 0.027 mmol), and methyl 2-bromoisonicotinate (115 mg, 0.534 mmol) in dioxane (2 mL) (4.6 mg, 5.8%). $^1$H NMR (400 MHz, CD$_3$CN) δ ppm 3.24-3.51 (m, 4H), 3.59-3.78 (m, 1H), 3.90 (s, 3H), 4.00-4.15 (m, 2H), 4.40-4.52 (m, 1H), 4.87-4.99 (m, 1H), 7.18-7.27 (m, 1H), 7.27-7.36 (m, 1H), 7.40-7.53 (m, 2H), 7.65-7.76 (m, 2H), 7.84-7.96 (m, 1H), 8.43-8.53 (m, 1H), 8.60-8.70 (m, 1H), 9.62-9.76 (m, 1H); ESI-MS m/z [M+H]$^+$ calc'd for C$_{24}$H$_{22}$N$_6$O$_3$, 443.18. found 443.3.

Example 201

(R)-2-(1H-indol-4-yl)-5-(5-methoxypyridin-3-yl)-5,6,6a,7,9,10-hexahydro-[1,4]oxazino[3,4-h]pteridine

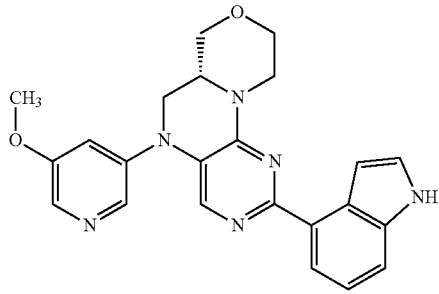 [SMILES: COc1cncc(N2C[C@@H]3COCCN3c3nc(-c4cccc5[nH]ccc45)ncc32)c1]

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 75 mg, 0.178 mmol), cesium carbonate (116 mg, 0.356 mmol), palladium (II)acetate (1.997 mg, 0.009 mmol), dicyclohexyl(2',4',6'-triisopropylbiphenyl-2-yl)phosphine (12.72 mg, 0.027 mmol), and 3-bromo-5-methoxypyridine (100 mg, 0.534 mmol) in dioxane (2 mL) (24 mg, 33%). $^1$H NMR (400 MHz, DMSO-d$_6$) δ ppm 3.53-3.68 (m, 4H), 3.87 (s, 3H), 3.90-4.08 (m, 3H), 4.09-4.19 (m, 1H), 4.79-4.87 (m, 1H), 7.04-7.12 (m, 1H), 7.23-7.33 (m, 1H), 7.44-7.52 (m, 1H), 7.54-7.62 (m, 1H), 7.63-7.76 (m, 3H), 8.14-8.23 (m, 1H), 8.25-8.33 (m, 1H), 11.48-11.61 (m, 1H); ESI-MS m/z [M+H]$^+$ calc'd for C$_{23}$H$_{22}$N$_6$O$_2$, 415.19. found 415.3.

Example 202

(R)-methyl 5-(2-(1H-indol-4-yl)-6a,7,9,10-tetrahydro-[1,4]oxazino[3,4-h]pteridin-5(6H)-yl)-2-methoxynicotinate

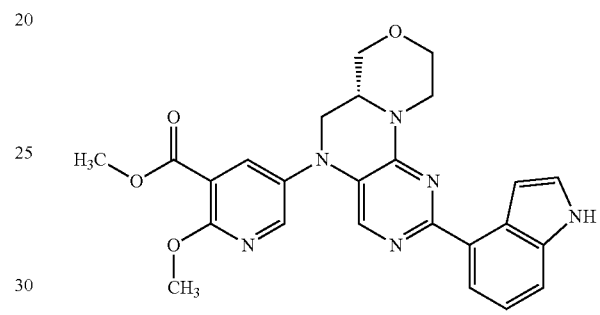

A TFA salt of the title compound was prepared in a manner similar to EXAMPLE 181 using (R)-2-(1-(tert-butyldimethylsilyl)-1H-indol-4-yl)-5,6,6a,7,9,10-hexahydro-[1,4]oxazino[3,4-h]pteridine (PREPARATION x12, 75 mg, 0.178 mmol), cesium carbonate (116 mg, 0.356 mmol), palladium (II)acetate (1.997 mg, 0.009 mmol), dicyclohexyl(2',4',6'-triisopropylbiphenyl-2-yl)phosphine (12.72 mg, 0.027 mmol), and methyl 5-bromo-2-methoxynicotinate (131 mg, 0.534 mmol) in dioxane (2 mL) (36 mg, 43%). $^1$H NMR (400 MHz, DMSO-d$_6$) δ ppm 3.54-3.69 (m, 4H), 3.72-3.80 (m, 1H), 3.83 (s, 3H), 3.97 (s, 3H), 4.08-4.18 (m, 1H), 4.73-4.85 (m, 1H), 7.02-7.09 (m, 1H), 7.23-7.31 (m, 1H), 7.38-7.44 (m, 1H), 7.54-7.60 (m, 1H), 7.61-7.72 (m, 2H), 8.18-8.25 (m, 1H), 8.44-8.50 (m, 1H), 11.46-11.57 (m, 1H); ESI-MS m/z [M+H]$^+$ calc'd for C$_{25}$H$_{24}$N$_6$O$_4$, 473.19. found 473.3.

Example 203

(R)-2-(2-(1H-indol-4-yl)-6a,7,9,10-tetrahydro-[1,4]oxazino[3,4-h]pteridin-5(6H)-yl)-N-(pyridin-4-yl)acetamide

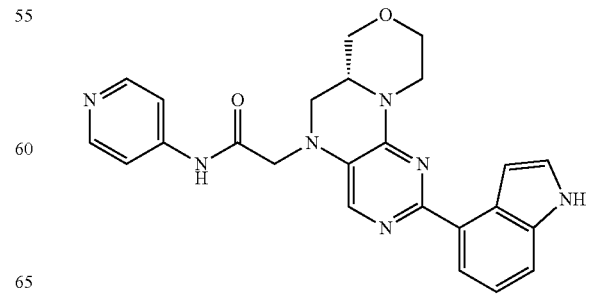

A TFA salt of the title compound was prepared in a manner similar to Example 2 using (R)-2-(2-chloro-6a,7,9,10-tetrahydro-[1,4]oxazino[3,4-h]pteridin-5(6H)-yl)-N-(pyridin-4-yl)acetamide (PREPARATION x70, 63.4 mg, 0.174 mmol), 1H-indol-4-ylboronic acid (56 mg, 0.348 mmol), and PdCl$_2$(dppf) (6.36 mg, 0.009 mmol) in dioxane (2 mL) and aqueous saturated NaHCO$_3$ (0.4 mL) (2 mg, 2.6%). ESI-MS m/z [M+H]$^+$ calc'd for C$_{24}$H$_{23}$N$_7$O$_2$, 442.20. found 442.4.

Example 204

(R)-2-(2-(1H-indol-4-yl)-6a,7,9,10-tetrahydro-[1,4]oxazino[3,4-h]pteridin-5(6H)-yl)-N-(2-methoxyethyl)acetamide

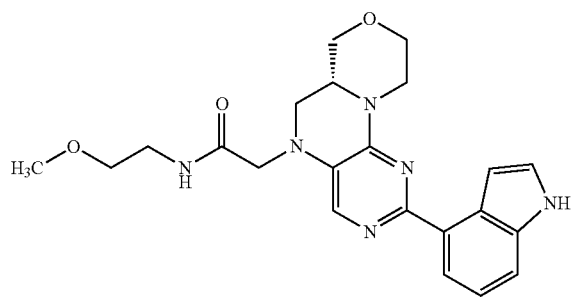 [SMILES: COCCNC(=O)CN1C[C@@H]2COCCN2c2nc(-c3cccc4[nH]ccc34)ncc21]

A TFA salt of the title compound was prepared in a manner similar to Example 2 using (R)-2-(2-chloro-6a,7,9,10-tetrahydro-[1,4]oxazino[3,4-h]pteridin-5(6H)-yl)-N-(2-methoxyethyl)acetamide (PREPARATION x71, 60 mg, 0.174 mmol), 1H-indol-4-ylboronic acid (56 mg, 0.348 mmol), and PdCl$_2$(dppf) (6.36 mg, 0.009 mmol) in dioxane (2 mL) and aqueous saturated NaHCO$_3$ (0.4 mL) (10 mg, 14%). ESI-MS m/z [M+H]$^+$ calc'd for C$_{22}$H$_{26}$N$_6$O$_3$, 423.21. found 423.3.

Example 205

(R)-2-(2-(1H-indol-4-yl)-6a,7,9,10-tetrahydro-[1,4]oxazino[3,4-h]pteridin-5(6H)-yl)-N-(tetrahydro-2H-pyran-4-yl)acetamide

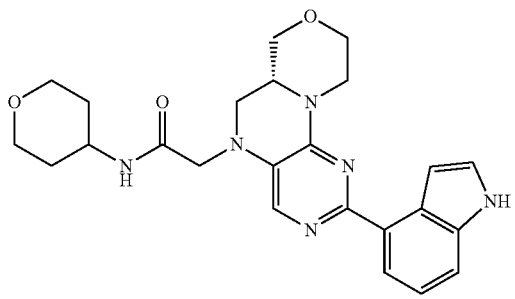 [SMILES: O=C(CN1C[C@@H]2COCCN2c2nc(-c3cccc4[nH]ccc34)ncc21)NC1CCOCC1]

A TFA salt of the title compound was prepared in a manner similar to Example 2 using (R)-2-(2-chloro-6a,7,9,10-tetrahydro-[1,4]oxazino[3,4-h]pteridin-5(6H)-yl)-N-(tetrahydro-2H-pyran-4-yl)acetamide (PREPARATION x72, 64.6 mg, 0.174 mmol), 1H-indol-4-ylboronic acid (56 mg, 0.348 mmol), and PdCl$_2$(dppf) (6.36 mg, 0.009 mmol) in dioxane (2 mL) and aqueous saturated NaHCO$_3$ (0.4 mL) (3 mg, 4%). $^1$H NMR (400 MHz, CD$_3$CN) δ ppm 1.41-1.49 (m, 2H), 1.75 (m, 4H), 3.22-3.49 (m, 6H), 3.59-3.73 (m, 1H), 3.75-4.14 (m, 6H), 4.78-4.94 (m, 1H), 6.71-6.82 (m, 1H), 7.05-7.14 (m, 1H), 7.25-7.35 (m, 1H), 7.35-7.41 (m, 1H), 7.43-7.53 (m, 1H), 7.63-7.77 (m, 2H), 9.67-9.83 (m, 1H); ESI-MS m/z [M+H]$^+$ calc'd for C$_{24}$H$_{28}$N$_6$O$_3$, 449.23. found 449.4.

Example 206

(R)-2-(2-(1H-indol-4-yl)-6a,7,9,10-tetrahydro-[1,4]oxazino[3,4-h]pteridin-5(6H)-yl)-N-(1-methyl-1H-pyrazol-4-yl)acetamide

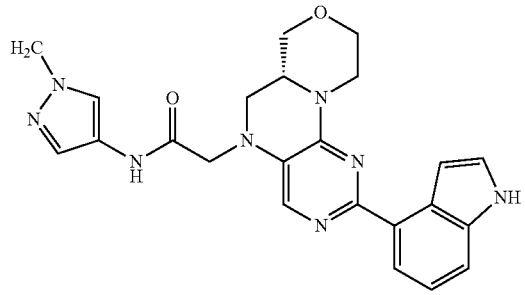 [SMILES: Cn1cc(NC(=O)CN2C[C@@H]3COCCN3c3nc(-c4cccc5[nH]ccc45)ncc32)cn1]

A TFA salt of the title compound was prepared in a manner similar to Example 2 using (R)-2-(2-chloro-6a,7,9,10-tetrahydro-[1,4]oxazino[3,4-h]pteridin-5(6H)-yl)-N-(1-methyl-1H-pyrazol-4-yl)acetamide (PREPARATION x73, 63.9 mg, 0.174 mmol), 1H-indol-4-ylboronic acid (56 mg, 0.348 mmol), and PdCl$_2$(dppf) (6.36 mg, 0.009 mmol) in dioxane (2 mL) and aqueous saturated NaHCO$_3$ (0.4 mL) (9 mg, 11%). $^1$H NMR (400 MHz, DMSO-d$_6$) δ ppm 3.28-3.55 (m, 8H), 3.59-3.69 (m, 1H), 3.76-3.84 (m, 3H), 3.90-4.17 (m, 4H), 4.30-4.46 (m, 1H), 4.66-4.82 (m, 1H), 6.93-7.07 (m, 1H), 7.20-7.33 (m, 1H), 7.41-7.49 (m, 1H), 7.50-7.74 (m, 4H), 7.83-7.93 (m, 1H), 10.17-10.30 (m, 1H), 11.44-11.67 (m, 1H); ESI-MS m/z [M+H]$^+$ calc'd for C$_{23}$H$_{24}$N$_8$O$_2$, 445.21 found 445.3.

Example 207

(R)-2-(2-(1H-indol-4-yl)-6a,7,9,10-tetrahydro-[1,4]oxazino[3,4-h]pteridin-5(6H)-yl)-N-cyclopropylacetamide

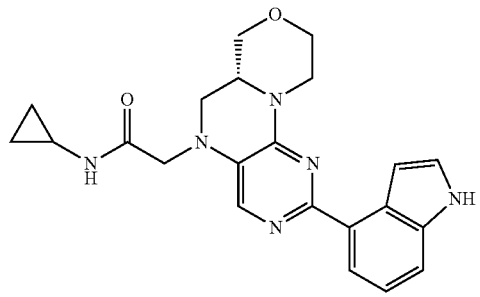 [SMILES: O=C(CN1C[C@@H]2COCCN2c2nc(-c3cccc4[nH]ccc34)ncc21)NC1CC1]

A TFA salt of the title compound was prepared in a manner similar to Example 2 using (R)-2-(2-chloro-6a,7,9,10-tetrahydro-[1,4]oxazino[3,4-h]pteridin-5(6H)-yl)-N-cyclopropylacetamide (PREPARATION x74, 56.9 mg, 0.174 mmol), 1H-indol-4-ylboronic acid (56 mg, 0.348 mmol), and PdCl$_2$(dppf) (6.36 mg, 0.009 mmol) in dioxane (2 mL) and aqueous saturated NaHCO$_3$ (0.4 mL) (6 mg, 8.6%). $^1$H NMR (400 MHz, DMSO-d$_6$) δ ppm 0.39-0.51 (m, 2H), 0.59-0.71 (m, 2H), 2.60-2.73 (m, 1H), 3.21-3.31 (m, 4H), 3.55-3.69 (m, 1H), 3.77-3.95 (m, 2H), 3.95-4.04 (m, 1H), 4.05-4.18 (m, 2H), 4.64-4.77 (m, 1H), 6.96-7.12 (m, 1H), 7.19-7.33 (m, 1H), 7.38-7.48 (m, 1H), 7.50-7.77 (m, 3H), 8.15-8.26 (m, 1H), 11.41-11.62 (m, 1H); ESI-MS m/z [M+H]⁺ calc'd for C$_{22}$H$_{24}$N$_6$O$_2$, 405.20 found 405.3.

Example 208

(R)-2-(2-(1H-indol-4-yl)-6a,7,9,10-tetrahydro-[1,4]oxazino[3,4-h]pteridin-5(6H)-yl)-N-(2-cyanopropan-2-yl)acetamide

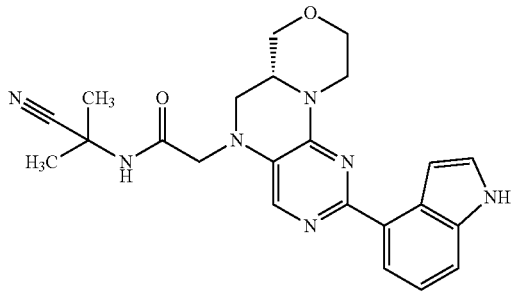 [SMILES: CC(C)(C#N)NC(=O)CN1C[C@@H]2COCCN2c2nc(-c3cccc4[nH]ccc34)ncc21]

A TFA salt of the title compound was prepared in a manner similar to Example 2 using (R)-2-(2-chloro-6a,7,9,10-tetrahydro-[1,4]oxazino[3,4-h]pteridin-5(6H)-yl)-N-(2-cyanopropan-2-yl)acetamide (PREPARATION x75, 61.6 mg, 0.174 mmol), 1H-indol-4-ylboronic acid (56 mg, 0.348 mmol), and PdCl$_2$(dppf) (6.36 mg, 0.009 mmol) in dioxane (2 mL) and aqueous saturated NaHCO$_3$ (0.4 mL) (26.4 mg, 35%). $^1$H NMR (400 MHz, DMSO-d$_6$) δ ppm 1.62 (d, J=2.02 Hz, 6H), 3.24-3.37 (m, 4H), 3.56-3.69 (m, 2H), 3.81-4.17 (m, 4H), 4.22-4.37 (m, 1H), 4.62-4.82 (m, 1H), 6.93-7.12 (m, 1H), 7.19-7.35 (m, 1H), 7.39-7.53 (m, 1H), 7.53-7.76 (m, 3H), 8.66-8.90 (m, 1H), 11.41-11.69 (m, 1H); ESI-MS m/z [M+H]⁺ calc'd for C$_{23}$H$_{25}$N$_7$O$_2$, 432.21 found 432.4.

Example 209

2-((R)-2-(1H-indol-4-yl)-6a,7,9,10-tetrahydro-[1,4]oxazino[3,4-h]pteridin-5(6H)-yl)-N-(tetrahydrofuran-3-yl)acetamide

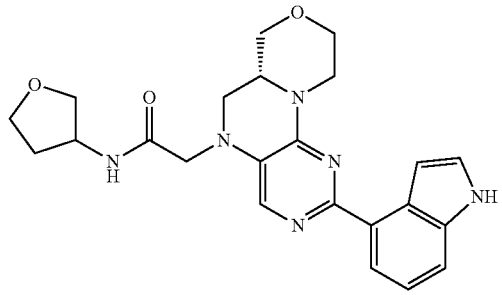 [SMILES: O=C(CN1C[C@@H]2COCCN2c2nc(-c3cccc4[nH]ccc34)ncc21)NC1CCOC1]

A TFA salt of the title compound was prepared in a manner similar to Example 2 using 2-((R)-2-chloro-6a,7,9,10-tetrahydro-[1,4]oxazino[3,4-h]pteridin-5(6H)-yl)-N-(tetrahydrofuran-3-yl)acetamide (PREPARATION x76, 62.1 mg, 0.174 mmol), 1H-indol-4-ylboronic acid (56 mg, 0.348 mmol), and PdCl$_2$(dppf) (6.36 mg, 0.009 mmol) in dioxane (2 mL) and aqueous saturated NaHCO$_3$ (0.4 mL) (5.4 mg, 7%). $^1$H NMR (400 MHz, DMSO-d$_6$) δ ppm 1.69-1.82 (m, 1H), 2.04-2.15 (m, 1H), 2.98-3.09 (m, 1H), 3.14-3.24 (m, 1H), 3.45-3.86 (m, 9H), 3.87-3.96 (m, 1H), 4.02-4.12 (m, 2H), 4.21-4.33 (m, 1H), 4.50-4.59 (m, 1H), 7.05-7.16 (m, 1H), 7.26-7.33 (m, 1H), 7.34-7.45 (m, 2H), 7.54-7.64 (m, 1H), 7.87-7.96 (m, 1H), 8.27-8.38 (m, 1H), 11.06-11.17 (m, 1H); ESI-MS m/z [M+H]⁺ calc'd for C$_{23}$H$_{26}$N$_6$O$_3$, 435.21 found 435.4.

Example 210

1-((R)-2-(1H-indol-4-yl)-6a,7,9,10-tetrahydro-[1,4]oxazino[3,4-h]pteridin-5(6H)-yl)-4,4-dimethylpentan-3-amine

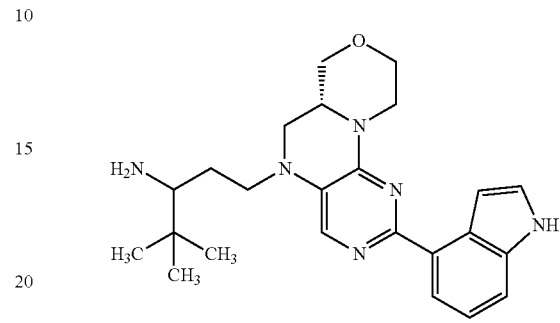

The title compound was prepared in a manner similar to EXAMPLE 193 using tert-butyl (1-((R)-2-(1H-indol-4-yl)-6a,7,9,10-tetrahydro-[1,4]oxazino[3,4-h]pteridin-5(6H)-yl)-4,4-dimethylpentan-3-yl)carbamate (PREPARATION x78) in CH$_2$Cl$_2$ (0.5 mL) and trifluoroacetic acid (0.5 mL) (11.7 mg, 76%). $^1$H NMR (400 MHz, DMSO-d$_6$) δ ppm 1.02 (s, 9H), 1.51-1.75 (m, 1H), 1.91-2.08 (m, 1H), 3.02-3.39 (m, 4H), 3.53-3.65 (m, 6H), 3.80-3.96 (m, 1H), 3.97-4.16 (m, 2H), 4.60-4.76 (m, 1H), 6.96-7.12 (m, 1H), 7.20-7.33 (m, 1H), 7.47-7.88 (m, 4H), 11.33-11.59 (m, 1H); ESI-MS m/z [M+H]⁺ calc'd for C$_{24}$H$_{32}$N$_6$O, 421.27 found 421.4.

Example 211

(R)-2-(2-(2-(difluoromethyl)-1H-benzo[d]imidazol-1-yl)-6a,7,9,10-tetrahydro-[1,4]oxazino[3,4-h]pteridin-5(6H)-yl)-N-((tetrahydro-2H-pyran-4-yl)methyl)acetamide

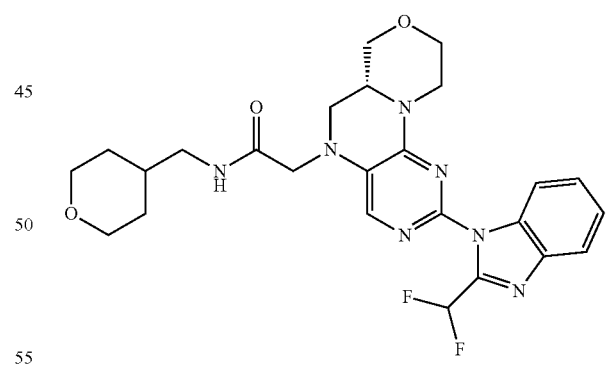

A mixture of (R)-2-(2-chloro-6a,7,9,10-tetrahydro-[1,4]oxazino[3,4-h]pteridin-5(6H)-yl)-N-((tetrahydro-2H-pyran-4-yl)methyl)acetamide (PREPARATION x26, 50 mg, 0.131 mmol), 2-(difluoromethyl)-1H-benzo[d]imidazole (24.22 mg, 0.144 mmol), cesium carbonate (64.0 mg, 0.196 mmol), tris(dibenzylideneacetone)dipalladium(0) (11.99 mg, 0.013 mmol), and 2-dicyclohexylphosphino-2',4',6'-tri-iso-propyl-1,1'-biphenyl (12.48 mg, 0.026 mmol) in DMF (500 μL) was heated to 130° C. in a microwave for 40 minutes. Additional tris(dibenzylideneacetone)dipalladium(0) (11.99 mg, 0.013 mmol) and 2-dicyclohexylphosphino-2',4',6'-tri-iso-propyl- 1,1'-biphenyl (12.48 mg, 0.026 mmol) were added to the reaction mixture, which was subsequently heated to 130° C. in the microwave for 1 hour. After addition of EtOAc and water, the mixture was extracted with EtOAc (2×). The combined extracts were washed with Na$_2$SO$_4$, filtered, and concentrated in vacuo. The residue was purified by flash column chromatography (NH-silica, gradient 30-100%, EtOAc/hexane) and then by preparatory HPLC using a 20-45% CH$_3$CN gradient in H$_2$O (with 0.05% TFA). The pure fractions were combined and lyophilized to give a TFA salt of the title compound as a yellow solid (11.3 mg, 13.8%). $^1$H NMR (400 MHz, DMSO-d$_6$) δ ppm 1.07-1.26 (m, 2H), 1.49-1.72 (m, 3H), 2.93-3.43 (m, 8H), 3.51-3.61 (m, 1H), 3.68-3.77 (m, 1H), 3.79-3.88 (m, 3H), 3.91-3.98 (m, 1H), 4.00-4.14 (m, 2H), 4.32-4.40 (m, 1H), 7.34-7.47 (m, 2H), 7.50 (s, 1H), 7.56-7.86 (m, 2H), 8.09-8.21 (m, 2H); ESI-MS m/z [M+H]$^+$ calc'd for C$_{25}$H$_{29}$F$_2$N$_7$O$_3$, 514.24. found 514.3.

Example 212

(R)-2-(2-(1H-indol-4-yl)-6a,7,9,10-tetrahydro-[1,4]oxazino[3,4-h]pteridin-5(6H)-yl)-N-methyl-N-((tetrahydro-2H-pyran-4-yl)methyl)acetamide

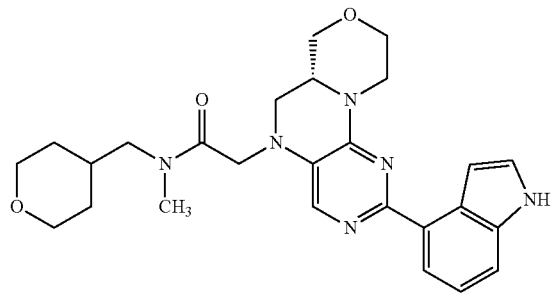 [SMILES: CN(CC1CCOCC1)C(=O)CN1C[C@@H]2COCCN2c2nc(-c3cccc4[nH]ccc34)ncc21]

A mixture of (R)-2-(2-chloro-6a,7,9,10-tetrahydro-[1,4]oxazino[3,4-h]pteridin-5(6H)-yl)-N-methyl-N-((tetrahydro-2H-pyran-4-yl)methyl)acetamide (PREPARATION x79, 70 mg, 0.177 mmol), indole-4-boronic acid (42.7 mg, 0.265 mmol), tetrakis(triphenylphosphine)palladium(0) (20.43 mg, 0.018 mmol), and sodium carbonate (37.5 mg, 0.354 mmol) in 1,4-dioxane (0.7 mL) and water (0.35 mL) was heated to 120° C. for 1 hour in a microwave. After cooling to room temperature, the reaction mixture was diluted with EtOAc, washed with water and brine, dried over Na$_2$SO$_4$, filtered, and concentrated in vacuo. The residue was purified by column chromatography (silica-NH, gradient 0-10% MeOH/CHCl$_3$) to afford the title compound as an off-white solid (36.8 mg, 43.7%). $^1$H NMR (400 MHz, DMSO-d$_6$) δ ppm 1.04-1.61 (m, 4H), 1.78-1.97 (m, 1H), 2.80-3.09 (m, 4H), 3.12-3.38 (m, 7H), 3.58 (t, J=9.98 Hz, 2H), 3.78-4.16 (m, 5H), 4.41-4.60 (m, 2H), 7.11 (t, J=7.71 Hz, 1H), 7.26-7.64 (m, 4H), 7.86-7.95 (m, 1H), 11.11 (br s, 1H); ESI-MS m/z [M+H]$^+$ calc'd for C$_{26}$H$_{32}$N$_6$O$_3$, 477.26. found 477.3.

Example 213

(S)-tert-butyl 2-(2-(1H-indol-4-yl)-6a,7,9,10-tetrahydro-[1,4]oxazino[3,4-h]pteridin-5(6H)-yl)acetate

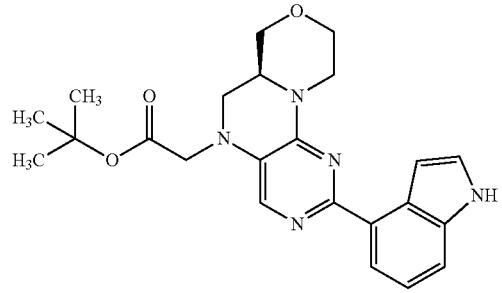 [SMILES: CC(C)(C)OC(=O)CN1C[C@H]2COCCN2c2nc(-c3cccc4[nH]ccc34)ncc21]

A mixture of (S)-tert-butyl 2-(2-chloro-6a,7,9,10-tetrahydro-[1,4]oxazino[3,4-h]pteridin-5(6H)-yl)acetate (PREPARATION x80, 100 mg, 0.293 mmol), indole-4-boronic acid (70.8 mg, 0.440 mmol), tetrakis(triphenylphosphine)palladium(0) (33.9 mg, 0.029 mmol), and sodium carbonate (62.2 mg, 0.587 mmol) in 1,4-dioxane (1 mL) and water (0.5 mL) was heated to 120° C. for 1 hour in a microwave. After cooling to room temperature, the reaction mixture was diluted with EtOAc, filtered through Celite, washed with water and brine, dried over Na$_2$SO$_4$, filtered, and concentrated in vacuo. The residue was purified via flash column chromatography (silica-NH, gradient 10-80% EtOAc/hexane) to afford the title compound as an off-white solid (112 mg, 91%). $^1$H NMR (400 MHz, DMSO-d$_6$) δ ppm 1.38-1.48 (m, 9H), 2.98-3.09 (m, 1H), 3.15-3.40 (m, 3H), 3.52-3.64 (m, 2H), 3.87-4.11 (m, 3H), 4.28 (d, J=17.94 Hz, 1H), 4.52-4.60 (m, 1H), 7.12 (t, J=7.71 Hz, 1H), 7.29-7.44 (m, 3H), 7.51-7.68 (m, 1H), 7.93 (dd, J=7.45, 0.88 Hz, 1H), 11.12 (br s, 1H); ESI-MS m/z [M+H]$^+$ calc'd for C$_{23}$H$_{27}$N$_5$O$_3$, 422.22. found 422.3.

Example 214

(R)-2-(2-(4-(hydroxymethyl)phenyl)-6a,7,9,10-tetrahydro-[1,4]oxazino[3,4-h]pteridin-5(6H)-yl)-N-((tetrahydro-2H-pyran-4-yl)methyl)acetamide

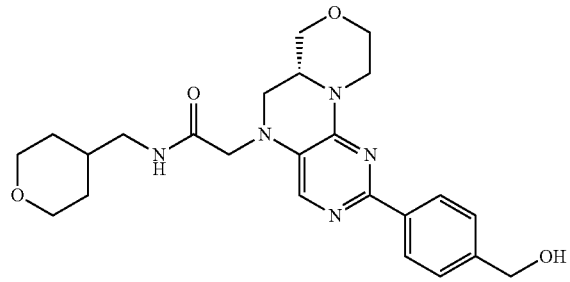 [SMILES: O=C(CN1C[C@@H]2COCCN2c2nc(-c3ccc(CO)cc3)ncc21)NCC1CCOCC1]

A mixture of (R)-2-(2-chloro-6a,7,9,10-tetrahydro-[1,4]oxazino[3,4-h]pteridin-5(6H)-yl)-N-((tetrahydro-2H-pyran-4-yl)methyl)acetamide (PREPARATION x26, 50 mg, 0.131 mmol), 4-(hydroxymethyl)phenylboronic acid (29.8 mg, 0.196 mmol), tetrakis(triphenylphosphine)palladium(0) (15.13 mg, 0.013 mmol), and sodium carbonate (27.8 mg, 0.262 mmol) in 1,4-dioxane (0.5 mL) and water (0.25 mL) was heated to 120° C. for 1 hour in a microwave. After cooling to room temperature, the reaction mixture was diluted with EtOAc, washed with water and brine, dried over Na$_2$SO$_4$, filtered, and concentrated in vacuo. The residue was purified by column chromatography (silica-NH, gradient 0-10% MeOH/CHCl$_3$) to afford a white solid, which was recrystallized from EtOH/EtOAc to give the title compound as an off-white solid (19.0 mg, 32.0%). $^1$H NMR (400 MHz, DMSO-d$_6$) δ ppm 1.02-1.21 (m, 2H), 1.48-1.71 (m, 3H), 2.91-3.02 (m, 3H), 3.12-3.32 (m, 5H), 3.50-3.67 (m, 2H), 3.73-4.08 (m, 6H), 4.49-4.61 (m, 3H), 5.19 (t, J=5.68 Hz, 1H), 7.34 (d, J=8.59 Hz, 2H), 7.47-7.51 (m, 1H), 8.08 (t, J=5.94 Hz, 1H), 8.16 (d, J=8.34 Hz, 2H); ESI-MS m/z [M+H]$^+$ calc'd for C$_{24}$H$_{31}$N$_5$O$_4$, 454.24. found 454.4.

Example 215

(R)-2-(2-(2-(hydroxymethyl)phenyl)-6a,7,9,10-tetrahydro-[1,4]oxazino[3,4-h]pteridin-5(6H)-yl)-N-((tetrahydro-2H-pyran-4-yl)methyl)acetamide

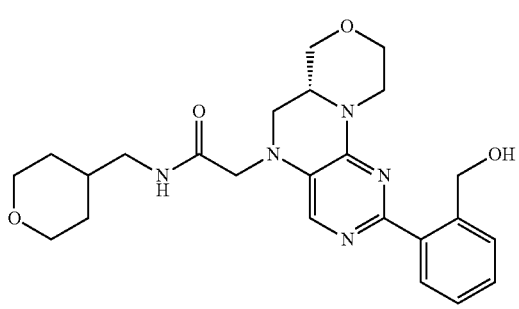 [SMILES: O=C(CN1C[C@@H]2COCCN2c2nc(-c3ccccc3CO)ncc21)NCC1CCOCC1]

The title compound was prepared in a manner similar to EXAMPLE 214 using 2-(hydroxymethyl)phenylboronic acid (29.8 mg, 0.196 mmol) in place of 4-(hydroxymethyl) phenylboronic acid. $^1$H NMR (400 MHz, DMSO-d$_6$) δ ppm 0.99-1.18 (m, 2H), 1.42-1.65 (m, 3H), 2.84-2.99 (m, 3H), 3.06-3.31 (m, 5H), 3.42-3.61 (m, 2H), 3.69-4.04 (m, 6H), 4.34-4.40 (m, 1H), 4.54-4.60 (m, 2H), 5.64-5.69 (m, 1H), 7.19-7.31 (m, 2H), 7.43-7.48 (m, 2H), 7.83 (dd, J=7.58, 1.77 Hz, 1H), 8.03 (t, J=5.81 Hz, 1H); ESI-MS m/z [M+H]$^+$ calc'd for C$_{24}$H$_{31}$N$_5$O$_4$, 454.24. found 454.4.

Example 216

(R)-2-(2-(3-(methoxymethyl)phenyl)-6a,7,9,10-tetrahydro-[1,4]oxazino[3,4-h]pteridin-5(6H)-yl)-N-((tetrahydro-2H-pyran-4-yl)methyl)acetamide

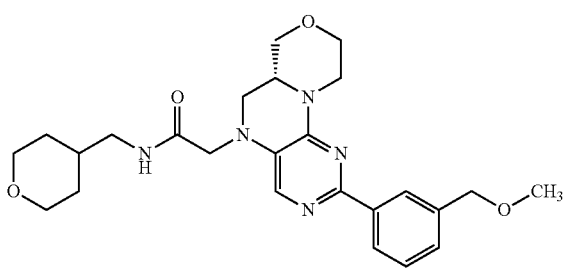 [SMILES: COCc1cccc(-c2ncc3c(n2)N2CCOC[C@H]2CN3CC(=O)NCC2CCOCC2)c1]

The title compound was prepared in a manner similar to EXAMPLE 214 using 3-(methoxymethyl)phenylboronic acid (32.6 mg, 0.196 mmol) in place of 4-(hydroxymethyl) phenylboronic acid. $^1$H NMR (400 MHz, DMSO-d$_6$) δ ppm 1.03-1.25 (m, 2H), 1.48-1.74 (m, 3H), 2.91-3.04 (m, 3H), 3.31 (s, 8H), 3.51-3.68 (m, 2H), 3.75-4.09 (m, 6H), 4.46 (s, 2H), 4.56 (d, J=11.87 Hz, 1H), 7.27-7.42 (m, 2H), 7.49-7.55 (m, 1H), 8.05-8.18 (m, 3H); ESI-MS m/z [M+H]$^+$ calc'd for C$_{25}$H$_{33}$N$_5$O$_4$, 468.26. found 468.4.

Example 217

(R)-2-(2-(3-(difluoromethoxy)phenyl)-6a,7,9,10-tetrahydro-[1,4]oxazino[3,4-h]pteridin-5(6H)-yl)-N-((tetrahydro-2H-pyran-4-yl)methyl)acetamide

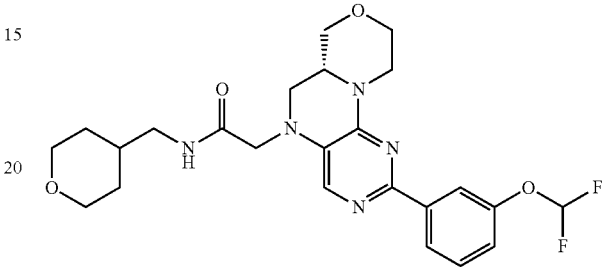

The title compound was prepared in a manner similar to EXAMPLE 214 using 3-(difluoromethoxy)-benzeneboronic acid (36.9 mg, 0.196 mmol) in place of 4-(hydroxymethyl) phenylboronic acid. $^1$H NMR (400 MHz, DMSO-d$_6$) δ ppm 1.04-1.22 (m, 2H), 1.44-1.72 (m, 3H), 2.92-3.04 (m, 3H), 3.11-3.38 (m, 5H), 3.51-3.68 (m, 2H), 3.77-3.93 (m, 4H), 4.00-4.10 (m, 2H), 4.50-4.59 (m, 1H), 7.08-7.55 (m, 4H), 7.94 (s, 1H), 8.06-8.11 (m, 2H); ESI-MS m/z [M+H]$^+$ calc'd for C$_{24}$H$_{29}$F$_2$N$_5$O$_4$, 490.22. found 490.3.

Example 218

(R)-2-(2-(3-cyanophenyl)-6a,7,9,10-tetrahydro-[1,4]oxazino[3,4-h]pteridin-5(6H)-yl)-N-((tetrahydro-2H-pyran-4-yl)methyl)acetamide

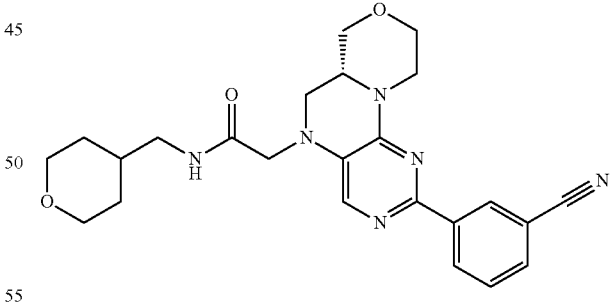

The title compound was prepared in a manner similar to EXAMPLE 214 using 3-cyanophenylboronic acid (28.9 mg, 0.196 mmol) in place of 4-(hydroxymethyl)phenylboronic acid. $^1$H NMR (400 MHz, DMSO-d$_6$) δ ppm 1.13 (qd, J=12.21, 4.80 Hz, 2H), 1.48-1.72 (m, 3H), 2.92-3.04 (m, 3H), 3.13-3.40 (m, 5H), 3.50-3.68 (m, 2H), 3.77-3.86 (m, 3H), 3.90 (dd, J=10.99, 3.41 Hz, 1H), 4.00-4.11 (m, 2H), 4.57-4.62 (m, 1H), 7.53 (s, 1H), 7.59-7.66 (m, 1H), 7.82 (dt, J=7.71, 1.33 Hz, 1H), 8.09 (t, J=5.94 Hz, 1H), 8.47-8.54 (m, 2H); ESI-MS m/z [M+H]$^+$ calc'd for C$_{24}$H$_{28}$N$_6$O$_3$, 449.23. found 449.3.

Example 219

(R)-2-(2-(2-fluoro-5-(hydroxymethyl)phenyl)-6a,7,9,10-tetrahydro-[1,4]oxazino[3,4-h]pteridin-5(6H)-yl)-N-((tetrahydro-2H-pyran-4-yl)methyl)acetamide

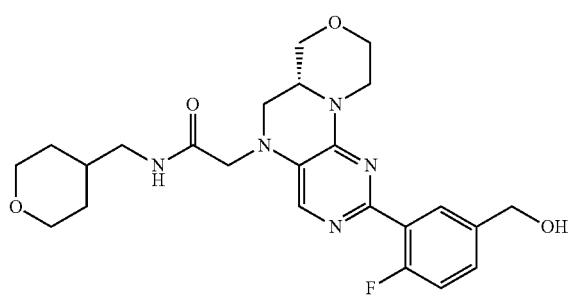 [SMILES: O=C(CN1C[C@@H]2COCCN2c2nc(-c3cc(CO)ccc3F)ncc21)NCC1CCOCC1]

The title compound was prepared in a manner similar to EXAMPLE 214 using 2-fluoro-5-hydroxymethylphenylboronic acid (43.2 mg, 0.196 mmol) in place of 4-(hydroxymethyl)phenylboronic acid. $^1$H NMR (400 MHz, DMSO-$d_6$) δ ppm 1.06-1.25 (m, 2H), 1.48-1.72 (m, 3H), 2.87-3.05 (m, 3H), 3.12-3.36 (m, 5H), 3.47-3.56 (m, 1H), 3.57-3.67 (m, 1H), 3.75-3.85 (m, 3H), 3.89 (dd, J=11.12, 3.28 Hz, 1H), 3.97-4.08 (m, 2H), 4.39-4.46 (m, 1H), 4.49 (d, J=5.56 Hz, 2H), 5.24 (t, J=5.81 Hz, 1H), 7.15 (dd, J=10.99, 8.46 Hz, 1H), 7.27-7.37 (m, 1H), 7.51 (s, 1H), 7.84 (dd, J=7.58, 2.27 Hz, 1H), 8.09 (t, J=5.94 Hz, 1H); ESI-MS m/z [M+H]$^+$ calc'd for $C_{24}H_{30}FN_5O_4$, 472.23. found 472.3.

Example 220

(R)-2-(2-(4-fluoro-3-(hydroxymethyl)phenyl)-6a,7,9,10-tetrahydro-[1,4]oxazino[3,4-h]pteridin-5(6H)-yl)-N-((tetrahydro-2H-pyran-4-yl)methyl)acetamide

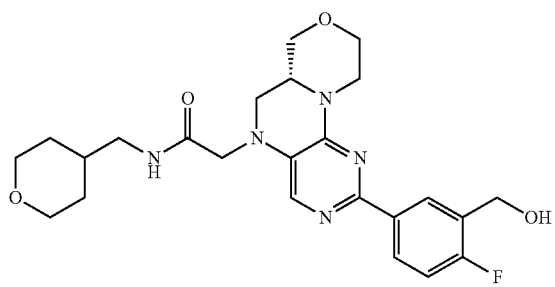 [SMILES: O=C(CN1C[C@@H]2COCCN2c2nc(-c3ccc(F)c(CO)c3)ncc21)NCC1CCOCC1]

The title compound was prepared in a manner similar to EXAMPLE 214 using 4-fluoro-3-hydroxymethylphenylboronic acid (43.2 mg, 0.196 mmol) in place of 4-(hydroxymethyl)phenylboronic acid. $^1$H NMR (400 MHz, DMSO-$d_6$) δ ppm 1.13 (qd, J=12.13, 4.04 Hz, 2H), 1.48-1.73 (m, 3H), 2.92-3.03 (m, 3H), 3.11-3.32 (m, 5H), 3.49-3.67 (m, 2H), 3.74-3.93 (m, 4H), 3.98-4.08 (m, 2H), 4.52-4.59 (m, 3H), 5.32 (t, J=5.81 Hz, 1H), 7.15 (dd, J=9.85, 8.59 Hz, 1H), 7.49 (s, 1H), 8.05-8.16 (m, 2H), 8.33 (dd, J=7.58, 2.27 Hz, 1H); ESI-MS m/z [M+H]$^+$ calc'd for $C_{24}H_{30}FN_5O_4$, 472.23. found 472.4.

Example 221

(R)-2-(2-(6-aminopyridin-3-yl)-6a,7,9,10-tetrahydro-[1,4]oxazino[3,4-h]pteridin-5(6H)-yl)-N-((tetrahydro-2H-pyran-4-yl)methyl)acetamide

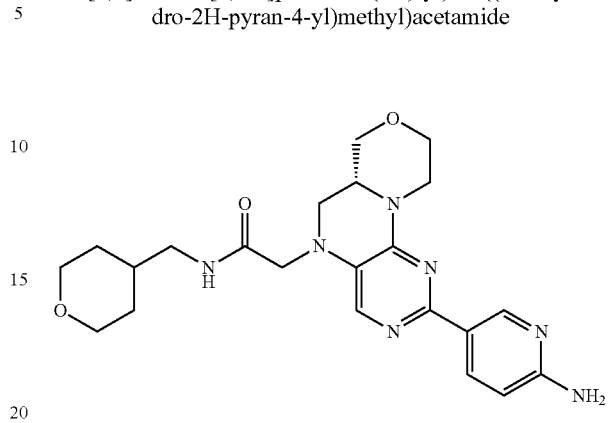

The title compound was prepared in a manner similar to EXAMPLE 214 using 2-amino-5-(4,4,5,5-tetramethyl-1,3,2-dioxaborolan-2-yl)pyridine (43.2 mg, 0.196 mmol) in place of 4-(hydroxymethyl)phenylboronic acid. $^1$H NMR (400 MHz, DMSO-$d_6$) δ ppm 1.13 (qd, J=12.13, 4.04 Hz, 2H), 1.48-1.73 (m, 3H), 2.92-3.03 (m, 3H), 3.11-3.32 (m, 5H), 3.49-3.67 (m, 2H), 3.74-3.93 (m, 4H), 3.98-4.08 (m, 2H), 4.52-4.59 (m, 3H), 5.32 (t, J=5.81 Hz, 1H), 7.15 (dd, J=9.85, 8.59 Hz, 1H), 7.49 (s, 1H), 8.05-8.16 (m, 2H), 8.33 (dd, J=7.58, 2.27 Hz, 1H); ESI-MS m/z [M+H]$^+$ calc'd for $C_{22}H_{29}N_7O_3$, 440.24. found 440.4.

Example 222

(R)-2-(2-(4-(3-methylureido)phenyl)-6a,7,9,10-tetrahydro-[1,4]oxazino[3,4-h]pteridin-5(6H)-yl)-N-((tetrahydro-2H-pyran-4-yl)methyl)acetamide

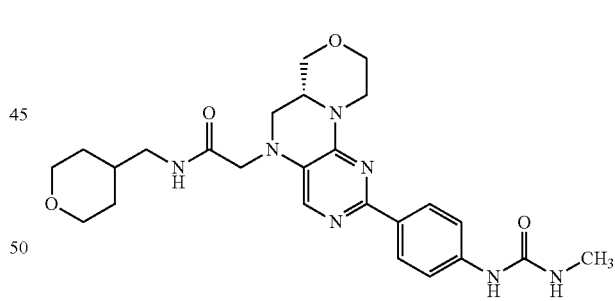

A mixture of (R)-2-(2-chloro-6a,7,9,10-tetrahydro-[1,4]oxazino[3,4-h]pteridin-5(6H)-yl)-N-((tetrahydro-2H-pyran-4-yl)methyl)acetamide (PREPARATION x26, 50 mg, 0.131 mmol), 1-methyl-3-[4-(4,4,5,5-tetramethyl-1,3,2-dioxaborolane-2-yl)phenyl]-urea (54.2 mg, 0.196 mmol), tetrakis(triphenylphosphine)palladium(0) (15.13 mg, 0.013 mmol), and sodium carbonate (27.8 mg, 0.262 mmol) in 1,4-dioxane (0.5 mL) and water (0.25 mL) was heated to 120° C. for 1 hour in a microwave. After cooling to room temperature, the reaction mixture was diluted with EtOAc, washed with water and brine, dried over $Na_2SO_4$, filtered, and concentrated in vacuo. The residue was purified by flash column chromatography (silica-NH, gradient 0-10% MeOH/CHCl$_3$) and then by preparatory HPLC using a 5-30% CH$_3$CN gradient in H$_2$O (with 0.05% TFA). The pure fractions were combined and lyophilized to give a TFA salt of the title compound as a white solid (12.0 mg, 15.0%).

$^1$H NMR (400 MHz, DMSO-d$_6$) δ ppm 1.08-1.25 (m, 2H), 1.49-1.71 (m, 3H), 2.66 (d, J=4.55 Hz, 3H), 2.99 (t, J=6.32 Hz, 2H), 3.16-3.32 (m, 5H), 3.43 (dd, J=11.62, 4.04 Hz, 1H), 3.53-3.63 (m, 1H), 3.77-4.22 (m, 7H), 4.82 (d, J=12.88 Hz, 1H), 6.18-6.28 (m, 1H), 7.31 (s, 1H), 7.59 (d, J=8.84 Hz, 2H), 8.03 (d, J=9.09 Hz, 2H), 8.13 (t, J=5.81 Hz, 1H), 9.01 (br s, 1H); ESI-MS m/z [M+H]$^+$ calc'd for C$_{25}$H$_{33}$N$_7$O$_4$, 496.26. found 496.4.

Example 223

(R)—N-((tetrahydro-2H-pyran-4-yl)methyl)-2-(2-(thiophen-3-yl)-6a,7,9,10-tetrahydro-[1,4]oxazino[3,4-h]pteridin-5(6H)-yl)acetamide

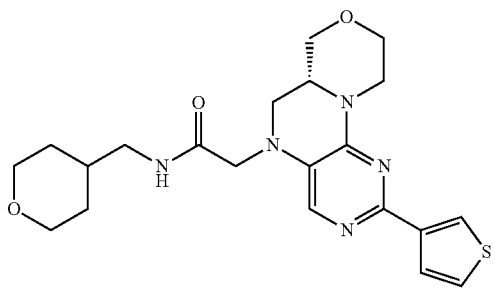 [SMILES: O=C(CN1C[C@@H]2COCCN2c2nc(-c3ccsc3)ncc21)NCC1CCOCC1]

A TFA salt of the title compound was prepared in a manner similar to EXAMPLE 222 using 3-thiopheneboronic acid (25.1 mg, 0.196 mmol) in place of 1-methyl-3-[4-(4,4,5,5-tetramethyl-1,3,2-dioxaborolane-2-yl)phenyl]-urea. $^1$H NMR (400 MHz, DMSO-d$_6$) δ ppm 1.06-1.25 (m, 2H), 1.48-1.73 (m, 3H), 2.99 (t, J=6.19 Hz, 2H), 3.15-3.31 (m, 5H), 3.44 (dd, J=11.75, 4.17 Hz, 1H), 3.53-3.65 (m, 1H), 3.77-4.22 (m, 7H), 4.82 (d, J=12.63 Hz, 1H), 7.35 (s, 1H), 7.72-7.83 (m, 2H), 8.14 (t, J=5.94 Hz, 1H), 8.48 (br s, 1H); ESI-MS m/z [M+H]$^+$ calc'd for C$_{21}$H$_{27}$N$_5$O$_3$S, 430.19. found 430.3.

Example 224

(R)-2-(2-(4-acetamidophenyl)-6a,7,9,10-tetrahydro-[1,4]oxazino[3,4-h]pteridin-5(6H)-yl)-N-((tetrahydro-2H-pyran-4-yl)methyl)acetamide

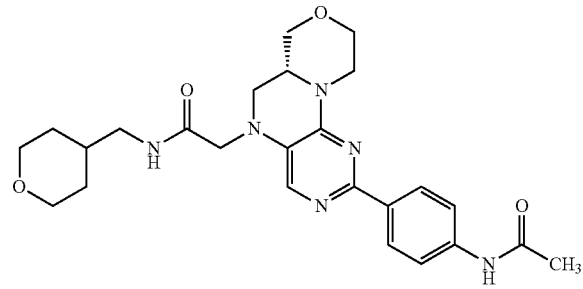 [SMILES: CC(=O)Nc1ccc(-c2ncc3c(n2)N2CCOC[C@H]2CN3CC(=O)NCC2CCOCC2)cc1]

A TFA salt of the title compound was prepared in a manner similar to EXAMPLE 222 using 4-acetamidophenylboronic acid (35.2 mg, 0.196 mmol) in place of 1-methyl-3-[4-(4,4,5,5-tetramethyl-1,3,2-dioxaborolane-2-yl)phenyl]-urea. $^1$H NMR (400 MHz, DMSO-d$_6$) δ ppm 1.14 (qd, J=11.87, 4.29 Hz, 2H), 1.48-1.72 (m, 3H), 2.09 (s, 3H), 3.00 (t, J=6.32 Hz, 2H), 3.15-3.33 (m, 5H), 3.44 (dd, J=11.75, 4.17 Hz, 1H), 3.53-3.64 (m, 1H), 3.79-4.10 (m, 6H), 4.17 (d, J=17.18 Hz, 1H), 4.82 (d, J=12.38 Hz, 1H), 7.37 (s, 1H), 7.77 (d, J=8.84 Hz, 2H), 8.07-8.19 (m, 3H), 10.31 (s, 1H); ESI-MS m/z [M+H]$^+$ calc'd for C$_{25}$H$_{32}$N$_6$O$_4$, 481.25. found 481.4.

Example 225

(R)-2-(2-(1-methyl-1H-pyrazol-5-yl)-6a,7,9,10-tetrahydro-[1,4]oxazino[3,4-h]pteridin-5(6H)-yl)-N-((tetrahydro-2H-pyran-4-yl)methyl)acetamide

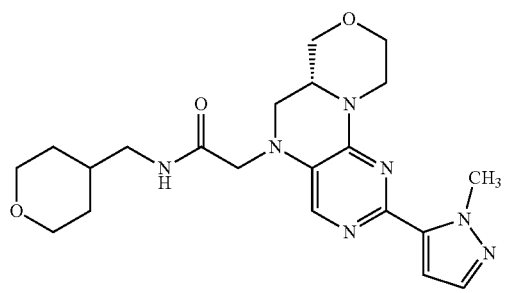 [SMILES: Cn1nccc1-c1ncc2c(n1)N1CCOC[C@H]1CN2CC(=O)NCC1CCOCC1]

A TFA salt of the title compound was prepared in a manner similar to EXAMPLE 222 using 1-methyl-5-(4,4,5,5-tetramethyl-[1,3,2]dioxaborolan-2-yl)-1H-pyrazole (40.9 mg, 0.196 mmol) in place of 1-methyl-3-[4-(4,4,5,5-tetramethyl-1,3,2-dioxaborolane-2-yl)phenyl]-urea. $^1$H NMR (400 MHz, DMSO-d$_6$) δ ppm 1.05-1.30 (m, 2H), 1.49-1.74 (m, 3H), 2.96-3.03 (m, 2H), 3.10-3.31 (m, 5H), 3.42 (dd, J=11.75, 3.92 Hz, 1H), 3.52-3.63 (m, 1H), 3.74-4.07 (m, 6H), 4.10-4.24 (m, 4H), 4.52 (d, J=12.38 Hz, 1H), 6.90 (d, J=1.77 Hz, 1H), 7.46 (s, 1H), 7.52 (d, J=2.02 Hz, 1H), 8.13 (t, J=5.94 Hz, 1H); ESI-MS m/z [M+H]$^+$ calc'd for C$_{21}$H$_{29}$N$_7$O$_3$, 428.24. found 428.4.

Example 226

(R)-2-(2-(5-(hydroxymethyl)thiophen-2-yl)-6a,7,9,10-tetrahydro-[1,4]oxazino[3,4-h]pteridin-5(6H)-yl)-N-((tetrahydro-2H-pyran-4-yl)methyl)acetamide

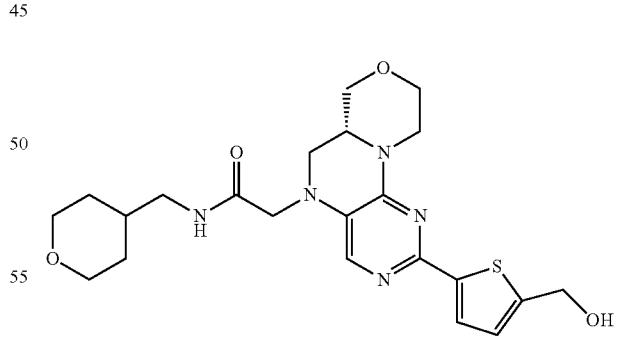

A TFA salt of the title compound was prepared in a manner similar to EXAMPLE 222 using 5-hydroxymethylthiophene-2-boronic acid (31.0 mg, 0.196 mmol) in place of 1-methyl-3-[4-(4,4,5,5-tetramethyl-1,3,2-dioxaborolan-2-yl)phenyl]-urea. $^1$H NMR (400 MHz, DMSO-d$_6$) δ ppm 1.05-1.30 (m, 2H), 1.49-1.74 (m, 3H), 2.96-3.03 (m, 2H), 3.10-3.31 (m, 5H), 3.42 (dd, J=11.75, 3.92 Hz, 1H), 3.52-3.63 (m, 1H), 3.74-4.07 (m, 6H), 4.10-4.24 (m, 4H), 4.52 (d, J=12.38 Hz, 1H), 6.90 (d, J=1.77 Hz, 1H), 7.46 (s, 1H), 7.52 (d, J=2.02 Hz, 1H), 8.13 (t, J=5.94 Hz, 1H); ESI-MS m/z [M+H]$^+$ calc'd for C$_{22}$H$_{29}$N$_5$O$_4$S, 460.20. found 460.3.

Example 227

(R)-5-(2-(1H-indol-4-yl)-6a,7,9,10-tetrahydro-[1,4]oxazino[3,4-h]pteridin-5(6H)-yl)-2-methylpentan-2-ol

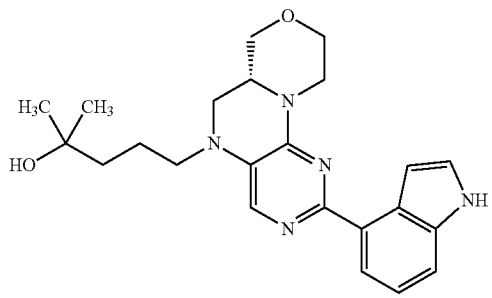 [SMILES: CC(C)(O)CCCN1C[C@@H]2COCCN2c2nc(-c3cccc4[nH]ccc34)ncc21]

To a 25 mL pear flask was added (R)-5-(2-(1H-indol-4-yl)-6a,7,9,10-tetrahydro-[1,4]oxazino[3,4-h]pteridin-5(6H)-yl)-2-methylpentan-2-yl acetate (PREPARATION x82, 48 mg, 0.107 mmol) in methanol (3 mL) to give a yellow solution. Aqueous NaOH (3N, 0.4 mL) was added and the mixture was stirred at 50° C. for 4 hours, before being cooled to room temperature. The reaction mixture was partitioned between saturated NaHCO$_3$ and ethyl acetate, and the aqueous layer was extracted a second time with ethyl acetate. The combined organic layers were dried over MgSO$_4$, filtered, and concentrated. After trituration with Et$_2$O, the solid product was dried in vacuo to give the title compound as an off-white solid (31 mg, 71%). $^1$H NMR (400 MHz, DMSO-d$_6$) δ ppm 1.10 (s, 6H), 1.32-1.48 (m, 2H), 1.53-1.73 (m, 2H), 2.95-3.10 (m, 2H), 3.11-3.25 (m, 2H), 3.26-3.40 (m, 2H), 3.50-3.64 (m, 2H), 3.93 (dd, J=10.99, 3.16 Hz, 1H), 4.06 (dd, J=11.49, 3.16 Hz, 1H), 4.19 (s, 1H), 4.52 (d, J=11.62 Hz, 1H), 7.11 (t, J=7.71 Hz, 1H), 7.29-7.44 (m, 3H), 7.77 (s, 1H), 7.93 (dd, J=7.45, 0.88 Hz, 1H), 11.11 (br s, 1H); ESI-MS m/z [M+H]$^+$ calc'd for C$_{23}$H$_{29}$N$_5$O$_2$, 408.24. found 408.3.

Example 228

2-((2-(1H-indol-4-yl)-6a,7,9,10-tetrahydro-[1,4]oxazino[3,4-h]pteridin-5(6H)-yl)methyl)-4-methylbenzamide

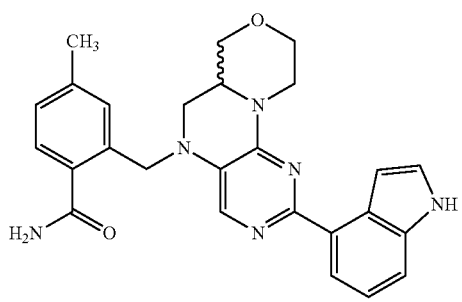 [SMILES: Cc1ccc(C(N)=O)c(CN2CC3COCCN3c3nc(-c4cccc5[nH]ccc45)ncc32)c1]

To a 10 mL vial were added 2-((2-chloro-6a,7,9,10-tetrahydro-[1,4]oxazino[3,4-h]pteridin-5(6H)-yl)methyl)-4-methylbenzamide (PREPARATION x84, 57 mg, 0.152 mmol), 1H-indol-4-ylboronic acid (49.1 mg, 0.305 mmol), and PdCl$_2$(dppf) (11.16 mg, 0.015 mmol) in dioxane (2 mL) and saturated NaHCO$_3$ (0.4 mL). The resulting orange suspension was heated to 100° C. and stirred overnight. The reaction mixture was subsequently diluted with EtOAc and washed with saturated NH$_4$Cl (3x). The combined organic layers were dried over MgSO$_4$, filtered, and concentrated. The product was purified by preparative HPLC, using a 20-45% CH$_3$CN gradient in H$_2$O (with 0.05% TFA). The pure fractions were combined and lyophilized to give the title compound as a yellow solid (23 mg, 33%). $^1$H NMR (400 MHz, DMSO-d$_6$) δ ppm 2.33 (s, 3H), 3.06-3.19 (m, 1H), 3.24-3.33 (m, 2H), 3.56-3.64 (m, 1H), 3.89-4.05 (m, 1H), 4.06-4.18 (m, 1H), 4.41-4.55 (m, 1H), 4.67-4.81 (m, 2H), 6.94-7.08 (m, 1H), 7.21-7.33 (m, 2H), 7.33-7.41 (m, 1H), 7.44-7.54 (m, 1H), 7.54-7.74 (m, 2H), 7.79-7.91 (m, 1H), 11.46-11.66 (m, 1H); ESI-MS m/z [M+H]$^+$ calc'd for C$_{26}$H$_{26}$N$_6$O$_2$, 455.2. found 455.3.

Example 229

1-cyclopropyl-3-(4-(6-oxo-5-(tetrahydro-2H-pyran-4-yl)-5,6,6a,7,9,10-hexahydro-[1,4]oxazino[3,4-h]pteridin-2-yl)phenyl)urea

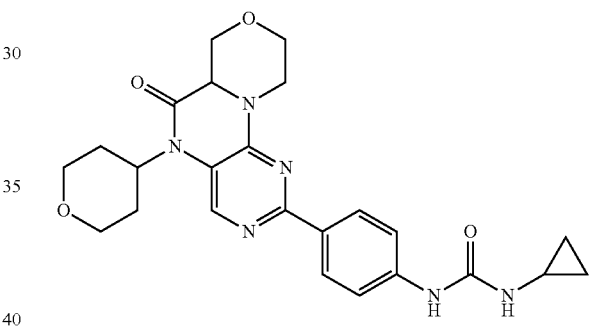

To a microwave reaction vial were added 2-chloro-5-(tetrahydro-2H-pyran-4-yl)-6a,7,9,10-tetrahydro-[1,4]oxazino[3,4-h]pteridin-6(5H)-one (PREPARATION x55, 0.040 g, 0.123 mmol), 1-cyclopropyl-3-(4-(4,4,5,5-tetramethyl-1,3,2-dioxaborolan-2-yl)phenyl)urea (0.041 g, 0.135 mmol), and PdCl$_2$(dppf) (0.018 g, 0.025 mmol) in saturated aq sodium bicarbonate (0.3 mL, 0.123 mmol) and dioxane (1.232 mL). The resulting suspension was heated by microwave irradiation at 100° C. for 1 hour, then filtered, and purified by preparatory HPLC using a 20-30% CH$_3$CN gradient in H$_2$O (with 0.05% TFA). The fractions were combined, concentrated in vacuo, and lyophilized to give the title compound as a white solid (13 mg, 23%). $^1$H NMR (400 MHz, DMSO-d$_6$) δ ppm 0.45-0.62 (m, 2H), 0.71-0.86 (m, 2H), 1.66-1.82 (m, 2H), 2.55-2.84 (m, 3H), 3.17-3.40 (m, 2H), 3.46-3.78 (m, 4H), 4.07 (td, J=12.19, 4.17 Hz, 3H), 4.30-4.46 (m, 2H), 4.55 (dd, J=10.61, 3.79 Hz, 1H), 4.96 (dd, J=13.64, 1.77 Hz, 2H), 7.67 (d, J=8.84 Hz, 2H), 8.01-8.26 (m, 3H); ESI-MS m/z [M+H]$^+$ calc'd for C$_{24}$H$_{28}$N$_6$O$_4$, 465.2. found 465.4.

TABLE 1, below, lists PI3Kδ inhibition data for many of the compounds described in the examples, where larger pIC$_{50}$ values represent higher potency. Most of the compounds were tested in accordance with the assay described on page 39 of the specification.

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. It is to be understood that the above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references, including patents, patent applications and publications, are herein incorporated by reference in their entirety and for all purposes.

TABLE 1

PI3Kδ Inhibition ($pIC_{50}$) for Example (Ex) Compounds

| Ex | $pIC_{50}$ |
|---|---|
| 1 | 7.5 |
| 2 | 7.3 |
| 3 | 8.3 |
| 4 | 8.4 |
| 5 | 8.0 |
| 6 | 8.0 |
| 7 | 8.1 |
| 8 | <5.0 |
| 9 | <5.0 |
| 10 | 5.5 |
| 11 | <5.0 |
| 12 | 5.1 |
| 13 | 7.8 |
| 14 | 5.3 |
| 15 | 6.4 |
| 16 | 5.2 |
| 17 | 7.4 |
| 18 | 6.4 |
| 19 | 8.0 |
| 20 | 6.3 |
| 21 | 5.9 |
| 22 | 7.7 |
| 23 | 8.3 |
| 24 | 7.2 |
| 25 | 6.8 |
| 26 | 6.6 |
| 27 | 6.6 |
| 28 | 6.2 |
| 29 | 8.3 |
| 30 | 8.9 |
| 31 | 8.1 |
| 32 | 7.1 |
| 33 | 7.9 |
| 34 | 7.9 |
| 35 | 8.0 |
| 36 | 6.9 |
| 37 | 6.5 |
| 38 | 7.9 |
| 39 | 7.7 |
| 40 | 7.8 |
| 41 | 7.5 |
| 42 | 6.3 |
| 43 | 6.4 |
| 44 | 6.5 |
| 45 | 6.6 |
| 46 | 6.5 |
| 47 | 6.8 |
| 48 | 6.6 |
| 49 | 6.7 |
| 50 | 6.5 |
| 51 | 6.6 |
| 52 | 6.4 |
| 53 | 6.6 |
| 54 | 6.3 |
| 55 | 6.2 |
| 56 | 5.5 |
| 57 | 6.1 |
| 58 | 6.3 |

TABLE 1-continued

PI3Kδ Inhibition ($pIC_{50}$) for Example (Ex) Compounds

| Ex | $pIC_{50}$ |
|---|---|
| 59 | 7.2 |
| 60 | 7.5 |
| 61 | 6.2 |
| 62 | 6.1 |
| 63 | 5.6 |
| 64 | 7.4 |
| 65 | |
| 66 | |
| 67 | 8.3 |
| 68 | 7.3 |
| 69 | 5.6 |
| 70 | 6.7 |
| 71 | 6.4 |
| 72 | 6.9 |
| 73 | 7.7 |
| 74 | 7.2 |
| 75 | 6.5 |
| 76 | 7.5 |
| 77 | 7.3 |
| 78 | 7.7 |
| 79 | 7.3 |
| 80 | 7.2 |
| 81 | 7.8 |
| 82 | 7.9 |
| 83 | 6.0 |
| 84 | 6.9 |
| 85 | 7.9 |
| 86 | 8.1 |
| 87 | 7.1 |
| 88 | 8.2 |
| 89 | 7.2 |
| 90 | 8.3 |
| 91 | 9.1 |
| 92 | 8.7 |
| 93 | 8.3 |
| 94 | 8.6 |
| 95 | 9.1 |
| 96 | 6.2 |
| 97 | 6.0 |
| 98 | 5.2 |
| 99 | 8.2 |
| 100 | 5.4 |
| 101 | 6.5 |
| 102 | 6.7 |
| 103 | 6.9 |
| 104 | 6.7 |
| 105 | 5.1 |
| 106 | 8.1 |
| 107 | 6.4 |
| 108 | 7.5 |
| 109 | 5.1 |
| 110 | 5.5 |
| 111 | 5.8 |
| 112 | 7.5 |
| 113 | 6.3 |
| 114 | 6.7 |
| 115 | 6.2 |
| 116 | 5.8 |
| 117 | 6.1 |
| 118 | 7.0 |
| 119 | 5.6 |
| 120 | 5.1 |
| 121 | 7.5 |
| 122 | 6.0 |
| 123 | 9.1 |
| 124 | 5.4 |
| 125 | 8.0 |
| 126 | 7.0 |
| 127 | 6.9 |
| 128 | 6.3 |
| 129 | 7.0 |
| 130 | 6.9 |
| 131 | 6.9 |
| 132 | 5.2 |
| 133 | 7.0 |
| 134 | <7.0 |

TABLE 1-continued

PI3Kδ Inhibition (pIC$_{50}$) for Example (Ex) Compounds

| Ex | pIC$_{50}$ |
|---|---|
| 135 | 7.0 |
| 136 | 6.3 |
| 137 | 6.3 |
| 138 | 5.5 |
| 139 | 7.1 |
| 140 | 6.2 |
| 141 | <5.0 |
| 142 | 7.7 |
| 143 | 5.7 |
| 144 | 8.6 |
| 145 | 7.6 |
| 146 | 7.5 |
| 147 | 7.7 |
| 148 | 8.4 |
| 149 | 6.7 |
| 150 | 8.3 |
| 151 | 5.3 |
| 152 | 6.3 |
| 153 | 7.4 |
| 154 | 6.9 |
| 155 | 7.6 |
| 156 | 6.5 |
| 157 | 7.4 |
| 158 | 8.1 |
| 159 | 8.6 |
| 160 | 7.0 |
| 161 | 8.4 |
| 162 | 8.2 |
| 163 | 7.5 |
| 164 | 7.1 |
| 165 | 6.1 |
| 166 | 7.2 |
| 167 | 6.0 |
| 168 | <5.0 |
| 169 | 8.1 |
| 170 | 8.2 |
| 171 | 8.5 |
| 172 | 8.3 |
| 173 | 6.8 |
| 174 | 8.1 |
| 175 | 8.8 |
| 176 | 8.8 |
| 177 | 8.7 |
| 178 | 8.8 |
| 179 | 7.3 |
| 180 | 6.4 |
| 181 | 7.1 |
| 182 | 7.8 |
| 183 | 6.4 |
| 184 | 6.4 |
| 185 | 8.0 |
| 186 | 7.3 |
| 187 | 6.9 |
| 188 | 7.4 |
| 189 | 8.1 |
| 190 | 7.6 |
| 191 | 8.5 |
| 192 | 8.5 |
| 193 | 6.1 |
| 194 | 8.5 |
| 195 | 8.5 |
| 196 | 8.2 |
| 197 | 5.5 |
| 198 | 7.8 |
| 199 | 6.0 |
| 200 | 7.0 |
| 201 | 7.9 |
| 202 | 8.6 |
| 203 | 6.4 |
| 204 | 6.8 |
| 205 | 6.7 |
| 206 | 7.3 |
| 207 | 6.6 |
| 208 | 6.4 |
| 209 | 7.0 |
| 210 | <5.0 |
| 211 | 7.7 |
| 212 | 7.4 |
| 213 | 5.0 |
| 214 | 5.7 |
| 215 | 5.3 |
| 216 | 6.0 |
| 217 | 6.1 |
| 218 | 5.9 |
| 219 | 7.0 |
| 220 | 6.6 |
| 221 | 6.9 |
| 222 | 7.5 |
| 223 | 6.1 |
| 224 | 6.5 |
| 225 | 5.8 |
| 226 | 6.3 |
| 227 | 7.8 |
| 228 | 6.8 |
| 229 | 7.5 |

What is claimed is:

1. A compound of Formula 1

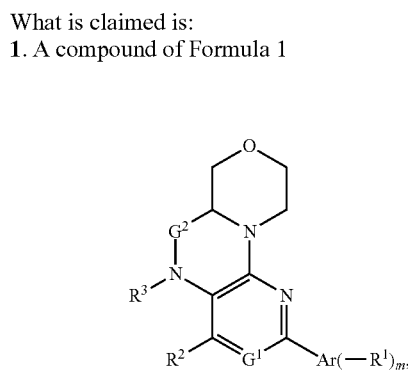

or a pharmaceutically acceptable salt therefore, wherein:
$G^1$ is selected from N and $CR^7$;
$G^2$ is selected from C=O and $CH_2$;
Ar is $C_{1-10}$ heteroaryl;
m is 0, 1, 2, 3, or 4;
n is 0, 1, 2 or 3;
each $R^1$ is independently selected from cyano, halo, hydroxy, nitro, oxo, optionally substituted $C_{1-6}$ alkyl, optionally substituted $C_{1-4}$ alkoxy, optionally substituted $C_{2-4}$ alkenyl, optionally substituted $C_{2-4}$ alkynyl, optionally substituted $C_{3-8}$ cycloalkyl, optionally substituted $C_{3-6}$ heterocyclyl, optionally substituted $C_{6-14}$ aryl, optionally substituted $C_{6-14}$ aryloxy, optionally substituted $C_{1-10}$ heteroaryl, optionally substituted $C_{1-10}$ heteroaryloxy, —C(O)OR$^4$, —OC(O)R$^4$, —N(R$^4$)R$^5$, —NHC(O)N(R)R$^9$, —S(O)$_2$R$^6$, —S(O)$_2$N(R$^4$)R$^5$, —C(O)N(R$^8$)R$^9$, —NHC(O)OR$^{10}$, —NHS(O)$_2$NHR$^8$, —NHS(O)$_2$R$^6$, —NHC(O)NHN(R$^8$)R$^9$, —NHC(S)N(R$^8$)R$^9$, —NHC(=NR$^{11}$)N(R)R$^9$, —NHC(SR$^{12}$)N(R)R$^9$, and —NHC(=NR$^{11}$)OR$^{13}$;
$R^2$ is selected from hydrogen, cyano, halo, hydroxy, nitro, optionally substituted $C_{1-6}$ alkyl, optionally substituted $C_{1-4}$ alkoxy, optionally substituted $C_{2-4}$ alkenyl, optionally substituted $C_{2-4}$ alkynyl, optionally substituted $C_{3-6}$ heterocyclyl, optionally substituted $C_{6-14}$ aryl, optionally substituted $C_{6-14}$ aryloxy, optionally substituted $C_{1-10}$ heteroaryl, —C(O)OR$^4$, —OC(O)R$^4$, —N(R$^4$)R$^5$, and —S(O)$_2$R$^6$;
$R^3$ is selected from hydrogen, optionally substituted $C_{1-6}$ alkyl, optionally substituted $C_{3-8}$ cycloalkyl, optionally substituted $C_{3-6}$ heterocyclyl, optionally substituted $C_{6-14}$ aryl, optionally substituted $C_{1-10}$ heteroaryl, —(CH$_2$)$_n$N(R$^4$)R$^5$, —(CH$_2$)$_n$C(O)N(R$^4$)R$^5$, and —S(O)$_2$R$^6$;

each R$^4$ and R$^5$ is independently selected from hydrogen, optionally substituted $C_{1-6}$ alkyl, optionally substituted $C_{3-8}$ cycloalkyl, optionally substituted phenyl, optionally substituted $C_{3-6}$ heterocyclyl, and optionally substituted $C_{1-10}$ heteroaryl;

each R$^6$ is independently selected from optionally substituted $C_{1-6}$ alkyl, optionally substituted $C_{3-8}$ cycloalkyl, optionally substituted phenyl, optionally substituted $C_{3-6}$ heterocyclyl, and optionally substituted $C_{1-10}$ heteroaryl;

R$^7$ is selected from hydrogen, cyano, halo, hydroxy, nitro, optionally substituted $C_{1-4}$ alkyl, optionally substituted $C_{1-4}$ alkoxy, —C(O)OR$^4$, —C(O)N(R$^4$)R$^5$, —N(R$^4$)R$^5$, —NHC(O)R$^4$, —NHC(O)N(R$^4$)R$^5$, —OC(O)N(R$^4$)R$^5$, —NHC(O)OR$^6$, —S(O)$_2$R$^6$, —NHS(O)$_2$R$^6$, and —S(O)$_2$N(R$^4$)R$^5$;

each R$^8$ and R$^9$ is independently selected from hydrogen, optionally substituted $C_{1-6}$ alkyl, optionally substituted $C_{3-8}$ cycloalkyl, optionally substituted $C_{6-14}$ aryl, optionally substituted $C_{3-6}$ heterocyclyl, and optionally substituted $C_{1-10}$ heteroaryl;

each R$^{10}$ is independently selected from optionally substituted $C_{1-6}$ alkyl, optionally substituted $C_{3-8}$ cycloalkyl, optionally substituted $C_{6-14}$ aryl, optionally substituted $C_{3-6}$ heterocyclyl, and optionally substituted $C_{1-10}$ heteroaryl;

each R$^{11}$ is independently selected from hydrogen, cyano, nitro, optionally substituted $C_{1-6}$ alkyl, optionally substituted $C_{1-4}$ alkoxy, optionally substituted $C_{3-8}$ cycloalkyl, optionally substituted $C_{3-6}$ heterocyclyl, optionally substituted $C_{6-14}$ aryl, and optionally substituted $C_{1-10}$ heteroaryl;

each R$^{12}$ is independently selected from optionally substituted $C_{1-6}$ alkyl and optionally substituted phenyl;

each R$^{13}$ is independently selected from optionally substituted $C_{1-6}$ alkyl, optionally substituted $C_{3-8}$ cycloalkyl, and optionally substituted $C_{6-14}$ aryl;

each R$^{14}$ and R$^{15}$ is independently selected from hydrogen, $C_{1-6}$ alkyl, $C_{3-8}$ cycloalkyl, optionally substituted phenyl, $C_{3-6}$ heterocyclyl, and $C_{1-10}$ heteroaryl; and each R$^{16}$ is independently selected from $C_{1-6}$ alkyl, $C_{3-8}$ cycloalkyl, optionally substituted phenyl, $C_{3-6}$ heterocyclyl, and $C_{1-10}$ heteroaryl;

wherein:

each optionally substituted $C_{1-6}$ alkyl is independently substituted with from 0 to 7 substituents independently selected from cyano, halo, hydroxy, oxo, optionally substituted $C_{1-4}$ alkyl, $C_{1-4}$ alkoxy, $C_{2-4}$ alkenyl, optionally substituted $C_{3-8}$ cycloalkyl, optionally substituted $C_{3-6}$ heterocyclyl, optionally substituted $C_{1-10}$ heteroaryl, optionally substituted phenyl, optionally substituted $C_{6-14}$ aryloxy, —SR$^{14}$, —C(O)OR$^{14}$, —N(R$^{14}$)R$^{15}$, —C(O)N(R$^{14}$)R$^{15}$, and —S(O)$_2$R$^{16}$;

each optionally substituted $C_{1-4}$ alkoxy is independently substituted with from 0 to 6 substituents independently selected from cyano, halo, hydroxy, oxo, $C_{2-4}$ alkenyl, $C_{1-4}$ alkoxy, optionally substituted $C_{3-8}$ cycloalkyl, optionally substituted $C_{1-10}$ heteroaryl, optionally substituted phenyl, —C(O)N(R$^{14}$)R$^{15}$, and —C(O)OR$^{14}$;

each optionally substituted $C_{2-4}$ alkenyl is independently substituted with from 0 to 3 substituents independently selected from cyano, halo, hydroxy, oxo, $C_{1-4}$ alkoxy, $C_{3-8}$ cycloalkyl, optionally substituted $C_{1-10}$ heteroaryl, optionally substituted phenyl, —C(O)N(R$^{14}$)R$^{15}$, and —C(O)OR$^{14}$;

each optionally substituted $C_{2-4}$ alkynyl is independently substituted with from 0 to 3 substituents independently selected from cyano, halo, hydroxy, oxo, $C_{1-4}$ alkoxy, $C_{3-8}$ cycloalkyl, optionally substituted $C_{1-10}$ heteroaryl, optionally substituted phenyl, —C(O)N(R$^{14}$)R$^{15}$, and —C(O)OR$^{14}$;

each optionally substituted $C_{3-8}$ cycloalkyl is independently substituted with from 0 to 6 substituents independently selected from cyano, halo, hydroxy, nitro, oxo, optionally substituted $C_{1-4}$ alkyl, $C_{1-4}$ alkoxy, $C_{2-4}$ alkenyl, $C_{3-8}$ cycloalkyl, $C_{3-8}$ cycloalkoxy, optionally substituted $C_{1-10}$ heteroaryl, optionally substituted phenyl, —C(O)N(R$^{14}$)R$^{15}$, —C(O)N(R$^{14}$)R$^{15}$, —N(R$^{14}$)R$^{15}$, —NHC(O)R$^{14}$, —NHC(O)OR$^{14}$, and —C(O)OR$^{14}$;

each optionally substituted $C_{1-10}$ heteroaryl is independently substituted with from 0 to 5 substituents independently selected from cyano, halo, hydroxy, oxo, nitro, optionally substituted $C_{1-4}$ alkyl, $C_{1-4}$ alkoxy, $C_{3-8}$ cycloalkyl, optionally substituted $C_{3-6}$ heterocyclyl, $C_{1-10}$ heteroaryl, optionally substituted phenyl, —C(O)N(R$^{14}$)R$^{15}$, —N(R$^{14}$)R$^{15}$, —C(O)N(R$^{14}$)R$^{15}$, —OC(O)NR$^{14}$R$^{15}$, —NHC(O)OR$^{16}$, —NHS(O)$_2$R$^{16}$, —S(O)$_2$N(R$^{14}$)R$^{15}$, —NHC(O)N(R$^{14}$)R$^{15}$, —C(O)OR$^{14}$, and —S(O)$_2$R$^{16}$;

each optionally substituted $C_{1-10}$ heteroaryloxy is independently substituted with from 0 to 5 substituents independently selected from cyano, halo, hydroxy, nitro, oxo, optionally substituted $C_{1-4}$ alkyl, $C_{1-4}$ alkoxy, trifluoromethyl, optionally substituted phenyl, and —S(O)$_2$R$^{16}$;

each optionally substituted $C_{3-6}$ heterocyclyl is independently substituted with from 0 to 4 substituents independently selected from cyano, halo, hydroxy, nitro, oxo, optionally substituted $C_{1-4}$ alkyl, optionally substituted $C_{1-4}$ alkoxy, $C_{2-4}$ alkenyl, optionally substituted $C_{3-8}$ cycloalkyl, $C_{3-8}$ cycloalkoxy, $C_{3-6}$ heterocyclyl, $C_{1-10}$ heteroaryl, optionally substituted phenyl, —C(O)N(R$^{14}$)R$^{15}$, —C(O)N(R$^{14}$)R$^{15}$, —N(R$^{14}$)R$^{15}$, and —C(O)OR$^{14}$;

each optionally substituted $C_{1-4}$ alkyl is independently substituted with from 0 to 5 substituents independently selected from cyano, halo, hydroxy, nitro, oxo, optionally substituted $C_{1-4}$ alkoxy, $C_{2-4}$ alkenyl, $C_{3-8}$ cycloalkyl, $C_{3-8}$ cycloalkoxy, $C_{3-6}$ heterocyclyl, $C_{1-10}$ heteroaryl, phenyl, —SR$^{14}$, —C(O)N(R$^{14}$)R$^5$, —N(R$^{14}$)R$^5$, —C(O)OR$^{14}$, and —S(O)$_2$R$^{16}$;

each optionally substituted $C_{6-14}$ aryl is independently substituted with from 0 to 5 substituents independently selected from cyano, halo, hydroxy, nitro, oxo, optionally substituted $C_{1-4}$ alkyl, $C_{1-4}$ alkoxy, $C_{2-4}$ alkenyl, $C_{1-10}$ heteroaryl, trifluoromethyl, trifluoromethoxy, —N(R$^{14}$)R$^{15}$, —C(O)N(R$^{14}$)R$^5$, —OC(O)N(R$^{14}$)R$^5$, —NHC(O)OR$^{16}$, —NHS(O)$_2$R$^{16}$, —S(O)$_2$N(R$^{14}$)R$^5$, —NHC(O)N(R$^{14}$)R$^{15}$, —C(O)OR$^{14}$, and —S(O)$_2$R$^{16}$;

each optionally substituted $C_{6-14}$ aryloxy is independently substituted with from 0 to 5 substituents independently selected from cyano, halo, hydroxy, nitro, oxo, optionally substituted $C_{1-4}$ alkyl, $C_{1-4}$ alkoxy, $C_{2-4}$ alkenyl, trifluoromethyl, trifluoromethoxy, —N(R$^{14}$)R$^{15}$, C(O)N(R$^{14}$)R$^{15}$, —OC(O)N(R$^{14}$)R$^{15}$, —NHC(O)OR$^{16}$, —NHS(O)$_2$R$^{16}$, —S(O)$_2$N(R$^{14}$)R$^{15}$, —NHC(O)N(R$^{14}$)R$^{15}$, —C(O)OR$^{14}$, and —S(O)$_2$R$^{16}$;

each optionally substituted phenyl is independently substituted with from 0 to 5 substituents independently selected from cyano, halo, hydroxy, nitro, optionally substituted $C_{1-4}$ alkyl, $C_{1-4}$ alkoxy, $C_{2-4}$ alkenyl, $C_{1-10}$ heteroaryl, trifluoromethyl, trifluoromethoxy, —N($R^{14}$)$R^{15}$, —C(O)N($R^{14}$)$R^{15}$, —OC(O)N($R^{14}$)$R^{15}$, —NHC(O)O$R^{16}$, —NHS(O)$_2R^{16}$, —S(O)$_2$N($R^{14}$)$R^{15}$, —NHC(O)N($R^{14}$)$R^{15}$, —C(O)O$R^{14}$, and —S(O)$_2R^{16}$;

each of the aforementioned heteroaryl and heteroaryloxy moieties has independently one to four ring heteroatoms independently selected from N, O, and S, and each of the aforementioned heterocyclyl moieties is independently saturated or partially unsaturated and has one or two ring heteroatoms independently selected from N, O, and S.

2. A compound or pharmaceutically acceptable salt according to claim 1, wherein $G^1$ is N.

3. A compound or pharmaceutically acceptable salt according to claim 1, wherein $G^2$ is $CH_2$.

4. A compound or pharmaceutically acceptable salt according to claim 1, wherein Ar is a bicyclic $C_{5-9}$ heteroaryl having from 1 to 4 nitrogen heteroatoms.

5. A compound or pharmaceutically acceptable salt according to claim 4, wherein Ar is a bicyclic $C_{7-9}$ heteroaryl having from 1 to 2 nitrogen heteroatoms.

6. A compound or pharmaceutically acceptable salt according to claim 5, wherein Ar is selected from indolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, benzimidazolyl, and indazolyl.

7. A compound or pharmaceutically acceptable salt according to claim 6, wherein Ar is selected from indol-4-yl, 1H-pyrrolo[2,3-b]pyridin-4-yl, 1H-pyrrolo[2,3-c]pyridin-4-yl, and 1H-pyrrolo[3,2-c]pyridin-4-yl.

8. A compound or pharmaceutically acceptable salt according to claim 1, wherein $R^3$ is selected from optionally substituted $C_{1-6}$ alkyl, optionally substituted $C_{6-14}$ aryl, optionally substituted $C_{1-10}$ heteroaryl, and —S(O)$_2R^6$.

9. A compound or pharmaceutically acceptable salt according to claim 1, wherein $R^2$ is hydrogen.

10. A compound according to claim 1, which is selected from the following compounds:
- 5-(5,6,6a,7,9,10-hexahydro-[1,4]oxazino[3,4-h]pteridin-2-yl)pyrimidin-2-amine;
- 2-(1H-indol-4-yl)-5,6,6a,7,9,10-hexahydro-[1,4]oxazino[3,4-h]pteridine;
- 5-(cyclopropylmethyl)-2-(1H-indol-4-yl)-5,6,6a,7,9,10-hexahydro-[1,4]oxazino[3,4-h]pteridine;
- 5-(5-(4-(methylsulfonyl)benzyl)-5,6,6a,7,9,10-hexahydro-[1,4]oxazino[3,4-h]pteridin-2-yl)pyrimidin-2-amine;
- 5-(2-chloro-4-(methylsulfonyl)benzyl)-2-(1H-indol-4-yl)-5,6,6a,7,9,10-hexahydro-[1,4]oxazino[3,4-h]pteridine;
- 5-(5-(2-chloro-4-(methylsulfonyl)benzyl)-5,6,6a,7,9,10-hexahydro-[1,4]oxazino[3,4-h]pteridin-2-yl)pyrimidin-2-amine;
- 2-(6-methoxy-1H-indol-3-yl)-5,6,6a,7,9,10-hexahydro-[1,4]oxazino[3,4-h]pteridine;
- 2-(7-methoxy-1H-indol-3-yl)-5,6,6a,7,9,10-hexahydro-[1,4]oxazino[3,4-h]pteridine;
- 2-(1H-benzo[d]imidazol-4-yl)-5,6,6a,7,9,10-hexahydro-[1,4]oxazino[3,4-h]pteridine;
- 2-(7-chloro-1H-indol-3-yl)-5,6,6a,7,9,1-hexahydro-[,4]oxazino[3,4-h]pteridine;
- 4-(5,6,6a,7,9,10-hexahydro-[1,4]oxazino[3,4-h]pteridin-2-yl)-1H-indol-2-ol;
- 2-(4-((2-(1H-indol-4-yl)-6a,7,9,10-tetrahydro-[1,4]oxazino[3,4-h]pteridin-5(6H)-yl)methyl)phenyl)propan-2-ol;
- 2-(2-methoxypyridin-4-yl)-5,6,6a,7,9,10-hexahydro-[1,4]oxazino[3,4-h]pteridine;
- 2-(1H-pyrrolo[2,3-b]pyridin-4-yl)-5,6,6a,7,9,10-hexahydro-[1,4]oxazino[3,4-h]pteridine;
- 2-(7-fluoro-3-methyl-1H-indol-4-yl)-5-(4-(methylsulfonyl)benzyl)-5,6,6a,7,9,10-hexahydro-[1,4]oxazino[3,4-h]pteridine;
- 2-(7-fluoro-1H-indol-4-yl)-5-(4-(methylsulfonyl)benzyl)-5,6,6a,7,9,10-hexahydro-[1,4]oxazino[3,4-h]pteridine;
- 2-(1H-indol-4-yl)-5-tosyl-5,6,6a,7,9,10-hexahydro-[1,4]oxazino[3,4-h]pteridine;
- 2-(1H-indol-4-yl)-5-(4-(methylsulfonyl)benzyl)-5,6,6a,7,9,10-hexahydro-[1,4]oxazino[3,4-h]pteridine;
- 1-(2-(1H-indol-4-yl)-6a,7,9,10-tetrahydro-[1,4]oxazino[3,4-h]pteridin-5(6H)-yl)-2-(4-methoxyphenyl)ethanone;
- 5-(4-(methylsulfonyl)benzyl)-2-(2-(trifluoromethyl)-1H-indol-4-yl)-5,6,6a,7,9,10-hexahydro-[1,4]oxazino[3,4-h]pteridine;
- 2-(1H-indazol-4-yl)-5-(4-(methylsulfonyl)benzyl)-5,6,6a,7,9,10-hexahydro-[1,4]oxazino[3,4-h]pteridine;
- 5-(4-(methylsulfonyl)benzyl)-2-(1H-pyrrolo[2,3-c]pyridin-4-yl)-5,6,6a,7,9,10-hexahydro-[1,4]oxazino[3,4-h]pteridine;
- 5-(4-(methylsulfonyl)benzyl)-2-(1H-pyrrolo[3,2-b]pyridin-6-yl)-5,6,6a,7,9,10-hexahydro-[1,4]oxazino[3,4-h]pteridine;
- 5-(4-(methylsulfonyl)benzyl)-2-(1H-pyrrolo[2,3-b]pyridin-5-yl)-5,6,6a,7,9,10-hexahydro-[1,4]oxazino[3,4-h]pteridine;
- 2-(1H-indol-4-yl)-4-methyl-5-(4-(methylsulfonyl)benzyl)-5,6,6a,7,9,10-hexahydro-[1,4]oxazino[3,4-h]pteridine;
- 5-(cyclopropylmethyl)-2-(1H-indol-4-yl)-4-methyl-5,6,6a,7,9,10-hexahydro-[1,4]oxazino[3,4-h]pteridine;
- (S)-2-(1H-indol-4-yl)-5-(4-(methylsulfonyl)benzyl)-5,6,6a,7,9,10-hexahydro-[1,4]oxazino[3,4-h]pteridine;
- (R)-2-(1H-indol-4-yl)-5-(4-(methylsulfonyl)benzyl)-5,6,6a,7,9,10-hexahydro-[1,4]oxazino[3,4-h]pteridine;
- (R)-5-(4-(methylsulfonyl)benzyl)-2-(1H-pyrrolo[2,3-c]pyridin-4-yl)-5,6,6a,7,9,10-hexahydro-[1,4]oxazino[3,4-h]pteridine;
- (R)-5-((5-ethyl-1,3,4-oxadiazol-2-yl)methyl)-2-(1H-indol-4-yl)-5,6,6a,7,9,10-hexahydro-[1,4]oxazino[3,4-h]pteridine;
- 2-(1H-indol-4-yl)-5-(2-phenoxyethyl)-5,6,6a,7,9,10-hexahydro-[1,4]oxazino[3,4-h]pteridine;
- 2-(1H-indol-4-yl)-5-((5-(thiophen-2-yl)-1,3,4-oxadiazol-2-yl)methyl)-5,6,6a,7,9,10-hexahydro-[1,4]oxazino[3,4-h]pteridine;
- 3-(2-(1H-indol-4-yl)-6a,7,9,10-tetrahydro-[1,4]oxazino[3,4-h]pteridin-5(6H)-yl)-N-(furan-2-ylmethyl)propanamide;
- 5-((5-ethyl-1,3,4-oxadiazol-2-yl)methyl)-2-(1H-indol-4-yl)-5,6,6a,7,9,10-hexahydro-[1,4]oxazino[3,4-h]pteridine;
- 5-((1-cyclopropyl-1H-tetrazol-5-yl)methyl)-2-(1H-indol-4-yl)-5,6,6a,7,9,10-hexahydro-[1,4]oxazino[3,4-h]pteridine;
- 2-(1H-indol-4-yl)-5-((2-phenyloxazol-4-yl)methyl)-5,6,6a,7,9,10-hexahydro-[1,4]oxazino[3,4-h]pteridine;
- 2-(1H-indol-4-yl)-5-((5-phenyl-1,3,4-oxadiazol-2-yl)methyl)-5,6,6a,7,9,1-hexahydro-[1,4]oxazino[3,4-h]pteridine;
- 2-(1H-indol-4-yl)-5-(oxazol-2-ylmethyl)-5,6,6a,7,9,10-hexahydro-[1,4]oxazino[3,4-h]pteridine;

2-(1H-indol-4-yl)-5-((1-phenyl-1H-1,2,3-triazol-4-yl)methyl)-5,6,6a,7,9,1-hexahydro-[1,4]oxazino[3,4-h]pteridine;
2-(2-(1H-indol-4-yl)-6a,7,9,10-tetrahydro-[1,4]oxazino[3,4-h]pteridin-5(6H)-yl)-N-(2-methylbenzyl)acetamide;
2-(2-(1H-indol-4-yl)-6a,7,9,10-tetrahydro-[1,4]oxazino[3,4-h]pteridin-5(6H)-yl)-N-isopropylacetamide;
2-(2-(1H-indol-4-yl)-6a,7,9,10-tetrahydro-[1,4]oxazino[3,4-h]pteridin-5(6H)-yl)-N,N-dimethylacetamide;
2-(2-(1H-indol-4-yl)-6a,7,9,10-tetrahydro-[1,4]oxazino[3,4-h]pteridin-5(6H)-yl)-N-isopropyl-N-methylacetamide;
2-((2-(1H-indol-4-yl)-6a,7,9,10-tetrahydro-[1,4]oxazino[3,4-h]pteridin-5(6H)-yl)methyl)benzonitrile;
2-((2-(1H-indol-4-yl)-6a,7,9,10-tetrahydro-[1,4]oxazino[3,4-h]pteridin-5(6H)-yl)methyl)-4-fluorobenzonitrile;
4-((2-(1H-indol-4-yl)-6a,7,9,10-tetrahydro-[1,4]oxazino[3,4-h]pteridin-5(6H)-yl)methyl)-3-methoxybenzonitrile;
1-(2-(1H-indol-4-yl)-6a,7,9,10-tetrahydro-[1,4]oxazino[3,4-h]pteridin-5(6H)-yl)-2-phenylethanone;
1-(2-(1H-indol-4-yl)-6a,7,9,10-tetrahydro-[1,4]oxazino[3,4-h]pteridin-5(6H)-yl)-2-(thiophen-2-yl)ethanone;
1-(2-(1H-indol-4-yl)-6a,7,9,10-tetrahydro-[1,4]oxazino[3,4-h]pteridin-5(6H)-yl)-2-(3-methoxyphenyl)ethanone;
1-(2-(1H-indol-4-yl)-6a,7,9,10-tetrahydro-[1,4]oxazino[3,4-h]pteridin-5(6H)-yl)-2-(thiophen-3-yl)ethanone;
1-(2-(1H-indol-4-yl)-6a,7,9,10-tetrahydro-[1,4]oxazino[3,4-h]pteridin-5(6H)-yl)-2-(benzofuran-3-yl)ethanone;
benzyl 2-(1H-indol-4-yl)-6a,7,9,10-tetrahydro-[1,4]oxazino[3,4-h]pteridine-5(6H)-carboxylate;
2-(2,6-difluorophenyl)-1-(2-(indolin-4-yl)-6a,7,9,10-tetrahydro-[1,4]oxazino[3,4-h]pteridin-5(6H)-yl)ethanone;
1-(2-(2-(difluoromethyl)-1H-benzo[d]imidazol-1-yl)-6a,7,9,10-tetrahydro-[1,4]oxazino[3,4-h]pteridin-5(6H)-yl)ethanone;
1-(2-(2-methyl-1H-benzo[d]imidazol-1-yl)-6a,7,9,10-tetrahydro-[1,4]oxazino[3,4-h]pteridin-5(6H)-yl)ethanone;
tert-butyl ((1r,4r)-4-((2-(1H-indol-4-yl)-6a,7,9,10-tetrahydro-[1,4]oxazino[3,4-h]pteridin-5(6H)-yl)methyl)cyclohexyl)carbamate;
(1r,4r)-4-((2-(1H-indol-4-yl)-6a,7,9,10-tetrahydro-[1,4]oxazino[3,4-h]pteridin-5(6H)-yl)methyl)cyclohexanamine;
3-((2-(1H-indol-4-yl)-6a,7,9,10-tetrahydro-[1,4]oxazino[3,4-h]pteridin-5(6H)-yl)methyl)benzonitrile;
3-((2-(1H-indol-4-yl)-6a,7,9,10-tetrahydro-[1,4]oxazino[3,4-h]pteridin-5(6H)-yl)methyl)-4-fluorobenzonitrile;
2-(1H-pyrrolo[2,3-b]pyridin-3-yl)-5,6,6a,7,9,10-hexahydro-[1,4]oxazino[3,4-h]pteridine;
2-(benzo[d][1,3]dioxol-4-yl)-5,6,6a,7,9,1-hexahydro-[1,4]oxazino[3,4-h]pteridine;
(R)-2-(2-(difluoromethyl)-1H-benzo[d]imidazol-1-yl)-5-(4-(methylsulfonyl)benzyl)-5,6,6a,7,9,10-hexahydro-[1,4]oxazino[3,4-h]pteridine;
(R)-tert-butyl 2-(2-(1H-indol-4-yl)-6a,7,9,10-tetrahydro-[1,4]oxazino[3,4-h]pteridin-5(6H)-yl)acetate;
(R)-2-(2-(1H-indol-4-yl)-6a,7,9,10-tetrahydro-[1,4]oxazino[3,4-h]pteridin-5(6H)-yl)acetic acid;
(R)-2-(2-(1H-indol-4-yl)-6a,7,9,10-tetrahydro-[1,4]oxazino[3,4-h]pteridin-5(6H)-yl)-N-(cyclopropylmethyl)acetamide;
(R)-2-(2-(1H-indol-4-yl)-6a,7,9,10-tetrahydro-[1,4]oxazino[3,4-h]pteridin-5(6H)-yl)-N-(2-hydroxy-2-methylpropyl)acetamide;
(R)-2-(2-(1H-indol-4-yl)-6a,7,9,10-tetrahydro-[1,4]oxazino[3,4-h]pteridin-5(6H)-yl)-N-((1H-pyrazol-3-yl)methyl)acetamide;
(R)-2-(2-(1H-indol-4-yl)-6a,7,9,10-tetrahydro-[1,4]oxazino[3,4-h]pteridin-5(6H)-yl)-N-((tetrahydro-2H-pyran-4-yl)methyl)acetamide;
2-((2-(1H-indol-4-yl)-6a,7,9,10-tetrahydro-[1,4]oxazino[3,4-h]pteridin-5(6H)-yl)methyl)benzamide;
2-((2-(1H-indol-4-yl)-6a,7,9,10-tetrahydro-[1,4]oxazino[3,4-h]pteridin-5(6H)-yl)methyl)-4-fluorobenzamide;
3-((2-(1H-indol-4-yl)-6a,7,9,10-tetrahydro-[1,4]oxazino[3,4-h]pteridin-5(6H)-yl)methyl)benzamide;
3-((2-(1H-indol-4-yl)-6a,7,9,10-tetrahydro-[1,4]oxazino[3,4-h]pteridin-5(6H)-yl)methyl)-4-fluorobenzamide;
4-((2-(1H-indol-4-yl)-6a,7,9,10-tetrahydro-[1,4]oxazino[3,4-h]pteridin-5(6H)-yl)methyl)benzamide;
4-((2-(1H-indol-4-yl)-6a,7,9,10-tetrahydro-[1,4]oxazino[3,4-h]pteridin-5(6H)-yl)methyl)-3-methoxybenzamide;
2-(1H-indol-4-yl)-5-((6-methylpyridin-2-yl)methyl)-5,6,6a,7,9,10-hexahydro-[1,4]oxazino[3,4-h]pteridine;
5-((5-cyclopropyl-1,3,4-oxadiazol-2-yl)methyl)-2-(1H-indol-4-yl)-5,6,6a,7,9,10-hexahydro-[1,4]oxazino[3,4-h]pteridine;
5-((S)-2,3-dihydro-1H-inden-1-yl)-2-(1H-pyrazol-4-yl)-6a,7,9,10-tetrahydro-[1,4]oxazino[3,4-h]pteridin-6(5H)-one;
5-((S)-1-phenylethyl)-2-(1H-pyrazol-3-yl)-6a,7,9,10-tetrahydro-[1,4]oxazino[3,4-h]pteridin-6(5H)-one;
2-(1H-indol-6-yl)-5-(4-(methylsulfonyl)benzyl)-6a,7,9,10-tetrahydro-[1,4]oxazino[3,4-h]pteridin-6(5H)-one;
ethyl 5-(5-(4-(methylsulfonyl)benzyl)-6-oxo-5,6,6a,7,9,10-hexahydro-[1,4]oxazino[3,4-h]pteridin-2-yl)nicotinate;
2-(6-aminopyridin-3-yl)-5-(4-(methylsulfonyl)benzyl)-6a,7,9,10-tetrahydro-[1,4]oxazino[3,4-h]pteridin-6(5H)-one;
5-(4-(methylsulfonyl)benzyl)-2-(1H-pyrrolo[2,3-b]pyridin-5-yl)-6a,7,9,10-tetrahydro-[1,4]oxazino[3,4-h]pteridin-6(5H)-one;
N-methyl-5-(5-(4-(methylsulfonyl)benzyl)-6-oxo-5,6,6a,7,9,10-hexahydro-[1,4]oxazino[3,4-h]pteridin-2-yl)picolinamide;
2-(1H-indazol-5-yl)-5-(4-(methylsulfonyl)benzyl)-6a,7,9,10-tetrahydro-[1,4]oxazino[3,4-h]pteridin-6(5H)-one;
N-(5-(5-(4-(methylsulfonyl)benzyl)-6-oxo-5,6,6a,7,9,10-hexahydro-[1,4]oxazino[3,4-h]pteridin-2-yl)pyridin-2-yl)acetamide;
5-(4-(methylsulfonyl)benzyl)-2-(2-oxo-2,3-dihydro-1H-benzo[d]imidazol-5-yl)-6a,7,9,10-tetrahydro-[1,4]oxazino[3,4-h]pteridin-6(5H)-one;
5-(4-(methylsulfonyl)benzyl)-2-(1H-pyrrolo[3,2-b]pyridin-6-yl)-6a,7,9,10-tetrahydro-[1,4]oxazino[3,4-h]pteridin-6(5H)-one;
2-(1H-indol-4-yl)-5-(4-(methylsulfonyl)benzyl)-6a,7,9,10-tetrahydro-[1,4]oxazino[3,4-h]pteridin-6(5H)-one;
2-(1H-indazol-6-yl)-5-(4-(methylsulfonyl)benzyl)-6a,7,9,10-tetrahydro-[1,4]oxazino[3,4-h]pteridin-6(5H)-one;
2-(2-aminopyrimidin-5-yl)-5-(4-(methylsulfonyl)benzyl)-6a,7,9,10-tetrahydro-[1,4]oxazino[3,4-h]pteridin-6(5H)-one;
2-(1-methyl-1H-pyrazol-5-yl)-5-(4-(methylsulfonyl)benzyl)-6a,7,9,10-tetrahydro-[1,4]oxazino[3,4-h]pteridin-6(5H)-one;

2-(1H-indol-5-yl)-5-(4-(methylsulfonyl)benzyl)-6a,7,9,10-tetrahydro-[1,4]oxazino[3,4-h]pteridin-6(5H)-one;
2-(3-methyl-1H-pyrazol-4-yl)-5-(4-(methylsulfonyl)benzyl)-5,6,6a,7,9,10-hexahydro-[1,4]oxazino[3,4-h]pteridine;
2-(7-chloro-1H-indol-3-yl)-5-(4-(methylsulfonyl)benzyl)-6a,7,9,10-tetrahydro-[1,4]oxazino[3,4-h]pteridin-6(5H)-one;
2-(2-hydroxy-1H-indol-4-yl)-5-(4-(methylsulfonyl)benzyl)-6a,7,9,10-tetrahydro-[1,4]oxazino[3,4-h]pteridin-6(5H)-one;
2-(6-methoxy-1H-indol-3-yl)-5-(4-(methylsulfonyl)benzyl)-6a,7,9,10-tetrahydro-[1,4]oxazino[3,4-h]pteridin-6(5H)-one;
5-(4-(methylsulfonyl)benzyl)-2-(1H-pyrrolo[2,3-b]pyridin-3-yl)-6a,7,9,10-tetrahydro-[1,4]oxazino[3,4-h]pteridin-6(5H)-one;
2-(7-methoxy-1H-indol-3-yl)-5-(4-(methylsulfonyl)benzyl)-6a,7,9,10-tetrahydro-[1,4]oxazino[3,4-h]pteridin-6(5H)-one;
2-(1H-benzo[d]imidazol-4-yl)-5-(4-(methylsulfonyl)benzyl)-6a,7,9,10-tetrahydro-[1,4]oxazino[3,4-h]pteridin-6(5H)-one;
2-(2-methoxypyridin-4-yl)-5-(4-(methylsulfonyl)benzyl)-6a,7,9,10-tetrahydro-[1,4]oxazino[3,4-h]pteridin-6(5H)-one;
2-(4-aminopyridin-2-yl)-5-(4-(methylsulfonyl)benzyl)-6a,7,9,10-tetrahydro-[1,4]oxazino[3,4-h]pteridin-6(5H)-one;
2-(7-fluoro-1H-indol-4-yl)-5-(4-(methylsulfonyl)benzyl)-6a,7,9,10-tetrahydro-[1,4]oxazino[3,4-h]pteridin-6(5H)-one;
2-(7-fluoro-3-methyl-1H-indol-4-yl)-5-(4-(methylsulfonyl)benzyl)-6a,7,9,10-tetrahydro-[1,4]oxazino[3,4-h]pteridin-6(5H)-one;
5-(4-(methylsulfonyl)benzyl)-2-(1H-pyrrolo[2,3-c]pyridin-4-yl)-6a,7,9,10-tetrahydro-[1,4]oxazino[3,4-h]pteridin-6(5H)-one;
5-benzyl-2-(1H-indol-4-yl)-6a,7,9,10-tetrahydro-[1,4]oxazino[3,4-h]pteridin-6(5H)-one;
5-(6-chloro-2,3-dihydro-1H-inden-1-yl)-2-(1H-indol-4-yl)-6a,7,9,10-tetrahydro-[1,4]oxazino[3,4-h]pteridin-6(5H)-one;
(R)-2-(1H-indol-4-yl)-6a,7,9,10-tetrahydro-[1,4]oxazino[3,4-h]pteridin-6(5H)-one;
(S)-2-(1H-indol-4-yl)-6a,7,9,10-tetrahydro-[1,4]oxazino[3,4-h]pteridin-6(5H)-one;
2-(benzo[d][1,3]dioxol-4-yl)-6a,7,9,10-tetrahydro-[1,4]oxazino[3,4-h]pteridin-6(5H)-one;
2-(1H-benzo[d]imidazol-4-yl)-6a,7,9,10-tetrahydro-[1,4]oxazino[3,4-h]pteridin-6(5H)-one;
(S)-2-(1H-indol-4-yl)-5-((S)-1-p-tolylethyl)-6a,7,9,10-tetrahydro-[1,4]oxazino[3,4-h]pteridin-6(5H)-one;
(R)-2-(1H-indol-4-yl)-5-((S)-1-p-tolylethyl)-6a,7,9,10-tetrahydro-[1,4]oxazino[3,4-h]pteridin-6(5H)-one;
5-(4-(methylsulfonyl)benzyl)-2-(1H-pyrrolo[2,3-b]pyridin-4-yl)-6a,7,9,10-tetrahydro-[1,4]oxazino[3,4-h]pteridin-6(5H)-one;
2-(2-methyl-1H-imidazol-1-yl)-5-(4-(methylsulfonyl)benzyl)-6a,7,9,10-tetrahydro-[1,4]oxazino[3,4-h]pteridin-6(5H)-one;
2-(2-(difluoromethyl)-1H-benzo[d]imidazol-1-yl)-5-((5-methyl-1,3,4-oxadiazol-2-yl)methyl)-6a,7,9,10-tetrahydro-[1,4]oxazino[3,4-h]pteridin-6(5H)-one;
2-(2-aminopyrimidin-5-yl)-5-((S)-1-(4-chlorophenyl)ethyl)-6a,7,9,10-tetrahydro-[1,4]oxazino[3,4-h]pteridin-6(5H)-one;
5-((S)-1-(4-chlorophenyl)ethyl)-2-(1H-indol-4-yl)-6a,7,9,10-tetrahydro-[1,4]oxazino[3,4-h]pteridin-6(5H)-one;
2-(1H-indol-4-yl)-5-(pyrimidin-2-ylmethyl)-5,6,6a,7,9,10-hexahydro-[1,4]oxazino[3,4-h]pteridine;
(R)-methyl 2-((2-(1H-indol-4-yl)-6a,7,9,10-tetrahydro-[1,4]oxazino[3,4-h]pteridin-5(6H)-yl)methyl)-4-methylbenzoate;
(R)-(2-((2-(1H-indol-4-yl)-6a,7,9,19,10-tetrahydro-[1,4]oxazino[3,4-h]pteridin-5(6H)-yl)methyl)-4-methylphenyl)methanol;
(R)-5-((5-ethyl-1,3,4-oxadiazol-2-yl)methyl)-2-(1H-pyrrolo[2,3-c]pyridin-4-yl)-5,6,6a,7,9,10-hexahydro-[1,4]oxazino[3,4-h]pteridine;
(R)-5-(5-((5-ethyl-1,3,4-oxadiazol-2-yl)methyl)-5,6,6a,7,9,10-hexahydro-[1,4]oxazino[3,4-h]pteridin-2-yl)pyridin-2-ol;
(R)-4-(2-(1H-indol-4-yl)-6a,7,9,10-tetrahydro-[1,4]oxazino[3,4-h]pteridin-5(6H)-yl)-2-methylbutan-2-ol;
(R)-4-(2-(1H-pyrrolo[2,3-c]pyridin-4-yl)-6a,7,9,10-tetrahydro-[1,4]oxazino[3,4-h]pteridin-5(6H)-yl)-2-methylbutan-2-ol;
(R)-2-(2-(1H-indol-4-yl)-6a,7,9,10-tetrahydro-[1,4]oxazino[3,4-h]pteridin-5(6H)-yl)ethanol;
(R)-2-(2-(1H-pyrrolo[2,3-c]pyridin-4-yl)-6a,7,9,10-tetrahydro-[1,4]oxazino[3,4-h]pteridin-5(6H)-yl)-N-((tetrahydro-2H-pyran-4-yl)methyl)acetamide;
(6aR)-2-(1H-indol-4-yl)-5-(1-(5-isobutyl-1,3,4-oxadiazol-2-yl)ethyl)-5,6,6a,7,9,10-hexahydro-[1,4]oxazino[3,4-h]pteridine;
(6aR)-5-(1-(5-ethyl-1,3,4-oxadiazol-2-yl)ethyl)-2-(1H-indol-4-yl)-5,6,6a,7,9,10-hexahydro-[1,4]oxazino[3,4-h]pteridine;
(R)-5-((5-ethyl-1,3,4-oxadiazol-2-yl)methyl)-2-(1H-pyrrolo[3,2-c]pyridin-1-yl)-5,6,6a,7,9,10-hexahydro-[1,4]oxazino[3,4-h]pteridine;
2-(1H-indol-4-yl)-5-phenyl-5,6,6a,7,9,10-hexahydro-[1,4]oxazino[3,4-h]pteridine;
(R)-2-(1H-indol-4-yl)-5-((1-methyl-1H-pyrazol-4-yl)methyl)-5,6,6a,7,9,10-hexahydro-[1,4]oxazino[3,4-h]pteridine;
(R)-5-(3-ethylphenyl)-2-(1H-indol-4-yl)-5,6,6a,7,9,1-hexahydro-[1,4]oxazino[3,4-h]pteridine;
(R)-5-(2-ethylphenyl)-2-(1H-indol-4-yl)-5,6,6a,7,9,1-hexahydro-[1,4]oxazino[3,4-h]pteridine;
(R)-2-(1H-indol-4-yl)-5-(oxazol-5-ylmethyl)-5,6,6a,7,9,10-hexahydro-[1,4]oxazino[3,4-h]pteridine;
(R)-2-(2-(1H-indol-4-yl)-6a,7,9,10-tetrahydro-[1,4]oxazino[3,4-h]pteridin-5(6H)-yl)benzonitrile;
(R)-2-(1H-indol-4-yl)-5-(o-tolyl)-5,6,6a,7,9,10-hexahydro-[1,4]oxazino[3,4-h]pteridine;
(R)-5-((3-ethylisoxazol-5-yl)methyl)-2-(1H-indol-4-yl)-5,6,6a,7,9,10-hexahydro-[1,4]oxazino[3,4-h]pteridine;
(R)-4-(2-(1H-indol-4-yl)-6a,7,9,10-tetrahydro-[1,4]oxazino[3,4-h]pteridin-5(6H)-yl)cyclohexanol;
(R)-ethyl 3-(2-(1H-indol-4-yl)-6a,7,9,10-tetrahydro-[1,4]oxazino[3,4-h]pteridin-5(6H)-yl)benzoate;
(R)-2-(1H-indol-4-yl)-5-(3-(methylsulfonyl)phenyl)-5,6,6a,7,9,10-hexahydro-[1,4]oxazino[3,4-h]pteridine;
(R)-2-(1H-indol-4-yl)-5-(tetrahydro-2H-pyran-4-yl)-5,6,6a,7,9,10-hexahydro-[1,4]oxazino[3,4-h]pteridine;
(R)-2,5-di(1H-indol-4-yl)-5,6,6a,7,9,10-hexahydro-[1,4]oxazino[3,4-h]pteridine;
(R)-5-(2-(1,3-dioxolan-2-yl)ethyl)-2-(1H-indol-4-yl)-5,6,6a,7,9,10-hexahydro-[1,4]oxazino[3,4-h]pteridine;
(R)-methyl 4-(2-(1H-indol-4-yl)-6a,7,9,10-tetrahydro-[1,4]oxazino[3,4-h]pteridin-5(6H)-yl)butanoate;

(R)-4-(2-(1H-indol-4-yl)-6a,7,9,10-tetrahydro-[1,4]ox-azino[3,4-h]pteridin-5(6H)-yl)butanoic acid;

(1R,4r)-4-(((R)-2-(1H-indol-4-yl)-6a,7,9,10-tetrahydro-[1,4]oxazino[3,4-h]pteridin-5(6H)-yl)methyl)cyclohexanamine;

(R)-ethyl 5-(2-(1H-indol-4-yl)-6a,7,9,10-tetrahydro-[1,4]oxazino[3,4-h]pteridin-5(6H)-yl)nicotinate;

(R)-methyl 5-(2-(1H-indol-4-yl)-6a,7,9,10-tetrahydro-[1,4]oxazino[3,4-h]pteridin-5(6H)-yl)nicotinate;

(R)-methyl 2-(2-(1H-indol-4-yl)-6a,7,9,10-tetrahydro-[1,4]oxazino[3,4-h]pteridin-5(6H)-yl)isonicotinate;

(R)-2-(1H-indol-4-yl)-5-(5-methoxypyridin-3-yl)-5,6,6a,7,9,10-hexahydro-[1,4]oxazino[3,4-h]pteridine;

(R)-methyl 5-(2-(1H-indol-4-yl)-6a,7,9,10-tetrahydro-[1,4]oxazino[3,4-h]pteridin-5(6H)-yl)-2-methoxynicotinate;

(R)-2-(2-(1H-indol-4-yl)-6a,7,9,10-tetrahydro-[1,4]oxazino[3,4-h]pteridin-5(6H)-yl)-N-(pyridin-4-yl)acetamide;

(R)-2-(2-(1H-indol-4-yl)-6a,7,9,10-tetrahydro-[1,4]oxazino[3,4-h]pteridin-5(6H)-yl)-N-(2-methoxyethyl)acetamide;

(R)-2-(2-(1H-indol-4-yl)-6a,7,9,10-tetrahydro-[1,4]oxazino[3,4-h]pteridin-5(6H)-yl)-N-(tetrahydro-2H-pyran-4-yl)acetamide;

(R)-2-(2-(1H-indol-4-yl)-6a,7,9,10-tetrahydro-[1,4]oxazino[3,4-h]pteridin-5(6H)-yl)-N-(1-methyl-1H-pyrazol-4-yl)acetamide;

(R)-2-(2-(1H-indol-4-yl)-6a,7,9,10-tetrahydro-[1,4]oxazino[3,4-h]pteridin-5(6H)-yl)-N-cyclopropylacetamide;

(R)-2-(2-(1H-indol-4-yl)-6a,7,9,10-tetrahydro-[1,4]oxazino[3,4-h]pteridin-5(6H)-yl)-N-(2-cyanopropan-2-yl)acetamide;

2-((R)-2-(1H-indol-4-yl)-6a,7,9,10-tetrahydro-[1,4]oxazino[3,4-h]pteridin-5(6H)-yl)-N-(tetrahydrofuran-3-yl)acetamide;

((R)-2-(1H-indol-4-yl)-6a,7,9,10-tetrahydro-[1,4]oxazino[3,4-h]pteridin-5(6H)-yl)-4,4-dimethylpentan-3-amine;

(R)-2-(2-(2-(difluoromethyl)-1H-benzo[d]imidazol-1-yl)-6a,7,9,10-tetrahydro-[1,4]oxazino[3,4-h]pteridin-5(6H)-yl)-N-((tetrahydro-2H-pyran-4-yl)methyl)acetamide;

(R)-2-(2-(1H-indol-4-yl)-6a,7,9,10-tetrahydro-[1,4]oxazino[3,4-h]pteridin-5(6H)-yl)-N-methyl-N-((tetrahydro-2H-pyran-4-yl)methyl)acetamide;

(S)-tert-butyl 2-(2-(1H-indol-4-yl)-6a,7,9,10-tetrahydro-[1,4]oxazino[3,4-h]pteridin-5(6H)-yl)acetate;

(R)-2-(2-(6-aminopyridin-3-yl)-6a,7,9,1-tetrahydro-[1,4]oxazino[3,4-h]pteridin-5(6H)-yl)-N-((tetrahydro-2H-pyran-4-yl)methyl)acetamide;

(R)—N-((tetrahydro-2H-pyran-4-yl)methyl)-2-(2-(thiophen-3-yl)-6a,7,9,10-tetrahydro-[1,4]oxazino[3,4-h]pteridin-5(6H)-yl)acetamide;

(R)-2-(2-(1-methyl-1H-pyrazol-5-yl)-6a,7,9,10-tetrahydro-[1,4]oxazino[3,4-h]pteridin-(6H)-yl)-N-((tetrahydro-2H-pyran-4-yl)methyl)acetamide;

(R)-2-(2-(5-(hydroxymethyl)thiophen-2-yl)-6a,7,9,10-tetrahydro-[1,4]oxazino[3,4-h]pteridin-5(6H)-yl)-N-((tetrahydro-2H-pyran-4-yl)methyl)acetamide;

(R)-5-(2-(1H-indol-4-yl)-6a,7,9,10-tetrahydro-[1,4]oxazino[3,4-h]pteridin-5(6H)-yl)-2-methylpentan-2-ol;

2-((2-(1H-indol-4-yl)-6a,7,9,10-tetrahydro-[1,4]oxazino[3,4-h]pteridin-5(6H)-yl)methyl)-4-methylbenzamide;

a stereoisomer of any of the aforementioned compounds; and a pharmaceutically acceptable salt of any of the aforementioned compounds or stereoisomers.

11. A pharmaceutical composition comprising:
a compound or pharmaceutically acceptable salt as defined in claim 1; and
a pharmaceutically acceptable excipient.

12. A method of treating a disease or condition in a subject, the method comprising administering to the subject an effective amount of a compound of Formula 1 or a pharmaceutically acceptable salt as defined in claim 1, wherein the disease or condition is selected from allergic rhinitis, asthma, atopic dermatitis, rheumatoid arthritis, multiple sclerosis, systemic lupus erythematosus, psoriasis, immune thrombocytopenic purpura, inflammatory bowel disease, chronic obstructive pulmonary disease, Sjögren's syndrome, ankylosing spondylitis, Behcet's disease, atherosclerosis, myocardial infarction, and thrombosis.

13. A combination comprising an effective amount of a compound or pharmaceutically acceptable salt as defined in claim 1 and a disease modifying antirheumatic drug.

* * * * *